(12) United States Patent
Rice et al.

(10) Patent No.: US 7,235,394 B1
(45) Date of Patent: Jun. 26, 2007

(54) FUNCTIONAL DNA CLONE FOR HEPATITIS C VIRUS (HCV) AND USES THEREOF

(75) Inventors: Charles M. Rice, University City, MO (US); Alexander A. Kolykhalov, St. Louis, MO (US)

(73) Assignee: Washington University, St. Louis, MO (US)

( * ) Notice: Subject to any disclaimer, the term of this patent is extended or adjusted under 35 U.S.C. 154(b) by 321 days.

(21) Appl. No.: 10/704,407

(22) Filed: Nov. 6, 2003

Related U.S. Application Data

(63) Continuation-in-part of application No. 09/917,563, filed on Jul. 27, 2001, now abandoned, which is a continuation of application No. 09/238,076, filed on Jan. 26, 1999, now abandoned, which is a continuation of application No. 08/811,566, filed on Mar. 4, 1997, now Pat. No. 6,127,116, which is a continuation-in-part of application No. 08/520,678, filed on Aug. 29, 1995, now Pat. No. 5,874,565.

(51) Int. Cl.
*C12N 7/00* (2006.01)
*C12N 7/02* (2006.01)
*C12N 5/10* (2006.01)
*C12P 21/00* (2006.01)
*C07H 21/04* (2006.01)

(52) U.S. Cl. ............... 435/239; 435/69.1; 435/70.1; 435/325; 435/320.1; 435/235.1; 536/23.72; 536/24.1

(58) Field of Classification Search ............ 435/235.1, 435/239, 325, 363, 320.1, 69.1, 70.1, 70.3, 435/366, 370, 5, 6; 424/93.1, 93.2, 93.21; 536/23.1, 23.7, 23.72, 24.1
See application file for complete search history.

(56) References Cited

U.S. PATENT DOCUMENTS

| | | |
|---|---|---|
| 4,631,211 A | 12/1986 | Houghten |
| 5,010,175 A | 4/1991 | Rutter et al. |
| 5,077,193 A | 12/1991 | Mishiro et al. |
| 5,106,726 A | 4/1992 | Wang |
| 5,176,994 A | 1/1993 | Mishiro et al. |
| 5,218,099 A | 6/1993 | Reyes et al. |
| 5,298,394 A | 3/1994 | Arima et al. |
| 5,312,737 A | 5/1994 | Bolling et al. |
| 5,350,671 A | 9/1994 | Houghton et al. |
| 5,371,017 A | 12/1994 | Houghton et al. |
| 5,372,928 A | 12/1994 | Miyamura et al. |
| 5,378,814 A | 1/1995 | Houghton et al. |
| 5,389,528 A | 2/1995 | Houghton et al. |
| 5,427,909 A | 6/1995 | Okamoto et al. |
| 5,428,145 A | 6/1995 | Okamoto et al. |
| 5,436,126 A | 7/1995 | Wang |
| 5,443,965 A | 8/1995 | Reyes et al. |
| 5,527,669 A | 6/1996 | Resnick et al. |
| 5,538,865 A | 7/1996 | Reyes et al. |
| 5,550,016 A | 8/1996 | Okamoto |
| 5,552,310 A | 9/1996 | Yoshikura et al. |
| 5,563,328 A * | 10/1996 | Mitra et al. ............ 800/294 |
| 5,576,302 A | 11/1996 | Cook et al. |
| 5,580,718 A | 12/1996 | Resnick et al. |
| 5,585,258 A | 12/1996 | Houghton et al. |
| 5,597,691 A | 1/1997 | Houghton et al. |
| 5,610,054 A | 3/1997 | Draper |
| 5,620,843 A | 4/1997 | Hellings et al. |
| 5,625,034 A | 4/1997 | Liao et al. |
| 5,625,043 A | 4/1997 | Priebe et al. |
| 5,641,654 A | 6/1997 | Maki et al. |
| 5,645,983 A | 7/1997 | Liao et al. |
| 5,654,179 A | 8/1997 | Lin |
| 5,656,731 A | 8/1997 | Urdea |
| 5,661,008 A * | 8/1997 | Almstedt et al. .......... 435/69.6 |
| 5,667,992 A | 9/1997 | Casey et al. |
| 5,670,152 A | 9/1997 | Weiner et al. |
| 5,670,153 A | 9/1997 | Weiner et al. |
| 5,677,124 A | 10/1997 | DuBois et al. |
| 5,679,342 A * | 10/1997 | Houghton et al. ........ 424/93.21 |
| 5,683,864 A | 11/1997 | Houghton et al. |
| 5,698,390 A | 12/1997 | Houghton et al. |
| 5,712,088 A | 1/1998 | Houghton et al. |
| 5,714,596 A | 2/1998 | Houghton et al. |
| 5,854,067 A * | 12/1998 | Newgard et al. .......... 435/366 |

(Continued)

FOREIGN PATENT DOCUMENTS

EP      1 267 167      12/2002

(Continued)

OTHER PUBLICATIONS

Blight et al., Science, vol. 290 No. 5498, pp. 1972-1974 (Dec. 2000).*
Bowie et al., Science, vol. 247 No. 4948, pp. 1306-1310 (Mar. 1990).*
Friebe et al., Journal of Virology, vol. 76 No. 11, pp. 5326-5338 (Jun. 2002).*
Ito et al., Journal of Virology, vol. 72 No. 11, pp. 8789-8796 (Nov. 1998).*
Lohmann et al., Science, vol. 285 No. 5424, pp. 110-113 (Jul. 1999).*
Tanaka et al., Journal of Virology, vol. 70 No. 5, pp. 3307-3312.*
Umlauft et al., Journal of Clinical Microbiology, vol. 34 No. 10, pp. 2552-2558 (Oct. 1996).*
Yi et al., Journal of Virology, vol. 77 No. 6, pp. 3557-3568 (Mar. 2003).*
Yoo et al., Journal of Virilogy, vol. 69 No. 1, pp. 32-38 (Jan. 1995).*
Lohmann et al., Science, vol. 285 No. 5424, pp. 110-113 (Jul. 1999).*

(Continued)

*Primary Examiner*—Bruce R. Campell
*Assistant Examiner*—Zacharaiah Lucas
(74) *Attorney, Agent, or Firm*—Thompson Coburn, LLP

(57) ABSTRACT

The present invention relates to the determination of an authentic HCV genome RNA sequences, to construction of infectious HCV DNA clones, and to use of the clones, or their derivatives, in therapeutic, vaccine, and diagnostic applications. The invention is also directed to HCV vectors, e.g., for gene therapy of gene vaccines.

23 Claims, 46 Drawing Sheets

U.S. PATENT DOCUMENTS

Figure 1:
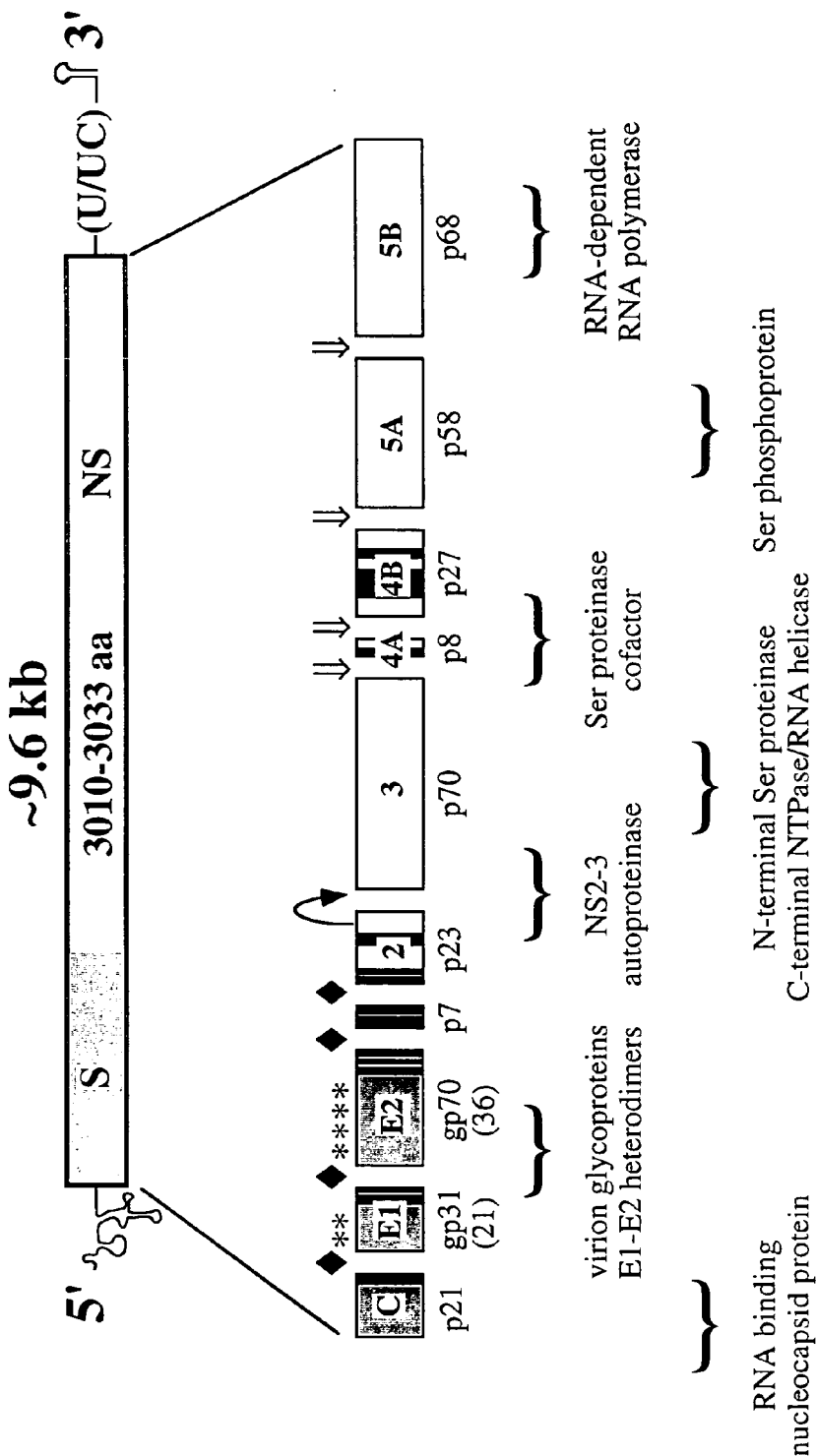

| | | | |
|---|---|---|---|
| 5,874,565 A | | 2/1999 | Rice et al. |
| 6,127,116 A | | 10/2000 | Rice et al. |
| 6,153,421 A | * | 11/2000 | Yanagi et al. ............ 435/235.1 |
| 6,165,715 A | * | 12/2000 | Collins et al. ................ 435/6 |
| 6,392,028 B1 | | 5/2002 | Rice et al. |
| 6,630,343 B1 | | 10/2003 | Bartenschlager |

FOREIGN PATENT DOCUMENTS

| | | |
|---|---|---|
| WO | WO96/34976 | 11/1996 |
| WO | WO97/08310 | 3/1997 |
| WO | WO99/04008 | 1/1999 |
| WO | WO01/89364 | 11/2001 |

OTHER PUBLICATIONS

Tanaka et al., Journal of Virology, vol. 70 No. 5, pp. 3307-3312 (1996).*

Umlauft et al., Journal of Clinical Microbiology, vol. 34 No. 10, pp. 2552-2558 (Oct. 1996).*

Yi et al., Journal of Virology, vol. 77 No. 6, pp. 3557-3568 (Mar. 2003).*

Verma et al., "Gene Therapy—Promises, Problems and Prospects", Nature, vol. 389, pp. 239-242 (1997).

Eck et al., "Gene-Based Therapy", The Pharmacological Basis of Therapeutics, Goodman and Gilman, Eds., pp. 77-101 (1996).

Orkin et al., "Report and Recommendations of the Panel to Assess the NIH Investment in Research on Gene Therapy", NIH (1995). Online at www.nih.gov/news/panelrep.html.

Houdebine, "Production of Pharmaceutical Proteins From Transgenic Animals", Journal of Biotechnology, vol. 34, pp. 269-287 (1994).

Lanford et al., "Advances in Model Systems for Hepatitis C Virus Research", Virology, vol. 293 No. 1, pp. 1-9 (Feb. 2002).

Zhu et al., "Replication of Hepatitis C Virus Subgenomes in Nonhepatic Epithelial and Mouse Hepatoma Cells", Journal of Virology, vol. 77 No. 17, pp. 9204-9210 (Sep. 2003).

Grobler et al., "Identification of a Key Determinant of Hepatitis C Virus Cell Culture Adaptation in Domain II of NS3 Helicase", The Journal of Biological Chemistry, vol. 278 No. 19, pp. 16741-16746 (May 2003).

Blight et al., "Highly Permissive Cell Lines for Subgenomic and Genomic Hepatitis C Virus RNA Replication", Journal of Virology, vol. 76 No. 24, pp. 13001-13014 (Dec. 2002).

Chung et al., "Hepatitis C virus replication is directly inhibited by IFN-alpha in a full-length binary expression system", Proceedings of the National Academy of Sciences, USA, vol. 98 No. 17, pp. 9847-9852 (Aug. 2001).

Bartenschlager et al., "Replication of the hepatitis C virsus in cell culture", Antiviral Research, vol. 60 No. 2, pp. 91-102 (Oct. 2003). Patent Cooperation Treaty; International Search Report; Jan. 3, 2005.

Barton and Flanegan, "Coupled translation and replication of poliovirus RNA in vitro: synthesis of functional 3D polymerase and infectious virus", J. Virol. 67:822-831 (1993).

Blight et al., "Immunohistochemical detection of the NS4 antigen of hepatitis C virus and its relation to histopathology", Amer. J. Path. 143:1568-1573 (1993).

Boyer et al., "Pathogenesis, diagnosis and management of hepatitis C", J. Hepatol. 32(1 Suppl.) 98-112 (2000).

Bredenbeek et al., "Sindbis virus expression vectors: packaging of RNA replicons by using defective helper RNAs", J. Virol. 67:6439-6446 (1993).

Butkiewicz et al., "Virus-specific cofactor requirement and chimeric hepatitis C virus/GB virus B nonstructural protein 3", J. Virol. 74, 4291-4301 (2000).

Carloni et al., "Susceptibility of human liver cell cultures to hepatitis C virus infection", Arch. Virol. (1993) [Suppl] 8:31-39.

Farci et al., "The outcome of acute hepatitis C predicted by the evolution of the viral quasispecies", Science 288:339-344 (2000).

Frolov et al., "Selection of RNA replicons capable of noncytopathic replication in mammalian cells", J. Virol., 73:3854-3856 (1999).

Gale et al., "Evidence That Hepatitis C Virus Resistance to Interferon Is Mediated Through Repression of the PKR Protein Kinase by the Nonstructural 5A Protein," Virology 230, 217-227 (1997).

Ghosh et al., "Hepatitis C virus NS5A protein modulates transcription through a novel cellular transcription factor SRCAP", J. Biol. Chem. 275:7184-7188 (2000).

Honda et al., "Natural variation in translational activities of the 5' nontranslated RNAs of hepatitis C virus genotypes 1a and 1b: evidence for a long-range RNA-RNA interaction outside of the internal ribosomal entry site", J. Virol. 73:4941-4951 (1999).

Hutchison et al., "A complete library of point substitution mutations in the glucocorticoid response element of mouse mammary tumor virus", Proc. Nat'l. Acad. Sci. USA 83:710-714 (1986).

Jansen et al., "Complete nucleotide sequence of a cell culture-adapted variant of hepatitis A virus: comparison with wild-type virus with restricted capacity for in vitro replication," Virology 163:299-307 (1988).

Kolykhalov et al., "Transmission of hepatitis C by intrahepatic inoculation with transcribed RNA", Science 277:570-574 (1997).

Krieger et al., "Enhancement of Hepatitis C Virus RNA replication by cell culture-adaptive mutations", J. Virol. 75:4614-4624 (2001).

Lai, Hepatology 27:299-302 (1998).

Lemm and Rice, "Assembly of functional Sindbis virus RNA replication complexes: requirement for coexpression of P123 and P34", J. Virol. 67:1905-1915 (1993).

Lemm et al., "Polypeptide requirements for assembly of functional Sindbis virus replication complexes: a model for the temporal regulation of minus- and plus-strand RNA synthesis", EMBO J. 13:2925-2934 (1994).

Lohmann et al., "Mutations in Hepatitis C Virus RNAs conferring cell culture adaptation", J. Virol. 75:1437-1449 (2001).

Lundkvist et al., "Cell culture adaptation of puumala hantavirus changes the infectivity for its natural reservoir, Clethrionomys glareolus, and leads to accumulation of mutants with altered genomic RNA S segment", J. Virol. 71:9515-9523 (1997).

Macejak et al., "Inhibition of hepatitis C virus (HCV)-RNA-dependent translation and replication of a chimeric HCV poliovirus using synthetic stabilized ribozymes", Hepatology 31:769-776 (2000).

Makimura et al., "Induction of antibodies against structural proteins of hepatitis C virus in mice using recombinant adenovirus", Vaccine 14:28-36 (1996).

Melnick and Wenner. In "Diagnostic Procedures for Viral and Rickettsial Infections, 4th Ed." (E.H. Lennette and N.J. Schmidt, Eds.), "Enteroviruses", pp. 529-553, American Public Health Association, Inc., New York (1969).

Miyamura et al., "Detection of antibody against antigen expressed by molecularly cloned hepatitis C virus cDNA: application to diagnosis and blood screening for posttransfusion hepatitis", Proc. Nat'l. Acad. Sci. USA 87:983-987 (1990).

Mizuno et al., "Virion-like structures in HeLa G cells transfected with the full-length sequence of the hepatitis C virus genome", Gastroenterology 1995 109:1933-1940 (1995).

Molla et al., "Cardioviral internal ribosomal entry site is functional in a genetically engineered dicistronic poliovirus", Nature 356: 255-257 (1992).

Moorman et al., "Infectious RNA transcribed from an engineered full-length cDNA template of the genome of a pestivirus", J. Virol. 70:763-770 (1996).

Murray et al., "Persistent replication of hepatitis C virus replicons expressing the beta-lactamase reporter in subpopulations of highly permissive Huh7 cells", J. Virol. 77:2928-2935 (2003).

Negro et al. Hepatology 14 116A:274 (1991).

Pileri et al., "Binding of hepatitis C virus to CD81", Science 282:938-941 (1998).

Purcell, "The hepatitis C virus: overview", Hepatology 26:11S-14S (1997).

Rice et al., "Production of infectious RNA transcripts from Sindbis virus cDNA clones: mapping of lethal mutations, rescue of a temperature-sensitive marker, and in vitro mutagenesis to generate defined mutants", J. Virol. 61: 3809-3819 (1987).

Tagawa, "Infection of human hepatocyte cell lines with hepatitis C virus in vitro", J. Gastroenterol. and Hepatol., 10:523-527 (1995).

Todd et al., "Replication-competent picornaviruses with complete genomic RNA 3' noncoding region deletions", *J. Virol.* 71:8868-8874 (1997).
Trowbridge et al., "Molecular cloning of an Australian isolate of hepatitis C virus", *Arch Virol.* 143:501-511 (1998).
Yanagi et al., "Transcripts from a single full-length cDNA clone of hepatitis C virus are infectious when directly transfected into the liver of a chimpanzee", *Proc. Nat'l. Acad. Sci. USA* 94:8738-8743 (1997).
Yanagi et al., "Transcripts of a chimeric cDNA clone of hepatitis C virus genotype 1b are infectious in vivo", *Virology* 244:161-172 (1998).
Yanagi et al., "Hepatitis C virus: an infectious molecular clone of a second major genotype (2a) and lack of viability in intertypic 1a and 2a chimeras", *Virology* 262:250-263 (1999).

* cited by examiner

A.

B.

```
#248       ............................................................
#227       ............................................................
#213       ............................................................
#211       ............................................................
#209       ............................................................
#12        ............................................................
GenBank    ............................................................
PCR-seq
cons.      ............................................................
       564 ACCTGGGCTCAGCCCGGGTACCCTTGGCCCCTCTATGGCAATGAGGGTTGCGGGTGGCG  623
        75 T  W  A  Q  P  G  Y  P  W  P  L  Y  G  N  E  G  C  G  W  A    94

#248       ............................................................
#227       ............................................................
#213       ............................................................
#211       ............................................................
#209       ...C........................................................
#12        ............................................................
GenBank    ............................................................
cons.      ............................................................
       624 GGATGGCTCCTGTCTCCCCGTGGCTCTCGGCCTAGCTGGGGCCCCACAGACCCCCGGCGT  683
        95 G  W  L  L  S  P  R  G  S  R  P  S  W  G  P  T  D  P  R  R   114

#248       ............................................................
#227       ............................................................
#213       ............................................................
#211       ............................................................
#209       ............................................................
#12        ................................A...........................
GenBank    ............................................................
cons.      ............................................................
       684 AGGTCGCGCAATTTGGGTAAGGTCATCGATACCCTTACGTGCGGCTTCGCCGACCTCATG  743
       115 R  S  R  N  L  G  K  V  I  D  T  L  T  C  G  F  A  D  L  M   134

#248       ............................................................
#227       ............................................................
#213       ............................................................
#211       ............................................................
#209       ............................................................
#12        ............................................................
GenBank    ............................................................
cons.      ............................................................
       744 GGGTACATACCGCTCGTCGGCGCCCCTCTTGGAGGCGCTGCCAGGGCCCTGGCGCATGGC  803
       135 G  Y  I  P  L  V  G  A  P  L  G  G  A  A  R  A  L  A  H  G   154

#248       ............................................................
#227       ............................................................
#213       ............................................................
#211       ..............................t.............................
#209       ..............................t.............................
#12        ............................................................
GenBank    ............................................................
cons.      ............................................................
       804 GTCCGGGTTCTGGAAGACGGCGTGAACTATGCAACAGGGAACCTTCCTGGTTGCTCTTTC  863
       155 V  R  V  L  E  D  G  V  N  Y  A  T  G  N  L  P  G  C  S  F   174
```

Figure 9AA

```
#248      ..............................................................
#227      ..............................................................
#213      .....................c........................................
#211      .......a......................................................
#209      .......a......................................................
#12       ..............................................................
GenBank   ..............................................................
cons.     ..............................................................
      864 TCTATCTTCCTTCTGGCCCTGCTCTCTTGCCTGACTGTGCCCGCTTCAGCCTACCAAGTG 923
      175 S   I   F   L   L   A   L   L   S   C   L   T   V   P   A   S   A   Y   Q   V   194

#248      ...................................c..........................
#227      ...................................c..........................
#213      ...................................c..........................
#211      ...................................c..........................
#209      ...................................c..........................
#12       ..............................................................
GenBank   ...................................c..........................
cons.     ...................................c..........................
      924 CGCAATTCCTCGGGGCTTTACCATGTCACCAATGATTGCCCTAATTCGAGTATTGTGTAC 983
      195 R   N   S   S   G   L   Y   H   V   T   N   D   C   P   N   S   S   I   V   Y   214

#248      ....................G.........................................
#227      ....................G.........................................
#213      ..............................................................
#211      .....a......A.................................................
#209      .....a......A................................................t
#12       ..............................................................
GenBank   ..............................................................
cons.     ..............................................................
      984 GAGGCGGCCGATGCCATCCTGCACACTCCGGGGTGTGTCCCTTGCGTTCGCGAGGGTAAC 1043
      215 E   A   A   D   A   I   L   H   T   P   G   C   V   P   C   V   R   E   G   N   234

#248      ..............................................................
#227      ......G.....................................t.................
#213      ..............................................................
#211      ...........................................G..................
#209      ..............................................................
#12       ..............................................................
GenBank   ..............................................................
cons.     ..............................................................
     1044 GCCTCGAGGTGTTGGGTGGCGGTGACCCCCACGGTGGCCACCAGGGACGGCAAACTCCCC 1103
      235 A   S   R   C   W   V   A   V   T   P   T   V   A   T   R   D   G   K   L   P   254

#248      ..........................................................g...
#227      ..........................................................g.T.
#213      ..........................................................g.T.
#211      ..........g.....c.........................................g...
#209      ................c.........................................g...
#12       ................G.........................................g...
GenBank   ..........................................................g...
cons.     ..........................................................g...
     1104 ACAACGCAGCTTCGACGTCATATCGATCTGCTTGTCGGGAGCGCCACCCTCTGCTCAGCC 1163
      255 T   T   Q   L   R   R   H   I   D   L   L   V   G   S   A   T   L   C   S   A   274
```

Figure 9AB

```
#248        ............................c..........................
#227        ............................c..........................
#213        ............................c..........................
#211        ......................................................C.....
#209        ............................c..........................
#12         ............................c..........................
GenBank     ............................c..........................
cons.       ............................c..........................
       1164 CTCTACGTGGGGGACCTGTGCGGGTCTGTTTTTCTTGTTGGTCAACTGTTTACCTTCTCT 1223
        275 L  Y  V  G  D  L  C  G  S  V  F  L  V  G  Q  L  F  T  F  S  294

#248        ........................GA............................
#227        ........................................................
#213        ........................................................
#211        ........................GA............................
#209        ........................................................
#12         ........................GA............................
GenBank     ........................GA............................
cons.       ........................GA............................
       1224 CCCAGGCGCCACTGGACGACGCAAAGCTGCAATTGTTCTATCTATCCCGGCCATATAACG 1283
        295 P  R  R  H  W  T  T  Q  S  C  N  C  S  I  Y  P  G  H  I  T  314

#248        ........................................................
#227        ..............g.........................................
#213        ........................................................
#211        ........................................................
#209        ....................................................c....c...
#12         ........................................................
GenBank     ..............A.........................................
cons.       ........................................................
       1284 GGTCATCGCATGGCATGGGATATGATGATGAACTGGTCCCCTACGGCAGCGTTGGTGGTA 1343
        315 G  H  R  M  A  W  D  M  M  M  N  W  S  P  T  A  A  L  V  V  334

#248        ..........................................c..........
#227        ........................................................
#213        ........................................................
#211        ........................................................
#209        ........................................................
#12         ..........................................c..........
GenBank     ..........a...............................c...c..........
PCR-seq     ........................................................
cons.       ........................................................
       1344 GCTCAGCTGCTCCGGATCCCACAAGCCATCATGGACATGATCGCTGGTGCTCACTGGGGA 1403
        335 A  Q  L  L  R  I  P  Q  A  I  M  D  M  I  A  G  A  H  W  G  354

#248        ........................................................
#227        ......T.................................................
#213        ......T.................................................
#211        ........................................................
#209        ........................................................
#12         ..............................G.........................
GenBank     ............AA..........................................
PCR-seq     ........................................................
cons.       ........................................................
       1404 GTCCTGGCGGGCATAGCGTATTTCTCCATGGTGGGGAACTGGGCGAAGGTCCTGGTAGTG 1463
        355 V  L  A  G  I  A  Y  F  S  M  V  G  N  W  A  K  V  L  V  V  374
```

Figure 9AC

```
#83        ................................................G.
#84        ..............t.................................. 
#86        .........................A.......................G.
#87        ................................................G.
#89        ................................................G.
#90        ................................................G.
#92        ..............t...........A.......................
#93        ..........................A.......................G.
#95        ------------------------------......A.......G.
#96        ................................................G.
#99        .............................--A.......G.
#101       ..........................A.......................G.
#248       ..............t...................................
#227       ................................................G.
#213       ..........................A.......................G.
#211       ................................................G.
#209       ..................................................
#12        ..............t...................................
GenBank    ..........................A.......................G.
PCR-seq    ..........................R.......................G.
cons.      ................................................G.
      1464 CTGCTGCTATTTGCCGGCGTCGACGCGGAAACCCACGTCACCGGGGGAAGTGCCGGCCAC 1523
       375  L  L  L  F  A  G  V  D  A  E  T  H  V  T  G  G  S  A  G  H  394

#83        ....TA.....cT..AC.................................
#84        ................C.......T.........................
#86        ................c.................................
#87        ...G........A...C.......T......T..................
#89        ....TA.....cT..AC.................................
#90        ....TA.....cT..AC.................................
#92        ...Gt...........C.......T......T..................
#93        ..................................................
#95        ..................................................
#96        ....TA.....cT..AC.................................
#99        ..................................................
#101       ................A.......G.........................
#248       ................C.......T.........................
#227       ..................................................
#213       ................A.................................
#211       ....TA.....cT..AC.................................
#209       ........C.........................................
#12        ................C.......T.........................
GenBank    ..................................................
PCR-seq    ..................................................
cons.      ..................................................
      1524 ACCACGGCTGGGCTTGTTGGTCTCCTTACACCAGGCGCCAAGCAGAACATCCAACTGATC 1583
       395  T  T  A  G  L  V  G  L  L  T  P  G  A  K  Q  N  I  Q  L  I  414
```

Figure 9AD

```
#83        ................................c.................t..............
#84        ................................................t..A.........A.
#86        ...........................................t.....t..A.........A.
#87        ..................................................t..A.........A.
#89        ................................c.................t..............
#90        ................................c.................t..............
#92        ....................................................t............A.
#93        ..........................................a........t..A.........A.
#95        ...........................................y.....t..A.........A.
#96        ................................c.................t..............
#99        ...........................G.......................t..A.........A.
#101       ...........................................t.....t..A.........A.
#248       .....................................................t..A.........A.
#227       ....................................................t..A.........A.
#213       ...........................................t.....t..A.........G.
#211       ................................c.................t..............
#209       ..................................................................
#12        ....................................................t..A.........A.
GenBank    ....................................................t..A.........A.
PCR-seq    ....................................................t..A.........A.
cons.      ....................................................t..A.........A.
      1584 AACACCAACGGCAGTTGGCACATCAATAGCACGGCCTTGAACTGCAACGATAGCCTTACC 1643
       415  N  T  N  G  S  W  H  I  N  S  T  A  L  N  C  N  D  S  L  T   434

#83        ...............................Aa.................................
#84        ...............................Aa.................................
#86        ...............................Aa.................................
#87        ........G....................TA..........................T.....
#89        ...............................Aa.................................
#90        ...............................Aa.................................
#92        ........G....................A.....G....................T...G.
#93        ...A...........................Ag.................................
#95        ...............................Aa.................................
#96        ...............................Aa.................................
#99        ...............................Ag.................................
#101       ...............................Aa.................................
#248       ...............................A..................................
#227       ...............................Ag.................................
#213       ...............................Aa...........................G.
#211       ...............................Aa.................................
#209       ....................................................................
#12        ...............................A..................................
GenBank    ...............................Ag.................................
PCR-seq    ...............................Ag.................................
cons.      ...............................Ag.................................
      1644 ACCGGCTGGTTAGCAGGGCTCTTCTATCGCCACAAATTCAACTCTTCAGGCTGTCCTGAG 1703
       435  T  G  W  L  A  G  L  F  Y  R  H  K  F  N  S  S  G  C  P  E   454
```

Figure 9AE

```
#83       ............................c...................c..t.........
#84       .............................................................t.........
#86       .............................................................t.........
#87       ............................................................c..t......C..
#89       ............................c....................c..t.........
#90       ............................c....................c..t.........
#92       ............................c....................c..t......C..
#93       ......T......................................................t.........
#95       .............................................................t.........
#96       .......................y................a.........y..t.........
#99       .............................................................t.........
#101      .............................................................t.........
#248      .....................................................G......t.........
#227      .............................................................t.........
#213      .............................................................t.........
#211      ............................c......................c..t.........
#209      ............................t.................................t.........
#12       .....................................................G......t.........
GenBank   .............................................................t.........
PCR-seq   .............................................................t.........
cons.     .............................................................t.........
     1704 AGGTTGGCCAGCTGCCGACGCCTTACCGATTTTGCCCAGGGCTGGGGTCCCATCAGTTAT 1763
      455 R   L   A   S   C   R   R   L   T   D   F   A   Q   G   W   G   P   I   S   Y   474

#83       ...............c....................c.........................
#84       ...............c....................c...T............A.......
#86       ...............c....................c................A.......
#87       ...............Cc...................c................A.......
#89       ...............c....................c................A.......
#90       ...............c....................c................A.......
#92       ...............Cc...................c.........................
#93       ...............c....................c................A.......
#95       ...............c....................c.........................
#96       ...............c....................c................r.......
#99       ...............c....................c.........................
#101      ...............c....................c.........................
#248      ...............c..t.................c.........................
#227      ...............c....................c..........c....A.......
#213      ...............c....................c.........................
#211      ...............c....................c..........c..............
#209      ...............c....................c.........................
#12       ...............c....................c.........................
GenBank   ...............c....................c.........................
PCR-seq   ...............c....................c.........................
cons.     ...............c....................c.........................
     1764 GCCAACGGAAGCGGCCTTGACGAACGCCCCTACTGTTGGCACTACCCTCCAAGACCTTGT 1823
      475 A   N   G   S   G   L   D   E   R   P   Y   C   W   H   Y   P   P   R   P   C   494
```

Figure 9AF

```
#248       ............................................t......
#227       ..t..........................................
#213       .............................................
#211       ..t..........................................
#209       .............................................
#12        .............................................
GenBank    .............................................
PCR-seq       ..........................................
cons.      .............................................
    1824 GGCATTGTGCCCGCAAAGAGCGTGTGTGGCCCGGTATATTGCTTCACTCCCAGCCCCGTG 1883
     495 G  I  V  P  A  K  S  V  C  G  P  V  Y  C  F  T  P  S  P  V  514

#248       .............................................
#227       .............................................
#213       .............................................
#211       .............................................
#209       .............................................
#12        ........g....................................
GenBank    .............................................
PCR-seq    .............................................
cons.      .............................................
    1884 GTGGTGGGAACGACCGACAGGTCGGGCGCGCCTACCTACAGCTGGGGTGCAAATGATACG 1943
     515 V  V  G  T  T  D  R  S  G  A  P  T  Y  S  W  G  A  N  D  T  534

#248       ........t....................A...............c......
#227       .............................................
#213       .............................................
#211       ..........................................C..
#209       .............................................
#12        ........t....................----------------
GenBank    .............................................
PCR-seq    .............................................
cons.      .............................................
    1944 GATGTCTTCGTCCTTAACAACACCAGGCCACCGCTGGGCAATTGGTTCGGTTGTACCTGG 2003
     535 D  V  F  V  L  N  N  T  R  P  P  L  G  N  W  F  G  C  T  W  554

#248       .............................................
#227       .............................................
#213       ...............................G.............
#211       .............................................
#209       .............................................
#12        -----------------,...........................
GenBank    .............................................
PCR-seq    .............................................
cons.      .............................................
    2004 ATGAACTCAACTGGATTCACCAAAGTGTGCGGAGCGCCCCCTTGTGTCATCGGAGGGGTG 2063
     555 M  N  S  T  G  F  T  K  V  C  G  A  P  P  C  V  I  G  G  V  574
```

Figure 9AG

```
#248       ................................t........g...............
#227       ................................t........g...............
#213       ..........................................................
#211       ................................t........g...............
#209       .............c..................t........g...............
#12        ................................t........g...............
GenBank    ..................................................T.......
PCR-seq    ................................t........g...............
cons.      ................................t........g...............
      2064 GGCAACAACACCTTGCTCTGCCCCACTGATTGCTTCCGCAAACATCCGGAAGCCACATAC 2123
       575 G  N  N  T  L  L  C  P  T  D  C  F  R  K  H  P  E  A  T  Y  594

#248       ..............................A............................
#227       ..............................A............................
#213       .............................................................
#211       ..............................A............................
#209       ..............................A............................
#12        ..............................A............................
GenBank    .............A................................................
PCR-seq    ..............................R............................
cons.      ..............................................................
      2124 TCTCGGTGCGGCTCCGGTCCCTGGATTACACCCAGGTGCATGGTCGACTACCCGTATAGG 2183
       595 S  R  C  G  S  G  P  W  I  T  P  R  C  M  V  D  Y  P  Y  R  614

#248       ....................c.......................................
#227       ....................c.......................................
#213       ....................c.......................................
#211       ....................c.......................................
#209       ....................c.......................................
#12        ....................c.......Y...............................
GenBank    ....................c.......................................
PCR-seq    ....................c.......................................
cons.      ....................c.......................................
      2184 CTTTGGCACTATCCTTGTACTATCAATTACACCATATTCAAAGTCAGGATGTACGTGGGA 2243
       615 L  W  H  Y  P  C  T  I  N  Y  T  I  F  K  V  R  M  Y  V  G  634

#248       ..............................................................
#227       ..............................................................
#213       ..............................................................
#211       ..............................................................
#209       ..............................................................
#12        ..............................................................
GenBank    ..............................................................
PCR-seq    ..............................................................
cons.      ..............................................................
      2244 GGGGTCGAGCACAGGCTGGAAGCGGCCTGCAACTGGACGCGGGGCGAACGCTGTGATCTG 2303
       635 G  V  E  H  R  L  E  A  A  C  N  W  T  R  G  E  R  C  D  L  654
```

Figure 9AH

```
#248        ............................g......................
#227        ...................................g................
#213        ............................g......................
#211        ...................................g................
#209        ...................................g................
#12         ...................................g................
GenBank     ............................g......................
cons.       .....................................................
       2304 GAAGACAGGGACAGGTCCGAGCTCAGCCCATTGCTGCTGTCCACCACACAGTGGCAGGTC  2363
        655 E   D   R   D   R   S   E   L   S   P   L   L   L   S   T   T   Q   W   Q   V    674

#248        ..................-------...........................
#227        .....................T..............................
#213        .....................T..............................
#211        .....................................................
#209        .....................................................
#12         .....................................................
GenBank     .....................................................
PCR-seq                       .......................................
cons.       .....................................................
       2364 CTTCCGTGTTCTTTCACGACCCTGCCAGCCTTGTCCACCGGCCTCATCCACCTCCACCAG  2423
        675 L   P   C   S   F   T   T   L   P   A   L   S   T   G   L   I   H   L   H   Q    694

#248        ..............................a......................
#227        ..............................a......................
#213        ..............................a......................
#211        ..............................a......................
#209        ..............................a..............C........
#12         ..............................a......................
GenBank     ..............................a......................
PCR-seq     ..............................a......................
cons.       ..............................a......................
       2424 AACATTGTGGACGTGCAGTACTTGTACGGGGTGGGGTCAAGCATCGCGTCCTGGGCCATT  2483
        695 N   I   V   D   V   Q   Y   L   Y   G   V   G   S   S   I   A   S   W   A   I    714

#248        ......................................c..............
#227        .....................................................
#213        .....................................................
#211        ......................................c..............
#209        ......................................c..............
#12         ......................................c..............
GenBank     ...............................................t......
PCR-seq     .....................................................
cons.       .....................................................
       2484 AAGTGGGAGTACGTCGTTCTCCTGTTCCTTCTGCTTGCAGACGCGCGCGTCTGCTCCTGC  2543
        715 K   W   E   Y   V   V   L   L   F   L   L   L   A   D   A   R   V   C   S   C    734
```

Figure 9AI

```
#248      ..............................................G.....
#227      ........................................A............
#213      ..............................................G.....
#211      ......................................................
#209      ......................................................
#12       ...........................................----------
GenBank   ......................................................
PCR-seq   ......................................................
cons.     ......................................................
     2544 TTGTGGATGATGTTACTCATATCCCAAGCGGAGGCGGCTTTGGAGAACCTCGTAATACTC 2603
      735 L  W  M  M  L  L  I  S  Q  A  E  A  A  L  E  N  L  V  I  L  754

#248      ......................................................
#227      ........c.....................t........................
#213      ......................................................
#211      ......................................................
#209      ......................................................
#12       ----..................................................
GenBank   ..............................t........................
PCR-seq   ......................................................
cons.     ......................................................
     2604 AATGCAGCATCCCTGGCCGGGACGCACGGTCTTGTGTCCTTCCTCGTGTTCTTCTGCTTT 2663
      755 N  A  A  S  L  A  G  T  H  G  L  V  S  F  L  V  F  F  C  F  774

#248      ..............................................T.....
#227      ......................................................
#213      ..............................................T.....
#211      ......................................................
#209      ......................................................
#12       ......................................................
GenBank   .........................................c............
cons.     ......................................................
     2664 GCGTGGTATCTGAAGGGTAGGTGGGTGCCCGGAGCGGTCTACGCCTTCTACGGGATGTGG 2723
      775 A  W  Y  L  K  G  R  W  V  P  G  A  V  Y  A  F  Y  G  M  W  794

#248      .................................G....................
#227      ......................................................
#213      ......................................................
#211      .............t.....................g....................
#209      .............t.....................g....................
#12       .............c...t.................g....................
GenBank   ......................................................
cons.     ......................................................
     2724 CCTCTCCTCCTGCTCCTGCTGGCGTTGCCTCAGCGGGCATACGCACTGGACACGGAGGTG 2783
      795 P  L  L  L  L  L  A  L  P  Q  R  A  Y  A  L  D  T  E  V  814
```

Figure 9AJ

```
#248       ..............................................g......
#227       ........................................G.......g......
#213       ................................................g......
#211       ................................................g......
#209       ................................................g......
#12        ................................................g......
GenBank    ................................................g......
PCR-seq    ..........................................g......
cons.      ................................................g......
      2784 GCCGCGTCGTGTGGCGGCGTTGTTCTTGTCGGGTTAATGGCGCTGACTCTGTCACCATAT 2843
       815 A  A  S  C  G  G  V  V  L  V  G  L  M  A  L  T  L  S  P  Y  834

#248       ............................................................
#227       ............................................................
#213       ....................................................G.......
#211       ..........C.................................................
#209       ..........C.................................................
#12        ..........C.................................................
GenBank    ............................................................
PCR-seq    ..........C.................................................
cons.      ..........C.................................................
      2844 TACAAGCGCTATATCAGCTGGTGCATGTGGTGGCTTCAGTATTTTCTGACCAGAGTAGAA 2903
       835 Y  K  R  Y  I  S  W  C  M  W  W  L  Q  Y  F  L  T  R  V  E  854

#248       ............................................................
#227       ............................................................
#213       ............................................................
#211       ............................................................
#209       ............................................................
#12        ............................................................
GenBank    ............................................................
PCR-seq    ............................................................
cons.      ............................................................
      2904 GCGCAACTGCACGTGTGGGTTCCCCCCCTCAACGTCCGGGGGGGCGCGATGCCGTCATC 2963
       855 A  Q  L  H  V  W  V  P  P  L  N  V  R  G  G  R  D  A  V  I  874

#248       ..............a...........c........................G........
#227       ..............a...........c..................................
#213       ..............a...........c.........................T........
#211       .....................................................T........
#209       ..............................................................
#12        ..........c...................................................
GenBank    .......C......a...........G.c.................................
PCR-seq    ..............r...........y...................................
cons.      ..............................................................
      2964 TTACTCATGTGTGTTGTACACCCGACTCTGGTATTTGACATCACCAAACTACTCCTGGCC 3023
       875 L  L  M  C  V  V  H  P  T  L  V  F  D  I  T  K  L  L  A  894
```

Figure 9AK

```
#248        ............................................................
#227        ............................................................
#213        ............................................................
#211        ............................................................
#209        ............................................................
#12         ............................................................
GenBank     ............................................................
PCR-seq     ............................................................
cons.       ............................................................
     3024 ATCTTCGGACCCCTTTGGATTCTTCAAGCCAGTTTGCTTAAAGTCCCCTACTTCGTGCGC  3083
      895 I  F  G  P  L  W  I  L  Q  A  S  L  L  K  V  P  Y  F  V  R    914

#248        ...............................G............................
#227        ............................................................
#213        ............................................................
#211        ............................................................
#209        ............................................................
#12         ...............................G............................
GenBank     ............................................................
PCR-seq     ............................................................
cons.       ............................................................
     3084 GTTCAAGGCCTTCTCCGGATCTGCGCGCTAGCGCGGAAGATAGCCGGAGGTCATTACGTG  3143
      915 V  Q  G  L  L  R  I  C  A  L  A  R  K  I  A  G  G  H  Y  V    934

#248        ....................a.......................................
#227        ....................a.......................................
#213        ....................a.......................................
#211        ....................a.......................................
#209        ....................a.......................................
#12         ............G.......a.......................................
GenBank     ....................a................G................G.t...
PCR-seq     ....................a.......................................
cons.       ....................a.......................................
     3144 CAAATGGCCATCATCAAGTTGGGGGCGCTTACTGGCACCTATGTGTATAACCATCTCACC  3203
      935 Q  M  A  I  I  K  L  G  A  L  T  G  T  Y  V  Y  N  H  L  T    954

#248        ............................................................
#227        ............................................................
#213        ..................................................c.........
#211        ..........................................................g.
#209        ............................................................
#12         .........................................A..................
GenBank     ............................................................
PCR-seq     ............................................................
cons.       ............................................................
     3204 CCTCTTCGAGACTGGGCGCACAACGGCCTGCGAGATCTGGCCGTGGCTGTGGAACCAGTC  3263
      955 P  L  R  D  W  A  H  N  G  L  R  D  L  A  V  E  P  V          974
```

Figure 9AL

```
#248      ............................................................
#227      ............................................................
#213      ............................................................
#211      ............................................................
#209      .........................................t..................
#12       ............................................................
GenBank   ............................................................
PCR-seq   ............................................................
cons.     ............................................................
     3264 GTCTTCTCCCGAATGGAGACCAAGCTCATCACGTGGGGGGCAGATACCGCCGCGTGCGGT 3323
      975 V  F  S  R  M  E  T  K  L  I  T  W  G  A  D  T  A  A  C  G   994

#248      ............................G...............................g...
#227      ..............................................................g...
#213      .........................C...................................g...
#211      .........................................t........................
#209      ..............................................................g...
#12       ............A.................................................g...
GenBank   ..............................................................g...
PCR-seq   ..............................................................g...
cons.     ..............................................................g...
     3324 GACATCATCAACGGCTTGCCCGTCTCTGCCCGTAGGGGCCAGGAGATACTGCTTGGACCA 3383
      995 D  I  I  N  G  L  P  V  S  A  R  R  G  Q  E  I  L  L  G  P  1014

#248      ........g...................................................
#227      ............................................................
#213      ............................................................
#211      ...........................................................a
#209      ............................................................
#12       ............................................................
GenBank   ............................................................
PCR-seq   ...
cons.     ............................................................
     3384 GCCGACGGAATGGTCTCCAAGGGGTGGAGGTTGCTGGCGCCCATCACGGCGTACGCCCAG 3443
     1015 A  D  G  M  V  S  K  G  W  R  L  L  A  P  I  T  A  Y  A  Q  1034

#248      .....................C......................................
#227      ............................................................
#213      ............................................................
#211      ............................................................
#209      ............................................................
#12       ..............................................A.............
GenBank   ............................................................
cons.     ............................................................
     3444 CAGACGAGAGGCCTCCTAGGGTGTATAATCACCAGCCTGACTGGCCGGGACAAAAACCAA 3503
     1035 Q  T  R  G  L  L  G  C  I  I  T  S  L  T  G  R  D  K  N  Q  1054
```

Figure 9AM

```
#248      ............................................................
#227      ...............a............................................
#213      ............................................................
#211      ............................................................
#209      ............................................................
#12       ............................................................
GenBank   ...........................g................................
cons.     ............................................................
     3504 GTGGAGGGTGAGGTCCAGATCGTGTCAACTGCTACCCAAACCTTCCTGGCAACGTGCATC 3563
     1055 V  E  G  E  V  Q  I  V  S  T  A  T  Q  T  F  L  A  T  C  I  1074

#248      ............................................................
#227      ............................................................
#213      ..........................................g.................
#211      ............................................................
#209      ............................................................
#12       ............................................................
GenBank   ............................................................
PCR-seq                             ........................
cons.     ............................................................
     3564 AATGGGGTATGCTGGACTGTCTACCACGGGGCCGGAACGAGGACCATCGCATCACCCAAG 3623
     1075 N  G  V  C  W  T  V  Y  H  G  A  G  T  R  T  I  A  S  P  K  1094

#248      ............................................................
#227      ........................................................c...
#213      ............................................................
#211      ............................................................
#209      ............................................................
#12       ............................................................
GenBank   ...............c....................t........c...............
PCR-seq   ............................................................
cons.     ............................................................
     3624 GGTCCTGTCATCCAGATGTATACCAATGTGGACCAAGACCTTGTGGGCTGGCCCGCTCCT 3683
     1095 G  P  V  I  Q  M  Y  T  N  V  D  Q  D  L  V  G  W  P  A  P  1114

#248      ...........................................c........c...
#227      ......................................................c...
#213      ......................................................c...
#211      ......................................................c...
#209      ............................................................
#12       ......................................................c...
GenBank   ......................................................c...
PCR-seq   ......................................................c...
cons.     ......................................................c...
     3684 CAAGGTTCCCGCTCATTGACACCCTGCACCTGCGGCTCCTCGGACCTTTACCTGGTTACG 3743
     1115 Q  G  S  R  S  L  T  P  C  T  C  G  S  S  D  L  Y  L  V  T  1134

#248      ..........t.................................................
#227      ..........t.................................................
#213      ..........t.................................................
#211      G...........................................................
#209      ............................................................
#12       ..........t.................................................
GenBank   ..........t.................................................
PCR-seq   ..........t.................................................
cons.     ..........t.................................................
     3744 AGGCACGCCGACGTCATTCCCGTGCGCCGGCGAGGTGATAGCAGGGGTAGCCTGCTTTCG 3803
     1135 R  H  A  D  V  I  P  V  R  R  R  G  D  S  R  G  S  L  L  S  1154
```

Figure 9AN

```
#248      ................t.g.................................
#227      ................t.g.................................
#213      ................t.g.................................
#211      ................t.g.................................
#209      ................t.g.................................
#12       ................t.g.................................
GenBank   ................t.g.............A...................
PCR-seq   ................t.g..................................
cons.     ................t.g..................................
     3804 CCCCGGCCCATTTCCTACCTAAAAGGCTCCTCGGGGGGTCCGCTGTTGTGCCCCGCGGGA 3863
     1155 P  R  P  I  S  Y  L  K  G  S  S  G  G  P  L  L  C  P  A  G  1174

#248      ............................................G.t..........
#227      ............................................G.t..........
#213      ............................................G.t..........
#211      ............................................G..............
#209      ........a...................................G..............
#12       ............................................G t...........
GenBank   ............................................G.t..........
PCR-seq   ............................................G.t...
cons.     ............................................G.t..........
     3864 CACGCCGTGGGCCTATTCAGGGCCGCGGTGTGCACCCGTGGAGTGACCAAGGCGGTGGAC 3923
     1175 H  A  V  G  L  F  R  A  A  V  C  T  R  G  V  T  K  A  V  D  1194

#248      C................G...........................
#227      .................G...........................
#213      .................G...........................
#211      .............................................
#209      .................G...........................
#12       .................G...........................
GenBank   .............................................
cons.     .............................................
     3924 TTTATCCCTGTGGAGAACCTAGAGACAACCATGAGATCCCCGGTGTTCACGGACAACTCC 3983
     1195 F  I  P  V  E  N  L  E  T  T  M  R  S  P  V  F  T  D  N  S  1214

#248      ...........................................................c
#227      ...........................................................c
#213      ...........................................................c
#211      ...........................................................c
#209      ...........................................................c
#12       ...........................................................c
GenBank   ...........................................................c
cons.     ...........................................................c
     3984 TCTCCACCAGCAGTGCCCCAGAGCTTCCAGGTGGCCCACCTGCATGCTCCCACCGGCAGT 4043
     1215 S  P  P  A  V  P  Q  S  F  Q  V  A  H  L  H  A  P  T  G  S  1234

#248      .............................................................
#227      .............................................................
#213      A............................................................
#211      .............................................................
#209      .............................................................
#12       .............................................................
GenBank   ..............................A.............................
cons.     .............................................................
     4044 GGTAAGAGCACCAAGGTCCCCGGCTGCGTACGCAGCCCAGGGCTACAAGGTGTTGGTGCTC 4103
     1235 G  K  S  T  K  V  P  A  A  Y  A  A  Q  G  Y  K  V  L  V  L  1254
```

Figure 9AO

```
#248       ............................................................t
#227       ............................................................t
#213       ............................................................t
#211       .....................A..........................................
#209       ................................................................
#12        ............................................................t
GenBank    ................a...........................................t
cons.      ............................................................t
      4104 AACCCCTCTGTTGCTGCAACGCTGGGCTTTGGTGCTTACATGTCCAAGGCCCATGGGGTC 4163
      1255 N  P  S  V  A  A  T  L  G  F  G  A  Y  M  S  K  A  H  G  V  1274

#248       ........................................t.....................
#227       ................................................................
#213       ......................................................c.....
#211       ................................................................
#209       ................................................................
#12        ..............g.................................................
GenBank    ................................................................
cons.      ................................................................
      4164 GATCCTAATATCAGGACCGGGGTGAGAACAATTACCACTGGCAGCCCCATCACGTACTCC 4223
      1275 D  P  N  I  R  T  G  V  R  T  I  T  T  G  S  P  I  T  Y  S  1294

#248       ..............................t.................
#227       ..............................t.................
#213       ..............................t.................
#211       ..............................t.................
#209       ................................................................
#12        ................................................................
GenBank    ..........................c.............t.....................
cons.      .............................t.................
      4224 ACCTACGGCAAGTTCCTTGCCGACGGCGGGTGCTCAGGAGGCGCTTATGACATAATAATT 4283
      1295 T  Y  G  K  F  L  A  D  G  G  C  S  G  G  A  Y  D  I  I  I  1314

#248       ................................................................
#227       ................................................................
#213       ................................................................
#211       ................................................................
#209       ................................................................
#12        ................................................................
GenBank    ..............................c.................
cons.      ................................................................
      4284 TGTGACGAGTGCCACTCCACGGATGCCACATCCATCTTGGGCATCGGCACTGTCCTTGAC 4343
      1315 C  D  E  C  H  S  T  D  A  T  S  I  L  G  I  G  T  V  L  D  1334

#248       ....................c..........................................
#227       ....................c..........................................
#213       ....................c..........................................
#211       ................................................................
#209       ................................................................
#12        ................................................................
GenBank    ....................c..........................................
cons.      ....................c..........................................
      4344 CAAGCAGAGACTGCGGGGGCGAGATTGGTTGTGCTCGCCACTGCTACCCCTCCGGGCTCC 4403
      1335 Q  A  E  T  A  G  A  R  L  V  V  L  A  T  A  T  P  P  G  S  1354
```

Figure 9AP

```
#248        ............................................................c
#227        ............................................................y
#213        .............................................................
#211        .............................................................
#209        .............................................................
#12         .............................................................
GenBank     ............................................................c
cons.       .............................................................
    4404 GTCACTGTGTCCCATCCTAACATCGAGGAGGTTGCTCTGTCCACCACCGGAGAGATCCCT 4463
    1355 V  T  V  S  H  P  N  I  E  E  V  A  L  S  T  T  G  E  I  P  1374

#248        ..t.........................................................c
#227        ..t.........................................................c
#213        ..t.........................................................c
#211        ..t.........................................................c
#209        ..t..........................................................
#12         ..t.............G............................................
GenBank     ..t.........................................................c
PCR-seq     ............................................................c
cons.       ..t.........................................................c
    4464 TTCTACGGCAAGGCTATCCCCCTCGAGGTGATCAAGGGGGGAAGACATCTCATCTTCTGT 4523
    1375 F  Y  G  K  A  I  P  L  E  V  I  K  G  G  R  H  L  I  F  C  1394

#248        .............................................................
#227        .............................................................
#213        .............................................................
#211        ..............................................A..............
#209        ..................t..........................................
#12         .............................................................
GenBank     .............................................................
PCR-seq     .............................................................
cons.       .............................................................
    4524 CACTCAAAGAAGAAGTGCGACGAGCTCGCCGCGAAGCTGGTCGCATTGGGCATCAATGCC 4583
    1395 H  S  K  K  K  C  D  E  L  A  A  K  L  V  A  L  G  I  N  A  1414

#248        .....................t.........................G............
#227        .....................t.........................G........A..
#213        .....................t..c......................G............
#211        .....................t..c......................G............
#209        ................................................G............
#12         ................................................G............
GenBank     .....................t.........................G............
PCR-seq     .....................t.........................G............
cons.       .....................t.........................G............
    4584 GTGGCCTACTACCGCGGACTTGACGTGTCTGTCATCCCGACCAACGGCGATGTTGTCGTC 4643
    1415 V  A  Y  Y  R  G  L  D  V  S  V  I  P  T  N  G  D  V  V  V  1434

#248        .............................................................
#227        .............................................................
#213        ..................t..........................................
#211        .............................................................
#209        .............................................................
#12         .............................................................
GenBank     .............................................................
PCR-seq     .............................................................
cons.       .............................................................
    4644 GTGTCGACCGATGCTCTCATGACTGGCTTTACCGGCGACTTCGACTCTGTGATAGACTGC 4703
    1435 V  S  T  D  A  L  M  T  G  F  T  G  D  F  D  S  V  I  D  C  1454
```

Figure 9AQ

```
#248      ............................................................
#227      ............................................................
#213      ............................................................
#211      ............................................................
#209      ............................................................
#12       .........................................G..................
GenBank   ..............t...............................................
PCR-seq   ............................................................
cons.     ............................................................
     4704 AACACGTGTGTCACTCAGACAGTCGATTTCAGCCTTGACCCTACCTTTACCATTGAGACA 4763
     1455 N   T   C   V   T   Q   T   V   D   F   S   L   D   P   T   F   T   I   E   T   1474

#248      ................................a...........................
#227      ................................a.........G..................
#213      ................................a............................
#211      ................................a............................
#209      ............................................................
#12       ............................................................
GenBank   ................................a............................
PCR-seq   ................................a.
cons.     ................................a............................
     4764 ACCACGCTCCCCCAGGATGCTGTCTCCAGGACTCAGCGCCGGGGCAGGACTGGCAGGGGG 4823
     1475 T   T   L   P   Q   D   A   V   S   R   T   Q   R   R   G   R   T   G   R   G   1494

#248      ..............t.A............................................
#227      ..........................................................a
#213      ............................................................
#211      ............................................................
#209      ............................................................
#12       ............................................................
GenBank   ..............t..............................................
cons.     ............................................................
     4824 AAGCCAGGCATCTACAGATTTGTGGCACCGGGGGAGCGCCCCTCCGGCATGTTCGACTCG 4883
     1495 K   P   G   I   Y   R   F   V   A   P   G   E   R   P   S   G   M   F   D   S   1514

#248      .......................................C.....................
#227      .....t.................................C.................t...
#213      .......................................C.....................
#211      .......................................C.....................
#209      .................G.....................C.....................
#12       .......................................C.....................
GenBank   .......................................C.....................
cons.     .......................................C.....................
     4884 TCCGTCCTCTGTGAGTGCTATGACGCGGGCTGTGCTTGGTATGAGCTCATGCCCGCCGAG 4943
     1515 S   V   L   C   E   C   Y   D   A   G   C   A   W   Y   E   L   M   P   A   E   1534

#248      ............................................................
#227      ............................................................
#213      ............................................................
#211      ............................................................
#209      ............................................................
#12       ............................................................
GenBank   ............................................................
cons.     ............................................................
     4944 ACTACAGTTAGGCTACGAGCGTACATGAACACCCCGGGGCTTCCCGTGTGCCAGGACCAT 5003
     1535 T   T   V   R   L   R   A   Y   M   N   T   P   G   L   P   V   C   Q   D   H   1554
```

Figure 9AR

```
#248       ............................t.....................
#227       ............................t.....................
#213       .................a..........t.....................
#211       ....G............a..........t.....................
#209       ..................................................
#12        ..................................................
GenBank    ....G.......................t.....................
cons.      ............................t.....................
      5004 CTTGAATTTTGGGAGGGCGTCTTTACGGGCCTCACCCATATAGATGCCCACTTTCTATCC 5063
      1555 L  E  F  W  E  G  V  F  T  G  L  T  H  I  D  A  H  F  L  S  1574

#248       ..................................................
#227       ..................................................
#213       ..............c...................................t
#211       ..............c....................................
#209       ..................................................
#12        ..................................................
GenBank    ..................................................
cons.      ..................................................
      5064 CAGACAAAGCAGAGTGGGGAGAACTTTCCTTACCTGGTAGCGTACCAAGCCACCGTGTGC 5123
      1575 Q  T  K  Q  S  G  E  N  F  P  Y  L  V  A  Y  Q  A  T  V  C  1594

#248       ..................................................
#227       ..................................................
#213       ..................................................
#211       ..................................................
#209       ..................................................
#12        ..................................................
GenBank    ..............................c...................
cons.      ..................................................
      5124 GCTAGGGCTCAAGCCCCTCCCCCATCGTGGGACCAGATGTGGAAGTGTTTGATCCGCCTT 5183
      1595 A  R  A  Q  A  P  P  P  S  W  D  Q  M  W  K  C  L  I  R  L  1614

#248       ..................................................
#227       ..................................................
#213       ..................................................
#211       ..................................................
#209       ..................................................
#12        ..................................................
GenBank    ..................................................
cons.      ..................................................
      5184 AAACCCACCCTCCATGGGCCAACACCCCTGCTATACAGACTGGGCGCTGTTCAGAATGAA 5243
      1615 K  P  T  L  H  G  P  T  P  L  L  Y  R  L  G  A  V  Q  N  E  1634

#248       ..................................................
#227       ..................................................
#213       ..................................................
#211       ..................................................
#209       ..................................................
#12        ..................................................
GenBank    ..................................................
cons.      ..................................................
      5244 GTCACCCTGACGCACCCAATCACCAAATACATCATGACATGCATGTCGGCCGACCTGGAG 5303
      1635 V  T  L  T  H  P  I  T  K  Y  I  M  T  C  M  S  A  D  L  E  1654
```

Figure 9AS

```
#248      ..................................................
#227      ..................................................
#213      ..................................................
#211      ..............................--------------------
#209      ..............................--------------------........
#12       ..................................................
GenBank   ..................................................
cons.     ..................................................
     5304 GTCGTCACGAGCACCTGGGTGCTCGTTGGCGGCGTCCTGGCTGCTCTGGCCGCGTATTGC   5363
     1655 V   V   T   S   T   W   V   L   V   G   G   V   L   A   A   L   A   A   Y   C   1674

#248      ...............................c..................
#227      ..................................................
#213      ..................................................
#211      -----------------------------.....................
#209      ..................................................
#12       ..................................................
GenBank   ...............................c..................
cons.     ..................................................
     5364 CTGTCAACAGGCTGCGTGGTCATAGTGGGCAGGATTGTCTTGTCCGGGAAGCCGGCAATT   5423
     1675 L   S   T   G   C   V   V   I   V   G   R   I   V   L   S   G   K   P   A   I   1694

#248      ..................................................
#227      ..................................................
#213      ..................................................
#211      ..................................................
#209      ..................................................
#12       ..................................................
GenBank   ..................................................
cons.     ..................................................
     5424 ATACCTGACAGGGAGGTTCTCTACCAGGAGTTCGATGAGATGGAAGAGTGCTCTCAGCAC   5483
     1695 I   P   D   R   E   V   L   Y   Q   E   F   D   E   M   E   E   C   S   Q   H   1714

#248      ..................................................
#227      ..................................................
#213      ..................................................
#211      ..................................................
#209      ..................................................
#12       ..................................................
GenBank   ..................................................
cons.     ..................................................
     5484 TTACCGTACATCGAGCAAGGGATGATGCTCGCTGAGCAGTTCAAGCAGAAGGCCCTCGGC   5543
     1715 L   P   Y   I   E   Q   G   M   M   L   A   E   Q   F   K   Q   K   A   L   G   1734

#248      ..................................................
#227      ...............................A..................
#213      ...............................A..............c...
#211      ...............................A..............c...
#209      ..................................................
#12       ..............c...............................G....
GenBank   ..................................................
cons.     ...............................A..................
     5544 CTCCTGCAGACCGCGTCCCGCCATGCAGAGGTTATCACCCCTGCTGTCCAGACCAACTGG   5603
     1735 L   L   Q   T   A   S   R   H   A   E   V   I   T   P   A   V   Q   T   N   W   1754
```

Figure 9AT

```
#248      .................t........................................c
#227      ............c.............................................c
#213      .................a.....t..........................g..c
#211      .................t................................g..c
#209      ..........................................................c
#12       ..........................................................c
GenBank   .................t........................................c
cons.     ..........................................................c
     5604 CAGAAACTCGAGGTCTTCTGGGCGAAGCACATGTGGAATTTCATCAGTGGGATACAATAT 5663
     1755 Q  K  L  E  V  F  W  A  K  H  M  W  N  F  I  S  G  I  Q  Y  1774

#248      ............................................................
#227      ............................................................
#213      ............................................................
#211      ............................................................
#209      ............................................................
#12       ............................................................
GenBank   ............................................................
cons.     ............................................................
     5664 TTGGCGGGCCTGTCAACGCTGCCTGGTAACCCCGCCATTGCTTCATTGATGGCTTTTACA 5723
     1775 L  A  G  L  S  T  L  P  G  N  P  A  I  A  S  L  M  A  F  T  1794

#248      ............................................................
#227      ............................................................
#213      .....t......................................................
#211      .....t......................................................
#209      ............................................................
#12       ............................................................
GenBank   ............................................................
cons.     ............................................................
     5724 GCTGCCGTCACCAGCCCACTAACCACTGGCCAAACCCTCCTCTTCAACATATTGGGGGGG 5783
     1795 A  A  V  T  S  P  L  T  T  G  Q  T  L  L  F  N  I  L  G  G  1814

#248      ...........................................t.........c...
#227      ............................................................
#213      ............................................................
#211      ............................................................
#209      .............................................t..............
#12       ........................................a...................
GenBank   ............................................................
cons.     ............................................................
     5784 TGGGTGGCTGCCCAGCTCGCCGCCCCCGGTGCCGCTACCGCCTTTGTGGGCGCTGGCTTA 5843
     1815 W  V  A  A  Q  L  A  A  P  G  A  A  T  A  F  V  G  A  G  L  1834

#248      ............................................................
#227      ............................................................
#213      ............................................................
#211      .....................................................c......
#209      ............................................................
#12       ............................................................
GenBank   .........aC...A.............................................c
cons.     ............................................................
     5844 GCTGGCGCCGCCATCGGCAGCGTTGGACTGGGGAAGGTCCTCGTGGACATTCTTGCAGGG 5903
     1835 A  G  A  A  I  G  S  V  G  L  G  K  V  L  V  D  I  L  A  G  1854
```

Figure 9AU

```
#248      ..................................................
#227      ...................g..............................
#213      ...................g..............................
#211      ...................g............c.................
#209      ..................................................
#12       ..................................................
GenBank   ...................g..............................
cons.     ..................................................
     5904 TATGGCGCGGGCGTGGCGGGAGCTCTTGTAGCATTCAAGATCATGAGCGGTGAGGTCCCC 5963
     1855 Y   G   A   G   V   A   G   A   L   V   A   F   K   I   M   S   G   E   V   P   1874

#248      ............................................................
#227      ............................................................
#213      ............................................................
#211      ............................................................
#209      ............................................................
#12       ............................................................
GenBank   ...........................a...............C....
cons.     ............................................................
     5964 TCCACGGAGGACCTGGTCAATCTGCTGCCCGCCATCCTCTCGCCTGGAGCCCTTGTAGTC 6023
     1875 S   T   E   D   L   V   N   L   L   P   A   I   L   S   P   G   A   L   V   V   1894

#248      ............................................................
#227      ............................................................
#213      ............................................................
#211      ............................................................
#209      ............................................................
#12       .....................................c......................
GenBank   ........Tt...T.............Gt...............................
cons.     ............................................................
     6024 GGTGTGGTCTGCGCAGCAATACTGCGCCGGCACGTTGGCCCGGGCGAGGGGGCAGTGCAA 6083
     1895 G   V   V   C   A   A   I   L   R   R   H   V   G   P   G   E   G   A   V   Q   1914

#248      ............................................................
#227      ............................................................
#213      .............t..............................................
#211      ............................................................
#209      ............................................................
#12       ............................................................
GenBank   ..........................................a.................
PCR-seq                               .................................
cons.     ............................................................
     6084 TGGATGAACCGGCTAATAGCCTTCGCCTCCCGGGGGAACCATGTTTCCCCCACGCACTAC 6143
     1915 W   M   N   R   L   I   A   F   A   S   R   G   N   H   V   S   P   T   H   Y   1934

#248      ............................................................
#227      ............................................................
#213      ............................................................
#211      ............................................................
#209      ............................................................
#12       ............................................................
GenBank   ............................................................
PCR-seq   ............................................................
cons.     ............................................................
     6144 GTGCCGGAGAGCGATGCAGCCGCCCGCGTCACTGCCATACTCAGCAGCCTCACTGTAACC 6203
     1935 V   P   E   S   D   A   A   A   R   V   T   A   I   L   S   S   L   T   V   T   1954
```

Figure 9AV

```
#248      ................----------------------------------
#227      .................................................t
#213      ...................g.............................t
#211      ...................g...........T.................t
#209      ...................g.....................g.......t
#12       ...................g.............................t
GenBank   ...................g.............................t
PCR-seq   ...................g.............................t
cons.     ...................g.............................t
     6204 CAGCTCCTGAGGCGACTACATCAGTGGATAAGCTCGGAGTGTACCACTCCATGCTCCGGC 6263
     1955 Q   L   L   R   R   L   H   Q   W   I   S   S   E   C   T   T   P   C   S   G   1974

#248      ------------------------------------------------------------
#227      ............................................................
#213      ............................................................
#211      ............................................................
#209      ............................................................
#12       ............................................................
GenBank   ............................................................
PCR-seq   ............................................................
cons.     ............................................................
     6264 TCCTGGCTAAGGGACATCTGGGACTGGATATGCGAGGTGCTGAGCGACTTTAAGACCTGG 6323
     1975 S   W   L   R   D   I   W   D   W   I   C   E   V   L   S   D   F   K   T   W   1994

#248      ------------------------------------------------------------
#227      ............................................................
#213      ............................................................
#211      ............................................................
#209      ............................................................
#12       ............................................................
GenBank   .......................................................C..
PCR-seq   ............................................................
cons.     ............................................................
     6324 CTGAAAGCCAAGCTCATGCCACAACTGCCTGGGATTCCCTTTGTGTCCTGCCAGCGCGGG 6383
     1995 L   K   A   K   L   M   P   Q   L   P   G   I   P   F   V   S   C   Q   R   G   2014

#248      --...........................................................
#227      ............................................................
#213      ............................................................
#211      ............................................................
#209      ............................................................
#12       ............................................................
GenBank   ............................................................
PCR-seq   ............................................................
cons.     ............................................................
     6384 TATAGGGGGGTCTGGCGAGGAGACGGCATTATGCACACTCGCTGCCACTGTGGAGCTGAG 6443
     2015 Y   R   G   V   W   R   G   D   G   I   M   H   T   R   C   H   C   G   A   E   2034
```

Figure 9AW

```
#248       ............................................................
#227       ............................................................
#213       ..............................................c.............
#211       ............................................................
#209       .............g..............................................
#12        .............g..............................................
GenBank    ...............................................A............
PCR-seq    ..................
cons.      ............................................................
      6444 ATCACTGGACATGTCAAAAACGGGACGATGAGGATCGTCGGTCCTAGGACCTGCAGGAAC 6503
      2035 I  T  G  H  V  K  N  G  T  M  R  I  V  G  P  R  T  C  R  N  2054

#248       ............................................................
#227       ............................................................
#213       .........................................---................
#211       ............................................................
#209       ............................................................
#12        ............................................................
GenBank    .................TT......t..................................
cons.      ............................................................
      6504 ATGTGGAGTGGGACGTTCCCCATTAACGCCTACACCACGGGCCCCTGTACTCCCCTTCCT 6563
      2055 M  W  S  G  T  F  P  I  N  A  Y  T  T  G  P  C  T  P  L  P  2074

#248       ............................................................
#227       ............................................................
#213       ............................................................
#211       ............................................................
#209       ..................................c.........................
#12        ..................................c.........................
GenBank    ............................................................
cons.      ............................................................
      6564 GCGCCGAACTATAAGTTCGCGCTGTGGAGGGTGTCTGCAGAGGAATACGTGGAGATAAGG 6623
      2075 A  P  N  Y  K  F  A  L  W  R  V  S  A  E  E  Y  V  E  I  R  2094

#248       ............................................................
#227       ............................................................
#213       ............................................................
#211       ............................................................
#209       ............................................................
#12        ............................................................
GenBank    ...............................c.............c.............
cons.      ............................................................
      6624 CGGGTGGGGGACTTCCACTACGTATCGGGTATGACTACTGACAATCTTAAATGCCCGTGC 6683
      2095 R  V  G  D  F  H  Y  V  S  G  M  T  T  D  N  L  K  C  P  C  2114

#248       .........................................................---
#227       ............................................................
#213       .............................................c..............
#211       ............................................................
#209       ............................................................
#12        ............................................................
GenBank    ............................................................
cons.      ............................................................
      6684 CAGATCCCATCGCCCGAATTTTTCACAGAATTGGACGGGGTGCGCCTACATAGGTTTGCG 6743
      2115 Q  I  P  S  P  E  F  F  T  E  L  D  G  V  R  L  H  R  F  A  2134
```

Figure 9AX

```
#248    ------------------------------------------------------------
#227    ............................................................
#213    ............................................................
#211    ............................................................
#209    ............................................................
#12     ............................................................
GenBank ............................................................
cons.   ............................................................
   6744 CCCCCTTGCAAGCCCTTGCTGCGGGAGGAGGTATCATTCAGAGTAGGACTCCACGAGTAC 6803
   2135 P   P   C   K   P   L   L   R   E   E   V   S   F   R   V   G   L   H   E   Y   2154

#248    ------------------------------------------------------------
#227    ............................................................
#213    ........................c...................................
#211    ............................................................
#209    ............................................................
#12     ............................................................
GenBank ............................................................
cons.   ............................................................
   6804 CCGGTGGGGTCGCAATTACCTTGCGAGCCCGAACCGGACGTAGCCGTGTTGACGTCCATG 6863
   2155 P   V   G   S   Q   L   P   C   E   P   E   P   D   V   A   V   L   T   S   M   2174

#248    ------------------------------------------------------------
#227    ............................................................
#213    ............................................................
#211    .................................g..........................
#209    ..........................................................g..a...
#12     ..........................................................g..a...
GenBank ............................................................
cons.   ............................................................
   6864 CTCACTGATCCCTCCCATATAACAGCAGAGGCGGCCGGGAGAAGGTTGGCGAGAGGGTCA 6923
   2175 L   T   D   P   S   H   I   T   A   E   A   A   G   R   R   L   A   R   G   S   2194

#248    ---------------------------------........................
#227    ............................................................
#213    .......................A.t..................................
#211    .........................t..................................
#209    .........................t..................................
#12     .........................t..................................
GenBank ............................................................
cons.   ............................................................
   6924 CCCCCTTCTATGGCCAGCTCCTCGGCCAGCCAGCTGTCCGCTCCATCTCTCAAGGCAACT 6983
   2195 P   P   S   M   A   S   S   S   A   S   Q   L   S   A   P   S   L   K   A   T   2214

#248    ............................................................
#227    ............................................................
#213    ............................................................
#211    ............................................................
#209    ............................................................
#12     ............................................................
GenBank ............................................................
cons.   ............................................................
   6984 TGCACCGCCAACCATGACTCCCCTGACGCCGAGCTCATAGAGGCTAACCTCCTGTGGAGG 7043
   2215 C   T   A   N   H   D   S   P   D   A   E   L   I   E   A   N   L   L   W   R   2234
```

Figure 9AY

```
#248       ............................................a......
#227       ........................................................
#213       ........................................................
#211       ........................................................
#209       ........................................................
#12        ........................................................
GenBank    ........................................................
cons.      ........................................................
      7044 CAGGAGATGGGCGGCAACATCACCAGGGTTGAGTCAGAGAACAAAGTGGTGATTCTGGAC 7103
      2235 Q  E  M  G  G  N  I  T  R  V  E  S  E  N  K  V  V  I  L  D  2254

#248       ........................................................
#227       ........................................................
#213       .............................................t..........
#211       ........................................................
#209       ........................................................
#12        ........................................................
GenBank    ........................................................
cons.      ........................................................
      7104 TCCTTCGATCCGCTTGTGGCAGAGGAGGATGAGCGGGAGGTCTCCGTACCCGCAGAAATT 7163
      2255 S  F  D  P  L  V  A  E  E  D  E  R  E  V  S  V  P  A  E  I  2274

#248       ...............................T........................
#227       ........................................................
#213       .........................c..............................
#211       ........................................................
#209       ...............................T........................
#12        .........................c..............................
GenBank    .............Ca..........c..............................
cons.      ........................................................
      7164 CTGCGGAAGTCTCGGAGATTCGCCCGGGCCCTGCCCGTTTGGGCGCGGCCGGACTACAAC 7223
      2275 L  R  K  S  R  R  F  A  R  A  L  P  V  W  A  R  P  D  Y  N  2294

#248       ........T...............................................
#227       ........................................................
#213       ........A...............................................
#211       ........A...............................................
#209       .......gA...............................................
#12        ........g...............................................
GenBank    ....T...................................................
cons.      ........................................................
      7224 CCCCCGCTAGTAGAGACGTGGAAAAAGCCTGACTACGAACCACCTGTGGTCCATGGCTGC 7283
      2295 P  P  L  V  E  T  W  K  K  P  D  Y  E  P  P  V  V  H  G  C  2314

#248       ........................................................
#227       ........................................................
#213       ...............A........................................
#211       ........................................................
#209       .....g..................................................
#12        .....g..................................................
GenBank    ........................................................
cons.      ........................................................
      7284 CCGCTACCACCTCCACGGTCCCCTCCTGTGCCTCCGCCTCGGAAAAAGCGTACGGTGGTC 7343
      2315 P  L  P  P  P  R  S  P  P  V  P  P  P  R  K  K  R  T  V  V  2334
```

Figure 9AZ

```
#248      ................T........................
#227      ................T........................
#213      ................T........................
#211      ................T........................
#209      ................T........c................
#12       .........................................
GenBank   .........................................
cons.     ................T........................
     7344 CTCACCGAATCAACCCTACCTACTGCCTTGGCCGAGCTTGCCACCAAAAGTTTTGGCAGC 7403
     2335 L  T  E  S  T  L  P  T  A  L  A  E  L  A  T  K  S  F  G  S  2354

#248      .............................C...........
#227      .............................C...........
#213      .............................C...........
#211      .............................C...........
#209      .............................C...........
#12       .............................C...........
GenBank   .............................C...........
cons.     .............................C...........
     7404 TCCTCAACTTCCGGCATTACGGGCGACAATATGACAACATCCTCTGAGCCCGCCCCTTCT 7463
     2355 S  S  T  S  G  I  T  G  D  N  M  T  T  S  E  P  A  P  S  2374

#248      .........................................
#227      .........................................
#213      .........................................
#211      .........................................
#209      .........................................
#12       .........................................
GenBank   .........................................
cons.     .........................................
     7464 GGCTGCCCCCCCGACTCCGACGTTGAGTCCTATTCTTCCATGCCCCCCCTGGAGGGGGAG 7523
     2375 G  C  P  P  D  S  D  V  E  S  Y  S  S  M  P  P  L  E  G  E  2394

#248      .........................................
#227      .........................................
#213      ..........C..............................
#211      .........................................
#209      ..........C..............................
#12       ..........C..............................
GenBank   ..........C..............................
PCR-seq                                 ..................
cons.     ..........C..............................
     7524 CCTGGGGATCCGGATTTCAGCGACGGGTCATGGTCGACGGTCAGTAGTGGGGCCGACACG 7583
     2395 P  G  D  P  D  F  S  D  G  S  W  S  T  V  S  S  G  A  D  T  2414

#248      ............................T............
#227      .........................................
#213      ............................T............
#211      ............................T............
#209      ............................T............
#12       ..g.........................T............
GenBank   ............................T............
PCR-seq   ............................T............
cons.     ............................T............
     7584 GAAGATGTCGTGTGCTGCTCAATGTCTTATACCTGGACAGGCGCACTCGTCACCCCGTGC 7643
     2415 E  D  V  V  C  C  S  M  S  Y  T  W  G  A  L  V  T  P  C  2434
```

Figure 9BA

```
#248      ..............................................................
#227      ..............................................................
#213      ..............................................................
#211      ..............................................................
#209      ..............................................................
#12       ....................t.........................t...............
GenBank   ........g.......................................................
PCR-seq   ..............................................................
cons.     ..............................................................
     7644 GCTGCGGAAGAACAAAAACTGCCCATCAACGCACTGAGCAACTCGTTGCTACGCCATCAC 7703
     2435 A  A  E  E  Q  K  L  P  I  N  A  L  S  N  S  L  L  R  H  H  2454

#248      ..............................................................
#227      ..............................................................
#213      ........g.......................................................
#211      ........g.......................................................
#209      ........g...........................a...........................
#12       ....a..g.........................................................
GenBank   ........g...........................A...........................
PCR-seq   ........g.......................................................
cons.     ........g.......................................................
     7704 AATCTGGTATATTCCACCACTTCACGCAGTGCTTGCCAAAGGCAGAAGAAAGTCACATTT 7763
     2455 N  L  V  Y  S  T  T  S  R  S  A  C  Q  R  Q  K  K  V  T  F  2474

#248      ..............................................................
#227      ..............................................................
#213      ..............................................................
#211      ..............................................................
#209      ..............................................................
#12       ..............................................................
GenBank   ..............................................................
PCR-seq   ..............................................................
cons.     ..............................................................
     7764 GACAGACTGCAAGTTCTGGACAGCCATTACCAGGACGTGCTCAAGGAGGTCAAAGCAGCG 7823
     2475 D  R  L  Q  V  L  D  S  H  Y  Q  D  V  L  K  E  V  K  A  A  2494

#248      ..............................................................
#227      ..............................................................
#213      ..............................................................
#211      ..............................................................
#209      ..............................................................
#12       ..........................................c...................
GenBank   ..........................................G...................
PCR-seq   ..............................................................
cons.     ..............................................................
     7824 GCGTCAAAAGTGAAGGCTAACTTGCTATCCGTAGAGGAAGCTTGCAGCCTGACGCCCCCA 7883
     2495 A  S  K  V  K  A  N  L  L  S  V  E  E  A  C  S  L  T  P  P  2514
```

Figure 9BB

```
#248      ..........t.................................................
#227      ............................................................
#213      ............................................................
#211      ..........t.................................................
#209      ............................................................
#12       ............................................................
GenBank   ............................................................
PCR-seq   ............................................................
cons.     ............................................................
     7884 CATTCAGCCAAATCCAAGTTTGGCTATGGGGCAAAAGACGTCCGTTGCCATGCCAGAAAG 7943
     2515 H   S   A   K   S   K   F   G   Y   G   A   K   D   V   R   C   H   A   R   K   2534

#248      ............................................................
#227      ............................................................
#213      ............................................................
#211      ............................................................
#209      ............................................................
#12       ............................................................
GenBank   ............................................................
PCR-seq   ............................................................
cons.     ............................................................
     7944 GCCGTAGCCCACATCAACTCCGTGTGGAAAGACCTTCTGGAAGACAGTGTAACACCAATA 8003
     2535 A   V   A   H   I   N   S   V   W   K   D   L   L   E   D   S   V   T   P   I   2554

#248      .......C................t.................a................
#227      .......C................t..................................
#213      .......C................t.................a................
#211      .......C................t.................a................
#209      .......C................t..................................
#12       .......C................t..................................
GenBank   .......C................t..................................
PCR-seq   .......C................t..................................
cons.     .......C................t..................................
     8004 GACACTATCATCATGGCCAAGAACGAGGTCTTCTGCGTTCAGCCTGAGAAGGGGGGTCGT 8063
     2555 D   T   I   I   M   A   K   N   E   V   F   C   V   Q   P   E   K   G   G   R   2574

#248      .................C..........................................
#227      ............................................................
#213      ............................................................
#211      ............................................................
#209      ............................................................
#12       ............................................................
GenBank   ............................................................
PCR-seq   ............................................................
cons.     ............................................................
     8064 AAGCCAGCTCGTCTCATCGTGTTCCCCGACCTGGGCGTGCGCGTGTGCGAGAAGATGGCC 8123
     2575 K   P   A   R   L   I   V   F   P   D   L   G   V   R   V   C   E   K   M   A   2594

#248      ......................g.....................................
#227      ............................................................
#213      ......................g.....................................
#211      ......................g.....................................
#209      ......................g.....................................
#12       ......................g.....................................
GenBank   ......................g......t..............................
cons.     ......................g.....................................
     8124 CTGTACGACGTGGTTAGCAAACTCCCCCTGGCCGTGATGGGAAGCTCCTACGGATTCCAA 8183
     2595 L   Y   D   V   V   S   K   L   P   L   A   V   M   G   S   S   Y   G   F   Q   2614
```

Figure 9BC

```
#248      ..........................................................
#227      ..........................................................
#213      ..........................................................
#211      ..........................................................
#209      ..............................................a...........
#12       ..............................................a...........
GenBank   ..........................................................
cons.     ..........................................................
     8184 TACTCACCAGGACAGCGGGTTGAATTCCTCGTGCAAGCGTGGAAGTCCAAGAAGACCCCG  8243
     2615 Y   S   P   G   Q   R   V   E   F   L   V   Q   A   W   K   S   K   K   T   P    2634

#248      .........T................................................
#227      .........T................................................
#213      .........T................................................
#211      .........T................................................
#209      .........T................................................
#12       .........T................................................
GenBank   .........T................................................
cons.     .........T................................................
     8244 ATGGGGTTCCCGTATGATACCCGCTGTTTTGACTCCACAGTCACTGAGAGCGACATCCGT  8303
     2635 M   G   F   P   Y   D   T   R   C   F   D   S   T   V   T   E   S   D   I   R    2654

#248      ..........................................................
#227      ..........................................................
#213      ..........................................................
#211      ..........................................................
#209      ..........................................................
#12       ...........................................c..............
GenBank   ..........................................................
cons.     ..........................................................
     8304 ACGGAGGAGGCAATTTACCAATGTTGTGACCTGGACCCCCAAGCCCGCGTGGCCATCAAG  8363
     2655 T   E   E   A   I   Y   Q   C   C   D   L   D   P   Q   A   R   V   A   I   K    2674

#248      ..........................................................
#227      ..........................................................
#213      ..........................................................
#211      ..........................................................
#209      ..........................................................
#12       ..........................................................
GenBank   ..............................................t...........
cons.     ..........................................................
     8364 TCCCTCACTGAGAGGCTTTATGTTGGGGGCCCTCTTACCAATTCAAGGGGGGAAAACTGC  8423
     2675 S   L   T   E   R   L   Y   V   G   G   P   L   T   N   S   R   G   E   N   C    2694

#248      .....c....................................................
#227      .....c....................................................
#213      .....c....................................................
#211      .....c....................................................
#209      .....c....................................................
#12       .....c....................................................
GenBank   .....c.................A..................................
cons.     .....c....................................................
     8424 GGCTATCGCAGGTGCCGCGCGAGCGGCGTACTGACAACTAGCTGTGGTAACACCCTCACT  8483
     2695 G   Y   R   R   C   R   A   S   G   V   L   T   T   S   C   G   N   T   L   T    2714
```

Figure 9BD

```
#248      ..................T.c.......................
#227      ..................T.........................
#213      ..................T.........................
#211      ..................T.........................
#209      ..................T..........A..............
#12       ..................T.........................
GenBank   C.................T.........................
cons.     ..................T.........................
     8484 TGCTACATCAAGGCCCGGGCAGCCCGTCGAGCCGCAGGGCTCCAGGACTGCACCATGCTC 8543
     2715 C  Y  I  K  A  R  A  A  R  R  A  A  G  L  Q  D  C  T  M  L  2734

#248      ............................................
#227      ...............................A............
#213      ............................................
#211      ............................................
#209      ........................................t...
#12       .............c..............................
GenBank   ............................................
cons.     ............................................
     8544 GTGTGTGGCGACGACTTAGTCGTTATCTGTGAAAGTGCGGGGGTCCAGGAGGACGCGGCG 8603
     2735 V  C  G  D  D  L  V  V  I  C  E  S  A  G  V  Q  E  D  A  A  2754

#248      .............c..............................
#227      .............c..............................
#213      .............c..............................
#211      .............c..............................
#209      .............c..............................
#12       .............c..............................
GenBank   .............c..............................
cons.     .............c..............................
     8604 AGCCTGAGAGCCTTTACGGAGGCTATGACCAGGTACTCCGCCCCCCCCGGGGACCCCCCA 8663
     2755 S  L  R  A  F  T  E  A  M  T  R  Y  S  A  P  P  G  D  P  P  2774

#248      ............................................
#227      ..................................C.........
#213      ............................................
#211      ............................................
#209      ............................................
#12       ............c.........................t.....
GenBank   ............................................
cons.     ............................................
     8664 CAACCAGAATACGACTTGGAGCTTATAACATCATGCTCCTCCAACGTGTCAGTCGCCCAC 8723
     2775 Q  P  E  Y  D  L  E  L  I  T  S  C  S  S  N  V  S  V  A  H  2794

#248      .............g..............................
#227      ............................................
#213      .............g..............................
#211      .............g......C.......................
#209      .............g..................t...........
#12       ............gC..............................
GenBank   .............g..............................
cons.     .............g..............................
     8724 GACGGCGCTGGAAAAAGGGTCTACTACCTTACCCGTGACCCTACAACCCCCCTCGCGAGA 8783
     2795 D  G  A  G  K  R  V  Y  Y  L  T  R  D  P  T  T  P  L  A  R  2814
```

Figure 9BE

```
#248        ................................................................
#227        ................................................................
#213        ................................................................
#211        ................................................................
#209        ................................................................
#12         ................................................................
GenBank     ................................................................
cons.       ................................................................
       8784 GCCGCGTGGGAGACAGCAAGACACACTCCAGTCAATTCCTGGCTAGGCAACATAATCATG 8843
       2815 A   A   W   E   T   A   R   H   T   P   V   N   S   W   L   G   N   I   I   M 2834

#248        ................................................................
#227        ................................................................
#213        ................................................................
#211        .........................C......................................
#209        ................................................................
#12         .........................---------------------------------------
GenBank     .........................C......................................
cons.       ................................................................
       8844 TTTGCCCCCACACTGTGGGCGAGGATGATACTGATGACCCATTTCTTTAGCGTCCTCATA 8903
       2835 F   A   P   T   L   W   A   R   M   I   L   M   T   H   F   F   S   V   L   I 2854

#248        ...............................G................................
#227        ...............................G................................
#213        ...............................G................................
#211        ...............................G................................
#209        ...............................G................................
#12         ..............c................Gg...............................
GenBank     ..............c.....c..........G.................................
cons.       ...............................G.................................
       8904 GCCAGGGATCAGCTTGAACAGGCTCTTAACTGTGAGATCTACGCAGCCTGCTACTCCATA 8963
       2855 A   R   D   Q   L   E   Q   A   L   N   C   E   I   Y   A   A   C   Y   S   I 2874

#248        .........G..........................................C....
#227        ....................................................C....
#213        ....................................................C....
#211        ....................................................C....
#209        ....................................................C....
#12         ....................................................C....
GenBank     ....................................................C....
cons.       ....................................................C....
       8964 GAACCACTGGATCTACCTCCAATCATTCAAAGACTCCATGGCCTCAGCGCATTTTTACTC 9023
       2875 E   P   L   D   L   P   P   I   I   Q   R   L   H   G   L   S   A   F   L   L 2894

#248        ................A................................................
#227        ................A................................................
#213        ................A................................................
#211        ................A................................................
#209        ................A................................................
#12         ................A................................................
GenBank     ................A.t..............................................
PCR-seq     ..................................................................
cons.       ................A.................................................
       9024 CACAGTTACTCTCCAGGTGAAGTCAATAGGGTGGCCGCATGCCTCAGAAAACTTGGGGTC 9083
       2895 H   S   Y   S   P   G   E   V   N   R   V   A   A   C   L   R   K   L   G   V 2914
```

Figure 9BF

```
#248       ..............................t...........................
#227       ............................................................
#213       ...........................................................a
#211       ..............................t............................
#209       ...........................................................a
#12        ............g.................t.............................
GenBank    .............................T.................G....a
PCR-seq    ...........................................................a
cons.      ...........................................................a
     9084 CCGCCCTTGCGAGCTTGGAGACACCGGGCCCGGAGCGTCCGCGCTAGGCTTCTGTCCAGG  9143
     2915 P  P  L  R  A  W  R  H  R  A  R  S  V  R  A  R  L  L  S  R   2934

#248       ............................................................
#227       ............................................................
#213       ............................................................
#211       ............................................................
#209       ............................................................
#12        ...............................G............................
GenBank    .......A....................................................
cons.      ............................................................
     9144 GGAGGCAGGGCTGCCATATGTGGCAAGTACCTCTTCAACTGGGCAGTAAGAACAAAGCTC  9203
     2935 G  G  R  A  A  I  C  G  K  Y  L  F  N  W  A  V  R  T  K  L   2954

#248       ............................................................
#227       ............................................................
#213       ............................................................
#211       ............................................................
#209       ............................................................
#12        ............................................................
GenBank    ..........g...A.............................................
PCR-seq    .......................
cons.      ............................................................
     9204 AAACTCACTCCAATAGCGGCCGCTGGCCGGCTGGACTTGTCCGGTTGGTTCACGGCTGGC  9263
     2955 K  L  T  P  I  A  A  A  G  R  L  D  L  S  G  W  F  T  A  G   2974
```

Figure 9BG

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
       (A) LENGTH: 9646 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

```
GCCAGCCCCC TGATGGGGGC GACACTCCAC CATGAATCAC TCCCCTGTGA GGAACTACTG      60

TCTTCACGCA GAAAGCGTCT AGCCATGGCG TTAGTATGAG TGTCGTGCAG CCTCCAGGAC     120

CCCCCCTCCC GGGAGAGCCA TAGTGGTCTG CGGAACCGGT GAGTACACCG GAATTGCCAG     180

GACGACCGGG TCCTTTCTTG GATAAACCCG CTCAATGCCT GGAGATTTGG GCGTGCCCCC     240

GCAAGACTGC TAGCCGAGTA GTGTTGGGTC GCGAAAGGCC TTGTGGTACT GCCTGATAGG     300

GTGCTTGCGA GTGCCCCGGG AGGTCTCGTA GACCGTGCAC CATGAGCACG AATCCTAAAC     360

CTCAAAGAAA AACCAAACGT AACACCAACC GTCGCCCACA GGACGTCAAG TTCCCGGGTG     420

GCGGTCAGAT CGTTGGTGGA GTTTACTTGT TGCCGCGCAG GGGCCCTAGA TTGGGTGTGC     480

GCGCGACGAG GAAGACTTCC GAGCGGTCGC AACCTCGAGG TAGACGTCAG CCTATCCCCA     540

AGGCACGTCG GCCCGAGGGC AGGACCTGGG CTCAGCCCGG GTACCCTTGG CCCCTCTATG     600

GCAATGAGGG TTGCGGGTGG GCGGGATGGC TCCTGTCTCC CCGTGGCTCT CGGCCTAGCT     660

GGGGCCCCAC AGACCCCCGG CGTAGGTCGC GCAATTTGGG TAAGGTCATC GATACCCTTA     720

CGTGCGGCTT CGCCGACCTC ATGGGGTACA TACCGCTCGT CGGCGCCCCT CTTGGAGGCG     780

CTGCCAGGGC CCTGGCGCAT GGCGTCCGGG TTCTGGAAGA CGGCGTGAAC TATGCAACAG     840

GGAACCTTCC TGGTTGCTCT TTCTCTATCT TCCTTCTGGC CCTGCTCTCT TGCCTGACTG     900

TGCCCGCTTC AGCCTACCAA GTGCGCAATT CCTCGGGGCT TTACCATGTC ACCAATGATT     960

GCCCTAACTC GAGTATTGTG TACGAGGCGG CCGATGCCAT CCTGCACACT CCGGGGTGTG    1020

TCCCTTGCGT TCGCGAGGGT AACGCCTCGA GGTGTTGGGT GGCGGTGACC CCCACGGTGG    1080

CCACCAGGGA CGGCAAACTC CCCACAACGC AGCTTCGACG TCATATCGAT CTGCTTGTCG    1140

GGAGCGCCAC CCTCTGCTCG GCCCTCTACG TGGGGGACCT GTGCGGGTCT GTCTTTCTTG    1200

TTGGTCAACT GTTTACCTTC TCTCCCAGGC GCCACTGGAC GACGCAAGAC TGCAATTGTT    1260

CTATCTATCC CGGCCATATA ACGGGTCATC GCATGGCATG GGATATGATG ATGAACTGGT    1320

CCCCTACGGC AGCGTTGGTG GTAGCTCAGC TGCTCCGGAT CCCACAAGCC ATCATGGACA    1380

TGATCGCTGG TGCTCACTGG GGAGTCCTGG CGGGCATAGC GTATTCTCC ATGGTGGGA     1440

ACTGGGCGAA GGTCCTGGTA GTGCTGCTGC TATTTGCCGG CGTCGACGCG GAAACCCACG    1500

TCACCGGGGG AAGTGCCGGC CGCACCACGG CTGGGCTTGT TGGTCTCCTT ACACCAGGCG    1560

CCAAGCAGAA CATCCAACTG ATCAACACCA ACGGCAGTTG GCACATCAAT AGCACGGCCT    1620

TGAACTGCAA TGAAAGCCTT AACACCGGCT GGTTAGCAGG GCTCTTCTAT CAGCACAAAT    1680

TCAACTCTTC AGGCTGTCCT GAGAGGTTGG CCAGCTGCCG ACGCCTTACC GATTTTGCCC    1740

AGGGCTGGGG TCCTATCAGT TATGCCAACG GAAGCGGCCT CGACGAACGC CCCTACTGCT    1800

GGCACTACCC TCCAAGACCT TGTGGCATTG TGCCCGCAAA GAGCGTGTGT GGCCCGGTAT    1860

ATTGCTTCAC TCCCAGCCCC GTGGTGGTGG GAACGACCGA CAGGTCGGGC GCGCCTACCT    1920

ACAGCTGGGG TGCAAATGAT ACGGATGTCT TCGTCCTTAA CAACACCAGG CCACCGCTGG    1980

GCAATTGGTT CGGTTGTACC TGGATGAACT CAACTGGATT CACCAAAGTG TGCGGAGCGC    2040

CCCCTTGTGT CATCGGAGGG GTGGGCAACA ACACCTTGCT CTGCCCCACT GATTGTTTCC    2100

GCAAGCATCC GGAAGCCACA TACTCTCGGT GCGGCTCCGG TCCCTGGATT ACACCCAGGT    2160

GCATGGTCGA CTACCCGTAT AGGCTTTGGC ACTATCCTTG TACCATCAAT TACACCATAT    2220

TCAAAGTCAG GATGTACGTG GGAGGGGTCG AGCACAGGCT GGAAGCGGCC TGCAACTGGA    2280

CGCGGGGCGA ACGCTGTGAT CTGGAAGACA GGGACAGGTC CGAGCTCAGC CCATTGCTGC    2340
```

```
TGTCCACCAC ACAGTGGCAG GTCCTTCCGT GTTCTTTCAC GACCCTGCCA GCCTTGTCCA    2400

CCGGCCTCAT CCACCTCCAC CAGAACATTG TGGACGTGCA GTACTTGTAC GGGGTAGGGT    2460

CAAGCATCGC GTCCTGGGCC ATTAAGTGGG AGTACGTCGT TCTCCTGTTC CTCCTGCTTG    2520

CAGACGCGCG CGTCTGCTCC TGCTTGTGGA TGATGTTACT CATATCCCAA GCGGAGGCGG    2580

CTTTGGAGAA CCTCGTAATA CTCAATGCAG CATCCCTGGC CGGGACGCAC GGTCTTGTGT    2640

CCTTCCTCGT GTTCTTCTGC TTTGCGTGGT ATCTGAAGGG TAGGTGGGTG CCCGGAGCGG    2700

TCTACGCCTT CTACGGGATG TGGCCTCTCC TCCTGCTCCT GCTGGCGTTG CCTCAGCGGG    2760

CATACGCACT GGACACGGAG GTGGCCGCGT CGTGTGGCGG CGTTGTTCTT GTCGGGTTAA    2820

TGGCGCTGAC TCTGTCGCCA TATTACAAGC GCTACATCAG CTGGTGCATG TGGTGGCTTC    2880

AGTATTTTCT GACCAGAGTA GAAGCGCAAC TGCACGTGTG GGTTCCCCCC CTCAACGTCC    2940

GGGGGGGGCG CGATGCCGTC ATCTTACTCA TGTGTGTTGT ACACCCGACT CTGGTATTTG    3000

ACATCACCAA ACTACTCCTG GCCATCTTCG ACCCCTTTG GATTCTTCAA GCCAGTTTGC     3060

TTAAAGTCCC CTACTTCGTG CGCGTTCAAG GCCTTCTCCG GATCTGCGCG CTAGCGCGGA    3120

AGATAGCCGG AGGTCATTAC GTGCAAATGG CCATCATCAA GTTAGGGGCG CTTACTGGCA    3180

CCTATGTGTA TAACCATCTC ACCCCTCTTC GAGACTGGGC GCACAACGGC CTGCGAGATC    3240

TGGCCGTGGC TGTGGAACCA GTCGTCTTCT CCCGAATGGA GACCAAGCTC ATCACGTGGG    3300

GGGCAGATAC CGCCGCGTGC GGTGACATCA TCAACGGCTT GCCCGTCTCT GCCCGTAGGG    3360

GCCAGGAGAT ACTGCTTGGG CCAGCCGACG GAATGGTCTC CAAGGGGTGG AGGTTGCTGG    3420

CGCCCATCAC GGCGTACGCC CAGCAGACGA GAGGCCTCCT AGGGTGTATA ATCACCAGCC    3480

TGACTGGCCG GGACAAAAAC CAAGTGGAGG GTGAGGTCCA GATCGTGTCA ACTGCTACCC    3540

AAACCTTCCT GGCAACGTGC ATCAATGGGG TATGCTGGAC TGTCTACCAC GGGGCCGGAA    3600

CGAGGACCAT CGCATCACCC AAGGGTCCTG TCATCCAGAT GTATACCAAT GTGGACCAAG    3660

ACCTTGTGGG CTGGCCCGCT CCTCAAGGTT CCCGCTCATT GACACCCTGC ACCTGCGGCT    3720

CCTCGGACCT TTACCTGGTC ACGAGGCACG CCGATGTCAT TCCCGTGCGC CGGCGAGGTG    3780

ATAGCAGGGG TAGCCTGCTT TCGCCCCGGC CCATTTCCTA CTTGAAAGGC TCCTCGGGGG    3840

GTCCGCTGTT GTGCCCCGCG GGACACGCCG TGGGCCTATT CAGGGCCGCG GTGTGCACCC    3900

GTGGAGTGGC TAAGGCGGTG GACTTTATCC CTGTGGAGAA CCTAGAGACA ACCATGAGAT    3960

CCCCGGTGTT CACGGACAAC TCCTCTCCAC CAGCAGTGCC CCAGAGCTTC CAGGTGGCCC    4020

ACCTGCATGC TCCCACCGGC AGCGGTAAGA GCACCAAGGT CCCGGCTGCG TACGCAGCCC    4080

AGGGCTACAA GGTGTTGGTG CTCAACCCCT CTGTTGCTGC AACGCTGGGC TTTGGTGCTT    4140

ACATGTCCAA GGCCCATGGG GTTGATCCTA ATATCAGGAC CGGGGTGAGA ACAATTACCA    4200

CTGGCAGCCC CATCACGTAC TCCACCTACG GCAAGTTCCT TGCCGACGGC GGGTGCTCAG    4260

GAGGTGCTTA TGACATAATA ATTTGTGACG AGTGCCACTC CACGGATGCC ACATCCATCT    4320

TGGGCATCGG CACTGTCCTT GACCAAGCAG AGACTGCGGG GGCGAGACTG GTTGTGCTCG    4380

CCACTGCTAC CCCTCCGGGC TCCGTCACTG TGTCCCATCC TAACATCGAG GAGGTTGCTC    4440

TGTCCACCAC CGGAGAGATC CCTTTTTACG GCAAGGCTAT CCCCCTCGAG GTGATCAAGG    4500

GGGGAAGACA TCTCATCTTC TGCCACTCAA AGAAGAAGTG CGACGAGCTC GCCGCGAAGC    4560

TGGTCGCATT GGGCATCAAT GCCGTGGCCT ACTACCGCGG TCTTGACGTG TCTGTCATCC    4620

CGACCAGCGG CGATGTTGTC GTCGTGTCGA CCGATGCTCT CATGACTGGC TTTACCGGCG    4680

ACTTCGACTC TGTGATAGAC TGCAACACGT GTGTCACTCA GACAGTCGAT TTCAGCCTTG    4740
```

-continued

```
ACCCTACCTT TACCATTGAG ACAACCACGC TCCCCCAGGA TGCTGTCTCC AGGACTCAAC     4800

GCCGGGGCAG GACTGGCAGG GGGAAGCCAG GCATCTACAG ATTTGTGGCA CCGGGGGAGC     4860

GCCCCTCCGG CATGTTCGAC TCGTCCGTCC TCTGTGAGTG CTATGACGCG GGCTGTGCTT     4920

GGTATGAGCT CACGCCCGCC GAGACTACAG TTAGGCTACG AGCGTACATG AACACCCCGG     4980

GGCTTCCCGT GTGCCAGGAC CATCTTGAAT TTTGGGAGGG CGTCTTTACG GGCCTCACTC     5040

ATATAGATGC CCACTTTCTA TCCCAGACAA AGCAGAGTGG GGAGAACTTT CCTTACCTGG     5100

TAGCGTACCA AGCCACCGTG TGCGCTAGGG CTCAAGCCCC TCCCCCATCG TGGGACCAGA     5160

TGTGGAAGTG TTTGATCCGC CTTAAACCCA CCCTCCATGG GCCAACACCC CTGCTATACA     5220

GACTGGGCGC TGTTCAGAAT GAAGTCACCC TGACGCACCC AATCACCAAA TACATCATGA     5280

CATGCATGTC GGCCGACCTG GAGGTCGTCA CGAGCACCTG GGTGCTCGTT GGCGGCGTCC     5340

TGGCTGCTCT GGCCGCGTAT TGCCTGTCAA CAGGCTGCGT GGTCATAGTG GGCAGGATTG     5400

TCTTGTCCGG GAAGCCGGCA ATTATACCTG ACAGGGAGGT TCTCTACCAG GAGTTCGATG     5460

AGATGGAAGA GTGCTCTCAG CACTTACCGT ACATCGAGCA AGGGATGATG CTCGCTGAGC     5520

AGTTCAAGCA GAAGGCCCTC GGCCTCCTGC AGACCGCGTC CCGCCAAGCA GAGGTTATCA     5580

CCCCTGCTGT CCAGACCAAC TGGCAGAAAC TCGAGGTCTT CTGGGCGAAG CACATGTGGA     5640

ATTTCATCAG TGGGATACAA TACTTGGCGG GCCTGTCAAC GCTGCCTGGT AACCCCGCCA     5700

TTGCTTCATT GATGGCTTTT ACAGCTGCCG TCACCAGCCC ACTAACCACT GGCCAAACCC     5760

TCCTCTTCAA CATATTGGGG GGGTGGGTGG CTGCCCAGCT CGCCGCCCCC GGTGCCGCTA     5820

CCGCCTTTGT GGGCGCTGGC TTAGCTGGCC CCGCCATCGG CAGCGTTGGA CTGGGGAAGG     5880

TCCTCGTGGA CATTCTTGCA GGGTATGGCG CGGGCGTGGC GGGAGCTCTT GTAGCATTCA     5940

AGATCATGAG CGGTGAGGTC CCCTCCACGG AGGACCTGGT CAATCTGCTG CCCGCCATCC     6000

TCTCGCCTGG AGCCCTTGTA GTCGGTGTGG TCTGCGCAGC AATACTGCGC CGGCACGTTG     6060

GCCCGGGCGA GGGGGCAGTG CAATGGATGA ACCGGCTAAT AGCCTTCGCC TCCCGGGGGA     6120

ACCATGTTTC CCCCACGCAC TACGTGCCGG AGAGCGATGC AGCCGCCCGC GTCACTGCCA     6180

TACTCAGCAG CCTCACTGTA ACCCAGCTCC TGAGGCGACT GCATCAGTGG ATAAGCTCGG     6240

AGTGTACCAC TCCATGCTCC GGTTCCTGGC TAAGGGACAT CTGGGACTGG ATATGCGAGG     6300

TGCTGAGCGA CTTTAAGACC TGGCTGAAAG CCAAGCTCAT GCCACAACTG CCTGGGATTC     6360

CCTTTGTGTC CTGCCAGCGC GGGTATAGGG GGTCTGGCG AGGAGACGGC ATTATGCACA     6420

CTCGCTGCCA CTGTGGAGCT GAGATCACTG GACATGTCAA AAACGGGACG ATGAGGATCG     6480

TCGGTCCTAG GACCTGCAGG AACATGTGGA GTGGGACGTT CCCCATTAAC GCCTACACCA     6540

CGGGCCCCTG TACTCCCCTT CCTGCGCCGA ACTATAAGTT CGCGCTGTGG AGGGTGTCTG     6600

CAGAGGAATA CGTGGAGATA AGGCGGGTGG GGGACTTCCA CTACGTATCG GGTATGACTA     6660

CTGACAATCT TAAATGCCCG TGCCAGATCC CATCGCCCGA ATTTTTCACA GAATTGGACG     6720

GGGTGCGCCT ACATAGGTTT GCGCCCCCTT GCAAGCCCTT GCTGCGGGAG GAGGTATCAT     6780

TCAGAGTAGG ACTCCACGAG TACCCGGTGG GGTCGCAATT ACCTTGCGAG CCCGAACCGG     6840

ACGTAGCCGT GTTGACGTCC ATGCTCACTG ATCCCTCCCA TATAACAGCA GAGGCGGCCG     6900

GGAGAAGGTT GGCGAGAGGG TCACCCCCTT CTATGGCCAG CTCCTCGGCC AGCCAGCTGT     6960

CCGCTCCATC TCTCAAGGCA ACTTGCACCG CCAACCATGA CTCCCCTGAC GCCGAGCTCA     7020

TAGAGGCTAA CCTCCTGTGG AGGCAGGAGA TGGGCGGCAA CATCACCAGG GTTGAGTCAG     7080
```

-continued

```
AGAACAAAGT GGTGATTCTG GACTCCTTCG ATCCGCTTGT GGCAGAGGAG GATGAGCGGG    7140
AGGTCTCCGT ACCCGCAGAA ATTCTGCGGA AGTCTCGGAG ATTCGCCCGG GCCCTGCCCG    7200
TTTGGGCGCG GCCGGACTAC AACCCCCCGC TAGTAGAGAC GTGGAAAAAG CCTGACTACG    7260
AACCACCTGT GGTCCATGGC TGCCCGCTAC CACCTCCACG GTCCCTCCT GTGCCTCCGC     7320
CTCGGAAAAA GCGTACGGTG GTCCTCACCG AATCAACCCT ATCTACTGCC TTGGCCGAGC    7380
TTGCCACCAA AAGTTTTGGC AGCTCCTCAA CTTCCGGCAT TACGGGCGAC AATACGACAA    7440
CATCCTCTGA GCCCGCCCCT TCTGGCTGCC CCCCGACTC CGACGTTGAG TCCTATTCTT     7500
CCATGCCCCC CCTGGAGGGG GAGCCTGGGG ATCCGGATCT CAGCGACGGG TCATGGTCGA    7560
CGGTCAGTAG TGGGGCCGAC ACGGAAGATG TCGTGTGCTG CTCAATGTCT TATTCCTGGA    7620
CAGGCGCACT CGTCACCCCG TGCGCTGCGG AAGAACAAAA ACTGCCCATC AACGCACTGA    7680
GCAACTCGTT GCTACGCCAT CACAATCTGG TGTATTCCAC CACTTCACGC AGTGCTTGCC    7740
AAAGGCAGAA GAAAGTCACA TTTGACAGAC TGCAAGTTCT GGACAGCCAT TACCAGGACG    7800
TGCTCAAGGA GGTCAAAGCA GCGGCGTCAA AAGTGAAGGC TAACTTGCTA TCCGTAGAGG    7860
AAGCTTGCAG CCTGACGCCC CCACATTCAG CCAAATCCAA GTTTGGCTAT GGGGCAAAAG    7920
ACGTCCGTTG CCATGCCAGA AAGGCCGTAG CCCACATCAA CTCCGTGTGG AAAGACCTTC    7980
TGGAAGACAG TGTAACACCA ATAGACACTA CCATCATGGC CAAGAACGAG GTTTTCTGCG    8040
TTCAGCCTGA GAAGGGGGGT CGTAAGCCAG CTCGTCTCAT CGTGTTCCCC GACCTGGGCG    8100
TGCGCGTGTG CGAGAAGATG GCCCTGTACG ACGTGGTTAG CAAGCTCCCC CTGGCCGTGA    8160
TGGGAAGCTC CTACGGATTC AATACTCAC CAGGACAGCG GGTTGAATTC CTCGTGCAAG     8220
CGTGGAAGTC CAAGAAGACC CCGATGGGGT TCTCGTATGA TACCCGCTGT TTTGACTCCA    8280
CAGTCACTGA GAGCGACATC CGTACGGAGG AGGCAATTTA CCAATGTTGT GACCTGGACC    8340
CCCAAGCCCG CGTGGCCATC AAGTCCCTCA CTGAGAGGCT TTATGTTGGG GGCCCTCTTA    8400
CCAATTCAAG GGGGGAAAAC TGCGGCTACC GCAGGTGCCG CGCGAGCGGC GTACTGACAA    8460
CTAGCTGTGG TAACCCCTC ACTTGCTACA TCAAGGCCCG GGCAGCCTGT CGAGCCGCAG     8520
GGCTCCAGGA CTGCACCATG CTCGTGTGTG GCGACGACTT AGTCGTTATC TGTGAAAGTG    8580
CGGGGGTCCA GGAGGACGCG GCGAGCCTGA GAGCCTTCAC GGAGGCTATG ACCAGGTACT    8640
CCGCCCCCCC CGGGGACCCC CCACAACCAG AATACGACTT GGAGCTTATA ACATCATGCT    8700
CCTCCAACGT GTCAGTCGCC CACGACGGCG CTGGAAAGAG GGTCTACTAC CTTACCCGTG    8760
ACCCTACAAC CCCCCTCGCG AGAGCCGCGT GGGAGACAGC AAGACACACT CCAGTCAATT    8820
CCTGGCTAGG CAACATAATC ATGTTTGCCC CCACACTGTG GGCGAGGATG ATACTGATGA    8880
CCCATTTCTT TAGCGTCCTC ATAGCCAGGG ATCAGCTTGA ACAGGCTCTT AACTGTGAGA    8940
TCTACGGAGC CTGCTACTCC ATAGAACCAC TGGATCTACC TCCAATCATT CAAAGACTCC    9000
ATGGCCTCAG CGCATTTTCA CTCCACAGTT ACTCTCCAGG TGAAATCAAT AGGGTGGCCG    9060
CATGCCTCAG AAAACTTGGG GTCCCGCCCT TGCGAGCTTG GAGACACCGG GCCCGGAGCG    9120
TCCGCGCTAG GCTTCTGTCC AGAGGAGGCA GGGCTGCCAT ATGTGGCAAG TACCTCTTCA    9180
ACTGGGCAGT AAGAACAAAG CTCAAACTCA CTCCAATAGC GGCCGCTGGC CGGCTGGACT    9240
TGTCCGGTTG GTTCACGGCT GGCTACAGCG GGGGAGACAT TTATCACAGC GTGTCTCATG    9300
CCCGGCCCCG CTGGTTCTGG TTTTGCCTAC TCCTGCTCGC TGCAGGGGTA GGCATCTACC    9360
TCCTCCCCAA CCGATGAAGG TTGGGGTAAA CACTCCGGCC TCTTAGGCCA TTTCCTGTTT    9420
TTTTTTTTTT TTTTTTTTTT TTTTTTTTTT TTTTTTTTTT TTTTTTTCT TTTTTTTTTT     9480
```

```
TTTTTTCCTT TTTTTTTTTT TTTTTTTTCT TTCCTTCTTT TTTCCTTTCT TTTCCTTCCT    9540

TCTTTAATGG TGGCTCCATC TTAGCCCTAG TCACGGCTAG CTGTGAAAGG TCCGTGAGCC    9600

GCATGACTGC AGAGAGTGCT GATACTGGCC TCTCTGCAGA TCATGT                   9646
```

(2) INFORMATION FOR SEQ ID NO: 2:

(i) SEQUENCE CHARACTERISTICS:
        (A) LENGTH: 3012 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 2:

```
Met Ser Thr Asn Pro Lys Pro Gln Arg Lys Thr Lys Arg Asn Thr Asn
1               5                  10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65              70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145             150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225             230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
```

-continued

```
                290                 295                 300
Asn Cys Ser Ile Tyr Pro Gly His Ile Thr Gly His Arg Met Ala Trp
305                 310                 315                 320

Asp Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
                340                 345                 350

Trp Gly Val Leu Ala Gly Ile Ala Tyr Phe Ser Met Val Gly Asn Trp
                355                 360                 365

Ala Lys Val Leu Val Leu Leu Phe Ala Gly Val Asp Ala Glu
370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
                435                 440                 445

Ser Ser Gly Cys Pro Glu Arg Leu Ala Ser Cys Arg Arg Leu Thr Asp
450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Gly Thr Thr Asp Arg Ser Gly Ala Pro Thr Tyr Ser
                515                 520                 525

Trp Gly Ala Asn Asp Thr Asp Val Phe Val Leu Asn Asn Thr Arg Pro
                530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Met
                595                 600                 605

Val Asp Tyr Pro Tyr Arg Leu Trp His Tyr Pro Cys Thr Ile Asn Tyr
610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
                690                 695                 700

Val Gly Ser Ser Ile Ala Ser Trp Ala Ile Lys Trp Glu Tyr Val Val
705                 710                 715                 720
```

-continued

```
Leu Leu Phe Leu Leu Ala Asp Ala Arg Val Cys Ser Cys Leu Trp
            725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Arg Trp Val Pro
770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
            850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Ile Cys Ala Leu Ala Arg Lys Ile
            915                 920                 925

Ala Gly Gly His Tyr Val Gln Met Ala Ile Ile Lys Leu Gly Ala Leu
            930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Gln
            995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Thr Gln Thr Phe Leu Ala Thr
                1060                1065                1070

Cys Ile Asn Gly Val Cys Trp Thr Val Tyr His Gly Ala Gly Thr Arg
            1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135
```

-continued

Ala Asp Val Ile Pro Val Arg Arg Gly Asp Ser Arg Gly Ser Leu
        1140                1145                1150

Leu Ser Pro Arg Pro Ile Ser Tyr Leu Lys Gly Ser Ser Gly Pro
        1155                1160                1165

Leu Leu Cys Pro Ala Gly His Ala Val Gly Leu Phe Arg Ala Val
        1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
            1205                1210                1215

Pro Ala Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Ile
        1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Ser Thr Asp Ala Leu
1425                1430                1435                1440

Met Thr Gly Phe Thr Gly Asp Phe Asp Ser Val Ile Asp Cys Asn Thr
            1445                1450                1455

Cys Val Thr Gln Thr Val Asp Phe Ser Leu Asp Pro Thr Phe Thr Ile
            1460                1465                1470

Glu Thr Thr Thr Leu Pro Gln Asp Ala Val Ser Arg Thr Gln Arg Arg
        1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile

-continued

```
            1555                1560                1565
Asp Ala His Phe Leu Ser Gln Thr Lys Gln Ser Gly Glu Asn Phe Pro
    1570                1575                1580
Tyr Leu Val Ala Tyr Gln Ala Thr Val Cys Ala Arg Ala Gln Ala Pro
1585                1590                1595                1600
Pro Pro Ser Trp Asp Gln Met Trp Lys Cys Leu Ile Arg Leu Lys Pro
                1605                1610                1615
Thr Leu His Gly Pro Thr Pro Leu Leu Tyr Arg Leu Gly Ala Val Gln
            1620                1625                1630
Asn Glu Val Thr Leu Thr His Pro Ile Thr Lys Tyr Ile Met Thr Cys
        1635                1640                1645
Met Ser Ala Asp Leu Glu Val Val Thr Ser Thr Trp Val Leu Val Gly
    1650                1655                1660
Gly Val Leu Ala Ala Leu Ala Ala Tyr Cys Leu Ser Thr Gly Cys Val
1665                1670                1675                1680
Val Ile Val Gly Arg Ile Val Leu Ser Gly Lys Pro Ala Ile Ile Pro
                1685                1690                1695
Asp Arg Glu Val Leu Tyr Gln Glu Phe Asp Glu Met Glu Glu Cys Ser
            1700                1705                1710
Gln His Leu Pro Tyr Ile Glu Gln Gly Met Met Leu Ala Glu Gln Phe
        1715                1720                1725
Lys Gln Lys Ala Leu Gly Leu Leu Gln Thr Ala Ser Arg Gln Ala Glu
    1730                1735                1740
Val Ile Thr Pro Ala Val Gln Thr Asn Trp Gln Lys Leu Glu Val Phe
1745                1750                1755                1760
Trp Ala Lys His Met Trp Asn Phe Ile Ser Gly Ile Gln Tyr Leu Ala
                1765                1770                1775
Gly Leu Ser Thr Leu Pro Gly Asn Pro Ala Ile Ala Ser Leu Met Ala
            1780                1785                1790
Phe Thr Ala Ala Val Thr Ser Pro Leu Thr Thr Gly Gln Thr Leu Leu
        1795                1800                1805
Phe Asn Ile Leu Gly Gly Trp Val Ala Ala Gln Leu Ala Ala Pro Gly
    1810                1815                1820
Ala Ala Thr Ala Phe Val Gly Ala Gly Leu Ala Gly Ala Ala Ile Gly
1825                1830                1835                1840
Ser Val Gly Leu Gly Lys Val Leu Val Asp Ile Leu Ala Gly Tyr Gly
                1845                1850                1855
Ala Gly Val Ala Gly Ala Leu Val Ala Phe Lys Ile Met Ser Gly Glu
            1860                1865                1870
Val Pro Ser Thr Glu Asp Leu Val Asn Leu Leu Pro Ala Ile Leu Ser
        1875                1880                1885
Pro Gly Ala Leu Val Val Gly Val Val Cys Ala Ala Ile Leu Arg Arg
    1890                1895                1900
His Val Gly Pro Gly Glu Gly Ala Val Gln Trp Met Asn Arg Leu Ile
1905                1910                1915                1920
Ala Phe Ala Ser Arg Gly Asn His Val Ser Pro Thr His Tyr Val Pro
                1925                1930                1935
Glu Ser Asp Ala Ala Ala Arg Val Thr Ala Ile Leu Ser Ser Leu Thr
            1940                1945                1950
Val Thr Gln Leu Leu Arg Arg Leu His Gln Trp Ile Ser Ser Glu Cys
        1955                1960                1965
Thr Thr Pro Cys Ser Gly Ser Trp Leu Arg Asp Ile Trp Asp Trp Ile
    1970                1975                1980
```

-continued

```
Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045

Pro Arg Thr Cys Arg Asn Met Trp Ser Gly Thr Phe Pro Ile Asn Ala
                2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
                2100                2105                2110

Pro Cys Gln Ile Pro Ser Pro Glu Phe Phe Thr Glu Leu Asp Gly Val
                2115                2120                2125

Arg Leu His Arg Phe Ala Pro Pro Cys Lys Pro Leu Leu Arg Glu Glu
                2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190

Gly Ser Pro Pro Ser Met Ala Ser Ser Ala Ser Gln Leu Ser Ala
                2195                2200                2205

Pro Ser Leu Lys Ala Thr Cys Thr Ala Asn His Asp Ser Pro Asp Ala
                2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
                2245                2250                2255

Asp Pro Leu Val Ala Glu Glu Asp Glu Arg Glu Val Ser Val Pro Ala
                2260                2265                2270

Glu Ile Leu Arg Lys Ser Arg Arg Phe Ala Arg Ala Leu Pro Val Trp
                2275                2280                2285

Ala Arg Pro Asp Tyr Asn Pro Pro Leu Val Glu Thr Trp Lys Lys Pro
                2290                2295                2300

Asp Tyr Glu Pro Pro Val Val His Gly Cys Pro Leu Pro Pro Pro Arg
2305                2310                2315                2320

Ser Pro Pro Val Pro Pro Arg Lys Lys Arg Thr Val Val Leu Thr
                2325                2330                2335

Glu Ser Thr Leu Ser Thr Ala Leu Ala Glu Leu Ala Thr Lys Ser Phe
                2340                2345                2350

Gly Ser Ser Ser Thr Ser Gly Ile Thr Gly Asp Asn Thr Thr Thr Ser
                2355                2360                2365

Ser Glu Pro Ala Pro Ser Gly Cys Pro Pro Asp Ser Asp Val Glu Ser
                2370                2375                2380

Tyr Ser Ser Met Pro Pro Leu Glu Gly Glu Pro Gly Asp Pro Asp Leu
2385                2390                2395                2400
```

-continued

Ser Asp Gly Ser Trp Ser Thr Val Ser Gly Ala Asp Thr Glu Asp
            2405                2410                2415

Val Val Cys Cys Ser Met Ser Tyr Ser Trp Thr Gly Ala Leu Val Thr
                2420                2425                2430

Pro Cys Ala Ala Glu Glu Gln Lys Leu Pro Ile Asn Ala Leu Ser Asn
            2435                2440                2445

Ser Leu Leu Arg His His Asn Leu Val Tyr Ser Thr Thr Ser Arg Ser
    2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
            2485                2490                2495

Lys Val Lys Ala Asn Leu Leu Ser Val Glu Glu Ala Cys Ser Leu Thr
            2500                2505                2510

Pro Pro His Ser Ala Lys Ser Lys Phe Gly Tyr Gly Ala Lys Asp Val
            2515                2520                2525

Arg Cys His Ala Arg Lys Ala Val Ala His Ile Asn Ser Val Trp Lys
            2530                2535                2540

Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
            2565                2570                2575

Ala Arg Leu Ile Val Phe Pro Asp Leu Gly Val Arg Val Cys Glu Lys
            2580                2585                2590

Met Ala Leu Tyr Asp Val Val Ser Lys Leu Pro Leu Ala Val Met Gly
            2595                2600                2605

Ser Ser Tyr Gly Phe Gln Tyr Ser Pro Gly Gln Arg Val Glu Phe Leu
            2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
            2675                2680                2685

Ser Arg Gly Glu Asn Cys Gly Tyr Arg Arg Cys Arg Ala Ser Gly Val
            2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile

```
                        2820            2825            2830
Ile Met Phe Ala Pro Thr Leu Trp Ala Arg Met Ile Leu Met Thr His
        2835            2840            2845

Phe Phe Ser Val Leu Ile Ala Arg Asp Gln Leu Glu Gln Ala Leu Asn
2850            2855            2860

Cys Glu Ile Tyr Gly Ala Cys Tyr Ser Ile Glu Pro Leu Asp Leu Pro
2865            2870            2875            2880

Pro Ile Ile Gln Arg Leu His Gly Leu Ser Ala Phe Ser Leu His Ser
        2885            2890            2895

Tyr Ser Pro Gly Glu Ile Asn Arg Val Ala Ala Cys Leu Arg Lys Leu
        2900            2905            2910

Gly Val Pro Pro Leu Arg Ala Trp Arg His Arg Ala Arg Ser Val Arg
        2915            2920            2925

Ala Arg Leu Leu Ser Arg Gly Gly Arg Ala Ala Ile Cys Gly Lys Tyr
        2930            2935            2940

Leu Phe Asn Trp Ala Val Arg Thr Lys Leu Lys Leu Thr Pro Ile Ala
2945            2950            2955            2960

Ala Ala Gly Arg Leu Asp Leu Ser Gly Trp Phe Thr Ala Gly Tyr Ser
        2965            2970            2975

Gly Gly Asp Ile Tyr His Ser Val Ser His Ala Arg Pro Arg Trp Phe
        2980            2985            2990

Trp Phe Cys Leu Leu Leu Leu Ala Ala Gly Val Gly Ile Tyr Leu Leu
        2995            3000            3005

Pro Asn Arg Glx
    3010
```

(2) INFORMATION FOR SEQ ID NO: 3:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO: 3:

GCCAGCCCCC TGATGGGGGC GACACTCCAC CATGAATC                      38

(2) INFORMATION FOR SEQ ID NO: 4:

(i) SEQUENCE CHARACTERISTICS:
        (A) LENGTH: 98 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO: 4:

GGTGGCTCCA TCTTAGCCCT AGTCACGGCT AGCTGTGAAA GGTCCGTGAG CCGCATGACT     60

GCAGAGAGTG CTGATACTGG CCTCTCTGCT GATCATGT                      98

(2) INFORMATION FOR SEQ ID NO: 5:

(i) SEQUENCE CHARACTERISTICS:
        (A) LENGTH: 12980 base pairs (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

```
GCCAGCCCCC TGATGGGGGC GACACTCCAC CATGAATCAC TCCCCTGTGA GGAACTACTG    60
TCTTCACGCA GAAAGCGTCT AGCCATGGCG TTAGTATGAG TGTCGTGCAG CCTCCAGGAC   120
CCCCCCTCCC GGGAGAGCCA TAGTGGTCTG CGGAACCGGT GAGTACACCG GAATTGCCAG   180
GACGACCGGG TCCTTTCTTG GATAAACCCG CTCAATGCCT GGAGATTTGG GCGTGCCCCC   240
GCAAGACTGC TAGCCGAGTA GTGTTGGGTC GCGAAAGGCC TTGTGGTACT GCCTGATAGG   300
GTGCTTGCGA GTGCCCCGGG AGGTCTCGTA GACCGTGCAC CATGAGCACG AATCCTAAAC   360
CTCAAAGAAA AACCAAACGT AACACCAACC GTCGCCCACA GGACGTCAAG TTCCCGGGTG   420
GCGGTCAGAT CGTTGGTGGA GTTTACTTGT TGCCGCGCAG GGGCCCTAGA TTGGGTGTGC   480
GCGCGACGAG GAAGACTTCC GAGCGGTCGC AACCTCGAGG TAGACGTCAG CCTATCCCCA   540
AGGCACGTCG GCCCGAGGGC AGGACCTGGG CTCAGCCCGG GTACCTTGG CCCCTCTATG    600
GCAATGAGGG TTGCGGGTGG GCGGGATGGC TCCTGTCTCC CCGTGGCTCT CGGCCTAGCT   660
GGGGCCCCAC AGACCCCCGG CGTAGGTCGC GCAATTTGGG TAAGGTCATC GATACCCTTA   720
CGTGCGGCTT CGCCGACCTC ATGGGGTACA TACCGCTCGT CGGCGCCCCT CTTGGAGGCG   780
CTGCCAGGGC CCTGGCGCAT GGCGTCCGGG TTCTGGAAGA CGGCGTGAAC TATGCAACAG   840
GGAACCTTCC TGGTTGCTCT TTCTCTATCT TCCTTCTGGC CCTGCTCTCT TGCCTGACCG   900
TGCCCGCTTC AGCCTACCAA GTGCGCAATT CCTCGGGGCT TTACCATGTC ACCAATGATT   960
GCCCTAACTC GAGTATTGTG TACGAGGCGG CCGATGCCAT CCTGCACACT CCGGGGTGTG  1020
TCCCTTGCGT TCGCGAGGGT AACGCCTCGA GGTGTTGGGT GGCGGTGACC CCCACGGTGG  1080
CCACCAGGGA CGGCAAACTC CCCACAACGC AGCTTCGACG TCATATCGAT CTGCTTGTCG  1140
GGAGCGCCAC CCTCTGCTCG GCCCTCTACG TGGGGGACCT GTGCGGGTCT GTCTTTCTTG  1200
TTGGTCAACT GTTTACCTTC TCTCCCAGGC GCCACTGGAC GACGCAAGAC TGCAATTGTT  1260
CTATCTATCC CGGCCATATA ACGGGTCATC GCATGGCATG GGATATGATG ATGAACTGGT  1320
CCCCTACGGC AGCGTTGGTG GTAGCTCAGC TGCTCCGGAT CCCACAAGCC ATCATGGACA  1380
TGATCGCTGG TGCTCACTGG GGAGTCCTGG CGGGCATAGC GTATTTCTCC ATGGTGGGGA  1440
ACTGGGCGAA GGTCCTGGTA GTGCTGCTGC TATTTGCCGG CGTCGACGCG GAAACCCACG  1500
TCACCGGGGG AAGTGCCGGC CGCACCACGG CTGGGCTTGT TGGTCTCCTT ACACCAGGCG  1560
CCAAGCAGAA CATCCAACTG ATCAACACCA ACGGCAGTTG GCACATCAAT AGCACGGCCT  1620
TGAACTGCAA TGAAAGCCTT AACACCGGCT GGTTAGCAGG GCTCTTCTAT CAGCACAAAT  1680
TCAACTCTTC AGGCTGTCCT GAGAGGTTGG CCAGCTGCCG ACGCCTTACC GATTTTGCCC  1740
AGGGCTGGGG TCCTATCAGT TATGCCAACG GAAGCGGCCT CGACGAACGC CCCTACTGCT  1800
GGCACTACCC TCCAAGACCT TGTGGCATTG TGCCCGCAAA GAGCGTGTGT GGCCCGGTAT  1860
ATTGCTTCAC TCCCAGCCCC GTGGTGGTGG GAACGACCGA CAGGTCGGGC GCGCCTACCT  1920
ACAGCTGGGG TGCAAATGAT ACGGATGTCT TCGTCCTTAA CAACACCAGG CCACCGCTGG  1980
GCAATTGGTT CGGTTGTACC TGGATGAACT CAACTGGATT CACCAAAGTG TGCGGAGCGC  2040
```

```
CCCCTTGTGT CATCGGAGGG GTGGGCAACA ACACCTTGCT CTGCCCCACT GATTGTTTCC    2100

GCAAGCATCC GGAAGCCACA TACTCTCGGT GCGGCTCCGG TCCCTGGATT ACACCCAGGT    2160

GCATGGTCGA CTACCCGTAT AGGCTTTGGC ACTATCCTTG TACCATCAAT TACACCATAT    2220

TCAAAGTCAG GATGTACGTG GGAGGGGTCG AGCACAGGCT GGAAGCGGCC TGCAACTGGA    2280

CGCGGGGCGA ACGCTGTGAT CTGGAAGACA GGGACAGGTC CGAGCTCAGC CCATTGCTGC    2340

TGTCCACCAC ACAGTGGCAG GTCCTTCCGT GTTCTTTCAC GACCCTGCCA GCCTTGTCCA    2400

CCGGCCTCAT CCACCTCCAC CAGAACATTG TGGACGTGCA GTACTTGTAC GGGGTAGGGT    2460

CAAGCATCGC GTCCTGGGCC ATTAAGTGGG AGTACGTCGT TCTCCTGTTC CTCCTGCTTG    2520

CAGACGCGCG CGTCTGCTCC TGCTTGTGGA TGATGTTACT CATATCCCAA GCGGAGGCGG    2580

CTTTGGAGAA CCTCGTAATA CTCAATGCAG CATCCCTGGC CGGGACGCAC GGTCTTGTGT    2640

CCTTCCTCGT GTTCTTCTGC TTTGCGTGGT ATCTGAAGGG TAGGTGGGTG CCCGGAGCGG    2700

TCTACGCCTT CTACGGGATG TGGCCTCTCC TCCTGCTCCT GCTGGCGTTG CCTCAGCGGG    2760

CATACGCACT GGACACGGAG GTGGCCGCGT CGTGTGGCGG CGTTGTTCTT GTCGGGTTAA    2820

TGGCGCTGAC TCTGTCGCCA TATTACAAGC GCTACATCAG CTGGTGCATG TGGTGGCTTC    2880

AGTATTTTCT GACCAGAGTA GAAGCGCAAC TGCACGTGTG GGTTCCCCCC CTCAACGTCC    2940

GGGGGGGGCG CGATGCCGTC ATCTTACTCA TGTGTGTTGT ACACCCGACT CTGGTATTTG    3000

ACATCACCAA ACTACTCCTG GCCATCTTCG GACCCCTTTG GATTCTTCAA GCCAGTTTGC    3060

TTAAAGTCCC CTACTTCGTG CGCGTTCAAG GCCTTCTCCG GATCTGCGCG CTAGCGCGGA    3120

AGATAGCCGG AGGTCATTAC GTGCAAATGG CCATCATCAA GTTAGGGGCG CTTACTGGCA    3180

CCTATGTGTA TAACCATCTC ACCCCTCTTC GAGACTGGGC GCACAACGGC CTGCGAGATC    3240

TGGCCGTGGC TGTGGAACCA GTCGTCTTCT CCCGAATGGA GACCAAGCTC ATCACGTGGG    3300

GGGCAGATAC CGCCGCGTGC GGTGACATCA TCAACGGCTT GCCCGTCTCT GCCCGTAGGG    3360

GCCAGGAGAT ACTGCTTGGG CCAGCCGACG GAATGGTCTC CAAGGGGTGG AGGTTGCTGG    3420

CGCCCATCAC GGCGTACGCC CAGCAGACGA GAGGCCTCCT AGGGTGTATA ATCACCAGCC    3480

TGACTGGCCG GGACAAAAAC CAAGTGGAGG GTGAGGTCCA GATCGTGTCA ACTGCTACCC    3540

AAACCTTCCT GGCAACGTGC ATCAATGGGG TATGCTGGAC TGTCTACCAC GGGGCCGGAA    3600

CGAGGACCAT CGCATCACCC AAGGGTCCTG TCATCCAGAT GTATACCAAT GTGGACCAAG    3660

ACCTTGTGGG CTGGCCCGCT CCTCAAGGTT CCCGCTCATT GACACCCTGC ACCTGCGGCT    3720

CCTCGGACCT TTACCTGGTC ACGAGGCACG CCGATGTCAT TCCCGTGCGC CGGCGAGGTG    3780

ATAGCAGGGG TAGCCTGCTT TCGCCCCGGC CCATTTCCTA CTTGAAAGGC TCCTCGGGGG    3840

GTCCGCTGTT GTGCCCCGCG GGACACGCCG TGGGCCTATT CAGGGCCGCG GTGTGCACCC    3900

GTGGAGTGGC TAAGGCGGTG GACTTTATCC CTGTGGAGAA CCTAGAGACA ACCATGAGAT    3960

CCCCGGTGTT CACGGACAAC TCCTCTCCAC CAGCAGTGCC CCAGAGCTTC CAGGTGGCCC    4020

ACCTGCATGC TCCCACCGGC AGCGGTAAGA GCACCAAGGT CCCGGCTGCG TACGCAGCCC    4080

AGGGCTACAA GGTGTTGGTG CTCAACCCCT CTGTTGCTGC AACGCTGGGC TTTGGTGCTT    4140

ACATGTCCAA GGCCCATGGG GTTGATCCTA ATATCAGGAC CGGGGTGAGA ACAATTACCA    4200

CTGGCAGCCC CATCACGTAC TCCACCTACG GCAAGTTCCT TGCCGACGGC GGGTGCTCAG    4260

GAGGTGCTTA TGACATAATA ATTTGTGACG AGTGCCACTC CACGGATGCC ACATCCATCT    4320

TGGGCATCGG CACTGTCCTT GACCAAGCAG AGACTGCGGG GGCGAGACTG GTTGTGCTCG    4380
```

```
CCACTGCTAC CCCTCCGGGC TCCGTCACTG TGTCCCATCC TAACATCGAG GAGGTTGCTC    4440

TGTCCACCAC CGGAGAGATC CCCTTTTACG GCAAGGCTAT CCCCCTCGAG GTGATCAAGG    4500

GGGGAAGACA TCTCATCTTC TGCCACTCAA AGAAGAAGTG CGACGAGCTC GCCGCGAAGC    4560

TGGTCGCATT GGGCATCAAT GCCGTGGCCT ACTACCGCGG TCTTGACGTG TCTGTCATCC    4620

CGACCAGCGG CGATGTTGTC GTCGTGTCGA CCGATGCTCT CATGACTGGC TTTACCGGCG    4680

ACTTCGACTC TGTGATAGAC TGCAACACGT GTGTCACTCA GACAGTCGAT TTCAGCCTTG    4740

ACCCTACCTT TACCATTGAG ACAACCACGC TCCCCCAGGA TGCTGTCTCC AGGACTCAAC    4800

GCCGGGGCAG GACTGGCAGG GGGAAGCCAG GCATCTACAG ATTTGTGGCA CCGGGGGAGC    4860

GCCCCTCCGG CATGTTCGAC TCGTCCGTCC TCTGTGAGTG CTATGACGCG GGCTGTGCTT    4920

GGTATGAGCT CACGCCCGCC GAGACTACAG TTAGGCTACG AGCGTACATG AACACCCCGG    4980

GGCTTCCCGT GTGCCAGGAC CATCTTGAAT TTTGGGAGGG CGTCTTTACG GGCCTCACTC    5040

ATATAGATGC CCACTTTCTA TCCCAGACAA AGCAGAGTGG GGAGAACTTT CCTTACCTGG    5100

TAGCGTACCA AGCCACCGTG TGCGCTAGGG CTCAAGCCCC TCCCCCATCG TGGGACCAGA    5160

TGTGGAAGTG TTTGATCCGC CTTAAACCCA CCCTCCATGG GCCAACACCC CTGCTATACA    5220

GACTGGGCGC TGTTCAGAAT GAAGTCACCC TGACGCACCC AATCACCAAA TACATCATGA    5280

CATGCATGTC GGCCGACCTG GAGGTCGTCA CGAGCACCTG GGTGCTCGTT GGCGGCGTCC    5340

TGGCTGCTCT GGCCGCGTAT TGCCTGTCAA CAGGCTGCGT GGTCATAGTG GGCAGGATTG    5400

TCTTGTCCGG GAAGCCGGCA ATTATACCTG ACAGGGAGGT TCTCTACCAG GAGTTCGATG    5460

AGATGGAAGA GTGCTCTCAG CACTTACCGT ACATCGAGCA AGGGATGATG CTCGCTGAGC    5520

AGTTCAAGCA GAAGGCCCTC GGCCTCCTGC AGACCGCGTC CCGCCAAGCA GAGGTTATCA    5580

CCCCTGCTGT CCAGACCAAC TGGCAGAAAC TCGAGGTCTT CTGGGCGAAG CACATGTGGA    5640

ATTTCATCAG TGGGATACAA TACTTGGCGG GCCTGTCAAC GCTGCCTGGT AACCCCGCCA    5700

TTGCTTCATT GATGGCTTTT ACAGCTGCCG TCACCAGCCC ACTAACCACT GGCCAAACCC    5760

TCCTCTTCAA CATATTGGGG GGGTGGGTGG CTGCCCAGCT CGCCGCCCCC GGTGCCGCTA    5820

CCGCCTTTGT GGGCGCTGGC TTAGCTGGCG CCGCCATCGG CAGCGTTGGA CTGGGGAAGG    5880

TCCTCGTGGA CATTCTTGCA GGGTATGGCG CGGGCGTGGC GGGAGCTCTT GTAGCCTTCA    5940

AGATCATGAG CGGTGAGGTC CCCTCCACGG AGGACCTGGT CAATCTGCTG CCCGCCATCC    6000

TCTCGCCTGG AGCCCTTGTA GTCGGTGTGG TCTGCGCAGC AATACTGCGC CGGCACGTTG    6060

GCCCGGGCGA GGGGGCAGTG CAATGGATGA ACCGGCTAAT AGCCTTCGCC TCCCGGGGGA    6120

ACCATGTTTC CCCCACGCAC TACGTGCCGG AGAGCGATGC AGCCGCCCGC GTCACTGCCA    6180

TACTCAGCAG CCTCACTGTA ACCCAGCTCC TGAGGCGACT GCATCAGTGG ATAAGCTCGG    6240

AGTGTACCAC TCCATGCTCC GGTTCCTGGC TAAGGGACAT CTGGGACTGG ATATGCGAGG    6300

TGCTGAGCGA CTTTAAGACC TGGCTGAAAG CCAAGCTCAT GCCACAACTG CCTGGGATTC    6360

CCTTTGTGTC CTGCCAGCGC GGGTATAGGG GGGTCTGGCG AGGAGACGGC ATTATGCACA    6420

CTCGCTGCCA CTGTGGAGCT GAGATCACTG GACATGTCAA AAACGGGACG ATGAGGATCG    6480

TCGGTCCTAG GACCTGCAGG AACATGTGGA GTGGGACGTT CCCCATTAAC GCCTACACCA    6540

CGGGCCCCTG TACTCCCCTT CCTGCGCCGA ACTATAAGTT CGCGCTGTGG AGGGTGTCTG    6600

CAGAGGAATA CGTGGAGATA AGGCGGGTGG GGGACTTCCA CTACGTATCG GTATGACTA    6660

CTGACAATCT TAAATGCCCG TGCCAGATCC CATCGCCCGA ATTTTTCACA GAATTGGACG    6720

GGGTGCGCCT ACATAGGTTT GCGCCCCCTT GCAAGCCCTT GCTGCGGGAG GAGGTATCAT    6780
```

```
TCAGAGTAGG ACTCCACGAG TACCCGGTGG GGTCGCAATT ACCTTGCGAG CCCGAACCGG    6840

ACGTAGCCGT GTTGACGTCC ATGCTCACTG ATCCCTCCCA TATAACAGCA GAGGCGGCCG    6900

GGAGAAGGTT GGCGAGAGGG TCACCCCCTT CTATGGCCAG CTCCTCGGCC AGCCAGCTGT    6960

CCGCTCCATC TCTCAAGGCA ACTTGCACCG CCAACCATGA CTCCCCTGAC GCCGAGCTCA    7020

TAGAGGCTAA CCTCCTGTGG AGGCAGGAGA TGGGCGGCAA CATCACCAGG GTTGAGTCAG    7080

AGAACAAAGT GGTGATTCTG GACTCCTTCG ATCCGCTTGT GGCAGAGGAG GATGAGCGGG    7140

AGGTCTCCGT ACCCGCAGAA ATTCTGCGGA AGTCTCGGAG ATTCGCCCGG GCCCTGCCCG    7200

TTTGGGCGCG GCCGGACTAC AACCCCCCGC TAGTAGAGAC GTGGAAAAAG CCTGACTACG    7260

AACCACCTGT GGTCCATGGC TGCCCGCTAC CACCTCCACG GTCCCCTCCT GTGCCTCCGC    7320

CTCGGAAAAA GCGTACGGTG GTCCTCACCG AATCAACCCT ATCTACTGCC TTGGCCGAGC    7380

TTGCCACCAA AAGTTTTGGC AGCTCCTCAA CTTCCGGCAT TACGGGCGAC AATACGACAA    7440

CATCCTCTGA GCCCGCCCCT TCTGGCTGCC CCCCGACTC CGACGTTGAG TCCTATTCTT     7500

CCATGCCCCC CCTGGAGGGG GAGCCTGGGG ATCGGATCT CAGCGACGGG TCATGGTCGA     7560

CGGTCAGTAG TGGGGCCGAC ACGGAAGATG TCGTGTGCTG CTCAATGTCT TATTCCTGGA    7620

CAGGCGCACT CGTCACCCCG TGCGCTGCGG AAGAACAAAA ACTGCCCATC AACGCACTGA    7680

GCAACTCGTT GCTACGCCAT CACAATCTGG TGTATTCCAC CACTTCACGC AGTGCTTGCC    7740

AAAGGCAGAA GAAAGTCACA TTTGACAGAC TGCAAGTTCT GGACAGCCAT TACCAGGACG    7800

TGCTCAAGGA GGTCAAAGCA GCGGCGTCAA AAGTGAAGGC TAACTTGCTA TCCGTAGAGG    7860

AAGCTTGCAG CCTGACGCCC CCACATTCAG CCAAATCCAA GTTTGGCTAT GGGGCAAAAG    7920

ACGTCCGTTG CCATGCCAGA AAGGCCGTAG CCCACATCAA CTCCGTGTGG AAAGACCTTC    7980

TGGAAGACAG TGTAACACCA ATAGACACTA CCATCATGGC CAAGAACGAG GTTTTCTGCG    8040

TTCAGCCTGA GAAGGGGGGT CGTAAGCCAG CTCGTCTCAT CGTGTTCCCC GACCTGGGCG    8100

TGCGCGTGTG CGAGAAGATG GCCCTGTACG ACGTGGTTAG CAAGCTCCCC CTGGCCGTGA    8160

TGGGAAGCTC CTACGGATTC CAATACTCAC CAGGACAGCG GGTTGAATTC CTCGTGCAAG    8220

CGTGGAAGTC CAAGAAGACC CCGATGGGGT TCTCGTATGA TACCCGCTGT TTTGACTCCA    8280

CAGTCACTGA GAGCGACATC CGTACGGAGG AGGCAATTTA CCAATGTTGT GACCTGGACC    8340

CCCAAGCCCG CGTGGCCATC AAGTCCCTCA CTGAGAGGCT TTATGTTGGG GGCCCTCTTA    8400

CCAATTCAAG GGGGGAAAAC TGCGGCTACC GCAGGTGCCG CGCGAGCGGC GTACTGACAA    8460

CTAGCTGTGG TAACACCCTC ACTTGCTACA TCAAGGCCCG GGCAGCCTGT CGAGCCGCAG    8520

GGCTCCAGGA CTGCACCATG CTCGTGTGTG GCGACGACTT AGTCGTTATC TGTGAAAGTG    8580

CGGGGGTCCA GGAGGACGCG GCGAGCCTGA GAGCCTTCAC GGAGGCTATG ACCAGGTACT    8640

CCGCCCCCCC CGGGGACCCC CCACAACCAG AATACGACTT GGAGCTTATA ACATCATGCT    8700

CCTCCAACGT GTCAGTCGCC CACGACGGCG CTGGAAAGAG GGTCTACTAC CTTACCCGTG    8760

ACCCTACAAC CCCCCTCGCG AGAGCCGCGT GGGAGACAGC AAGACACACT CCAGTCAATT    8820

CCTGGCTAGG CAACATAATC ATGTTTGCCC CCACACTGTG GGCGAGGATG ATACTGATGA    8880

CCCATTTCTT TAGCGTCCTC ATAGCCAGGG ATCAGCTTGA ACAGGCTCTT AACTGTGAGA    8940

TCTACGGAGC CTGCTACTCC ATAGAACCAC TGGATCTACC TCCAATCATT CAAAGACTCC    9000

ATGGCCTCAG CGCATTTTCA CTCCACAGTT ACTCTCCAGG TGAAATCAAT AGGGTGGCCG    9060

CATGCCTCAG AAAACTTGGG GTCCCGCCCT TGCGAGCTTG GAGACACCGG GCCCGGAGCG    9120
```

```
TCCGCGCTAG GCTTCTGTCC AGAGGAGGCA GGGCTGCCAT ATGTGGCAAG TACCTCTTCA    9180
ACTGGGCAGT AAGAACAAAG CTCAAACTCA CTCCAATAGC GGCCGCTGGC CGGCTGGACT    9240
TGTCCGGTTG GTTCACGGCT GGCTACAGCG GGGGAGACAT TTATCACAGC GTGTCTCATG    9300
CCCGGCCCCG CTGGTTCTGG TTTTGCCTAC TCCTGCTCGC TGCAGGGGTA GGCATCTACC    9360
TCCTCCCCAA CCGATGAAGG TTGGGGTAAA CACTCCGGCC TCTTAGGCCA TTTCCTGTTT    9420
TTTTTTTTTT TTTTTTTTTT TTTTTTTTTT TTTTTTTTTT TTTTTTTTTT CTTTTTTTTT    9480
TTTTTTTTCC TTTTTTTTTT TTTTTTTTTT CTTTCCTTCT TTTTTCCTTT CTTTTCCTTC    9540
CTTCTTTAAT GGTGGCTCCA TCTTAGCCCT AGTCACGGCT AGCTGTGAAA GGTCCGTGAG    9600
CCGCATGACT GCAGAGAGTG CTGATACTGG CCTCTCTGCA GATCATGTCG CATTCACGCG    9660
TTCGAATTAA TTAACTAGTG GGAATACGCG GGGTATGCCG CGTTTTAGCA TATTGACGAC    9720
CCAATTCTCA TGTTTGACAG CTTATCATCG ATAAGCTTTA ATGCGGTAGT TTATCACAGT    9780
TAAATTGCTA ACGCAGTCAG GCACCGTGTA TGAAATCTAA CAATGCGCTC ATCGTCATCC    9840
TCGGCACCGT CACCCTGGAT GCTGTAGGCA TAGGCTTGGT TATGCCGGTA CTGCCGGGCC    9900
TCTTGCGGGA TATCGTCCAT TCCGACAGCA TCGCCAGTCA CTATGGCGTG CTGCTAGCGC    9960
TATATGCGTT GATGCAATTT CTATGCGCAC CCGTTCTCGG AGCACTGTCC GACCGCTTTG   10020
GCCGCCGCCC AGTCCTGCTC GCTTCGCTAC TTGGAGCCAC TATCGACTAC GCGATCATGG   10080
CGACCACACC CGTCCTGTGG ATCCTCTACG CCGGACGCAT CGTGGCCGGC ATCACCGGCG   10140
CCACAGGTGC GGTTGCTGGC GCCTATATCG CCGACATCAC CGATGGGGAA GATCGGGCTC   10200
GCCACTTCGG GCTCATGAGC GCTTGTTTCG GCGTGGGTAT GGTGGCAGGC CCCGTGGCCG   10260
GGGGACTGTT GGGCGCCATC TCCTTGCATG CACCATTCCT TGCGGCGGCG GTGCTCAACG   10320
GCCTCAACCT ACTACTGGGC TGCTTCCTAA TGCAGGAGTC GCATAAGGGA GAGCGTCGAC   10380
CGATGCCCTT GAGAGCCTTC AACCCAGTCA GCTCCTTCCG GTGGGCGCGG GGCATGACTA   10440
TCGTCGCCGC ACTTATGACT GTCTTCTTTA TCATGCAACT CGTAGGACAG GTGCCGGCAG   10500
CGCTCTGGGT CATTTTCGGC GAGGACCGCT TTCGCTGGAG CGCGACGATG ATCGGCCTGT   10560
CGCTTGCGGT ATTCGGAATC TTGCACGCCC TCGCTCAAGC CTTCGTCACT GGTCCCGCCA   10620
CCAAACGTTT CGGCGAGAAG CAGGCCATTA TCGCCGGCAT GGCGGCCGAC GCGCTGGGCT   10680
ACGTCTTGCT GGCGTTCGCG ACGCGAGGCT GGATGGCCTT CCCCATTATG ATTCTTCTCG   10740
CTTCCGGCGG CATCGGGATG CCCGCGTTGC AGGCCATGCT GTCCAGGCAG GTAGATGACG   10800
ACCATCAGGG ACAGCTTCAA GGATCGCTCG CGGCTCTTAC CAGCCTAACT TCGATCACTG   10860
GACCGCTGAT CGTCACGCGC ATTTATGCCG CCTCGGCGAG CACATGGAAC GGGTTGGCAT   10920
GGATTGTAGG CGCCGCCCTA TACCTTGTCT GCCTCCCCGC GTTGCGTCGC GGTGCATGGA   10980
GCCGGGCCAC CTCGACCTGA ATGGAAGCCG GCGGCACCTC GCTAACGGAT TCACCACTCC   11040
AAGAATTGGA GCCAATCAAT TCTTGCGGAG AACTGTGAAT GCGCAAACCA ACCCTTGGCA   11100
GAACATATCC ATCGCGTCCG CCATCTCCAG CAGCCGCACG CGGCGCATCT CGGGCAGCGT   11160
TGGGTCCTGG CCACGGGTGC GCATGATCGT GCTCCTGTCG TTGAGGACCC GGCTAGGCTG   11220
GCGGGGTTGC CTTACTGGTT AGCAGAATGA ATCACCGATA CGCGAGCGAA CGTGAAGCGA   11280
CTGCTGCTGC AAAACGTCTG CGACCTGAGC AACAACATGA ATGGTCTTCG GTTTCCGTGT   11340
TTCGTAAAGT CTGGAAACGC GGAAGTCAGC GCCCTGCACC ATTATGTTCC GGATCTGCAT   11400
CGCAGGATGC TGCTGGCTAC CCTGTGGAAC ACCTACATCT GTATTAACGA AGCGCTGGCA   11460
TTGACCCTGA GTGATTTTTC TCTGGTCCCG CCGCATCCAT ACCGCCAGTT GTTTACCCTC   11520
```

```
ACAACGTTCC AGTAACCGGG CATGTTCATC ATCAGTAACC CGTATCGTGA GCATCCTCTC    11580

TCGTTTCATC GGTATCATTA CCCCCATGAA CAGAAATTCC CCCTTACACG GAGGCATCAA    11640

GTGACCAAAC AGGAAAAAAC CGCCCTTAAC ATGGCCCGCT TTATCAGAAG CCAGACATTA    11700

ACGCTTCTGG AGAAACTCAA CGAGCTGGAC GCGGATGAAC AGGCAGACAT CTGTGAATCG    11760

CTTCACGACC ACGCTGATGA GCTTTACCGC AGCTGCCTCG CGCGTTTCGG TGATGACGGT    11820

GAAAACCTCT GACACATGCA GCTCCCGGAG ACGGTCACAG CTTGTCTGTA AGCGGATGCC    11880

GGGAGCAGAA AAGCCCGTCA GGGCGCGTCA GCGGGTGTTG GCGGGTGTCG GGGCGCAGCC    11940

ATGACCCAGT CACGTAGCGA TAGCGGAGTG TATACTGGCT TAACTATGCG GCATCAGAGC    12000

AGATTGTACT GAGAGTGCAC CATATGCGGT GTGAAATACC GCACAGATGC GTAAGGAGAA    12060

AATACCGCAT CAGGCGCTCT TCCGCTTCCT CGCTCACTGA CTCGCTGCGC TCGGTCGTTC    12120

GGCTGCGGCG AGCGGTATCA GCTCACTCAA AGGCGGTAAT ACGGTTATCC ACAGAATCAG    12180

GGGATAACGC AGGAAAGAAC ATGTGAGCAA AAGGCCAGCA AAAGGCCAGG AACCGTAAAA    12240

AGGCCGCGTT GCTGGCGTTT TTCCATAGGC TCCGCCCCCC TGACGAGCAT CACAAAAATC    12300

GACGCTCAAG TCAGAGGTGG CGAAACCCGA CAGGACTATA AAGATACCAG GCGTTTCCCC    12360

CTGGAAGCTC CCTCGTGCGC TCTCCTGTTC CGACCCTGCC GCTTACCGGA TACCTGTCCG    12420

CCTTTCTCCC TTCGGGAAGC GTGGCGCTTT CTCATAGCTC ACGCTGTAGG TATCTCAGTT    12480

CGGTGTAGGT CGTTCGCTCC AAGCTGGGCT GTGTGCACGA ACCCCCCGTT CAGCCCGACC    12540

GCTGCGCCTT ATCCGGTAAC TATCGTCTTG AGTCCAACCC GGTAAGACAC GACTTATCGC    12600

CACTGGCAGC AGCCACTGGT AACAGGATTA GCAGAGCGAG GTATGTAGGC GGTGCTACAG    12660

AGTTCTTGAA GTGGTGGCCT AACTACGGCT ACACTAGAAG GACAGTATTT GGTATCTGCG    12720

CTCTGCTGAA GCCAGTTACC TTCGGAAAAA GAGTTGGTAG CTCTTGATCC GGCAAACAAA    12780

CCACCGCTGG TAGCGGTGGT TTTTTTGTTT GCAAGCAGCA GATTACGCGC AGAAAAAAAG    12840

GATCTCAAGA AGATCCTTTG ATCTTTTCTA CGGGGTCTGA CGCTCAGTGG AACGAAAACT    12900

CACGTTAAGG GATTTTGGTC ATGAGATTAT CAAAAAGGAT CTTCACCTAG ATCCTTTTCT    12960

AGATAATACG ACTCACTATA                                                 12980
```

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO: 6:

```
GGCGACACTC CACCATAGAT C                                                  21
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

```
        (iii) HYPOTHETICAL: NO (xi) SEQUENCE DESCRIPTION: SEQ ID NO: 7:

TGGCACTACC CTCCAAGACC                                              20

(2) INFORMATION FOR SEQ ID NO: 8:

(i) SEQUENCE CHARACTERISTICS:
             (A) LENGTH: 27 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (xi) SEQUENCE DESCRIPTION: SEQ ID NO: 8:

ATGACACAAG GGGGCGCTCC GCACACT                                      27

(2) INFORMATION FOR SEQ ID NO: 9:

(i) SEQUENCE CHARACTERISTICS:
             (A) LENGTH: 18 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (xi) SEQUENCE DESCRIPTION: SEQ ID NO: 9:

TCCTGCTTGT GGATGATG                                                18

(2) INFORMATION FOR SEQ ID NO: 10:

(i) SEQUENCE CHARACTERISTICS:
             (A) LENGTH: 16 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (xi) SEQUENCE DESCRIPTION: SEQ ID NO: 10:

TAGTTTGGTG ATGTCA                                                  16

(2) INFORMATION FOR SEQ ID NO: 11:

(i) SEQUENCE CHARACTERISTICS:
             (A) LENGTH: 17 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (xi) SEQUENCE DESCRIPTION: SEQ ID NO: 11:

ACATAGGTGC CAGTAAG                                                 17

(2) INFORMATION FOR SEQ ID NO: 12:

(i) SEQUENCE CHARACTERISTICS:
             (A) LENGTH: 16 base pairs
```

```
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO: 12:

CTGGCAACGT GCATCA                                                16

(2) INFORMATION FOR SEQ ID NO: 13:

(i) SEQUENCE CHARACTERISTICS:
         (A) LENGTH: 18 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (xi) SEQUENCE DESCRIPTION: SEQ ID NO: 13:

GGGTGAGAAC AATTACCA                                              18

(2) INFORMATION FOR SEQ ID NO: 14:

(i) SEQUENCE CHARACTERISTICS:
         (A) LENGTH: 16 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (xi) SEQUENCE DESCRIPTION: SEQ ID NO: 14:

ATTGATGCCC AATGCG                                                16

(2) INFORMATION FOR SEQ ID NO: 15:

(i) SEQUENCE CHARACTERISTICS:
         (A) LENGTH: 17 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (xi) SEQUENCE DESCRIPTION: SEQ ID NO: 15:

ACTGCCTGGG ATTCCCT                                               17

(2) INFORMATION FOR SEQ ID NO: 16:

(i) SEQUENCE CHARACTERISTICS:
         (A) LENGTH: 18 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (xi) SEQUENCE DESCRIPTION: SEQ ID NO: 16:

CCACAGTGGC AGCGAGTG                                              18
```

(2) INFORMATION FOR SEQ ID NO: 17:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO: 17:

```
CATGGACGTC AACACG                                                  16
```

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO: 18:

```
AATCTTCACC GGTTGGGGAG GAGGTAGATG                                   30
```

(2) INFORMATION FOR SEQ ID NO: 19:

(i) SEQUENCE CHARACTERISTICS:
        (A) LENGTH: 9416 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO: 19:

```
GCCAGCCCCC TGATGGGGGC GACACTCCAC CATAGATCAC TCCCCTGTGA GGAACTACTG    60

TCTTCACGCA GAAAGCGTCT AGCCATGGCG TTAGTATGAG TGTCGTGCAG CCTCCAGGAC   120

CCCCCCTCCC GGGAGAGCCA TAGTGGTCTG CGGAACCGGT GAGTACACCG GAATTGCCAG   180

GACGACCGGG TCCTTTCTTG GATAAACCCG CTCAATGCCT GGAGATTTGG GCGTGCCCCC   240

GCAAGACTGC TAGCCGAGTA GTGTTGGGTC GCGAAAGGCC TTGTGGTACT GCCTGATAGG   300

GTGCTTGCGA GTGCCCCGGG AGGTCTCGTA GACCGTGCAC CATGAGCACG AATCCTAAAC   360

CTCAAAGAAA AACCAAACGT AACACCAACC GTCGCCCACA GGACGTCGAG TTCCGGGTG    420

GCGGTCAGAT CGTTGGTGGA GTTTACTTGT TGCCGCGCAG GGGCCCTAGA TTGGGTGTGC   480

GCGCGACGAG GAAGACTTCC GAGCGGTCGC AACCTCGTGG TAGACGTCAG CCTATCCCCA   540

AGGCACGTCG GCCCGAGGGC AGGACCTGGG CTCAGCCCGG GTACCCTTGG CCCCTCTATG   600

GCAATGAGGG TTGCGGGTGG GCGGGATGGC TCCTGTCTCC CCGTGGCTCT CGGCCTAGCT   660

GGGGCCCCAC AGACCCCCGG CGTAGGTCGC GCAATTTGGG TAAGGTCATC GATACCCTTA   720

CGTGCGGCTT CGCCGACCTC ATGGGGTACA TACCGCTCGT CGGCGCCCCT CTTGGAGGCG   780

CTGCCAGGGC CCTGGCGCAT GGCGTCCGGG TTCTGGAAGA CGGCGTGAAC TATGCAACAG   840

GGAACCTTCC TGGTTGCTCT TTCTCTATCT TCCTTCTGGC CCTGCTCTCT TGCCTGACTG   900
```

-continued

```
TGCCCGCTTC AGCCTACCAA GTGCGCAATT CCTCGGGGCT TTACCATGTC ACCAATGATT    960

GCCCTAATTC GAGTATTGTG TACGAGGCGG CCGATGCCAT CCTGCACACT CCGGGGTGTG   1020

TCCCTTGCGT TCGCGAGGGT AACGCCTCGA GGTGTTGGGT GGCGGTGACC CCACGGTGG    1080

CCACCAGGGA CGGCAAACTC CCCACAACGC AGCTTCGACG TCATATCGAT CTGCTTGTCG   1140

GGAGCGCCAC CCTCTGCTCA GCCCTCTACG TGGGGACCT GTGCGGGTCT GTTTTTCTTG    1200

TTGGTCAACT GTTTACCTTC TCTCCCAGGC GCCACTGGAC GACGCAAAGC TGCAATTGTT   1260

CTATCTATCC CGGCCATATA ACGGGTCATC GCATGGCATG GGATATGATG ATGAACTGGT   1320

CCCCTACGGC AGCGTTGGTG GTAGCTCAGC TGCTCCGGAT CCCACAAGCC ATCATGGACA   1380

TGATCGCTGG TGCTCACTGG GGAGTCCTGG CGGGCATAGC GTATTTCTCC ATGGTGGGGA   1440

ACTGGGCGAA GGTCCTGGTA GTGCTGCTGC TATTTGCCGG CGTCGACGCG GAAACCCACG   1500

TCACCGGGGG AAGTGCCGGC CACACCACGG CTGGGCTTGT TGGTCTCCTT ACACCAGGCG   1560

CCAAGCAGAA CATCCAACTG ATCAACACCA ACGGCAGTTG GCACATCAAT AGCACGGCCT   1620

TGAACTGCAA CGATAGCCTT ACCACCGGCT GGTTAGCAGG GCTCTTCTAT CGCCACAAAT   1680

TCAACTCTTC AGGCTGTCCT GAGAGGTTGG CCAGCTGCCG ACGCCTTACC GATTTTGCCC   1740

AGGGCTGGGG TCCCATCAGT TATGCCAACG GAAGCGGCCT TGACGAACGC CCCTACTGTT   1800

GGCACTACCC TCCAAGACCT TGTGGCATTG TGCCCGCAAA GAGCGTGTGT GGCCCGGTAT   1860

ATTGCTTCAC TCCCAGCCCC GTGGTGGTGG GAACGACCGA CAGGTCGGGC GCGCCTACCT   1920

ACAGCTGGGG TGCAAATGAT ACGGATGTCT TCGTCCTTAA CAACACCAGG CCACCGCTGG   1980

GCAATTGGTT CGGTTGTACC TGGATGAACT CAACTGGATT CACCAAAGTG TGCGGAGCGC   2040

CCCCTTGTGT CATCGGAGGG GTGGGCAACA ACACCTTGCT CTGCCCCACT GATTGCTTCC   2100

GCAAACATCC GGAAGCCACA TACTCTCGGT GCGGCTCCGG TCCCTGGATT ACACCCAGGT   2160

GCATGGTCGA CTACCCGTAT AGGCTTTGGC ACTATCCTTG TACTATCAAT TACACCATAT   2220

TCAAAGTCAG GATGTACGTG GGAGGGGTCG AGCACAGGCT GGAAGCGGCC TGCAACTGGA   2280

CGCGGGGCGA ACGCTGTGAT CTGGAAGACA GGGACAGGTC CGAGCTCAGC CCATTGCTGC   2340

TGTCCACCAC ACAGTGGCAG GTCCTTCCGT GTTCTTTCAC GACCCTGCCA GCCTTGTCCA   2400

CCGGCCTCAT CCACCTCCAC CAGAACATTG TGGACGTGCA GTACTTGTAC GGGGTGGGGT   2460

CAAGCATCGC GTCCTGGGCC ATTAAGTGGG AGTACGTCGT TCTCCTGTTC CTTCTGCTTG   2520

CAGACGCGCG CGTCTGCTCC TGCTTGTGGA TGATGTTACT CATATCCCAA GCGGAGGCGG   2580

CTTTGGAGAA CCTCGTAATA CTCAATGCAG CATCCCTGGC CGGGACGCAC GGTCTTGTGT   2640

CCTTCCTCGT GTTCTTCTGC TTTGCGTGGT ATCTGAAGGG TAGGTGGGTG CCCGGAGCGG   2700

TCTACGCCTT CTACGGGATG TGGCCTCTCC TCCTGCTCCT GCTGGCGTTG CCTCAGCGGG   2760

CATACGCACT GGACACGGAG GTGGCCGCGT CGTGTGGCGG CGTTGTTCTT GTCGGGTTAA   2820

TGGCGCTGAC TCTGTCACCA TATTACAAGC GCTATATCAG CTGGTGCATG TGGTGGCTTC   2880

AGTATTTTCT GACCAGAGTA GAAGCGCAAC TGCACGTGTG GGTTCCCCCC CTCAACGTCC   2940

GGGGGGGGCG CGATGCCGTC ATCTTACTCA TGTGTGTTGT ACACCCGACT CTGGTATTTG   3000

ACATCACCAA ACTACTCCTG GCCATCTTCG GACCCCTTTG GATTCTTCAA GCCAGTTTGC   3060

TTAAAGTCCC CTACTTCGTG CGCGTTCAAG GCCTTCTCCG GATCTGCGCG CTAGCGCGGA   3120

AGATAGCCGG AGGTCATTAC GTGCAAATGG CCATCATCAA GTTGGGGCG CTTACTGGCA    3180

CCTATGTGTA TAACCATCTC ACCCCTCTTC GAGACTGGGC GCACAACGGC CTGCGAGATC   3240
```

```
TGGCCGTGGC TGTGGAACCA GTCGTCTTCT CCCGAATGGA GACCAAGCTC ATCACGTGGG    3300

GGGCAGATAC CGCCGCGTGC GGTGACATCA TCAACGGCTT GCCCGTCTCT GCCCGTAGGG    3360

GCCAGGAGAT ACTGCTTGGA CCAGCCGACG GAATGGTCTC CAAGGGGTGG AGGTTGCTGG    3420

CGCCCATCAC GGCGTACGCC CAGCAGACGA GAGGCCTCCT AGGGTGTATA ATCACCAGCC    3480

TGACTGGCCG GGACAAAAAC CAAGTGGAGG GTGAGGTCCA GATCGTGTCA ACTGCTACCC    3540

AAACCTTCCT GGCAACGTGC ATCAATGGGG TATGCTGGAC TGTCTACCAC GGGGCCGGAA    3600

CGAGGACCAT CGCATCACCC AAGGGTCCTG TCATCCAGAT GTATACCAAT GTGGACCAAG    3660

ACCTTGTGGG CTGGCCCGCT CCTCAAGGTT CCCGCTCATT GACACCCTGC ACCTGCGGCT    3720

CCTCGGACCT TTACCTGGTT ACGAGGCACG CCGACGTCAT TCCCGTGCGC CGGCGAGGTG    3780

ATAGCAGGGG TAGCCTGCTT TCGCCCCGGC CCATTTCCTA CCTAAAAGGC TCCTCGGGGG    3840

GTCCGCTGTT GTGCCCCGCG GGACACGCCG TGGGCCTATT CAGGGCCGCG GTGTGCACCC    3900

GTGGAGTGAC CAAGGCGGTG GACTTTATCC CTGTGGAGAA CCTAGAGACA CCATGAGAT    3960

CCCCGGTGTT CACGGACAAC TCCTCTCCAC CAGCAGTGCC CCAGAGCTTC CAGGTGGCCC    4020

ACCTGCATGC TCCCACCGGC AGTGGTAAGA GCACCAAGGT CCCGGCTGCG TACGCAGCCC    4080

AGGGCTACAA GGTGTTGGTG CTCAACCCCT CTGTTGCTGC AACGCTGGGC TTTGGTGCTT    4140

ACATGTCCAA GGCCCATGGG GTCGATCCTA ATATCAGGAC CGGGGTGAGA ACAATTACCA    4200

CTGGCAGCCC CATCACGTAC TCCACCTACG GCAAGTTCCT TGCCGACGGC GGGTGCTCAG    4260

GAGGCGCTTA TGACATAATA ATTTGTGACG AGTGCCACTC CACGGATGCC ACATCCATCT    4320

TGGGCATCGG CACTGTCCTT GACCAAGCAG AGACTGCGGG GGCGAGATTG GTTGTGCTCG    4380

CCACTGCTAC CCCTCCGGGC TCCGTCACTG TGTCCCATCC TAACATCGAG GAGGTTGCTC    4440

TGTCCACCAC CGGAGAGATC CCTTTCTACG GCAAGGCTAT CCCCCTCGAG GTGATCAAGG    4500

GGGGAAGACA TCTCATCTTC TGTCACTCAA AGAAGAAGTG CGACGAGCTC GCCGCGAAGC    4560

TGGTCGCATT GGGCATCAAT GCCGTGGCCT ACTACCGCGG ACTTGACGTG TCTGTCATCC    4620

CGACCAACGG CGATGTTGTC GTCGTGTCGA CCGATGCTCT CATGACTGGC TTTACCGGCG    4680

ACTTCGACTC TGTGATAGAC TGCAACACGT GTGTCACTCA GACAGTCGAT TTCAGCCTTG    4740

ACCCTACCTT TACCATTGAG ACAACCACGC TCCCCCAGGA TGCTGTCTCC AGGACTCAGC    4800

GCCGGGGCAG GACTGGCAGG GGGAAGCCAG GCATCTACAG ATTTGTGGCA CCGGGGGAGC    4860

GCCCCTCCGG CATGTTCGAC TCGTCCGTCC TCTGTGAGTG CTATGACGCG GGCTGTGCTT    4920

GGTATGAGCT CATGCCCGCC GAGACTACAG TTAGGCTACG AGCGTACATG AACACCCCGG    4980

GGCTTCCCGT GTGCCAGGAC CATCTTGAAT TTTGGGAGGG CGTCTTTACG GGCCTCACCC    5040

ATATAGATGC CCACTTTCTA TCCCAGACAA AGCAGAGTGG GGAGAACTTT CCTTACCTGG    5100

TAGCGTACCA AGCCACCGTG TGCGCTAGGG CTCAAGCCCC TCCCCCATCG TGGGACCAGA    5160

TGTGGAAGTG TTTGATCCGC CTTAAACCCA CCCTCCATGG GCCAACACCC CTGCTATACA    5220

GACTGGGCGC TGTTCAGAAT GAAGTCACCC TGACGCACCC AATCACCAAA TACATCATGA    5280

CATGCATGTC GGCCGACCTG GAGGTCGTCA CGAGCACCTG GGTGCTCGTT GGCGGCGTCC    5340

TGGCTGCTCT GGCCGCGTAT TGCCTGTCAA CAGGCTGCGT GGTCATAGTG GGCAGGATTG    5400

TCTTGTCCGG GAAGCCGGCA ATTATACCTG ACAGGGAGGT TCTCTACCAG GAGTTCGATG    5460

AGATGGAAGA GTGCTCTCAG CACTTACCGT ACATCGAGCA AGGGATGATG CTCGCTGAGC    5520

AGTTCAAGCA GAAGGCCCTC GGCCTCCTGC AGACCGCGTC CCGCCATGCA GAGGTTATCA    5580

CCCCTGCTGT CCAGACCAAC TGGCAGAAAC TCGAGGTCTT CTGGGCGAAG CACATGTGGA    5640
```

```
ATTTCATCAG TGGGATACAA TATTTGGCGG GCCTGTCAAC GCTGCCTGGT AACCCCGCCA   5700

TTGCTTCATT GATGGCTTTT ACAGCTGCCG TCACCAGCCC ACTAACCACT GGCCAAACCC   5760

TCCTCTTCAA CATATTGGGG GGTGGGTGG CTGCCCAGCT CGCCGCCCCC GGTGCCGCTA    5820

CCGCCTTTGT GGGCGCTGGC TTAGCTGGCG CCGCCATCGG CAGCGTTGGA CTGGGGAAGG   5880

TCCTCGTGGA CATTCTTGCA GGGTATGGCG CGGGCGTGGC GGGAGCTCTT GTAGCATTCA   5940

AGATCATGAG CGGTGAGGTC CCCTCCACGG AGGACCTGGT CAATCTGCTG CCCGCCATCC   6000

TCTCGCCTGG AGCCCTTGTA GTCGGTGTGG TCTGCGCAGC AATACTGCGC GGCACGTTG    6060

GCCCGGGCGA GGGGGCAGTG CAATGGATGA ACCGGCTAAT AGCCTTCGCC TCCCGGGGA    6120

ACCATGTTTC CCCCACGCAC TACGTGCCGG AGAGCGATGC AGCCGCCCGC GTCACTGCCA   6180

TACTCAGCAG CCTCACTGTA ACCCAGCTCC TGAGGCGACT ACATCAGTGG ATAAGCTCGG   6240

AGTGTACCAC TCCATGCTCC GGCTCCTGGC TAAGGGACAT CTGGGACTGG ATATGCGAGG   6300

TGCTGAGCGA CTTTAAGACC TGGCTGAAAG CCAAGCTCAT GCCACAACTG CCTGGGATTC   6360

CCTTTGTGTC CTGCCAGCGC GGGTATAGGG GGTCTGGCG AGGAGACGGC ATTATGCACA    6420

CTCGCTGCCA CTGTGGAGCT GAGATCACTG GACATGTCAA AAACGGGACG ATGAGGATCG   6480

TCGGTCCTAG GACCTGCAGG AACATGTGGA GTGGGACGTT CCCCATTAAC GCCTACACCA   6540

CGGGCCCCTG TACTCCCCTT CCTGCGCCGA ACTATAAGTT CGCGCTGTGG AGGGTGTCTG   6600

CAGAGGAATA CGTGGAGATA AGGCGGGTGG GGGACTTCCA CTACGTATCG GTATGACTA    6660

CTGACAATCT TAAATGCCCG TGCCAGATCC CATCGCCCGA ATTTTTCACA GAATTGGACG   6720

GGGTGCGCCT ACATAGGTTT GCGCCCCCTT GCAAGCCCTT GCTGCGGGAG GAGGTATCAT   6780

TCAGAGTAGG ACTCCACGAG TACCCGGTGG GGTCGCAATT ACCTTGCGAG CCCGAACCGG   6840

ACGTAGCCGT GTTGACGTCC ATGCTCACTG ATCCCTCCCA TATAACAGCA GAGGCGGCCG   6900

GGAGAAGGTT GGCGAGAGGG TCACCCCCTT CTATGGCCAG CTCCTCGGCC AGCCAGCTGT   6960

CCGCTCCATC TCTCAAGGCA ACTTGCACCG CCAACCATGA CTCCCCTGAC GCCGAGCTCA   7020

TAGAGGCTAA CCTCCTGTGG AGGCAGGAGA TGGGCGGCAA CATCACCAGG GTTGAGTCAG   7080

AGAACAAAGT GGTGATTCTG GACTCCTTCG ATCCGCTTGT GGCAGAGGAG GATGAGCGGG   7140

AGGTCTCCGT ACCCGCAGAA ATTCTGCGGA AGTCTCGGAG ATTCGCCCGG CCCTGCCCG    7200

TTTGGGCGCG GCCGGACTAC AACCCCCCGC TAGTAGAGAC GTGGAAAAAG CCTGACTACG   7260

AACCACCTGT GGTCCATGGC TGCCCGCTAC CACCTCCACG GTCCCCTCCT GTGCCTCCGC   7320

CTCGGAAAAA GCGTACGGTG GTCCTCACCG AATCAACCCT ACCTACTGCC TTGGCCGAGC   7380

TTGCCACCAA AAGTTTTGGC AGCTCCTCAA CTTCCGGCAT TACGGGCGAC AATATGACAA   7440

CATCCTCTGA GCCCGCCCCT TCTGGCTGCC CCCCGACTC CGACGTTGAG TCCTATTCTT     7500

CCATGCCCCC CCTGGAGGGG GAGCCTGGGG ATCCGGATTT CAGCGACGGG TCATGGTCGA   7560

CGGTCAGTAG TGGGGCCGAC ACGGAAGATG TCGTGTGCTG CTCAATGTCT TATACCTGGA   7620

CAGGCGCACT CGTCACCCCG TGCGCTGCGG AAGAACAAAA ACTGCCCATC AACGCACTGA   7680

GCAACTCGTT GCTACGCCAT CACAATCTGG TATATTCCAC CACTTCACGC AGTGCTTGCC   7740

AAAGGCAGAA GAAAGTCACA TTTGACAGAC TGCAAGTTCT GGACAGCCAT TACCAGGACG   7800

TGCTCAAGGA GGTCAAAGCA GCGGCGTCAA AAGTGAAGGC TAACTTGCTA TCCGTAGAGG   7860

AAGCTTGCAG CCTGACGCCC CCACATTCAG CCAAATCCAA GTTTGGCTAT GGGGCAAAAG   7920

ACGTCCGTTG CCATGCCAGA AAGGCCGTAG CCCACATCAA CTCCGTGTGG AAAGACCTTC   7980
```

```
TGGAAGACAG TGTAACACCA ATAGACACTA TCATCATGGC CAAGAACGAG GTCTTCTGCG    8040

TTCAGCCTGA GAAGGGGGGT CGTAAGCCAG CTCGTCTCAT CGTGTTCCCC GACCTGGGCG    8100

TGCGCGTGTG CGAGAAGATG GCCCTGTACG ACGTGGTTAG CAAACTCCCC CTGGCCGTGA    8160

TGGGAAGCTC CTACGGATTC CAATACTCAC CAGGACAGCG GGTTGAATTC CTCGTGCAAG    8220

CGTGGAAGTC CAAGAAGACC CCGATGGGGT TCCCGTATGA TACCCGCTGT TTTGACTCCA    8280

CAGTCACTGA GAGCGACATC CGTACGGAGG AGGCAATTTA CCAATGTTGT GACCTGGACC    8340

CCCAAGCCCG CGTGGCCATC AAGTCCCTCA CTGAGAGGCT TTATGTTGGG GGCCCTCTTA    8400

CCAATTCAAG GGGGGAAAAC TGCGGCTATC GCAGGTGCCG CGCGAGCGGC GTACTGACAA    8460

CTAGCTGTGG TAACACCCTC ACTTGCTACA TCAAGGCCCG GGCAGCCCGT CGAGCCGCAG    8520

GGCTCCAGGA CTGCACCATG CTCGTGTGTG GCGACGACTT AGTCGTTATC TGTGAAAGTG    8580

CGGGGGTCCA GGAGGACGCG GCGAGCCTGA GAGCCTTTAC GGAGGCTATG ACCAGGTACT    8640

CCGCCCCCCC CGGGGACCCC CCACAACCAG AATACGACTT GGAGCTTATA ACATCATGCT    8700

CCTCCAACGT GTCAGTCGCC CACGACGGCG CTGGAAAAAG GGTCTACTAC CTTACCCGTG    8760

ACCCTACAAC CCCCCTCGCG AGAGCCGCGT GGGAGACAGC AAGACACACT CCAGTCAATT    8820

CCTGGCTAGG CAACATAATC ATGTTTGCCC CCACACTGTG GGCGAGGATG ATACTGATGA    8880

CCCATTTCTT TAGCGTCCTC ATAGCCAGGG ATCAGCTTGA ACAGGCTCTT AACTGTGAGA    8940

TCTACGCAGC CTGCTACTCC ATAGAACCAC TGGATCTACC TCCAATCATT CAAAGACTCC    9000

ATGGCCTCAG CGCATTTTTA CTCCACAGTT ACTCTCCAGG TGAAGTCAAT AGGGTGGCCG    9060

CATGCCTCAG AAAACTTGGG GTCCCGCCCT TGCGAGCTTG GAGACACCGG GCCCGGAGCG    9120

TCCGCGCTAG GCTTCTGTCC AGGGGAGGCA GGGCTGCCAT ATGTGGCAAG TACCTCTTCA    9180

ACTGGGCAGT AAGAACAAAG CTCAAACTCA CTCCAATAGC GGCCGCTGGC CGGCTGGACT    9240

TGTCCGGTTG GTTCACGGCT GGCTACAGCG GGGGAGACAT TTATCACAGC GTGTCTCATG    9300

CCCGGCCCCG CTGGTTCTGG TTTTGCCTAC TCCTGCTCGC TGCAGGGGTA GGCATCTACC    9360

TCCTCCCCAA CCGGTGAAGA TTGGGCTAAC CACTCCAGGC CAATAGGCCA TCCCCT       9416
```

(2) INFORMATION FOR SEQ ID NO: 20:

(i) SEQUENCE CHARACTERISTICS:
        (A) LENGTH: 3011 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO: 20:

```
Met Ser Thr Asn Pro Lys Pro Gln Arg Lys Thr Lys Arg Asn Thr Asn
1               5                   10                  15

Arg Arg Pro Gln Asp Val Glu Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80
```

-continued

```
Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Ser Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Ser Ala Gly His Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Asp Ser
            420                 425                 430

Leu Thr Thr Gly Trp Leu Ala Gly Leu Phe Tyr Arg His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495
```

```
Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
            530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
            565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
            595                 600                 605

Val Asp Tyr Pro Tyr Arg Leu Trp His Tyr Pro Cys Thr Ile Asn Tyr
            610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Arg Trp Val Pro
            770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
```

-continued

```
            915                 920                 925
Ala Gly Gly His Tyr Val Gln Met Ala Ile Ile Lys Leu Gly Ala Leu
        930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Val Phe
                965                 970                 975
Ser Arg Met Glu Thr Lys Leu Ile Thr Trp Gly Ala Asp Thr Ala Ala
            980                 985                 990
Cys Gly Asp Ile Ile Asn Gly Leu Pro Val Ser Ala Arg Arg Gly Gln
        995                 1000                1005
Glu Ile Leu Leu Gly Pro Ala Asp Gly Met Val Ser Lys Gly Trp Arg
    1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Thr Gln Thr Phe Leu Ala Thr
            1060                1065                1070
Cys Ile Asn Gly Val Cys Trp Thr Val Tyr His Gly Ala Gly Thr Arg
        1075                1080                1085
Thr Ile Ala Ser Pro Lys Gly Pro Val Ile Gln Met Tyr Thr Asn Val
    1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
            1140                1145                1150
Leu Ser Pro Arg Pro Ile Ser Tyr Leu Lys Gly Ser Ser Gly Gly Pro
        1155                1160                1165
Leu Leu Cys Pro Ala Gly His Ala Val Gly Leu Phe Arg Ala Ala Val
    1170                1175                1180
Cys Thr Arg Gly Val Thr Lys Ala Val Asp Phe Ile Pro Val Glu Asn
1185                1190                1195                1200
Leu Glu Thr Thr Met Arg Ser Pro Val Phe Thr Asp Asn Ser Ser Pro
                1205                1210                1215
Pro Ala Val Pro Gln Ser Phe Gln Val Ala His Leu His Ala Pro Thr
            1220                1225                1230
Gly Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly Phe
    1250                1255                1260
Gly Ala Tyr Met Ser Lys Ala His Gly Val Asp Pro Asn Ile Arg Thr
1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Ile
            1300                1305                1310
Ile Ile Cys Asp Glu Cys His Ser Thr Asp Ala Thr Ser Ile Leu Gly
        1315                1320                1325
Ile Gly Thr Val Leu Asp Gln Ala Glu Thr Ala Gly Ala Arg Leu Val
    1330                1335                1340
```

```
Val Leu Ala Thr Ala Thr Pro Pro Gly Ser Val Thr Val Ser His Pro
1345                1350                1355                1360

Asn Ile Glu Glu Val Ala Leu Ser Thr Thr Gly Ile Pro Phe Tyr
                1365                1370                1375

Gly Lys Ala Ile Pro Leu Glu Val Ile Lys Gly Gly Arg His Leu Ile
                1380                1385                1390

Phe Cys His Ser Lys Lys Cys Asp Glu Leu Ala Ala Lys Leu Val
                1395                1400                1405

Ala Leu Gly Ile Asn Ala Val Ala Tyr Tyr Arg Gly Leu Asp Val Ser
                1410                1415                1420

Val Ile Pro Thr Asn Gly Asp Val Val Val Ser Thr Asp Ala Leu
1425                1430                1435                1440

Met Thr Gly Phe Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
                1460                1465                1470

Glu Thr Thr Thr Leu Pro Gln Asp Ala Val Ser Arg Thr Gln Arg Arg
                1475                1480                1485

Gly Arg Thr Gly Arg Gly Lys Pro Gly Ile Tyr Arg Phe Val Ala Pro
                1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Met Pro Ala Glu Thr Thr
                1525                1530                1535

Val Arg Leu Arg Ala Tyr Met Asn Thr Pro Gly Leu Pro Val Cys Gln
                1540                1545                1550

Asp His Leu Glu Phe Trp Glu Gly Val Phe Thr Gly Leu Thr His Ile
                1555                1560                1565

Asp Ala His Phe Leu Ser Gln Thr Lys Gln Ser Gly Glu Asn Phe Pro
                1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
                1620                1625                1630

Asn Glu Val Thr Leu Thr His Pro Ile Thr Lys Tyr Ile Met Thr Cys
                1635                1640                1645

Met Ser Ala Asp Leu Glu Val Val Thr Ser Thr Trp Val Leu Val Gly
1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
                1685                1690                1695

Asp Arg Glu Val Leu Tyr Gln Glu Phe Asp Glu Met Glu Glu Cys Ser
                1700                1705                1710

Gln His Leu Pro Tyr Ile Glu Gln Gly Met Met Leu Ala Glu Gln Phe
                1715                1720                1725

Lys Gln Lys Ala Leu Gly Leu Leu Gln Thr Ala Ser Arg His Ala Glu
                1730                1735                1740

Val Ile Thr Pro Ala Val Gln Thr Asn Trp Gln Lys Leu Glu Val Phe
1745                1750                1755                1760
```

-continued

Trp Ala Lys His Met Trp Asn Phe Ile Ser Gly Ile Gln Tyr Leu Ala
                1765                1770                1775
Gly Leu Ser Thr Leu Pro Gly Asn Pro Ala Ile Ala Ser Leu Met Ala
            1780                1785                1790
Phe Thr Ala Ala Val Thr Ser Pro Leu Thr Thr Gly Gln Thr Leu Leu
        1795                1800                1805
Phe Asn Ile Leu Gly Gly Trp Val Ala Ala Gln Leu Ala Ala Pro Gly
    1810                1815                1820
Ala Ala Thr Ala Phe Val Gly Ala Gly Leu Ala Gly Ala Ala Ile Gly
1825                1830                1835                1840
Ser Val Gly Leu Gly Lys Val Leu Val Asp Ile Leu Ala Gly Tyr Gly
                1845                1850                1855
Ala Gly Val Ala Gly Ala Leu Val Ala Phe Lys Ile Met Ser Gly Glu
            1860                1865                1870
Val Pro Ser Thr Glu Asp Leu Val Asn Leu Leu Pro Ala Ile Leu Ser
        1875                1880                1885
Pro Gly Ala Leu Val Val Gly Val Val Cys Ala Ala Ile Leu Arg Arg
    1890                1895                1900
His Val Gly Pro Gly Glu Gly Ala Val Gln Trp Met Asn Arg Leu Ile
1905                1910                1915                1920
Ala Phe Ala Ser Arg Gly Asn His Val Ser Pro Thr His Tyr Val Pro
                1925                1930                1935
Glu Ser Asp Ala Ala Ala Arg Val Thr Ala Ile Leu Ser Ser Leu Thr
            1940                1945                1950
Val Thr Gln Leu Leu Arg Arg Leu His Gln Trp Ile Ser Ser Glu Cys
        1955                1960                1965
Thr Thr Pro Cys Ser Gly Ser Trp Leu Arg Asp Ile Trp Asp Trp Ile
    1970                1975                1980
Cys Glu Val Leu Ser Asp Phe Lys Thr Trp Leu Lys Ala Lys Leu Met
1985                1990                1995                2000
Pro Gln Leu Pro Gly Ile Pro Phe Val Ser Cys Gln Arg Gly Tyr Arg
                2005                2010                2015
Gly Val Trp Arg Gly Asp Gly Ile Met His Thr Arg Cys His Cys Gly
            2020                2025                2030
Ala Glu Ile Thr Gly His Val Lys Asn Gly Thr Met Arg Ile Val Gly
        2035                2040                2045
Pro Arg Thr Cys Arg Asn Met Trp Ser Gly Thr Phe Pro Ile Asn Ala
    2050                2055                2060
Tyr Thr Thr Gly Pro Cys Thr Pro Leu Pro Ala Pro Asn Tyr Lys Phe
2065                2070                2075                2080
Ala Leu Trp Arg Val Ser Ala Glu Glu Tyr Val Glu Ile Arg Arg Val
                2085                2090                2095
Gly Asp Phe His Tyr Val Ser Gly Met Thr Thr Asp Asn Leu Lys Cys
            2100                2105                2110
Pro Cys Gln Ile Pro Ser Pro Glu Phe Phe Thr Glu Leu Asp Gly Val
        2115                2120                2125
Arg Leu His Arg Phe Ala Pro Pro Cys Lys Pro Leu Leu Arg Glu Glu
    2130                2135                2140
Val Ser Phe Arg Val Gly Leu His Glu Tyr Pro Val Gly Ser Gln Leu
2145                2150                2155                2160
Pro Cys Glu Pro Glu Pro Asp Val Ala Val Leu Thr Ser Met Leu Thr
                2165                2170                2175
Asp Pro Ser His Ile Thr Ala Glu Ala Ala Gly Arg Arg Leu Ala Arg

-continued

```
              2180            2185            2190
Gly Ser Pro Pro Ser Met Ala Ser Ser Ala Ser Gln Leu Ser Ala
        2195            2200            2205
Pro Ser Leu Lys Ala Thr Cys Thr Ala Asn His Asp Ser Pro Asp Ala
    2210            2215            2220
Glu Leu Ile Glu Ala Asn Leu Leu Trp Arg Gln Met Gly Gly Asn
2225            2230            2235            2240
Ile Thr Arg Val Glu Ser Glu Asn Lys Val Val Ile Leu Asp Ser Phe
            2245            2250            2255
Asp Pro Leu Val Ala Glu Asp Glu Arg Glu Val Ser Val Pro Ala
        2260            2265            2270
Glu Ile Leu Arg Lys Ser Arg Arg Phe Ala Arg Ala Leu Pro Val Trp
    2275            2280            2285
Ala Arg Pro Asp Tyr Asn Pro Pro Leu Val Glu Thr Trp Lys Lys Pro
        2290            2295            2300
Asp Tyr Glu Pro Pro Val Val His Gly Cys Pro Leu Pro Pro Pro Arg
2305            2310            2315            2320
Ser Pro Pro Val Pro Pro Pro Arg Lys Lys Arg Thr Val Val Leu Thr
            2325            2330            2335
Glu Ser Thr Leu Pro Thr Ala Leu Ala Glu Leu Ala Thr Lys Ser Phe
        2340            2345            2350
Gly Ser Ser Ser Thr Ser Gly Ile Thr Gly Asp Asn Met Thr Thr Ser
        2355            2360            2365
Ser Glu Pro Ala Pro Ser Gly Cys Pro Pro Asp Ser Asp Val Glu Ser
        2370            2375            2380
Tyr Ser Ser Met Pro Pro Leu Glu Gly Glu Pro Gly Asp Pro Asp Phe
2385            2390            2395            2400
Ser Asp Gly Ser Trp Ser Thr Val Ser Ser Gly Ala Asp Thr Glu Asp
            2405            2410            2415
Val Val Cys Cys Ser Met Ser Tyr Thr Trp Thr Gly Ala Leu Val Thr
            2420            2425            2430
Pro Cys Ala Ala Glu Glu Gln Lys Leu Pro Ile Asn Ala Leu Ser Asn
        2435            2440            2445
Ser Leu Leu Arg His His Asn Leu Val Tyr Ser Thr Thr Ser Arg Ser
    2450            2455            2460
Ala Cys Gln Arg Gln Lys Lys Val Thr Phe Asp Arg Leu Gln Val Leu
2465            2470            2475            2480
Asp Ser His Tyr Gln Asp Val Leu Lys Glu Val Lys Ala Ala Ala Ser
            2485            2490            2495
Lys Val Lys Ala Asn Leu Leu Ser Val Glu Glu Ala Cys Ser Leu Thr
            2500            2505            2510
Pro Pro His Ser Ala Lys Ser Lys Phe Gly Tyr Gly Ala Lys Asp Val
        2515            2520            2525
Arg Cys His Ala Arg Lys Ala Val Ala His Ile Asn Ser Val Trp Lys
        2530            2535            2540
Asp Leu Leu Glu Asp Ser Val Thr Pro Ile Asp Thr Ile Met Ala
2545            2550            2555            2560
Lys Asn Glu Val Phe Cys Val Gln Pro Glu Lys Gly Gly Arg Lys Pro
            2565            2570            2575
Ala Arg Leu Ile Val Phe Pro Asp Leu Gly Val Arg Val Cys Glu Lys
        2580            2585            2590
Met Ala Leu Tyr Asp Val Val Ser Lys Leu Pro Leu Ala Val Met Gly
        2595            2600            2605
```

```
Ser Ser Tyr Gly Phe Gln Tyr Ser Pro Gly Gln Arg Val Glu Phe Leu
    2610                2615                2620

Val Gln Ala Trp Lys Ser Lys Lys Thr Pro Met Gly Phe Pro Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
        2675                2680                2685

Ser Arg Gly Glu Asn Cys Gly Tyr Arg Arg Cys Arg Ala Ser Gly Val
    2690                2695                2700

Leu Thr Thr Ser Cys Gly Asn Thr Leu Thr Cys Tyr Ile Lys Ala Arg
2705                2710                2715                2720

Ala Ala Arg Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asn
    2850                2855                2860

Cys Glu Ile Tyr Ala Ala Cys Tyr Ser Ile Glu Pro Leu Asp Leu Pro
2865                2870                2875                2880

Pro Ile Ile Gln Arg Leu His Gly Leu Ser Ala Phe Leu Leu His Ser
            2885                2890                2895

Tyr Ser Pro Gly Glu Val Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ser Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
            2980                2985                2990

Trp Phe Cys Leu Leu Leu Leu Ala Ala Gly Val Gly Ile Tyr Leu Leu
        2995                3000                3005

Pro Asn Arg
    3010
```

-continued

```
(2) INFORMATION FOR SEQ ID NO: 21:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO: 21:

TGTCGCATTC                                                                10
```

FUNCTIONAL DNA CLONE FOR HEPATITIS C VIRUS (HCV) AND USES THEREOF

CROSS-REFERENCE TO RELATED APPLICATIONS

This application is a continuation-in-part of U.S. patent application Ser. No. 09/917,563, filed Jul. 27, 2001, now abandoned; which is a continuation of U.S. patent application Ser. No. 09/238,076, filed Jan. 26, 1999, now abandoned, which is a continuation of U.S. patent application Ser. No. 08/811,566, filed Mar. 4, 1997, now U.S. Pat. No. 6,127,116, which is a continuation-in-part of U.S. patent application Ser. No. 08/520,678, filed Aug. 29, 1995, now U.S. Pat. No. 5,874,565.

GOVERNMENT SUPPORT

The research leading to the present invention was supported, at least in part, by grants from United States Public Health Service Grant Nos. CA57973 and AI31501. Accordingly, the Government may have certain rights in the invention.

FIELD OF THE INVENTION

The present invention relates to the determination of functional HCV virus genomic RNA sequences, to construction of infectious HCV DNA clones, and to use of the clones, or their derivatives, in therapeutic, vaccine, and diagnostic applications. The invention is also directed to HCV vectors, e.g., for gene therapy or gene vaccines.

BACKGROUND OF THE INVENTION

Brief General Overview of Hepatitis C Virus

After the development of diagnostic tests for hepatitis A virus and hepatitis B virus, an additional agent, which could be experimentally transmitted to chimpanzees [Alter et al., *Lancet* 1, 459–463 (1978); Hollinger et al., *Intervirology* 10, 60–68 (1978); Tabor et al., *Lancet* 1, 463–466 (1978)], become recognized as the major cause of transfusion-acquired hepatitis. cDNA clones corresponding to the causative non-A non-B (NANB) hepatitis agent, called hepatitis C virus (HCV), were reported in 1989 [Choo et al., *Science* 244, 359–362 (1989)]. This breakthrough has led to rapid advances in diagnostics, and in or understanding of the epidemiology, pathogenesis and molecular virology of HCV (see Houghton et al., *Curr Stud Hematol Blood Transfus* 61, 1–11 (1994) for review). Evidence of HCV infection is found throughout the world, and the prevalence of HCV-specific antibodies ranges from 0.4–2% in most countries to more than 14% in Egypt [Hibbs et al., *J. Inf. Dis.* 168, 789–790 (1993)]. Besides transmission via blood or blood products, or less frequently by sexual and congenital routes, sporadic cases, not associated with known risk factors, occur and account for more than 40% of HCV cases [Alter et al., *J. Am. Med. Assoc.* 264, 2231–2235 (1990); Mast and Alter, *Semin. Virol.* 4, 273–283 (1993)]. Infections are usually chronic [Alter al., *N. Eng. J. Med.* 327, 1899–1905 (1992)], and clinical outcomes range from an inapparent carrier state to acute hepatitis, chronic active hepatitis, and cirrhosis which is strongly associated with the development of hepatocellular carcinoma.

Although interferon (IFN)-α has been shown to be useful for the treatment of a minority of patients with chronic HCV infections [Davis et al., *N. Engl. J. Med.* 321, 1501–1506 (1989); DiBisceglie et al., *New Engl. J. Med.* 321, 1506–1510 (1989)] and subunit vaccines show some promise in the chimpanzee model [Choo et al., *Proc. Natl. Acad. Sci. USA* 91, 1294–1298 (1994)], future efforts are needed to develop more effective therapies and vaccines. The considerable diversity observed among different HCV isolates [for review, see Bukh et al., *Sem. Liver Dis.* 15, 41–63 (1995)], the emergence of genetic variants in chronically infected individuals [Enomoto et al., *J. Hepatol.* 17, 415–416 (1993); Hijikata et al., *Biochem. Biophys. Res. Comm.* 175, 220–228 (1991); Kato et al., *Biochem. Biophys. Res. Comm.* 189, 119–127 (1992); Kato et al., *J. Virol.* 67, 3923–3930 (1993); Kurosaki et al., *Hepatology* 18, 1293–1299 (1993); Lesniewski et al., *J. Med. Virol.* 40, 150–156 (1993); Ogata et al., *Proc. Natl. Acad. Sci. USA* 88, 3392–3396 (1991); Weiner et al., *Virology* 180, 842–848 (1991); Weiner et al., *Proc. Natl. Acad. Sci. USA* 89, 3468–3472 (1992)], and the lack of protective immunity elicited after HCV infection [Farci et al., *Science* 258, 135–140 (1992); Prince et al., *J. Infect. Dis.* 165, 438–443 (1992)] present major challenges towards these goals.

Molecular Biology of HCV

Classification. Based on its genome structure and virion properties, HCV has been classified as a separate genus in the flavivirus family, which includes two other genera: the flaviviruses (e.g., yellow fever (YF) virus) and the animal pestiviruses (e.g., bovine viral diarrhea virus (BVDV) and classical swine fever virus (CSFV)) [Francki et al., *Arch. Virol.* Suppl. 2, 223 (1991)]. All members of this family have enveloped virions that contain a positive-strand RNA genome encoding all known virus-specific proteins via translation of a single long open reading frame (ORF).

Structure and physical properties of the virion. Little information is available on the structure and replication of HCV. Studies have been hampered by the lack of a cell culture system able to support efficient virus replication and the typically low titers of infectious virus present in serum. The size of infectious virus, based on filtration experiments, is between 30–80 mm [Bradley et al., *Gastroenterology* 88, 773–779 (1985); He et al., *J. Infect. Dis.* 156, 636–640 (1987); Yuasa et al., *J. Gen. Virol.* 72, 2021–2024 (1991)]. Initial measurements of the buoyant density of infectious material in sucrose yielded a range of values, with the majority present in a low density pool of <1.1 g/ml [Bradley et al., *J. Med. Virol.* 34, 206–208 (1991)]. Subsequent studies have used RT/PCR to detect HCV-specific RNA as an indirect measure of potentially infectious virus present in sera from chronically infected humans or experimentally infected chimpanzees. From these studies, it has become increasingly clear that considerable heterogeneity exists between different clinical samples, and that many factors can affect the behavior of particles containing HCV RNA [Hijikata et al., *J. Virol.* 67, 1953–1958 (1993); Thomssen et al., *Med. Microbiol. Immunol.* 181, 293–300 (1992)]. Such factors include association with immunoglobulins [Hijikata et al., (1993) supra] or low density lipoprotein [Thomssen et al., 1992, supra; Thomssen et al., *Med. Microbiol. Immunol.* 182, 329–334 (1993)]. In highly infectious acute phase chimpanzee serum, HCV-specific RNA is usually detected in fractions of low buoyant density (1.03–1.1 g/ml) [Carrick et al., *J. Virol. Meth.* 39, 279–289 (1992); Hijikata et al., (1993) supra]. In other samples, the presence of HCV antibodies and formation of immune complexes correlate with particles of higher density and lower infectivity [Hijikata et al., (1993) supra]. Treatment of particles with chloroform, which destroys infectivity [Bradley et al., *J. Infect. Dis.* 148, 254–265 (1983); Feinstone et al., *Infect. Immun.* 41, 816–821 (1983)], or with nonionic detergents, produced RNA containing particles of higher density (1.17–1.25 g/ml) believed to represent HCV nucleocapsids [Hijikata et al., (1993); supra; Kanto et al., *Hepatology* 19, 296–302 (1994); Miyamoto et al., *J. Gen. Virol.* 73, 715–718 (1992)].

There have been reports of negative-sense HCV-specific RNAs in sera and plasma [see Fong et al., *Journal of Clinical Investigation* 88:1058–60 (1991)]. However, it seems unlikely that such RNAs are essential components of infectious particles since some sera with high infectivity can have low or undetectable levels of negative-strand RNA [Shimizu et al., *Proc. Natl. Acad. Sci. USA* 90: 6037–6041 (1993)].

The virion protein composition has not been rigorously determined, but putative HCV structural proteins include a basic C protein and two membrane glycoproteins, E1 and E2.

HCV replication. Early events in HCV replication are poorly understood. Cellular receptors for the HCV glycoproteins have not been identified. The association of some HCV particles with beta-lipoprotein and immunoglobulins raises the possibility that these host molecules may modulate virus uptake and tissue tropism. Studies examining HCV replication have been largely restricted to human patients or experimentally inoculated chimpanzees. In the chimpanzee model, HCV RNA is detected in the serum as early as three days post-inoculation and persists through the peak of serum alanine aminotransferase (ALT) levels (an indicator of liver damage) [Shimizu et al., *Proc. Natl. Acad. Sci. USA* 87: 6441–6444 (1990)]. The onset of viremia is followed by the appearance of indirect hallmarks of HCV infection of the liver. These include the appearance of a cytoplasmic antigen [Shimizu et al., (1990) supra] and ultrastructural changes in hepatocytes such as the formation of microtubular aggregates for which HCV previously was referred to as the chloroform-sensitive "tubule forming agent" or "TFA" [reviewed by Bradley, *Prog. Med. Virol.* 37: 101–135 (1990)]. As shown by the appearance of viral antigens [Blight et al., *Amer. J. Path.* 143: 1568–1573 (1993); Hiramatsu et al., *Hepatology* 16: 306–311 (1992); Krawczynski et al., *Gastroenterology* 103: 622–629 (1992); Yamada et al., *Digest Dis. Sci.* 38: 882–887 (1993)] and the detection of positive and negative sense RNAs [Fong et al., (1991) supra; Gunji et al., *Arch. Virol.* 134: 293–302 (1994); Haruna et al., *J. Hepatol.* 18: 96–100 (1993); Lamas et al., *J. Hepatol.* 16: 219–223 (1992); Nouri Aria et al., *J. Clin. Inves.* 91: 2226–34 (1993); Sherker et al., *J. Med. Virol.* 39: 91–96 (1993); Takehara et al., *Hepatology* 15: 387–390 (1992); Tanaka et al., *Liver* 13: 203–208 (1993)], hepatocytes appear to be a major site of HCV replication, particularly during acute infection [Negro et al., *Proc. Natl. Acad. Sci. USA* 89: 2247–2251 (1992)]. In later stages of HCV infection the appearance of HCV-specific antibodies, the persistence or resolution of viremia, and the severity of liver disease, vary greatly both in the chimpanzee model and in human patients. Although some liver damage may occur as a direct consequence of HCV infection and cytopathogenicity, the emerging consensus is that host immune responses, in particular virus-specific cytotoxic T lymphocytes, may play a more dominant role in mediating cellular damage.

It has been speculated that HCV may also replicate in extra-hepatic reservoir(s). In some cases, RT/PCR or in situ hybridization has shown an association of HCV RNA with peripheral blood mononuclear cells including T-cells, B-cells, and monocytes reviewed in Blight and Gowans, *Viral Hepatitis Rev.* 1: 143–155 (1995)]. Such tissue tropism could be relevant to the establishment of chronic infections and might also play a role in the association between HCV infection and certain immunological abnormalities such as mixed cryoglobulinemia [reviewed by Ferri et al., *Eur. J. Clin. Invest.* 23: 399–405 (1993)], glomerulonephritis, and rare non-Hodgkin's B-lymphomas [Ferri et al., (1993) supra; Kagawa et al., *Lancet* 341: 316–317 (1993)]. However, the detection of circulating negative strand RNA in serum, the difficulty in obtaining truly strand-specific RT/PCR [Gunji et al., (1994) supra], and the low numbers of apparently infected cells have made it difficult to obtain unambiguous evidence for replication in these tissues in vivo.

Genome structure. Full-length or nearly full-length genome sequences of numerous HCV isolates have been reported [see Lin et al., *J. Virol.* 68: 5063–5073 (1994a); Okamoto et al., *J. Gen. Virol.* 75: 629–635 (1994); Sakamoto et al., *J. Gen. Virol.* 75: 1761–1768 (1994) and citations therein]. Given the considerable genetic divergence among isolates, it is clear that several major HCV genotypes are distributed throughout the world. Those of greatest importance in the U.S. are genotype 1, subtypes 1a and 1b (see below and Ref. Bukh et al., (1995) supra for a discussion of genotype prevalence and distribution). HCV genome RNAs are ~9.6 kilobases in length (FIG. 1). The 5' NTR is 341–344 bases long and highly conserved. The length of the long ORF varies slightly among isolates, encoding polyproteins of 3010, 3011 or 3033 amino acids. The reported 3' NTR structures show considerable diversity both in composition and length (28–42 bases), and appear to terminate with poly (U) (see Chen et al., *Virology* 188:102–113 (1992); Okamoto et al., *J. Gen. Virol.* 72:2697–2704 (1991); Tokita et al., *J. Gen. Virol.* 66:1476–83 (1994)] except in one case (HCV-1, type 1a) which appears to contain a 3' terminal poly (A) tract [Han et al., *Proc. Natl. Acad. Sci. USA* 88:1711–1715 (1991)]. In contrast, our recent analysis suggests that the genome RNA of the H-strain (also type 1a) contains an internal polypyrimidine tract followed by a novel RNA element [pending patent application Ser. No. 08/520,678, filed Aug. 29, 1995, and International Patent Application No. PCT/US96/14033, filed Aug. 28, 1996]. The results presented in pending application Ser. No. 08/520,678 show that the genome RNA of this type 1a isolate does not terminate with a homopolymer tract as previously thought, but rather with a novel sequence of ~98 bases. Furthermore, this 3' NTR structure and the novel 3' terminal element are features common to all HCV genotypes which have thus far been examined [Kolykhalov et al., *J. Virol.* 70: 3363–3371 (1996); Tanaka et al., *Biochem. Biophys. Res. Comm.* 215: 744–749 (1996); Tanaka et al., *J. Virol.* 70:3307–12 (1996); Yamada et al., *Virology* 223:255–261 (1996)].

Translation and proteolytic processing. Several studies have used cell-free translation and transient expression in cell culture to examine the role of the 5' NTR in translation initiation [Fukushi et al., *Biochem. Biophys. Res. Comm.* 199: 425–432 (1994); Tsukiyama-Kohara et al., *J. Virol.* 66: 1476–1483 (1992); Wang et al., *J. Virol.* 67: 3338–3344 (1993); Yoo et al., *Virology* 191: 889–899 (1992)]. This highly conserved sequence contains multiple short AUG-initiated ORFs and shows significant homology with the 5' NTR region of pestiviruses [Bukh et al., *Proc. Natl. Acad. Sci. USA* 89: 4942–4946 (1992); Han et al., (1991) supra]. A series of stem-loop structures have been proposed on the basis of computer modeling and sensitivity to digestion by different ribonucleases [Brown et al., *Nucl. Acids Res.* 20: 5041–5045 (1992); Tsukiyama-Kohara et al., (1992) supra].

The results from several groups indicate that this element functions as an internal ribosome entry site (IRES) allowing efficient translation initiation at the first AUG of the long ORF [Fukushi et al., (1994) supra; Tsukiyama-Kohara et al., (1992) supra; Wang et al., (1993) supra; Yoo et al., (1992) supra]. Some of the predicted features of the HCV and pestivirus IRES elements are similar to one another [Brown et al., (1992) supra]. The ability of this element to function as an IRES suggests that HCV genome RNAs may lack a 5' cap structure.

The organization and processing of the HCV polyprotein (FIG. 1) appears to be most similar to that of the pestiviruses. At least 10 polypeptides have been identified and the order of these cleavage products in the polyprotein is NH2-C-E1-E2-p7-NS2-NS3-NS4A-NS4B-NS5A-NS5B-COOH. As shown in FIG. 1, proteolytic processing is mediated by host signal peptidase and two HCV-encoded proteinases, the NS2-3 autoproteinase and the NS3-4A serine proteinase [see Rice, In "Fields Virology" (B. N. Fields, D. M. Knipe and P. M. Howley, Eds.), Vol. pp. 931–960. Raven Press, New York (1996); Shimotohno et al., J. Hepatol. 22: 87–92 (1995) for reviews]. C is a basic protein believed to be the viral core or capsid protein; E1 and E2 are putative virion envelope glycoproteins; p7 is a hydrophobic protein of unknown function that is inefficiently cleaved from the E2 glycoprotein [Lin et al., (1994a) supra; Mizushima et al., J. Virol. 68: 6215–6222 (1994); Selby et al., Virology 204: 114–122 (1994)], and NS2-NS5B are likely nonstructural (NS) proteins which function in viral RNA replication complexes. In particular, besides its N-terminal serine proteinase domain, NS3 contains motifs characteristic of RNA helicases and has been shown to possess an RNA-stimulated NTPase activity [Suzich et al., J. Virol. 67, 6152–6158 (1993)]; NS5B contains the GDD motif characteristic of the RNA-dependent RNA polymerases of positive-strand RNA viruses.

HCV RNA replication. By analogy with flaviviruses, replication of the positive-sense HCV virion RNA is thought to occur via a minus-strand intermediate. This strategy can be described briefly as follows: (i) uncoating of the incoming virus particle releases the genomic plus-strand, which is translated to produce a single long polyprotein that is probably processed co- and post-translationally to produce individual structural and nonstructural proteins; (ii) the nonstructural proteins presumably form a replication complex that utilizes the virion RNA as template for the synthesis of minus strands; (iii) these minus strands in turn serve as templates for synthesis of plus strands, which can be used for additional translation of viral protein, minus strand synthesis, or packaging into progeny virions. Very few details about HCV replication process are available, due to the lack of a good experimental system for virus propagation. Detailed analyses of authentic HCV replication and other steps in the viral life cycle would be greatly facilitated by the development of an efficient system for HCV replication in cell culture.

Many attempts have been made to infect cultured cells with serum collected from HCV-infected individuals, and low levels of replication have been reported in a number of cells types infected by this method, including B-cell [Bertolini et al., Res. Virol. 144: 281–285 (1993); Nakajima et al., J. Virol. 70: 9925–9 (1996); Valli et al., Res. Virol. 146: 285–288 (1995)]. T-cell (Kato et al., Biochem. Biophys. Res. Commun. 206:863–9 (1996); Mizutani et al., Biochem. Biophys. Res. Commun. 227:822–826; Mizutani et al., J. Virol. 70: 7219–7223 (1996); Nakajima et al., (1996) supra; Shimizu and Yoshikura, J. Virol. 68: 8406–8408 (1994); Shimizu et al., Proc. Natl. Acad. Sci USA, 89: 5477–5481 (1992); Shimizu et al., Proc. Natl. Acad. Sci. USA, 90: 6037–6041 (1993)], and hepatocyte [Kato et al., Jpn. J. Cancer Res., 87: 787–92 (1996); Tagawa, J. Gastoenterol. and Hepatol., 10: 523–527 (1995)] cell lines, as well as peripheral blood monocular cells (PBMCs) [Cribier et al., J. Gen. Virol., 76: 2485–2491 (1995)], and primary cultures of human fetal hepatocytes [Carloni et al., Arch. Virol. Suppl. 8: 31–39 (1993); Cribier et al., (1995) supra; Iacovacci et al., Res. Virol., 144: 275–279 (1993)] or hepatocytes from adult chimpanzees [Lanford et al., Virology 202: 606–14 (1994)]. HCV replication has also been detected in primary hepatocytes derived from a human HCV patient that were infected with the virus in vivo prior to cultivation [Ito et al., J. Gen. Virol. 77: 1043–1054 (1996)] and in the human hepatoma cell line Huh7 following transfection with RNA transcribed in vitro from an HCV-1 cDNA clone [Yoo et al., J. Virol., 69: 32–38 (1995)]. The reported observation of replication in cells transfected with RNA derived from the HCV-1 clone was puzzling, since this clone lacks the 3'NTR sequence downstream of the homopolymer tract (see below). The most well-characterized cell-culture systems for HCV replication utilize a B-cell line (Daudi) or T-cell lines persistently infected with retroviruses (HPB-Ma or MT-2) [Kato et al., (1995) supra; Mizutani et al., Biochem Biophys Res. Comm., 227: 822–826 (1996a); Mizutani et al., (1996) supra; Nakajima et al., (1996) supra; Shimizu and Yoshikura, (1994) supra]; Shimizu, Proc. Natl. Acad. Sci. USA, 90: 6037–6041 (1993)]. HPBMa is infected with an amphotropic murine leukemia virus pseudotype of murine sarcoma virus, while MT-2 is infected with human T-cell lymphotropic virus type I (HTLV-I). Clones (HPBMa10-2 and MT-2C) that support HCV replication more efficiently than the uncloned population have been isolated for the two T-cell lines HPBMa and MT-2 [Mizutani et al. J. Virol. (1996) supra; Shimizu et al., (1993) supra]. However, the maximum levels of RNA replication obtained in these lines or in the Daudi lines after degradation of the input RNA is still only about $5 \times 10^4$ RNA molecules per $10^6$ cells [Mizutani et al., (1996); supra; Mizutani et al., (1996) supra] or $10^4$ RNA molecules per ml of culture medium [Nakajima et al., (1996) supra]. Although the level of replication is low, long-term infections of up to 198 days in one system [Mizutani et al., Biochem. Biophys. Res. Comm. 227: 822–826 (1996a)] and more than a year in another system [Nakajima et al., (1996) supra] have been documented, and infectious virus production has been demonstrated by serial cell-free or cell-mediated passage of the virus to naive cells.

However, efficient HCV replication has not been observed in any of the cell-culture systems described to date, and all of the groups that have attempted to establish such systems have encountered a number of problems, including the difficulty in distinguishing input RNA from plus strands produced by replication, the false detection of minus strands, and generally low titers of replicated RNA. Thus, despite these advances, more efficient cell-culture systems for HCV propagation are needed for the production of concentrated virus stocks, structural analysis of virion components, and improved analyses of intracellular viral processes, including RNA replication.

Virion assembly and release. This process has not been examined directly, but the lack of complex glycans, the ER localization of expressed HCV glycoproteins [Dubuisson et al., J. Virol. 68: 6147–6160 (1994); Ralston et al., J. Virol. 67: 6753–6761 (1993)] and the absence of these proteins on the cell surface [Dubuisson et al., (1994) supra; Spaete et al., Virology 188: 819–830 (1992)] suggest that initial virion morphogenesis may occur by budding into intracellular vesicles. Thus far, efficient particle formation and release has not been observed in transient expression assays, suggesting that essential viral or host factors are absent or blocked. HCV virion formation and release may be inefficient, since a substantial fraction of the virus remains cell-associated, as found for the pestiviruses. A recent study indicates that extracellular HCV particles partially purified from human plasma contain complex N-linked glycans, although these carbohydrate moieties were not shown to be specifically associated with E1 or E2 [Sato et al., *Virology* 196: 354–357 (1993)]. Complex glycans associated with glycoproteins on released virions would suggest transit through the trans-Golgi and movement of virions through the host secretory pathway. If this is correct, intracellular sequestration of HCV glycoproteins and virion formation might then play a role in the establishment of chronic infections by minimizing immune surveillance and preventing lysis of virus-infected cells via antibody and complement.

Genetic variability. As for all positive-strand RNA viruses, the RNA-dependent RNA polymerase (RDRP) of HCV (NS5B) is believed to lack a 3'-5' exonuclease proof reading activity for removal of misincorporated bases. Replication is therefore error-prone, leading to a "quasi-species" virus population consisting of a large number of variants [Martell et al., *J. Virol.* 66: 3225–3229 (1992); Martell et al., *J. Virol.* 68: 3425–3436 (1994)]. This variability is apparent at multiple levels. First, in a chronically infected individual, changes in the virus population occur over time [Ogata et al., (1991) supra; Okamoto et al., *Virology* 190: 894–899 (1992)]; and these changes may have important consequences for disease. A particularly interesting example is the N-terminal 30 residue segment of the E2 glycoprotein, which exhibits a much higher degree of variability than the rest of the polyprotein [for examples, see Higashi et al., *Virology* 197, 659–668, 1993; Hijikata et al., (1991) supra; Weiner et al., (1991) supra]. There is accumulating evidence that this hypervariable region, perhaps analogous to the V3 domain of HIV-1 gp120, may be under immune selection by circulating HCV-specific antibodies [Kato et al., (1993) supra; Taniguchi et al., *Virology* 195: 297–301 (1993); Weiner et al., (1992) supra. In this model, antibodies directed against this portion of E2 may contribute to virus neutralization and thus drive the selection of variants with substitutions that permit escape from neutralization. This plasticity suggests that a specific amino acid sequence in the E2 hypervariable region is not essential for other functions of the protein such as virion attachment, penetration, or assembly.

Genetic variability may also contribute to the spectrum of different responses observed after IFN-α treatment of chronically infected patients. Diminished serum ALT levels and improved liver histology, which usually correlates with a decrease in the level of circulating HCV RNA, is seen in ~40% of those treated [Greiser-Wilke et al., *J. Gen. Virol.* 72: 2015–2019 (1991)]. After treatment, approximately 70% of the responders relapse. In some cases, after a transient loss of circulating viral RNA, renewed viremia is observed during or after the course of treatment. While this might suggest the existence or generation of IFN-resistant HCV genotypes or variants, further work is needed to determine the relative contributions of virus genotype and host-specific differences in immune response.

Finally, sequence comparisons of different HCV isolates around the world have revealed enormous genetic diversity [reviewed in Ref. Bukh et al., (1995) supra]. Because of the lack biologically relevant serological assays such as cross-neutralization tests, HCV types (designated by numbers), subtypes (designated by letters), and isolates are currently grouped on the basis of nucleotide or amino acid sequence similarity. Amino acid sequence similarity between the most divergent genotypes can be a little as ~50%, depending upon the protein being compared. This diversity has important biological implications, particularly for diagnosis, vaccine design, and therapy.

Attempts by Others to Generate Infectious HCV Transcripts from cDNA

A recent paper [Yoo et al., *J. Virol.* 69: 32–38 (1995)] reports replication of transcribed HCV-1 RNA after transfection of Huh7 cells. In this paper, T7 transcripts from various derivatives of an HCV-1 cDNA clone were tested for their ability to replicate following transfection of the human hepatoma cell line, Huh7. Possible HCV replication was assessed by strand-specific RT/PCR (using 5' NTR primers) and metabolic labeling of HCV-specific RNAs with $^3$H-uridine. Apparently full-length transcripts, terminating with either poly (A) or poly (U), were positive by these assays, but those with a deletion of the 5' terminal 144 bases were not. In some cultures, HCV-specific RNA was detected in the culture media and this putative virus was used to reinfect fresh Huh7cells.

The present inventors have been unable to reproduce these results. It appears that this report describes transient replication, rather than authentic HCV infection, with replication and virus production. Some of the data appear self-contradictory. For instance, the positive control reported in this paper was productive transfection of Huh7 cells with RNA extracted from 1 ml of high HCV titer chimpanzee plasma. This extracted sample would contain a maximum of $10^7$ potentially infectious full-length HCV RNA molecules. Under optimum transfection conditions (other than microinjection), greater than $10^5$ RNA molecules of virion RNA (at least for poliovirus, Sindbis virus, or YF) are typically required to initiate a single infectious event. This suggests that in the reported HCV-1 experiment fewer than 100 cells would be productively transfected. Furthermore, at 16 days post-transfection, both positive- and negative-strand RNAs were reportedly detected after eight hours of metabolic labeling. The detection of negative-strand RNA by this method (both for transfected virion RNA and transcript RNA) suggests that HCV is capable of both efficient replication and spread, and that the level of HCV RNA synthesis is similar to that which would be expected for a more robust flavivirus, such as YF (at the peak of a high multiplicity infection). Yet Yoo et al. did not report detection of HCV antigens in these cells using a variety of antisera, nor were they able to report detection of full-length positive- or negative-strands by Northern analysis (which is much more sensitive than metabolic labeling with $^3$H-uridine). Finally, the critical experiment, demonstrating that RNA or virus derived from the HCV-1 clone is infectious in the chimpanzee model, has not been reported.

Importance of Infectious Clone Technology for HCV Research

Despite the great deal of progress made in the last several years a vast number of questions concerning HCV replication, pathogenesis, and immunity remain unanswered. The field is rapidly reaching a bottleneck where we understand some aspects of the functions of the HCV RNA genome and its encoded proteins, but have no way of experimentally testing structure/function questions in the context of authentic virus replication. Such analyses are critical for understanding each step in the virus life cycle to enable the design of protective vaccines, effective therapy, and HCV diagnostics.

Thus, there is a need in the art for authentic HCV genetic material for expression of infectious HCV RNA.

There is a further need in the art for authentic genetic material for expression of native HCV virions and viral particle proteins, which can, in turn, permit characterization of HCV virion structure.

The art also requires an in vitro culture method for infectious HCV, which would permit analysis of HCV receptor binding, cellular infection, replication, virion assembly, and release.

These and other needs in the art are addressed by the present invention.

The citation of any reference herein should not be construed as an admission that such reference is available as "Prior Art" to the instant application.

SUMMARY OF THE INVENTION

The present invention advantageously provides an authentic hepatitis C virus (HCV) DNA clone capable of replication, expression of functional HCV proteins, and infection in vivo and in vitro for development of antiviral therapeutics and diagnostics.

In a broad aspect, the present invention is directed to a genetically engineered hepatitis C virus (HCV) nucleic acid clone which comprises from 5' to 3' on the positive-sense nucleic acid a functional 5' non-translated region (NTR) comprising an extreme 5'-terminal conserved sequence, an open reading frame (ORF) encoding at least a portion of an HCV polyprotein whose cleavage products form functional components of HCV virus particles and RNA replication machinery, and a 3' non-translated region (NTR) comprising an extreme 3'-terminal conserved sequence, or a derivative thereof selected from the group consisting of adapted virus, live-attenuated virus, replication-competent non-infectious virus, and defective virus. It has been found by the present inventors that various manipulations, effected using genetic engineering techniques, are required to produce an authentic HCV nucleic acid, e.g., a cDNA that can be transcribed to produce infectious HCV RNA, or an infectious HCV RNA. By providing engineered authentic HCV nucleic acids, the present inventors have for the first time enabled dissection of HCV replication machinery and protein activity, and preparation of various HCV derivatives. Previously, since there was uncertainty about whether any given HCV clone contained an error or mutation that led to its inability to function, one could not be certain that starting material for further analysis of HCV was useful or simply due to an artifact. Thus, a major advantage of the present invention is that it provides authentic HCV, thus assuring that any modifications result in real changes rather than artifacts due to errors in the clones provided in the prior art.

A further advantage of the present invention is recognition of the characteristics of an infectious HCV genome, particularly in the polyprotein coding region. In a specific embodiment, the HCV nucleic acid has a consensus nucleic acid sequence determined from the sequence of a majority of at least three clones of an HCV isolate or genotype. Preferably, the HCV nucleic acid has at least a functional portion of a sequence as shown in SEQ ID NO:1, which represents a specific embodiment of the present invention exemplified herein. It should be noted that while SEQ ID NO:1 is a DNA sequence, the present invention contemplates the corresponding RNA sequence, and DNA and RNA complementary sequences as well. In a further embodiment, a region from an HCV isolate is substituted for a homologous region, e.g., of an HCV nucleic acid having a sequence of SEQ ID NO:1. In a further preferred embodiment, exemplified herein, the HCV nucleic acid is a DNA that codes on expression for a replication-competent HCV RNA replicon, or is itself a replication-competent HCV RNA replicon. In a specific example, infra, an HCV nucleic acid of the invention has a full length sequence as depicted in or corresponding to SEQ ID NO:1. Various modifications of the 5' and 3' are also contemplated by the invention. For example, the 5'-terminal sequence can be homologous or complementary to an RNA sequence selected from the group consisting of GCCAGCC; GGCCAGCC; UGCCAGCC; AGCCAGCC; AAGCCAGCC; GAGCCAGCC; GUGCCAGCC; and GCGCCAGCC, wherein the sequence GCCAGCC is the 5'-terminus of SEQ ID NO:3.

Still another advantage of the present invention is the demonstration of the importance of the complete 3'-NTR for an infectious HCV clone. The 3'-NTR, particularly the approximately 98 base extreme terminal sequence, which is highly conserved among HCV genotypes, is the subject of U.S. patent application Ser. No. 08/520,678, filed Aug. 29, 1995, which is incorporated herein by reference in its entirety; and PCT International Application No. PCT/US96/14033, filed Aug. 28, 1996, which is also incorporated herein by reference in its entirety. Thus, in a preferred aspect, the function 3'-NTR comprises a 3'-terminal sequence of approximately 98 bases that is highly conserved among HCV genotypes. In a specific embodiment, the 3'-NTR extreme terminus is homologous or complementary to a DNA having the sequence 5'-GGTGGCTCCATCT-TAGCCCTAGTCACGGCTAGCTGTGAAAG-GTCCGTGAGCCG CATGACTGCAGAGAGTGCT-GATACTGGCCTCTCTGCTGATCATGT-3' (SEQ ID NO:4). In a specific embodiment, exemplified in SEQ ID NO:1, the 3'-NTR comprises a long poly-pyrimidine region (e.g., about 133 bases); however, alternative length poly-pyrimidine regions are also encompassed, including short regions (about 75 bases), or regions that are shorter or longer. Naturally, in a positive strand HCV DNA nucleic acid, the poly-pyrimidine region is a poly(T/TC) region, and in an positive strand HCV RNA nucleic acid, the poly-pyrimidine region is a poly(U/UC) region.

According to various aspects of the invention, and HCV nucleic acid, including the polyprotein coding region, can be mutated or engineered to produce variants or derivatives with, e.g., silent mutations, conservative mutations, etc. Such clones may also be adapted, e.g., by selection for propagation in animals or in vitro. The present invention further permits creation of HCV chimeras, in which portions of the genome for other genotypes or isolates are substituted for the homologous region of an HCV clone, such as SEQ ID NO:1 or the deposited embodiment, infra. In still other embodiments, the invention provides methods for preparing, and clones comprising, polyprotein coding sequence from an HCV genotype selected from the group consisting of the HCV-1, HCV-1a, HCV-1b, HCV-1c, HCV-2a, HCV-2b, HCV-2c, HCV-3a, and any "quasi-species" variant thereof. In a further preferred aspect, silent nucleotide changes in the polyprotein coding regions (i.e., variations of the third base of a codon that encodes the same amino acid) are incorporated as markers of specific HCV clones.

In a further aspect of the invention, an HCV nucleic acid, including attenuated and defective variants thereof, can comprise a heterologous gene operatively associated with an expression control sequence, wherein the heterologous gene and expression control sequence are oriented on the positive-strand nucleic acid molecule. In a specific embodiment, the heterologous gene is inserted by a strategy selected from the group consisting of in-frame fusion with the HCV polyprotein coding sequence; and creation of an additional cistron. The heterologous gene can be an antibiotic resistance gene or a reporter gene. Alternatively, the heterologous gene can be a therapeutic gene, or a gene encoding a vaccine antigen, i.e., for gene therapy or gene vaccine applications, respectively. In a specific embodiment, where the heterologous gene is an antibiotic resistance gene, the antibiotic resistance gene is a neomycin resistance gene operatively associated with an internal ribosome entry site (IRES) inserted in an SfiI site in the 3'-NTR.

Naturally, as noted above, the HCV nucleic acid of the invention is selected from the group consisting of double stranded DNA, positive-sense cDNA, or negative-sense cDNA, or positive-sense RNA or negative-sense RNA. Thus, where particular sequences of nucleic acids of the invention are set forth, both DNA and corresponding RNA are intended, included positive and negative strands thereof.

An HCV DNA may be inserted in a plasmid vector for translation of the corresponding HCV RNA. Thus, the HCV DNA may comprise a promoter 5' of the 5'-NTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter. In specific examples, infra, phage T7 and SP6 promoters are employed. In a specific embodiment, the present invention is directed to a plasmid clone, p90/HCVFL [long poly(U)], harboring a full-length HCV cDNA which can be transcribed to produce infectious HCV RNA transcripts as deposited with the American Type Culture Collection (ATCC), 12301 Parklawn Drive, Rockville, Md. 20852, USA on Feb. 13, 1997, and assigned accession no. 97879, having a sequence as depicted in SEQ ID NO:5. Naturally, the invention also includes a derivative of this plasmid, selected from the group consisting of a derivative wherein a 5'-terminal sequence is homologous or complementary to an RNA sequence selected from the group consisting of GCCAGCC, GGCCACC, UGCCAGCC, AGCCAGCC, AAGCCAGCC, GAGCCAGCC, GUGCCAGCC, and GCGCCAGCC, wherein the sequence GCCAGCC is the 5'-terminus of SEQ ID NO:3, and a derivative wherein a 3'-NTR comprises a short poly-pyrimidine region (since the deposited embodiment has a long poly-pyrimidine region, which may be preferred). In a further embodiment, a derivative of the deposited embodiment may be selected from the group consisting of a derivative produced by substitution of homologous regions from other HCV isolates or genotypes; a derivative produced by mutagenesis; a derivative selected from the group consisting of adapted, live-attenuated, replication competent non-infectious, and defective variants; a derivative comprising a heterologous gene operatively associated with an expression control sequence; and a derivative consisting of a functional fragment of any of the above-mentioned derivatives. Alternatively, portions of the deposited DNA clone, such as the 5' NTR, the polyprotein coding regions, the 3'-NTR or more generally any coding or non-translated region of the HCV genome, can be substituted with a corresponding region from a different HCV genotype to generate a new chimeric infectious clone, or by extension, infectious clones of other isolates and genotypes. For example, an HCV-1b or -2a polyprotein coding region (or consensus polyprotein coding regions) can be substituted for the HCV-H (1a strain) polyprotein coding region of the deposited clone.

Naturally, the present invention further provides an HCV DNA or RNA transcribed from the full length HCV cDNA harbored in the plasmid clones set forth above.

Thus, the specific HCV genome itself provides an excellent starting material for deriving modified variants of HCV, since any modifications will result from changes to authentic virus, rather than artifacts resulting from an accumulation of changes and errors. The HCV DNA clones or RNAs of the invention can be used in numerous methods, or to derive authentic HCV components, as set forth below.

For example, the invention provides a method for identifying a cell line that is permissive for infection with HCV, comprising contacting a cell line in tissue culture with an infectious amount of HCV RNA, e.g., as produced from the plasmid clones recited above, and detecting replication of HCV in cells of the cell line. Naturally, the invention extends as well to a method for identifying an animal that is permissive for infection with HCV, comprising introducing an infectious amount of the HCV RNA, e.g., as produced by the plasmids above, to the animal, and detecting replication of HCV in the animal. By providing authentic infectious HCV, preferably comprising a dominant selectable marker, the invention further provides a method for selecting for HCV with adaptive mutations that permit higher levels of HCV replication in a permissive cell line or animal comprising contacting a cell line in culture, or introducing into an animal, an infectious amount of the HCV RNA, and detecting progressively increasing levels of HCV RNA in the cell line or the animal. In a specific embodiment, the adaptive mutation permits modification of HCV tropism. An intermediate implication of this aspect of the invention is creation of new valid animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof. As noted above, a particular advantage of the invention is that is represents the first successful preparation of an HCV DNA clone capable of initiating a productive infection in animals or cell lines.

Because the HCV DNA, e.g., plasmid vectors, of the invention encode authentic HCV components, expression of such vectors in a host cell line transfected, transformed, or transduced with the HCV DNA can be effected. For example, a baculovirus or plant expression system can be harnessed to express HCV virus particles or components thereof. Thus, a host cell line may be selected from the group consisting of a bacterial cell, a yeast cell, a plant cell, an insect cell, and a mammalian cell.

Because the invention provides, inter alia, infectious HCV RNA, the invention provides a method for infecting an animal with HCV which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared. In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Naturally, the invention extends to an in vitro cell line infected with HCV, wherein the HCV has a genomic RNA sequence as described above. In a specific embodiment, the cell line is a hepatocyte cell line. The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

By providing for insertion of heterologous genes in the HCV nucleic acids, e.g., DNA or RNA vectors, the present invention provides a method for transducing an animal susceptible to HCV infection with a heterologous gene, e.g., for gene therapy or gene vaccination, by administering an amount of the HCV RNA to the animal effective to infect the animal with the HCV RNA. In a specific embodiment, such an HCV vector is generated in HCV harbored in the plasmids, described above.

Also provided is an in vitro cell-free assay system for HCV comprising HCV genomic template RNA of the invention, e.g., as transcribed from a plasmid of the invention as set forth above, functional HCV replicase components, and an isotonic buffered medium comprising ribonucleotide triphosphate bases. These elements provide the replication machinery and raw materials (NTPs).

The authentic HCV viral particles and viral particle proteins are a preferred starting material as HCV antigens. Thus, in a further embodiment, the invention provides a method for producing antibodies to HCV comprising administering an immunogenic amount of HCV virus particles to an animal, and isolating anti-HCV antibodies from the animal. Such antibodies may be used diagnostically, e.g., to detect the presence of HCV, or they may be used therapeutically, e.g., in passive immunotherapy. A further method for producing antibodies to HCV comprises screening a human antibody library for reactivity with HCV virus particles of the invention and selecting a clone from the library that expresses an antibody reactive with the HCV virus particle. Naturally, in addition to generating antibodies, the authentic HCV viral particles and proteins of the invention represent preferred starting materials for an HCV vaccine. Preferably, a vaccine of the invention includes a pharmaceutically acceptable adjuvant.

The authentic materials provided herein provide a method for screening for agents capable of modulating HCV replication in vitro and in vivo. Such methods include administering a candidate agent to an HCV infected animal of the invention, and testing for an increase or decrease in a level of HCV infection or activity compared to a level of HCV infection or activity in the animal prior to administration of the candidate agent, wherein a decrease in the level of HCV infection or activity compared to the level of HCV infection or activity in the animal prior to administration of the candidate agent is indicative of the ability of the agent to inhibit HCV infection or activity. Testing for the level of HCV infection can be performed by measuring viral titer in a tissue sample from the animal; measuring viral proteins in a tissue sample from the animal; or measuring liver enzymes. Alternatively, the HCV genome used to infect the animal may include a heterologous gene operatively associated with an expression control sequence, wherein the heterologous gene and expression control sequence are oriented on the positive-strand nucleic acid molecules, and testing for the level of HCV activity comprises measuring the level of a marker protein in a tissue sample from the animal.

Alternatively, such analysis can proceed in vitro, e.g., by contacting a cell line infected by an infectious HCV RNA of claim with a candidate agent; and testing for an increase or decrease in a level of HCV infection or activity compared to a level of HCV infection or activity in a control cell line or in the cell line prior to administration of the candidate agent; wherein a decrease in the level of HCV infection or activity compared to the level of HCV infection or activity in a control cell line or in the cell line prior to administration of the candidate agent is indicative of the ability of the agent to inhibit HCV infection or activity. Testing for the level of HCV infection in vitro can be performed by measuring viral titer in the cells, culture medium, or both; and measuring viral proteins in the cells, culture medium, or both. Alternatively, when the HCV genome used to infect the cell line includes a heterologous gene operatively associated with an expression control sequence, wherein the heterologous gene and expression control sequence are oriented on the positive-strand nucleic acid molecule, and testing for the level of HCV activity comprises measuring the level of a marker protein in a tissue sample from the animal.

A further method for screening for agents capable of modulating HCV replication involves the cell free system described above. This method comprises contacting the in vitro system of the invention with a candidate agent; and testing for an increase or decrease in a level of HCV replication compared to a level of HCV replication in a control cell system or system prior to administration of the candidate agent; wherein a decrease in the level of HCV replication compared to the level of HCV replication in a control cell line or in the cell line prior to administration of the candidate agent is indicative of the ability of the agent to inhibit HCV infection or activity.

The invention includes a method for preparing an HCV nucleic acid comprising joining from 5' to 3' on the positive-sense DNA a functional 5' non-translated region (NTR) comprising an extreme 5'-terminal conserved sequence, a polyprotein coding region encoding HCV proteins that provide for expression of functional HCV proteins, and a 3' non-translated region (NTR) comprising an extreme 3'-terminal conserved sequence. The method may further comprise determining a consensus sequence for the 5'-NTR, polyprotein coding sequence, and 3'-NTR from a majority sequence of at least three clones of an HCV isolate or genotype. In a specific embodiment, the 3'-NTR comprises an extreme terminal sequence homologous to a DNA having the sequence 5'-GGTGGCTCCATCTTAGCCCTAGT-CACGGCTAGCTGTGAAAGGTCCGTGAGCCG CAT-GACTGCAGAGAGTGCTGATACTGGC-CTCTCTGCTGATCATGT-3' (SEQ ID NO:4). In a further specific embodiment, the HCV nucleic acid has a positive strand sequence as depicted in or corresponding to SEQ ID NO:1 comprising substitution of a homologous region from another HCV isolate or genotype.

The present invention also has significant diagnostic implications. In one embodiment, the invention provides an in vitro method for detecting antibodies to HCV in a biological sample from a subject comprising contacting a biological sample from a subject with HCV virus particles of the invention, e.g., prepared as described above, under conditions that permit binding of HCV-specific antibodies in the sample to the HCV virus particles; and detecting binding of antibodies in the sample to the HCV virus particles, wherein detecting binding of antibodies in the sample to the HCV virus particles is indicative of the presence of antibodies to HCV in the sample.

An alternative in vitro method for detecting the presence of HCV in a biological sample from a subject comprises contacting a cell line permissive for productive HCV infection with a biological sample, wherein the cell line has been modified to contain a transgene that express a reporter gene product expressed under control of a trans-acting factor produced by HCV; and detecting expression of the reporter gene product, wherein detection of expression of the reporter gene product is indicative of the presence of HCV in the biological sample from the subject. In a related embodiment, the invention provides an in vitro method for detecting the presence of HCV in a biological sample from a subject comprising contacting a cell line permissive for productive HCV infection with a biological sample, wherein the cell line has been modified to contain a defective virus transgene, which defective virus transgene will express a reporter gene product at high levels under control of a trans-acting factor produced by HCV; and detecting expression of the reporter gene product, wherein detection of expression of the reporter gene product is indicative of the presence of HCV in the biological sample from the subject. Thus, a significant advantage of the present invention is in providing permissive (or susceptible) cell lines for these in vitro diagnostics. In the foregoing methods, the biological sample is selected from the group consisting of blood, serum, plasma, blood cells, lymphocytes, and liver tissue biopsy.

In a related aspect, the invention also provides a test kit for HCV comprising authentic HCV virus components, and a diagnostic test kit for HCV comprising components derived from an authentic HCV virus.

Thus, a primary object of the present invention has been to provide a DNA encoding infectious HCV.

A related object of the invention is to provide infectious HCV genomic RNA from DNA clones.

Still another object of the invention is to provide attenuated HCV DNA or genomic RNA suitable for vaccine development, which can invade a cell but fails to propagate infectious virus.

Another object of the invention is to provide in vitro and in vivo models of HCV infection for testing anti-HCV (or antiviral) drugs, for evaluating drug resistance, and for testing attenuated HCV viral vaccines.

Still another object of the invention is to provide for expression of HCV virions or virus particle proteins that can be used to identify the HCV receptor, receptor binding antagonists, and in neutralization assays. In addition, expressed HCV virions or virus particle proteins can be used to develop more effective HCV vaccines, with antigens that are structurally identical to or closely related to native HCV.

A further object of the present invention is to provide HCV diagnostics based on the ability to detect infectious HCV using engineered reporter cells.

Yet another object is to provide authentic viral antigens, particularly viral particles, to assay for HCV-specific antibodies or generate HCV-specific antibodies.

These and other objects of the present invention will be elaborated by the drawings and the Detailed Description of the Invention.

BRIEF DESCRIPTION OF THE DRAWINGS

FIG. 1. (PRIOR ART). HCV genome structure, polyprotein processing, and protein features. At the top is depicted the viral genome with the structural and nonstructural protein coding regions, and the 5' and 3' NTRs, and the putative 3' secondary structure. Boxes below the genome indicate proteins generated by the proteolytic processing cascade. Putative structural proteins are indicated by shaded boxes and the nonstructural proteins by open boxes. Contiguous stretches of uncharged amino acids are shown by black bars. Asterisks denote proteins with N-linked glycans but do not necessarily indicate the position or number of sites utilized. Cleavage sites shown are for host signalase (♦), the NS2-3 proteinase (curved arrow), an the NS3-4A serine protease (↓).

FIG. 2. Strategies for expression of heterologous RNAs and proteins using HCV vectors. At the top is a diagram of the positive-polarity RNA virus HCV, which expresses mature viral proteins by translation of a single long ORF and proteolytic processing. The regions of the polyprotein encoding the structural proteins (STRUCTURAL) and the nonstructural proteins (REPLICASE) are indicated as lightly-shaded and open boxes, respectively. Below are shown a number of proposed replication-competent "replicon" expression constructs. The first four constructs (A–D) lack structural genes and would therefore require a helper system to enable packaging into infectious virions. Constructs E–G would not require helper functions for replication or packaging. Darkly shaded boxes indicate heterologous or foreign gene sequences (FG). Translation initiation (aug) and termination signals (trm) are indicated by open triangles and solid diamonds, respectively. Internal ribosomes entry sites (IRES) are shown as boxes with vertical stripes. Constructs A and H illustrate the expression of a heterologous product as an in-frame fusion with the HCV polyprotein. Such protein fusion junctions can be engineered such that processing is mediated either by host or viral proteinases (indicated by the arrow).

FIG. 3. Engineered cell lines for assaying HCV infection. Panel A. Depicts a cells expressing the three silent transgenes. Driven by nuclear promoter elements are: (i) an mRNA expressing a polyprotein protein consisting of HCV NS4A fused to Sindbis virus (Sin) nonstructural protein 4 (nsP4), (ii) a defective Sindbis virus replicon lacking the nsP4 coding region but a subgenomic promoter (arrow) driving expression of a reporter gene (black box), (iii) a defective Sindbis virus RNA lacking the nsPS but containing a ubiquitin-nsP4 fusion gene under the control of the subgenomic RNA promoter. The Sindbis replicton and defective RNA contain all the signals necessary for Sindbis virus-specific RNA replication, transcription and packaging signals (stem loop structure), but are silent in the absence of active nsP4. Panel B. Upon productive infection of a susceptible cells by HCV, the virus is uncoated, translated and begins replication (step 1). This results in the production of active NS3 serine proteinase (step 2) which cleaves at the HCV NS4A-Sindbis nsP4 junction (step 3) to produce active nsP4. nsP4 assembles with the other three Sindbis nsPs to form an active Sindbis replication complex (step 4) which can replicate both Sindbis specific RNAs and lead to transcription from the Sindbis virus subgenomic promoters (step 5). Ub-nsP4 expressed from the subgenomic RNA of the defective RNA is cleaved to form a more active form of the nsP4 polymerase which further amplifies replication and transcription of the Sindbis-specific RNAs (step 6). This leads to high levels of reporter gene expression (step 7).

FIG. 4. Initial set of constructs tested in the chimpanzee model (chimpanzee experiment I). Clones tested in the chimpanzee model before the correct HCV 5' and 3' termini had been cloned and determined. Diagrams indicate the T7 or SP6 promoter elements, the HCV cDNA, and the run-off sites used for production of transcripts terminating with either poly (A) or poly (U).

FIG. 5 (A and B). (A) Regions of HCV H77 amplified for the combinatorial library. At the top, a diagram of the HCV H cDNA is shown with the restriction sites used for cloning the combinatorial library (KpnI and NotI: open box) indicated. The region was cloned into a recipient vector, pTET/HCVΔBglII/5'+3' corr. This recipient vector contains HCV H77 consensus sequences for the 5' and 3' terminal regions, as shown in black. Approximate protein boundaries are also indicated. Below, fragments amplified by RT-PCR from HCV H77 RNA are denoted as A through G. The number above each segment refers to the minimum complexity of the region in the library. Primer pairs and exact positions are given in Tables 2 & 3. (B) Intermediate and final fragments in the assembly of the combinatorial library. As detailed in Tables 2 and 3, infra, intermediates in the assembly PCR process and their approximate locations in the HCV cDNA are shown.

FIG. 6. Assembly PCR method. A general scheme of the assembly PCR method is shown. Specific HCV fragments and primers used in assembly are listed in Table 3.

FIG. 7. Example of complexity determination by PCR of cDNA dilutions. For amplified regions A, D, and G, different dilutions of first-strand cDNA were checked for successful amplification by PCR. Products were analyzed on an agarose gel. From this analysis, the minimum complexity for these regions in the combinatorial library was 80, 10 and 10 molecules of cDNA, respectively.

FIG. 8 (A and B). Analysis of transcription efficiency through long poly (U/UC) tracts. Using conditions for optimal transcription of HCV RNAs in vitro, transcription products from several template DNAs are shown. (A) Lane 1, supercoiled pTET/HCVFL CMR/5' 3' corr. DNA; lane 2, XmnI-digested pTET/HCVFL CMR/5'3' corr. template (predicted size 11740 bases); lane 3, Hpa I-digested pTET/HCVFL CMR/5' 3' corr. template (predicted size ~9600 bases); lanes 4 and 5, transcribed RNA size markers of 11,750 and 9400 bases, respectively. Transcription reactions contained 3 mM UTP and 1 mM A,G, and CTP. (B) Lane 1, BsmI-digested p92/HCVFLlong pU/5'GG DNA (predicted size ~9600 bases); lane 2, XbaI-digested p92/HCVFLlong pU/5'GG DNA (predicted size ~13000 bases). Transcription reactions in panel B contained all four NTPs at 3 mM. In both panels, HCV RNA transcripts terminating in the poly (U/UC) tract would be ~9500 bases in length. Lanes M in both panels are HindIII-digested lambda DNA size markers.

FIG. 9. Sequence alignment for determining of the HCV H77 consensus sequence. An alignment of the HCV H sequences determined is shown. The nucleotide and amino acid sequences at the bottom of each block are for the HCV H CMR prototype sequence. Numbers of the sequenced clones from the combinatorial library are indicated at the left (SEQ ID NOS:19, 20. GenBank refers to the HCV-H sequence determined by Inchaupe et al. [*Proc. Natl. Acad. Sci. USA* 88:10292, 1991; Accession #M67463]. "cons." indicates the HCV H77 consensus sequence [SEQ ID NO:1]. Positions identical to the HCV H CMR sequence are indicated by dots; gaps in certain sequences by dashes. Where differences were found, lower case letters indicate silent nucleotide substitutions; upper case letters indicate that a particular nucleotide substitution results in a coding change.

FIG. 10. Steps in the directed construction of the consensus clone. The diagram indicates the region of each sequenced clone used for directed construction of the consensus clone. Primary fragments from each clone are indicated by hatched boxes, intermediate assembly subclones as open boxes, and the final clones and regions used for assembly of the full-length consensus clone as shaded boxes. Table 4 summarizes the details of the cloning steps.

FIG. 11. Features/markers of the ten full-length clones tested in chimpanzee experiment III. At the top is a schematic of the HCV H77 cDNA consensus RNA. The ten RNA transcripts used for the successful chimpanzee inoculation experiment are diagramed below. Additional 5' nucleotides and "short" versus "long" poly (U/UC) tracts are indicated. All clones/transcripts included two silent nucleotide substitutions as markers; position 899 (C instead of T; indicated by asterisks); and position 5936 (C instead of A; indicated by circled asterisks). Clones with additional 5' bases contained a mutation inactivating the XhoI site at position 514 (triangle). Clones with "short" versus "long" poly (U/UC) tracts were distinguished by A (black dot) versus G at position 8054, respectively.

FIG. 12. Serum samples from inoculated animals do not contain carryover template DNA. As shown, duplicate RNA samples (from 10 μl serum) from the indicated weeks post-inoculation without (lane 1) or with $10^2$ (lanes 2–7) or $10^3$ (lanes 8–14) molecules of added competitor RNA were amplified by RT-PCR with (+) or without (−) enzyme in the reverse transcription step [Kolykhalov et al., *J. Virol.* 70:3363 (1996)]. No specific PCR band was detected in the absence of cDNA synthesis, indicating that the HCV-specific nucleic acid signal was due to RNA. The analysis shown is for chimpanzee #1535, which received the highest level of inoculated HCV RNA and where the template DNA had not been degraded by digestion with DNase I.

FIG. 13. Circulating HCV RNA from inoculated animals is protected from RNAase. In lane 1, 10 μl serum was mixed with $3\times10^5$ molecules of competitor RNA, digested with 0.5 μg RNase A for 15 min at room temperature, extracted with RNAzol and utilized for nested RT-PCR as described in [Kolykhalov, 1996, supra]. For the sample shown in lane 2, competitor RNA was added after lysis with RNAzol (no RNAse treatment). In lane 3, 10 μl serum without competitor RNA was predigested with RNase A prior to extraction with RNAzol as in lane 1. Lane 4 is a negative control for RT-PCR. The experiment demonstrated that HCV RNA containing material from the transfected chimps is RNase-resistant under conditions where an excess of competitor RNA is completely destroyed. The sample analyzed was from chimpanzee #1536 at week 6, in which the RNA titer was $6\times10^6$ molecules/ml.

DETAILED DESCRIPTION OF THE INVENTION

As pointed out above, the present invention advantageously provides an authentic hepatitis C virus (HCV) nucleic acid, e.g., DNA or RNA, clone. A functional HCV nucleic acid of the invention advantageously provides for infection of susceptible animals and cell lines. Despite arduous efforts, infectious HCV has not previously been successfully cloned, thus precluding systematic evaluation of the virus's mechanisms of replication, receptor binding and cell invasion, development of antiviral therapeutic agents using in vitro and in vivo assay systems, and development of sensitive in vitro diagnostic assay systems. In addition, the clones of the invention now enable expression of HCV particles and particle proteins under conditions that permit proper processing, and thus expression of proteins that bear the closest possible structural resemblance to native HCV. Such particles and proteins are preferred for anti-HCV vaccine development. In addition, by identifying the elements of the HCV genome that are necessary for infection, the present inventors advantageously harness the properties of HCV that lead to chronic liver infection for preparation of gene therapy vectors. Such vectors are particularly useful since they target the liver, which is a source of many proteins and thus a desirable organ for expression of a soluble factor to supplement a deficiency in a subject.

The present invention is based, in part, on generation of a functional genotype 1a cDNA clone, which can be used as a basis for preparation of functional clones for other HCV genotypes (e.g., constructed and verified using similar methods). These products have a variety of applications for development of (i) more effective HCV therapies; (ii) HCV vaccines; (iii) HCV diagnostics; and (iv) HCV-based gene expression vectors. Examples of these applications are described below.

The current invention describes the determination of an HCV consensus sequence and the use of this information to construct full-length HCV cDNA clones capable of yielding replication-competent infectious RNA transcripts. The rigorous determination of terminal sequences, including the discovery of highly conserved sequences at the 5' and 3' ends, the use of less error-prone methods for amplifying and assembling HCV cDNA clones, and the assembly of clones reflecting a consensus sequence, all contributed to the success of the present invention.

The term "authentic" is used herein to refer to an HCV nucleic acid, whether a DNA (i.e., cDNA) or RNA, that provides for full genomic replication and production of functional HCV proteins, or components thereof. In a specific embodiment, an authentic HCV nucleic acid is infectious, e.g., in a chimpanzee model or in tissue culture, forms viral particles (i.e., virions), or both. However, an authentic HCV nucleic acid of the invention may also be attenuated, such that it only produces some (not all) functional HCV proteins, or it can productively infect cells without replication in the absence of a helper cell line or plasmid, etc. The authentic HCV exemplified in the present application contains all of the virus-encoded information, whether in RNA elements or encoded proteins, necessary for initiation of an HCV replication cycle that corresponds to replication of wild-type virus in vivo. The specific HCV clones described herein, including the embodiment deposited with the ATCC and variants thereof described or exemplified in this application, represent a preferred starting material for developing HCV therapeutics, vaccines, diagnostics, and expression vectors. In particular, use of the HCV nucleic acids of the invention assures that authentic HCV components are involved, since, unlike the cloned HCVs of the prior art, these components together provide an infectious protein. The specific starting materials described herein, and preferably the deposited plasmid clone harboring authentic HCV cDNA, can be modified as described herein, e.g., by site-directed mutagenesis, to produce a defective or attenuated derivative. Alternatively, sequences from other genotypes or isolates can be substituted for the homologous sequence of the specific embodiments described herein. For example, an authentic HCV nucleic acid of the invention may comprise the consensus 5' and 3' sequences disclosed herein, e.g., on a recipient plasmid, and a polyprotein coding region from another isolate or genotype (either a consensus region or one obtained by very high fidelity cloning) is substituted for the homologous polyprotein coding region of the HCV exemplified herein. In addition, the general characteristics for an authentic HCV as described herein, including but not limited to containing extreme 5' or 3' sequences, or both, containing an ORF that encodes a polyprotein whose cleavage products form functional components of HCV virus particles and RNA replication machinery, and, in a preferred embodiment, incorporate a consensus sequence of a specific isolate or genotype provide for obtaining authentic HCV clones.

In particular, the present invention provides for modifying or "correcting" non-functional HCV clones, e.g., that are incapable of genuine replication, that fail to produce HCV proteins, that do not produce HCV RNA as detected by Northern analysis, or that fail to infect susceptible animals or cell lines in vitro. By comparing an authentic HCV nucleic acid sequence of the invention, e.g., the cDNA sequence of SEQ ID NO:1, with the sequence of the non-functional HCV clone, defects in the non-functional clone can be identified and corrected. All of the methods for modifying nucleic acid sequences available to one of skill in the art to effect modifications in the non-functional HCV genome, including but not limited to site-directed mutagenesis, substitution of the functional sequence from an authentic HCV clone, e.g., of SEQ ID NO:1, for the homologous sequence in the non-functional clone, etc.

The term "consensus sequence" is used herein to refer to a functional HCV genomic sequence, or any portion thereof, including the 5'-NTR polyprotein coding sequence or portion thereof, and 3'-NTR, which is determined by identifying the consensus residues from three or more, preferably six or more, independent clones of a strain or genotype of HCV. In the Examples, infra, 5'-NTR (including some capsid proteins from the polyprotein coding region) and 3'-NTR (including some portion of the genome encoding the C-terminus of the polyprotein) consensus sequences were determined and incorporated in a recipient plasmid (Example 3). Consensus sequences for the majority of the polyprotein coding region from a KpnI site to a NotI site were also determined, as shown in FIG. 8 and Example 4, infra, which yielded a consensus sequence. Insertion of the KpnI and NotI portion of the polyprotein coding sequence are inserted in the recipient plasmid containing consensus 5' and 3' consensus sequences, yields an authentic HCV genomic DNA clone.

The authentic HCV nucleic acid of the invention preferably includes a 5'-NTR extreme conserved sequence comprising the 5'-terminal sequence GCCAGCC, which may have additional bases upstream of this conserved sequence without affecting functional activity of the HCV nucleic acid. In a preferred embodiment, the 5'-GCCAGCC includes from 0 to about 10 additional upstream bases; more preferably it includes from 0 to about 5 upstream bases; more preferably still it includes 0, one, or two upstream bases. In specific embodiments, the extreme 5'-terminal sequence may be GCCAGCC; GGCCAGCC; UGCCAGCC; AGCCAGCC; AAGCCAGCC; GAGCCAGCC; GUGCCAGCC; or GCGCCAGCC, wherein the sequence GCCAGCC is the 5'-terminus of SEQ ID NO:3.

In an authentic HCV nucleic acid of the invention, the 3'-NTR comprises a long poly-pyrimidine region. In positive-strand HCV RNA, the region corresponds to a poly(U)/poly(UC) tract. Naturally, in positive-strand HCV DNA, this is a poly(T)/poly(TC) tract. The Examples, infra, show that the polypyrimidine tract may be of variable length: both short (about 75 bases) and long (133 bases) are effective, although an HCV clone containing a long poly(U/UC) tract is found to be highly infectious. Longer tracts may be found in naturally occurring HCV isolates. Thus, an authentic HCV nucleic acid of the invention may have a variable length polypyrimidine tract.

In a specific embodiment of the invention, plasmid p90/HCVFL [long poly(U)] harboring a cDNA encoding an infectious HCV RNA under control of a phage promoter was deposited with the American Type Culture Collection (ATCC), 12301 Parklawn Drive, Rockville, Md., United States of America on Feb. 13, 1997 on behalf of Washington University School of Medicine for the purpose of compliance with the Budapest Treaty on the International Recognition of the Deposit of Microorganisms for the Purposes of Patent Protection in accordance with its provisions, and the provisions of 37 C.F.R. § 1.801 et seq.

The benefits of this technology are enormous and far reaching. Of immediate significance is use of HCV cDNA from these functional clones as starting material for studies on the functions of individual HCV proteins and RNA elements using biochemical, cell culture, and transgenic animal approaches. The use of functional cDNA will minimize the chances of obtaining negative or misleading results because of errors introduced during cDNA synthesis or PCR-amplification. Such clones will also provide defined starting material for future molecular genetic studies on many aspects of HCV biology in the context of authentic virus replication. Uses relevant to therapy and vaccine development include: (i) the generation of defined HCV virus stocks to develop in vitro and in vivo assays for virus neutralization, attachment, penetration and entry; (ii) structure/function studies on HCV proteins and RNA elements and identification of new antiviral targets; (iii) a systematic survey of cell culture systems and conditions to identify those that support HCV RNA replication and particle release; (iv) production of adapted HCV variants capable of more efficient replication in cell culture; (v) production of HCV variants with altered tissue or species tropism; (vi) establishment of alternative animal models for inhibitor evaluation including those supporting HCV replication; (vii) development of cell-free HCV replication assays; (viii) production of immunogenic HCV particles for vaccination; (ix) engineering of attenuated HCV derivatives as possible vaccine candidates; (x) engineering of attenuated or defective HCV derivatives for expression of heterologous gene products for gene therapy and vaccine application; (xi) utilization of the HCV glycoproteins for targeted delivery of therapeutic agents to the liver or other cell types with appropriate receptors.

Various terms are used herein, which have the following definitions:

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia of other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacile Calmette-Guerin*) and *Corynebacterium parvum*. Preferably, the adjuvant is pharmaceutically acceptable.

In a specific embodiment, the term "about" or "approximately" means within 20%, preferably within 10%, and more preferably within 5% of a given value or range.

The following subsections of the application, which further amplify the foregoing disclosure, are provided for convenience and not by way of limitation.

Functional Full-length Clones for Other HCV Isolates and Genotypes

Using the approaches described here, functional full-length clones for the other HCV genotypes can be built and utilized for biological studies and antiviral screening and evaluation. In this extension of the invention, libraries can be constructed using RNA from single-exposure patients with high RNA titers (greater than $10^6$/ml) and known clinical history. A consensus sequence for the isolate can be generated from the sequences of individual clones in the library. New recipient plasmids containing a promoter, 5' and 3' terminal consensus sequences (either determined for that isolate or from a different isolate e.g., HCV-H77), and a 3' restriction site for production of run-off transcripts can be constructed.

As less error-prone methods emerge, screening of a limited number of clones from combinatorial libraries may yield function clones. Alternatively, as described here, sequence of derived from multiple clones and directed assembly can be used to produce functional consensus clones.

Thus, the present invention contemplates isolation of other HCV genomic sequences, or consensus genomic sequences. In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait et. 1984); *Nucleic Acid Hybridization* [B. D. Hames & S. J. Higgins eds. (1985)]; *Transcription and Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

It should be appreciated that the terms HCV sequence, such as the "3' terminal sequence element," "3' terminus," "3' sequence element," are meant to encompass all of the following sequences: (i) an RNA sequence of the positive-sense genome RNA; (ii) the complement of this RNA sequence, i.e., the HCV negative-sense RNA; (iii) the DNA sequence corresponding to the positive-sense sequence of the RNA element; and (iv) the DNA sequence corresponding to the negative-sense sequence of the RNA element. Accordingly, nucleotide sequences displaying substantially equivalent or altered properties are likewise contemplated. These modifications may be deliberate, for example, such as modifications obtained through site-directed mutagenesis, or may be accidental, such as those obtained through mutations in hosts that are producers of the complex or its named subunits.

A "vector" is a replicon, such as a plasmid, phage, or cosmid, to which another DNA (or RNA) segment may be joined so as to bring about the replication of the attached segment. A "cassette" refers to a segment of DNA RNA that can be inserted into a vector at specific restriction sites. The segment of DNA or RNA encodes a polypeptide or RNA of interest, and the cassette and restriction sites are designed to ensure insertion of the cassette in the proper reading frame for transcription and translation.

Transcriptional and translational control sequences are DNA or RNA regulatory sequences, such as promoters, enhancers, polyadenylation signals, terminators, IRES elements, and the like, that provide for the expression of a coding sequence in a host cell. A coding sequence is "under the control of" or "operably (also operatively) associated with" transcriptional and translational control sequences in a cell when RNA polymerase transcribes the coding sequence into RNA. RNA sequences can also serve as expression control sequences by virtue of their ability to modulate translation, RNA stability, RNA replication, and RNA transcription (for RNA viruses).

A "promoter sequence" is a DNA or RNA regulatory region capable of binding RNA polymerase in a cell and initiating transcription of a downstream (3' direction) coding or noncoding sequence. Thus, promoter sequences can also be used to refer to analogous RNA sequences or structures of similar function in RNA virus replication and transcription. Preferred promoters for cell-free or bacterial expression of infections HCV DNA clones of the invention are the phage promoters T7, T3, and SP6. Alternatively, a nuclear promoter, such as cytomegalovirus immediate-early promoter, can be used. Indeed, depending on the system used, expression may be driven from a eukaryotic, prokaryotic, or viral promoter element. Promoters for expression of HCV RNA can provide for capped or uncapped transcripts.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) [Reeck et al., *Cell* 50:667 (1987)]. Such proteins (and their encoding genes) have a high degree of sequence similarity. The term "sequence similarity" in all its grammatical forms refers to the degree of identity or correspondence between nucleic acid or amino acid sequences of proteins that may or may not share a common evolutionary origin [see Reeck et al., supra]. However, in common usage and in the instant application, the term "homologous," when modified with an adverb such as "substantially" or "highly," may refer to sequence similarity and not a common evolutionary origin.

In a specific embodiment, two DNA or RNA sequences are "homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The term "corresponding to" in relation to nucleic acid or amino acid structure is used herein to refer similar or homologous sequences, whether the exact position is identical or different from the molecule to which the similarity or homology is measured. A nucleic acid or amino acid sequence alignment may include gaps. Thus, the term "corresponding to" refers to the sequence similarity or regions of homology, and not the numbering of the amino acid residues or nucleotide bases.

HCV genomic nucleic acids can be isolated from any source of infectious HCV, particularly from tissue samples (blood, plasma, serum, liver biopsy, leukocytes, etc.) from an infected human or simian, or other permissive animal species. Methods for obtaining genomic HCV clones or portions thereof are well known in the art, as described above [see, e.g., Sambrook et al., 1989, supra]. HCV isolates, including polyprotein coding region sequences, are described, for example, in International Patent Publication WO 89/04669, published Jun. 1, 1989 by Houghton et al.; International Patent Publication WO 90/11089, published Oct. 4, 1990 by Houghton et al.; U.S. Pat. No. 5,350,671, issued Sep. 27, 1994 to Houghton et al.; U.S. Pat. No.

5,372,928, issued Dec. 13, 1994 to Miyamura et al.; European Patent Application No. EP 0 521 318 A2, published Jan. 7, 1993 for Cho et al.; and European Patent Application No. EP 0 510 952 A1, published Oct. 28, 1992, each of which is incorporated herein by reference in its entirety. Representative genotypes further include, but are by no means restricted to, other 1a isolates, 1b, 1c, 2a, 2b, 2c, 3a, etc. [Bukh et al., (1995) supra; Simmonds, *Hepatology* 21: 570–83 (1995); Simmonds et al., *Hepatology* 19: 1321–1324 (1994); Simmonds et al., *J. Gen. Virol.* 77: 3013–3024 (19960]. For many subtypes and genotypes, enough sequence data are available to design primers for RT/PCR and PCR assembly.

In the molecular cloning genomic HCV RNA or DNA, DNA fragments are generated, e.g., by reverse transcription into cDNA and PCR. These fragments may be assembled to form a full length sequence. Preparation of many such fragments provides a combinatorial library of HCV clones. Such a library may yield an infectious clone; more likely, the consensus sequence should be determined by comparing the sequences of all or a significant number of clones from such a library. Enough clones should be evaluated so that a majority of bases at any divergent position are identical. Thus, a consensus may be determined by analyzing the sequence of at least three clones, preferably about five clones, and more preferably six or more clones. Naturally, the more error-prone the cloning method, the greater the number of clones that should be sequenced to yield an authentic HCV consensus sequence.

The consensus sequence can then be used to prepare an infectious HCV DNA clone. The fidelity of the resulting clones is preferably established by sequencing. However, selection can be carried out on the basis of the properties of the clone, e.g., if the clone encodes an infectious HCV RNA. Thus, successful preparation of an infectious HCV DNA clone may be detected by assays based on the physical, pathological, or immunological properties of an animal or cell culture transfected or infected with the clone. For example, cDNA clones can be selected that produce an HCV virion or virus particle protein that, e.g., has similar or identical physical-chemical, electrophoretic migration, isoelectric focusing, or non-equilibrium pH gel electrophoresis behavior, proteolytic digestion maps, or antigenic properties as known for native HCV or HCV virus particle proteins.

Components of functional HCV cDNA clones. Components of the functional HCV cDNA described in this invention can be used to develop cell-free, cell culture, chimeric virus, and animal-based screening assays for known or newly identified HCV antiviral targets as described infra. Examples of known or suspected targets and assays include [see Houghton, In "Fields Virology" (B. N. Fields, D. M. Knipe and P. M. Howley, Eds.), Vol. pp. 1035–1058. Raven Press, New York (1996); Rice, (1996) supra; Rice et al., *Antiviral Therapy* 1, Suppl. 4, 11–17 (1997); Shimotohno, *Hepatology* 21,:887–8 (1995) for reviews], but are not limited to, the following:

The highly conserved 5' NTR, which contains elements essential for translation of the incoming HCV genome RNA, is one target. It is also likely that this sequence, or its complement, contains RNA elements important for RNA replication and/or packaging. Potential therapeutic strategies include: antisense oligonucleotides (supra); trans-acting ribozymes (supra); RNA decoys; small molecule compounds interfering with the function of this element (these could act by binding to the RNA element itself or to cognate viral or cellular factors required for activity).

Another target is the HCV C (capsid or core) protein which is highly conserved and is associated with the following functions: RNA binding and specific encapsidation of HCV genome RNA; transcriptional modulation of cellular [Ray et al., *Virus Res.* 37: 209–220 (1995)] and other viral [Shih et al., *J. Virol.* 69: 1160–1171 (1995); Shih et al., *J. Virol.* 67: 5823–5832 (1993)] genes; cellular transformation [Ray et al., *J. Virol.* 70: 4438–4443 (1996a)]; prevention of apoptosis [Ray et al., *Virol.* 226: 176–182 (1996b)]; modulation of host immune response through binding to members of the TNF receptor superfamily [Matsumoto et al., *J. Virol.* 71: 1301–1309 (1997)].

The E1, E2, and E2-p7 glycoprotein which form the components of the virion envelope and are targets for potentially neutralizing antibodies. Key steps for intervention include: signal peptidase mediated cleavage of these precursors from the polyprotein [Lin et al., (1994a) supra]; ER assembly of the E1E2 glycoprotein complex and association of these proteins with cellular chaperones and folding machinery [Dubuisson et al., (1994) supra; Dubuisson and Rice, *J. Virol.* 70: 778–786 (1996)]; assembly of virus particles including interactions between the nucleocapsid and virion envelope; transport and release of virus particles; the association of virus particles with host components such as VLDL [Hijikata et al., (1993) supra; Thomssen et al., (1992) supra; Thomssen et al., *Med. Microbiol. Immunol.* 182: 329–334 (1993)] which may play a role in evasion of immune surveillance or in binding and entry of cells expressing the LDL receptor; conserved and variable determinants in the virion which are targets for neutralization by antibodies or which bind to antibodies and facilitate immune-enhanced infection of cells via interaction with cognate Fc receptors; conserved and variable determinants in the virion important for receptor binding and entry; virion determinants participating in entry, fusion with cellular membranes, and uncoating the incoming viral nucleocapsid.

The NS2-3 autoprotease, which is required for cleavage at the ⅔ site is a further target.

The NS3 serine protease and NS4A cofactor which form a complex and mediate four cleavages in the HCV polyprotein [see Rice, (1997) supra for review) is yet another suitable target. Targets include the serine protease activity itself; the tetrahedral $Zn^{2+}$ coordination site in the C-terminal domain of the serine protease; the NS3-NS4A cofactor interaction; the membrane association of NS4A; stabilization of NS3 by NS4A; transforming potential of the NS3 protease region [Sakamuro et al., *J Virol* 69: 3893–6 (1995)].

The NS3 RNA-simulated NTPase [Suzich et al., (1993) supra], RNA helicase [Jin and Peterson, *Arch Biochem Biophys* 323: 47–53 (1995); Kim et al., *Biochem. Biophys. Res. Commun.* 215: 160–6 (1995)], and RNA binding [Kanai et al., *FEBS Lett* 376: 221–4 (1995)] activities; the NS4A protein as a component of the RNA replication complex of as yet undefined function; the NS5A protein, another presumed replication component, is phosphorylated predominantly on serine residues [Tanji et al., *J. Virol.* 69: 3980–3986 (1995)] are all targets for drug development. Possible characteristics of the latter which could be targets for therapy include the kinase responsible for NS5A phosphorylation and its interaction with NS5A; the interaction with NS5A and other components of the HCV replication complex.

The NS5B RDRP, which is the enzyme responsible for the actual synthesis of HCV positive and negative-strand RNAs, is another target. Specific aspects of its activity include the polymerase activity itself [Behrens et al., *EMBO J.* 15: 12–22 (1996)]; interactions of NS5B with other replicase components, including the HCV RNAs; steps involved in the initiation of negative- and positive-strand RNA synthesis; phosphorylation of NS5B [Hwang et al., *Virology* 227: 438 (1997)].

Other targets include structural or nonstructural protein functions important for HCV RNA replication and/or modulation of host cell function. Possible hydrophobic protein components capable of forming channels important for viral entry, egress or modulation of host cell gene expression may be targeted.

The 3' NTR, especially the highly conserved elements (poly (U/UC) tract; 98-base terminal sequence) can be targeted. Therapeutic approaches parallel those described for the 5' NTR, except that this portion of the genome is likely to play a key role in the initiation of negative-strand synthesis. It may also be involved in other aspects of HCV RNA replication, including translation, RNA stability, or packaging.

The functional HCV cDNA clones encode all of the viral proteins and RNA elements required for RNA packaging. These elements can be targeted for development of antiviral compounds. Electrophoretic mobility shift, UV cross-linking, filter binding, and three-hybrid [SenGupta et al., *Proc. Natl. Acad. Sci. USA* 93: 8496–8501 (1996)] assays can be used to define the protein and RNA elements important for HCV RNA packaging and to establish assays to screen for inhibitors of this process. Such inhibitors might include small molecules or RNA decoys produced by selection in vitro [Gold et al., (1995) supra].

Complex HCV libraries can be prepared using PCR sherffling, or by incorporating randomized sequences, such as are generated in "peptide display" libraries. Using the "phage method" [Scott and Smith, 1990, *Science* 249: 386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). As noted above, and exemplified infra, clones from such libraries can be used to generate a consensus genomic sequence.

Due to the degeneracy of nucleotide coding sequences, other DNA sequences that encode substantially the same amino acid sequence as an HCV polyprotein coding region may be used in the practice of the present invention. These include but are not limited to homologous genes from other species, and nucleotide sequences comprising all or portions of HCV polyprotein genes altered by the substitution of different codons that encode the same amino acid residue within the sequence, thus producing a silent change. Such silent changes permit creation of genomic markers, which can be used to identify a particular infectious isolate in a multiple infection animal model. Likewise, the HCV genomic derivatives of the invention include, but are not limited to, those containing, as a primary amino acid sequence, all or part of the amino acid sequence of an HCV polyprotein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

In another embodiment, an authentic HCV clone can be modified to introduce amino acid substitutions that reduce or eliminate protein function. An authentic HCV clone can also be modified to introduce amino acid substitutions that alter viral tropism.

Moreover, since HCV lacks proofreading activity, the virus itself readily mutates, forming mutant "quasi-species" of HCV that are also contemplated as within the present invention. Such mutations are easily identified by sequencing isolates from a subject, as detailed herein.

The clones encoding HCV derivatives and analogs of the invention can be produced by various methods known in the art. The manipulations which result in their production can occur at the gene or protein level. For example, the cloned HCV genome sequence can be modified by any of numerous strategies known in the art [Sambrook et al., 1989, supra]. The genomic sequence can be cleaved at appropriate sites with restriction endonuclease(s), followed by further enzymatic modification if desired, isolated, and ligated in vitro. Alternatively, genomic fragments can be joined, e.g., with PCR, to create an HCV genome. In the production of the genomic nucleic acid derivative or analog of HCV, care should be taken to ensure that the modified genome remains within the same translational reading frame as the native HCV genome, uninterrupted by translational stop signals, in the region where the desired activity is encoded.

The HCV polyprotein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations provide for modification of the functional activity of the HCV, e.g., to attenuate viral activity, or create a defective virus, as set forth infra. Any technique for mutagenesis known in the art can be used, including but not limited to, in vitro site-directed mutagenesis [Hutchinson, C., et al., 1978, J. Biol. Chem. 253:6551: Zoller and Smith, 1984, DNA 3:479–488; Oliphant et al., 1986, Gene 44:177; Hutchinson et al., 1986, Proc. Natl. Acad. Sci. U.S.A. 83:710], use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61–70].

Adaptation of HCV for more efficient replication in cell culture or alternative hosts. As mentioned earlier, HCV replication in cell culture is inefficient. The engineering of dominant selectable markers under the control of the HCV replication machinery can also be used to select for adaptive mutations in the HCV replication machinery. Such adaptive mutations could be manifested, but are not restricted to: (i) altering the tropism of HCV RNA replication; (ii) altering viral products responsible for deleterious effects on host cells; (iii) increasing or decreasing HCV RNA replication efficiency; (iv) increasing or decreasing HCV RNA packaging efficiency and/or assembly and release of HCV particles; (v) altering cell tropism at the level of receptor binding and entry. Even if the sequence of an HCV original cDNA clone is incompatible with establishing replication in a particular cell type, mutations occurring during in vitro transcription, during the initial stages of HCV-mediated RNA synthesis, or incorporated in the template DNA by a variety of chemical or biological methods, supra, may allow replication in a particular cellular environment or animal host. The engineered dominant selectable marker, whose expression is dependent upon productive HCV RNA replication, can be used to select for adaptive mutations in either the HCV replication machinery or the transfected host cell, or both.

Chimeric HCV clones. Components of these functional clones can also be used to construct chimeric viruses for assay of HCV gene functions and inhibitors thereof [Filocamo et al., *J. Virol.* 71: 1417–1427 (1997); Hahm et al., *Virology* 226: 318–326 (1996); Lu and Wimmer, *Proc Natl Acad Sci USA* 93: 1412–7 (1996)]. In one such extension of the invention, functional HCV elements such as the 5' IRES, proteases, RNA helicase, polymerase, or 3' NTR are used to create chimeric derivatives of BVDV whose productive replication is dependent on one or more of these HCV elements. Such BVDV/HCV chimeras can then be used to screen for and evaluate antiviral strategies against these functional components.

In addition, dominant selectable markers can be used to select for mutations in the HCV replication machinery that allow higher levels of RNA replication or particle formation. In one example, engineered HCV derivatives expressing a mutant form of DHFR can be used to confer resistance to methotrexate (MTX). As a dominant selectable marker, mutant DHFR is inefficient since nearly stoichiometric amounts are required for MTX resistance. By successively increasing concentrations of MTX in the medium, increased quantities of DHFR will be required for continued survival of cells harboring the replicating HCV RNA. This selection scheme, or similar ones based on this concept, can result in the selection of mutations in the HCV RNA replication machinery allowing higher levels of HCV RNA replication and RNA accumulation. Similar selections can be applied for mutations allowing production of higher yields of HCV particles in cell culture or for mutant HCV particles with altered cell tropism. Such selection schemes involve harvesting HCV particles from culture supernatants or after cell disruption and selecting for MTX-resistant transducing particles by reinfection of naive cells.

The identified and isolated genomic RNA can be reverse transcribed into its cDNA. cDNA could also be made by "long" PCR to include the promoter and run-off site, or by using 3'-terminal consensus sequence-specific primers for insertion in an appropriate recipient vector. Any of these cDNAs may be inserted into an appropriate cloning vector, e.g., which comprises consensus 5'- and 3'-NTRs, along with a suitable promoter and 3'-runoff sequence. A clone that includes a primer and run-off sequence can be used directly for production of functional HCV RNA. A large number of vector-host systems known in the art may be used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, pTET, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

Expression of HCV RNA and Polypeptides

The HCV DNA, which codes for HCV RNA and HCV proteins, particularly HCV RNA replicase or virion proteins, can be inserted into an appropriate expression vector, i.e., a vector which contains the necessary elements for the transcription and translation of the inserted protein-coding sequence. Such elements are termed herein a "promoter." Thus, the HCV DNA of the invention is operationally (or operably) associated with a promoter in an expression vector of the invention. An expression vector also preferably includes a replication origin. The necessary transcriptional and translational signals can be provided on a recombinant expression vector. In a preferred embodiment for in vitro synthesis of functional RNAs, the T7, T3, or SP6 promoter is used.

Potential host-vector systems include but are not limited to mammalian cell systems infected with virus recombinant (e.g., vaccinia virus, adenovirus, Sindbis virus, Semliki Forest virus, etc.); insect cell systems infected with recombinant viruses (e.g., baculovirus); microorganisms such as yeast containing yeast vectors; plant cells; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The cell into which the recombinant vector comprising the HCV DNA clone has been introduced is cultured in an appropriate cell culture medium under conditions that provide for expression of HCV RNA or such HCV proteins by the cell. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of HCV RNA or protein may be controlled by any promoter/enhancer element known in the art, but these regulatory elements must be functional in the host selected for expression. Promoters which may be used to control expression include, but are not limited to, the SV40 early promoter region (Benoist and Chambon, 1981, Nature 290: 304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 73:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318: 533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX [Smith et al., 1988, Gene 67:31–40], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like known in the art.

In addition to the preferred sequencing analysis, expression vectors containing an HCV DNA clone of the invention can be identified by four general approaches: (a) PCR amplification of the desired plasmid DNA or specific mRNA, (b) nucleic acid hybridization, (c) presence or absence of selection marker gene functions, (d) analysis with appropriate restriction endonucleases and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to the HCV DNA. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In the fourth approach, recombinant expression vectors are identical by digestion with appropriate restriction enzymes. In the fifth approach, recombinant expression vectors can be identified by assaying for the activity, biochemical, or immunological characteristics of the gene product expressed by the recombinant, e.g., HCV RNA, HCV virions, or HCV viral proteins.

For example, in a baculovirus expression systems, both non-fusion transfer vectors, such as but not limited to pVL941 (BamHI cloning site; Summers), pVL1393 (BamHI, SmaI, XbaI, EcoRI, NotI, XmaIII, BglII, and PstI cloning site; Invitrogen), pVL1392 (BglII, PstI, NotI, XmaIII, EcoRI, XbaI, SmaI, and BamHI cloning site; Summers and Invitrogen), and pBlueBacIII (BamHI, BglII, PstI, NcoI, and HindIII cloning site, with blue/white recombinant screening possible; Invitrogen), and fusion transfer vectors, such as but not limited to pAc700 (BamHI and KpnI cloning site, in which the BamHI recognition site begins with the initiation codon; Summers), pAc701 and pAc702 (same as pAc700, with different reading frames), pAc360 (BamHI cloning site 36 base pairs downstream of a polyhedrin initiation codon; Invitrogen(195)), and pBlueBacHisA, B, C (three different reading frames, with BamHI, BglII, PstI, NcoI, and HindIII cloning site, an N-terminal peptide for ProBond purification, and blue/white recombinant screening of plaques; Invitrogen) can be used.

Examples of mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; [see Kaufman, *Current Protocols in Molecular Biology*, 16.12 (1991)]. Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamHI, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHI cloning site, inducible methallothionein IIa gene promoter, hygromycin selectable marker: Invitrogen), pREP8 (BamHI, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Regulatable mammalian expression vectors, can be used, such as Tet and rTet [Gossen and Bujard, *Proc. Natl. Acad. Sci. USA* 89:5547–51 (1992); Gossen et al., *Science* 268:1766–1769 (1995)]. Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors [see, Kaufman (1991) supra] for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Examples of yeast expression systems include the non-fusion pYES2 vector (XbaI, SphI, ShoI, NotI, GstXI, EcoRI, BstXI, BamHI, SacI, KpnI, and HindIII cloning sit; Invitrogen) or the fusion pYESHisA, B, C (XbaI, SphI, ShoI, NotI, BstXI, EcoRI, BamHI, SacI, KpnI, and HindIII cloning site, N-terminal peptide purified with ProBond resin and cleaved with enterokinase; Invitrogen), to mention just two, can be employed according to the invention.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Expression in yeast can produce a glycosylated product. Expression in eukaryotic cells can increase the likelihood of "native" glycosylation and folding of an HCV protein. Moreover, expression in mammalian cells can provide a tool for reconstituting, or constituting, native HCV virions or virus particle proteins.

Furthermore, different vector/host expression systems may affect processing reactions, such as proteolytic cleavages, to a different extent.

A variety of transfection methods, useful for other RNA virus studies, are enabled herein. Examples include microinjection, cell fusion, calcium-phosphatecationic liposomes such as lipofectin [Rice et al., New Biol. 1:285–296 (1989); see "HCV-based Gene Expression Vectors", infra], DE-dextran [Rice et al., J. Virol. 61: 3809–3819 (1987)], and electroporation [Bredenbeek et al., J. Virol. 67: 6439–6446 (1993); Lijeström et al., J. Virol. 65: 4107–4113 (1991)]. Scrape loading [Kumar et al., Biochem. Mol. Biol. Int. 32: 1059–1066 (1994)] and ballistic methods [Burkholder et al., J. Immunol. Meth. 165: 149–156 (1993)] may also be considered for cell types refractory to transfection by these other methods. A DNA vector transporter may be considered [see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990].

In Vitro Infection with HCV

Identification of cell lines supporting HCV replication. An important aspect of the invention is a method it provides for developing new and more effective anti-HCV therapy by conferring the ability to evaluate the efficacy of different therapeutic strategies using an authentic and standardized in vitro HCV replication system. Such assays are invaluable before moving on to trials using rare and valuable experimental animals, such as the chimpanzee, or HCV-infected human patients. As mentioned in the Background of the Invention, at best only trace levels of HCV replication have been observed in cell culture and most of the systems reported are not amenable for drug screening or evaluation. The most promising system reported to date is the HTLV1-infected MT-2C T-lymphocyte subline, which has been shown to support HCV replication with a signal:noise ratio of about 1000:1 [Mizutani et al., J. Virol., 70: 7219–23 (1996)]. It should be noted, however, that replication in this system is initiated by infection with a patient inoculum. Such a system may have utility, but will be limited by differences between inocula which affect cell tropism and the detection of replication.

The HCV infectious clone technology can be used to establish in vitro and in vivo systems for analysis of HCV replication and packaging. These include, but are not restricted to, (i) identification or selection of permissive cell types (for RNA replication, virion assembly and release); (ii) investigation of cell culture parameters (e.g., varying culture conditions, cell activation, etc.) or selection of adaptive mutations that increase the efficiency of HCV replication in cell cultures; and (iii) definition of conditions for efficient production of infectious HCV particles (either released into the culture supernatant or obtained after cell disruption). These and other readily apparent extensions of the invention have broad utility for HCV therapeutic, vaccine, and diagnostic development.

General approaches for identifying permissive cell types are outlined below. Optimal methods for RNA transfection (see also, supra) vary with cell type and are determined using RNA reporter constructs. These include, for example, bicistronic RNAs [Wang et al., J. Virol. 67: 3338–44 (1993)] with the structure 5'-CAT-HCV IRES-LUC-3' which are used both to optimize transfection conditions (CAT; chloramphenicol acetyltransferase activity) and to determine if the cell type is permissive for HCV IRES-mediated translation (LUC; luciferase activity). For actual HCV RNA transfection experiments, cotransfection with a 5' capped luciferase reporter RNA [Wang et al., (1993) supra] provides an internal standard for productive transfection and translation. Examples of cell types potentially permissive for HCV replication include, but are not restricted to, primary human cells (e.g., hepatocytes, T-cells, B-cells, foreskin fibroblasts) as well as continuous human cell lines (e.g., HepG2, Huh7, HUT78, HPB-Ma, MT-2, MT-2C, and other HTLV-I and HTLV-II infected T-cell lines, Namalawa, Daudi, EBV-transformed LCLs). In addition, cell lines of other species, especially those which are readily transfected with RNA and permissive for replication of flaviviruses or pestiviruses (e.g., SW-13, Vero, BHK-21, COS, PK-15, MBCK, etc.), can be tested. Cells are transfected using a method as described supra.

For replication assays, RNA transcripts are prepared using the functional clone and the corresponding non-functional, e.g., ΔGDD (see Examples) derivative, is used as a negative control for persistence of HCV RNA and antigen in the absence of productive replication. Template DNA (which complicates later analyses) is removed by repeated cycles of DNaseI treatment and acid phenol extraction followed by purification by either gel electrophoresis or gel filtration (less than one molecule of amplifiable DNA per $10^9$ molecules of transcript RNA). DNA-free RNA transcripts will be mixed with LUC reporter RNA and used to transfect cell cultures using optimal conditions determined above. After recovery of the cells, RNaseA is added to the media to digest excess input RNA and the cultures incubated for various periods of time. An early timepoint (~1 day post-transfection) will be harvested and analyzed for LUC activity (to verify productive transfection) and positive-strand RNA levels in the cells and supernatant (as a baseline). Samples are collected periodically for 2–3 weeks and assayed for positive-strand RNA levels by QC-RT/PCR [see Kolykhalov et al., (1996) supra]. Cell types showing a clear and reproducible difference between the intact infectious transcript and the non-functional derivative, e.g., ΔGDD deletion, control can be subjected to more thorough analyses to verify authentic replication. Such assays include measurement of negative-sense HCV RNA accumulation by QC-RT/PCR [Gunji et al., (1994) supra; Lanford et al., *Virology* 202: 606–14 (1994)]. Northern-blot hybridization, or metabolic labeling [Yoo et al., (1995) supra] and single cell methods, such as in situ hybridization [ISH; Gowans et al., In "Nucleic Acid Probes" (R. H. Symons, Eds.), Vol. pp. 139–158. CRC Press, Boca Raton, (1989)], in situ PCR [followed by ISH to detect only HCV-specific amplification products; Haase et al., *Proc. Natl. Acad. Sci. USA* 87: 4971–4975 (1990)], and immunohistochemistry.

HCV particles for studying virus-receptor interactions. In combination with the identification of cell lines which are permissive for HCV infection and replication, defined HCV stocks produced using the infectious clone technology can be used to evaluate the interaction of the HCV with cellular receptors. Assays can be set up which measure binding of the virus to susceptible cells or productive infection, and then used to screen for inhibitors of these processes.

Identification of cell lines for characterization of HCV receptors. Cell lines permissive for HCV RNA replication, as assayed by RNA transfection, can be screened for their ability to be infected by the virus. Cell lines permissive for RNA replication but which cannot be infected by the homologous virus may lack one or more host receptors required for HCV binding and entry. Such cells provide valuable tools for (i) functional identification and molecular cloning of HCV receptors and co-receptors; (ii) characterization of virus-receptor interactions; and (iii) developing assays to screen for compounds or biologics (e.g., antibodies, SELEX RNAs [Bartel and Szostak, In "RNA-protein interactions" (K. Nagai and I. W. Mattaj, Eds.), Vol. pp. 82–102, IRL Press, Oxford (1995); Gold et al., *Annu. Rev. Biochem.* 64: 763–797 (1995)], etc.) that inhibit these interactions.

Once defined in this manner, these HCV receptors serve not only as therapeutic targets but may also be expressed in transgenic animals rendering them susceptible to HCV infection [Koike et al., *Dev Biol Stand* 78: 101–7 (1993); Ren and Racaniello, *J Virol* 66: 296–304 (1992)]. Such transgenic animal models supporting HCV replication and spread have important applications for evaluating anti-HCV drugs.

The ability to manipulate the HCV glycoprotein structure using infectious clone technology, or by genetic manipulations as described supra, may also be used to create HCV variants with altered receptor specificity. In one example, HCV glycoproteins can be modified to express a heterologous binding domain for a known cell surface receptor. The approach should allow the engineering of HCV derivatives with altered tropism and perhaps extend infection to non-chimeric small animal models.

Alternative approaches for identifying permissive cell lines. Besides using the unmodified HCV RNA transcripts derived from functional clones, these functional HCV clones can be engineered to provide selectable markers for HCV replications. For instance, genes encoding dominant selectable markers can be expressed as part of the HCV polyprotein, or as separate cistrons located in permissive regions of the HCV RNA genome. Such engineered derivatives [see Bredenbeek and Rice, *Semin. Virol.* 3: 297"310 (1992) for review] have been successfully constructed for other RNA viruses such as Sindbis virus [Frolov et al., *Proc. Natl. Acad. Sci. U.S.A.* 93: 11371–11377 (1996)] or the flavivirus Kunjin [Khromykh and Westaway, *J. Virol.* 71: 1497–1505 (1997)]. Examples of selectable markers for mammalian cells include, but are not limited to, the genes encoding dihydrofolate reductase (DHFR; methotrexate resistance), thymidine kinase (tk; methotrexate resistance), puromycin acetyl transferase (pac; puromycin resistance), neomycin resistance (neo; resistance to neomycin or G418), mycophenolic acid resistance (gpt), hygromycin resistance, and resistance to zeocin. Other selectable markers can be used in different hosts such as yeast (ura3, his3, leu2, trp1). Strategies for functional expression of heterologous genes have been described [see Bredenbeek and Rice, (1992) supra for review]. Examples include (FIG. 2): (i) in-frame insertion into the viral polyprotein with cleavage(s) to produce the selectable marker protein mediated by cellular or viral proteases; (ii) creation of separate cistrons using engineered translational start and stop signals. Examples include, but are not restricted to, the use of internal ribosome entry site (IRES) RNA elements derived from cellular or viral mRNAs [Jang et al., *Enzyme* 44: 292–309 (1991); Macejak and Sarnow, *Nature* 353: 90–94 1991); Molla et al., *Nature* 356: 255–257 (1992)]. In a particular manifestation, a cassette including the EMCV IRES element and the neomycin resistance gene is inserted in the HCV H77 3' NTR hypervariable region. Transcribed RNAs are used to transfect human hepatocyte or other cell lines and the antibiotic G418 used for selecting resistant cell populations. In one manifestation of this approach, transcripts from pHCVFL/3'EM-CVIRESneo (infra) are used to transfect a variety of different cell lines.

Alterations of the HCV cDNA can be made to produce lines expressing convenient assayable markers as indirect indicators of HCV replication. Such self-replicating RNAs might include the entire HCV genome RNA or RNA replicons, where regions non-essential for RNA replication have been deleted. Assayable genes might include a second dominant selectable marker, or those encoding proteins with convenient assays. Examples include, but are not restricted to, β-galactosidase, β-glucuronidase, firefly or bacterial luciferase, green fluorescent protein (GFP) and humanized derivatives thereof, cell surface markers, and secreted markers. Such products are either assayed directly or may activate the expression or activity of additional reporters.

Animal Models for HCV Infection and Replication

In addition to chimpanzees, the present invention permits development of alternative animal models for studying HCV replication and evaluating novel therapeutics. Using the authentic HCV cDNA clones described in this invention as starting material, multiple approaches can be envisioned for establishing alternative animal models for HCV replication. In one manifestation, well-defined HCV stocks, produced by transfection of chimpanzees or by replication in cell culture, could be used to inoculate immunodeficient mice harboring human tissues capable of supporting HCV replication. An example of this art is the SCID:Hu mouse, where mice with a severe combined immunodeficiency are engrafted with various human (or chimpanzee) tissues, which could include, but are not limited to, fetal liver, adult liver, spleen, or peripheral blood mononuclear cells. Besides SCID mice, normal irradiated mice can serve as recipients for engraftment of human or chimpanzee tissues. These chimeric animals would then be substrates for HCV replication after either ex vivo or in vivo infection with defined virus-containing inocula.

In another manifestation, adaptive mutations allowing HCV replication in alternative species may produce variants which will be permissive for replication in these animals. For instance, adaptation HCV for replication and spread in either continuous rodent cell lines or primary tissues (such as hepatocytes) enables the virus to replication in small rodent models. Alternatively, complex libraries of HCV variants created by chemical or biological [Stemmer, *Proc. Natl. Acad. Sci. USA* 91:10747 (1994)] methods can be created and used for inoculation of potentially susceptible animals. Such animals could be either immunocompetent or immunodeficient, as described above. Variants capable of replication can be isolated, molecularly cloned and then the adaptive mutations incorporated into a full-length clone, which is functional for replication in the selected non-human species.

The functional activity of HCV can be evaluated transgenically. In this respect, a transgenic mouse model can be used [see, e.g., Wilmut et al., *Experientia* 47:905 (1991)]. The HCV RNA or DNA clone can be used to prepare transgenic vectors, including viral vectors, or cosmid clones (or phage clones). Cosmids may be introduced into transgenic mice using published procedures [Jaenisch, *Science*, 240:1468–1474 (1988)]. In the preparation of transgenic mice, embryonic stem cells are obtained from blastocyst embryos [Joyner, In *Gene Targeting: A Practical Approach, The Practical Approach Series*, Rickwood, D., and Hames, B. D., Eds., IRL Press: Oxford (1993)] and transfected with HCV DNA or RNA. Transfected cells are injected into early embryos, e.g., mouse embryos, as described [Hammer et al., *Nature* 315:680 (1985); Joyner, supra]. Various techniques for preparation of transgenic animals have been described [U.S. Pat. No. 5,530,177, issued Jun. 25, 1996; U.S. Pat. No. 5,898,604, issued Dec. 31, 1996]. Of particular interest are transgenic animal models in which the phenotypic or pathogenic effects of a transgene are studied. For example, the effects of a rat phosphoenolpyruvate carboxykinase-bovine growth hormone fusion gene has been studied in pigs [Wieghart et al., *J. Reprod. Fert., Suppl.* 41:89–96 (1996)]. Transgenic mice that express of a gene encoding a human amyloid precursor protein associated with Alzheimer's disease are used to study this disease and other disorders [International Patent Publication WO 96/06927, published Mar. 7, 1996; Quon et al., *Nature* 352:239 (1991)]. Transgenic mice have also been created for the hepatitis delta agent [Bolo et al., *J. Virol.* 69:5203 (1995)] and for hepatitis B virus [Chisar, *Curr. Top. Microbiol. Immunol.* 206:149 (1996)], and replication occurs in these engineered animals.

Thus, the functional cDNA clones described here, or parts thereof, can be used to create transgenic models relevant to HCV replication and pathogenesis. In one example, transgenic animals harboring the entire HCV genome can be created. Appropriate constructs for transgenic expression of the entire HCV genome in a transgenic mouse of the invention could include a nuclear promoter engineered to produce transcripts with the appropriate 5' terminus, the full-length HCV cDNA sequence, a cis-cleaving delta ribozyme [Ball, *J. Virol.* 66: 2335–2345 (1992); Pattnaik et al., *Cell* 69: 1011–1020 (1992)] to produce an authentic 3' terminus, followed possibly by signals that promote proper nuclear processing and transport to the cytoplasm (where HCV RNA replication occurs). Besides the entire HCV genome, animals can been engineered to express individual or various combinations of HCV proteins and RNA elements. For example, animals engineered to express an HCV gene product or reporter gene under the control of the HCV IRES can be used to evaluate therapies directed against this specific RNA target. Similar animal models can be envisioned for most known HCV targets.

Such alternative animal models are useful for (i) studying the effects of different antiviral agents on HCV replication in a whole animal system; (ii) examining potential direct cytotoxic effects of HCV gene products on hepatocytes and other cell types, defining the underlying mechanisms involved, and identifying and testing strategies for therapeutic intervention; and (iii) studying immune-mediated mechanisms of cell and tissue damage relevant to HCV pathogenesis and identifying and testing strategies for interfering with these processes.

Selection and Analysis of Drug-Resistant Variants

Cell lines and animal models supporting HCV replication can be used to examine the emergence of HCV variants with resistance to existing and novel therapeutics. Like all RNA viruses, the HCV replicase is presumed to lack proofreading activity and RNA replication is therefore error prone, giving rise to a high level of variation [Bukh et al., (1995) supra]. The variability manifests itself in the infected patient over time and in the considerable diversity observed between different isolates. The emergence of drug-resistant variants is likely to be an important consideration in the design and evaluation of HCV mono and combination therapies. HCV replication systems of the invention can be used to study the emergence of variants under various therapeutic formulations. These might include monotherapy or various combination therapies (e.g., IFN-$\alpha$, ribavirin, and new antiviral compounds). Resistant mutants can then be used to define the molecular and structural basis of resistance and to evaluate new therapeutic formulations, or in screening assays for effective anti-HCV drugs (infra).

Screening for Anti-HCV Agents

HCV-permissive cell lines or animal models (preferably rodent models) can be used to screen for novel inhibitors or to evaluate candidate anti-HCV therapies. Such therapies include, but would not be limited to, (i) antisense oligonucleotides or ribozymes targeted to conserved HCV RNA targets; (ii) injectable compounds capable of inhibiting HCV replication; and (iii) orally bioavailable compounds capable of inhibiting HCV replication. Targets for such formulations include, but are not restricted to, (i) conserved HCV RNA elements important for RNA replication and RNA packaging; (ii) HCV-encoded enzymes; (iii) protein-protein and protein-RNA interactions important for HCV RNA replication, virus assembly, virus release, viral receptor binding, viral entry, and initiation of viral RNA replication; (iv) virus-host interactions modulating the ability of HCV to establish chronic infections; (v) virus-host interactions modulating the severity of liver damage, including factors affecting apoptosis and hepatotoxicity; (vi) virus-host interactions leading to the development of more severe clinical outcomes including cirrhosis and hepatocellular carcinoma; and (vii) virus-host interactions resulting in other, less frequent, HCV-associated human diseases.

Evaluation of antisense and ribozyme therapies. The present invention extends to the preparation of antisense nucleotides and ribozymes that may be tested for the ability to interfere with HCV replication. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [see Marcus-Sekura, *Anal. Biochem.* 172:298 (1988)]. In the cell, they hybridize to that mRNA, forming a double stranded DNA:RNA or RNA:RNA molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., *J. Exp. Med.* 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

In the genetic antisense approach, expression of the wild-type allele is suppressed because of expression of antisense RNA. This technique has been used to inhibit TK synthesis in tissue culture and to produce phenotypes of the Kruppel mutation in *Drosophila*, and the Shiverer mutation in mice [Izant et al., *Cell*, 36:1007–1015 (1984); Green et al., *Annu. Rev. Biochem.*, 55:569–597 (1986); Katsuki et al., *Science*, 241:593–595 (1988)]. An important advance of this approach is that only a small portion of the gene need be expressed for effective inhibition of expression of the entire cognate mRNA. The antisense transgene will be placed under control of its own promoter or another promoter expressed in the correct cell type, and placed upstream of the SV40 polyA site.

Ribozymes are RNA molecules possessing the ability to specifically cleave other single stranded DNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.* 260:3030 (1988)]. Because they are sequence-specific, only mRNAs with particular sequences are inactivated.

Investigators have identified two types of ribozymes, *Tetrahymena*-type and "hammerhead"-type. *Tetrahymena*-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to *Tetrahymena*-type ribozymes for inactivating a specific mRNA species, and eighteen base recognition sequences are preferable to shorter recognition sequences.

Screening compound libraries for anti-HCV activity. Various natural product or synthetic libraries can be screened for anti-HCV activity in the in vitro or in vivo models provided by the invention. One approach to preparation of a combinatorial library uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [*14th International Congress of Biochemistry*, Volume 5, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested for anti-HCV activity.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028], and the like can be used to screen for anti-HCV compounds according to the present invention. These references, describe adaption of the library screening techniques in biological assays.

Defined/engineered HCV virus particles for neutralization assays. The functional clones described herein can be used to produce defined stocks of HCV-H particles for infectivity and neutralization assays. Homogeneous stocks can be produced in the chimpanzee model, in cell culture systems, or using various heterologous expression systems (e.g., baculovirus, yeast, mammalian cells; see supra). As described above, besides homogeneous virus preparations of HCV-H, stocks of other genotypes or isolates can be produced. These stocks can be used in cell culture or in vivo assays to define molecules or gene therapy approaches capable of neutralizing HCV particle production or infectivity. Examples of such molecules include, but are not restricted to, polyclonal antibodies, monoclonal antibodies, artificial antibodies with engineered/optimized specificity, single-chain antibodies (see the section on antibodies, infra), nucleic acids or derivatized nucleic acids selected for specific binding and neutralization, small orally bioavailable compounds, etc. Such neutralizing agents, targeted to conserved viral or cellular targets, can be either genotype or isolate-specific or broadly cross-reactive. They could be used either prophylactically or for passive immunotherapy to reduce viral load and perhaps increase the chances of more effective treatment in combination with other antiviral agents (e.g., IFN-α, ribavirin, etc.). Directed manipulation of HCV infectious clones can also be used to produce HCV stocks with defined changes in the glycoprotein hypervariable regions or in other epitopes to study mechanisms of antibody neutralization, CTL recognition, immune escape and immune enhancement. These studies will lead to identification of other virus-specific functions for anti-viral therapy.

Dissection of HCV Replication

Other HCV replication assays. For the first time, this invention allows directed molecular genetic dissection of HCV replication. Such analyses are expected to (i) validate antiviral targets which are currently being pursued; and (ii) uncover unexpected new aspects of HCV replication amenable to therapeutic intervention. Targets for immediate validation through mutagenesis studies include the following: the 5' NTR, the HCV polyprotein and cleavage products, and the 3' NTR. As described above, analyses using the infectious clone technology and permissive cell cultures can be used to compare parental and mutant replication phenotypes after transfection of cell cultures with infectious RNA. Even though RT-PCR allows sensitive detection of viral RNA accumulation, mutations which decrease the efficiency of RNA replication may be difficult to analyze, unless conditional mutations are recovered. As a complement to first cycle analyses, trans-complementation assays can be used to facilitate analysis of HCV mutant phenotypes and inhibitor screening. Heterologous systems (vaccinia, Sindbis, or non-viral) can be used to drive expression of the HCV RNA replicase proteins and/or packaging machinery [see Lemm and Rice, *J. Virol.* 67: 1905–1915 (1993a); Lemm and Rice, *J. Virol.* 67: 1916–1926 (1993b); Lemm et al., *EMBO J.* 13: 2925–2934 (1994); Li et al., *J. Virol.* 65: 6714–6723 (1991)]. If these elements are capable of functioning in trans, then co-expression of RNAs with appropriate cis-elements should result in RNA replication/packaging. Such systems therefore mimic steps in authentic RNA replication and virion assembly, but uncouple production of viral components from HCV replication. If HCV replication is somehow self-limiting, heterologous systems may drive significantly higher levels of RNA replication or particle production, facilitating analysis of mutant phenotypes and antiviral screening. A third approach is to devise cell-free systems for HCV template-dependent RNA replication. A coupled translation/replication and assembly system has been described for poliovirus in HeLa cells [Barton and Flanegan, *J. Virol.* 67: 822–831 (1993); Molla et al., *Science* 254: 1647–1651 (1991)], and a template-dependent in vitro assay for initiation of negative-strand synthesis has been established for Sindbis virus. Similar in vitro systems for HCV are invaluable for studying many aspects of HCV replication as well as for inhibitor screening and evaluation. An example of each of these strategies follows.

Trans-complementation of HCV RNA replication and/or packaging using viral or non-viral expression systems. Heterologous systems can be used to drive HCV replication. For example, the vaccinia/T7 cytoplasmic expression system has been extremely useful for trans-complementation of RNA virus replicase and packaging functions [see Ball, (1992) supra; Lemm and Rice, (1993a) supra; Lemm and Rice (1993b) supra; Lemm et al., (1994) supra; Pattnaik et al., (1992) supra; Pattnaik et al., *Virology* 206: 760–4 (1995); Porter et al., *J. Virol.* 69: 1548–1555 (1995)]. In brief, a vaccinia recombinant (vTF7-3) is used to express T7 RNA polymerase (T7RNApol) in the cell type of interest. Target cDNAs, positioned downstream from the T7 promoter, are delivered either as vaccinia recombinants or by plasmid transfection. This system leads to high level RNA and protein expression. A variation of this approach, which obviates the need for vaccinia (which could interfere with HCV RNA replication or virion formation), is the pT7T7 system where the T7 promoter drives expression of T7RNApol [Chen et al., *Nucleic Acids Res.* 22: 2114–2120. (1994)]. pT7T7 is mixed with T7RNApol (the protein) and co-transfected with the T7-driven target plasmid of interest. Added T7RNApol initiates transcription, leading to it own production and high level expression of the target gene. Using either approach, RNA transcripts with precise 5' and 3' termini can be produced using the T7 transcription start site (5') and the cis-cleaving HCV ribozyme (Rz) (3') [Ball, (1992) supra; Pattnaik et al., (1992) supra].

These or similar expression systems can be used to establish assays for HCV RNA replication and particle formation, and for evaluation of compounds which might inhibit these processes. In another extension of the HCV functional clone technology, T7-driven protein expression constructs and full-length HCV clones incorporating the HCV ribozyme following the 3' NTR are used. A typical experimental plan to validate the assay is described for pT7T7, although essentially similar assays can be envisioned using vTF7-3 or cell lines expressing the T7 RNA polymerase. HCV-permissive cells are co-transfected with pT7T7+T7RNApol+p90/HCVFLlong pU Rz (or a negative control, such as ΔGDD). At different times post-transfection, accumulation of HCV proteins and RNAs, driven by the PT7T7 system, are followed by Western and Northern blotting, respectively. To assay for HCV-specific replicase function, Act. D is added to block DNA-dependent T7 transcription [Lemm and Rice, (1993a), supra] and Act. D-resistant RNA synthesis is monitored by metabolic labeling. Radioactivity will be incorporated into full-length HCV RNAs for p90/HCVFL long pU/Rz, but not for p90/HCVFLΔGDD/Rz. This assay system, or elaborated derivatives, can be used to screen for inhibitors and to study their effects on HCV RNA replication.

Cell-free systems for assaying HCV replication and inhibitors thereof. Cell-free assays for studying HCV RNA replication and inhibitor screening can also be established using the functional cDNA clones described in this invention. Either virion or transcribed RNAs are used as substrate RNA. For HCV, full-length HCV RNAs transcribed in vitro can be used to program such in vitro systems and replication assayed essentially as described for poliovirus [see Barton et al., (1995) supra]. In case hepatocyte-specific or other factors are required for HCV RNA replication, the system can be supplemented with hepatocyte or other cell extracts, or alternatively, a comparable system can be established using cell lines which have been shown to be permissive for HCV replication.

One concern about this approach is that proper cell-free synthesis and processing of the HCV polyprotein must occur. Sufficient quantities of properly processed replicase components may be difficult to produce. To circumvent this problem, the T7 expression system can be used to express high levels of HCV replicase components in appropriate cells [see Lemm et al. (1997) supra]. P15 membrane fractions from these cells (with added buffer, $Mg^{2+}$, an ATP regenerating system, and NTPs) should be able to initiate and synthesize full-length negative-strand RNAs upon addition of HCV-specific template RNAs.

Establishment of either or both of these assays allows rapid and precise analysis of the effects of HCV mutations, host factors, involved in replication and inhibitors of the various steps in HCV RNA replication. These systems will also establish the requirements for helper systems for preparing replication-deficient HCV vectors.

Vaccination and Protective Immunity

There are still many unknown parameters that impact on development of effective HCV vaccines. It is clear in both man and the chimpanzee that some individuals can clear the infection. Also, 10–20% of those treated with IFN appear to show a sustained response as evidenced by lack of circulating HCV RNA. Other studies have shown a lack of protective immunity, as evidenced by successful reinfection with both homologous virus as well as with more distantly related HCV types [Farci et al., (1992) supra; Prince et al., (1992) supra]. Nonetheless, chimpanzees immunized with subunit vaccines consisting of E1E2 oligomers and vaccinia recombinants expressing these proteins are partially protected against low dose challenges [Choo et al., *Proc. natl. Acad. Sci. USA* 91:1294 (1994)]. The infectious clone technology described in this invention has utility not only for basic studies aimed at understanding the nature of protective immune responses against HCV, but also for novel vaccine production methods.

Active immunity against HCV can be induced by immunization (vaccination) with an immunogenic amount of an attenuated or inactivated HCV virion, or HCV virus particle proteins, preferably with an immunologically effective adjuvant. An "immunologically effective adjuvant" is a material that enhances the immune response.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA or RNA encoding the antigen into tissues of a subject for expression of the antigen by the cells of the subject's tissue. Such vaccines are termed herein "DNA vaccines," "genetic vaccination," or "nucleic acid-based vaccines." Methods of transfection as described above, such as DNA vectors or vector transporters, can be used for DNA vaccines.

DNA vaccines are described in International Patent Publication WO 95/20660 and International Patent Publication WO 93/19183, the disclosures of which are hereby incorporated by reference in their entireties. The ability of directly injected DNA that encodes a viral protein or genome to elicit a protective immune response has been demonstrated in numerous experimental systems [Conry et al., *Cancer Res.*, 54:1164–1168 (1994); Cox et al., *Virol.* 67:5664–5667 (1993); Davis et al., *Hum. Mole. Genet.* 2:1847–1851 (1993); Sedegah et al., *Proc. Natl. Acad. Sci.*, 91:9866–9870 (1994); Montgomery et al., *DNA Cell Bio.*, 12:777–783 (1993); Ulmer et al., *Science*, 259:1745–1749 (1993); Wang et al., *Proc. Natl. Acad. Sci.*, 90:4156–4160 (1993); Xiang et al., *Virology*, 199:132–140 (1994)]. Studies to assess this strategy in neutralization of influenza virus have used both envelope and internal viral proteins to induce the production of antibodies, but in particular have focused on the viral hemagglutinin protein (HA) [Fynan et al., *DNA Cell. Biol.*, 12:785–789 (1993A); Fynan et al., *Proc. Natl. Acad. Sci.*, 90:11478–11482 (1993B); Robinson et al., *Vaccine*, 11:957, (1993); Webster et al., *Vaccine*, 12:1495–1498 (1994)].

Vaccination through directly injecting DNA or RNA that encodes a protein to elicit a protective immune response produces both cell-mediated and humoral responses. This is analogous to results obtained with live viruses [Raz et al., *Proc. Natl. Acad. Sci.*, 91:9519–9523 (1994); Ulmer, 1993, supra; Wang, 1993, supra; Xiang, 1994, supra]. Studies with ferrets indicate that DNA vaccines against conserved internal viral proteins of influenza, together with surface glycoproteins, are more effective against antigenic variants of influenza virus than are either inactivated or subvirion vaccines [Donnelly et al., *Nat. Medicine*, 6:583–587 (1995)]. Indeed, reproducible immune responses to DNA encoding nucleoprotein have been reported in mice that last essentially for the lifetime of the animal [Yankauckas et al., *DNA Cell Biol.*, 12: 771–776 (1993)].

A vaccine of the invention can be administered via any parenteral route, including but not limited to intramuscular, intraperitoneal, intravenous, intraarterial (e.g., hepatic artery) and the like. Preferably, since the desired result of vaccination is to elucidate an immune response to HCV, administration directly, or by targeting or choice of a viral vector, indirectly, to lymphoid tissues, e.g., lymph nodes or spleen. Since immune cells are continually replicating, they are ideal target for retroviral vector-based nucleic acid vaccines, since retroviruses require replicating cells.

Passive immunity can be conferred to an animal subject suspected of suffering an infection with HCV by administering antiserum, neutralizing polyclonal antibodies, or a neutralizing monoclonal antibody against HCV to the patient. Although passive immunity does not confer long term protection, it can be a valuable tool for the treatment of an acute infection of a subject who has not been vaccinated. Preferably, the antibodies administered for passive immune therapy are autologous antibodies. For example, if the subject is a human, preferably the antibodies are of human origin or have been "humanized," in order to minimize the possibility of an immune response against the antibodies. In addition, genes encoding neutralizing antibodies can be introduced in vectors for expression in vivo, e.g., in hepatocytes.

Antibodies for passive immune therapy. Preferably, HCV virions or virus particle proteins prepared as described above are used as an immunogen to generate antibodies that recognize HCV. Such antibodies include but are not limited to polyclonal, monoclonal, chimeric, single chain, Fab fragments, and an Fab expression library. Various procedures known in the art may be used for the production of polyclonal antibodies to HCV. For the production of antibody, various host animals can be immunized by injection with the HCV virions or polypeptide, e.g., as describe infra, including but not limited to rabbits, mice, rats, sheep, goats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward HCV as described above, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals [International Patent Publication No. WO 89/12690, published 28 Dec. 1989]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for HCV together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce HCV-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

HCV particles for subunit vaccination. The functional HCV-H cDNA clone, and similarly constructed and verified clones for other genotypes, can be used to produce HCV-like particles for vaccination. Proper glycosylation, folding, and assembly of HCV particles may be important for producing appropriately antigenic and protective subunit vaccines. Several methods can be used for particle production. They include engineering of stable cell lines for inducible or constitutive expression of HCV-like particles (using bacterial, yeast or mammalian cells), or the use of higher level eukaryotic heterologous expression systems such as recombinant baculoviruses, vaccinia viruses [Moss, *Proc. Natl. Acad. Sci. U.S.A.* 93: 11341–11348 (1996)], or alphaviruses [Frolov et al., (1996) supra]. HCV particles for immunization may be purified from either the media or disrupted cells, depending upon their localization. Such purified HCV particles or mixtures of particles representing a spectrum of HCV genotypes, can be injected with our without various adjuvants to enhance immunogenicity.

Infectious non-replicating HCV particles. In another manifestation, HCV particles capable of receptor binding, entry, and translation of genome RNA can be produced. Heterologous expression approaches for production of such particles include, but are not restricted to, *E. coli*, yeast, or mammalian cell lines, appropriate host cells infected or harboring recombinant baculoviruses, recombinant vaccinia viruses, recombinant alphaviruses or RNA replicons, or recombinant adenoviruses, engineered to express appropriate HCV RNAs and proteins. In one example, two recombinant baculoviruses are engineered. One baculovirus expresses the HCV structural proteins (e.g., C-E1-E2-p7) required for assembly of HCV particles. A second recombinant expresses the entire HCV genome RNA, with precise 5' and 3' ends, except that a deletion, such as ΔGDD, is included to inactivate the HCV NS5B RDRP. Other mutations abolishing productive HCV replication could also be utilized instead or in combination. Coinfection of appropriate host cells (Sf9, Sf21, etc.) with both recombinants will produce high levels of HCV structural proteins and genome RNA for packaging into HCV-like particles. Such particles can be produced at high levels, purified, and used for vaccination. Once introduced into the vaccine, such particles will exhibit normal receptor binding and infection of HCV-susceptible cells. Entry will occur and the genome RNA will be translated to produce all of the normal HCV antigens, except that further replication of the genome will be completely blocked given the inactivated 5B polymerase. Such particles are expected to elicit effective CTL responses against structural and nonstructural HCV protein antigens. This vaccination strategy alone or preferably in conjunction with the subunit strategy described above can be used to elicit high levels of both neutralizing antibodies and CTL responses to help clear the virus. A variety of different HCV genome RNA sequences can be utilized to ensure broadly cross-reactive and protective immune responses. In addition, modification of the HCV particles, either through genetic engineering, or by derivatization in vitro, could be used to target infection to cells most effective at eliciting protective and long lasting immune responses.

Live-attenuated HCV derivatives. The ability to manipulate the HCV genome RNA sequence and thereby produce mutants with altered pathogenicity provides a means of constructing live-attenuated HCV mutants appropriate for vaccination. Such vaccine candidates express protective antigens but would be impaired in their ability to cause disease, establish chronic infections, trigger autoimmune responses, and transform cells. Naturally, infectious HCV virus of the invention can be attenuated, inactivated, or killed by chemical or heat treatment.

HCV-based Gene Expression Vectors

Figure 2:
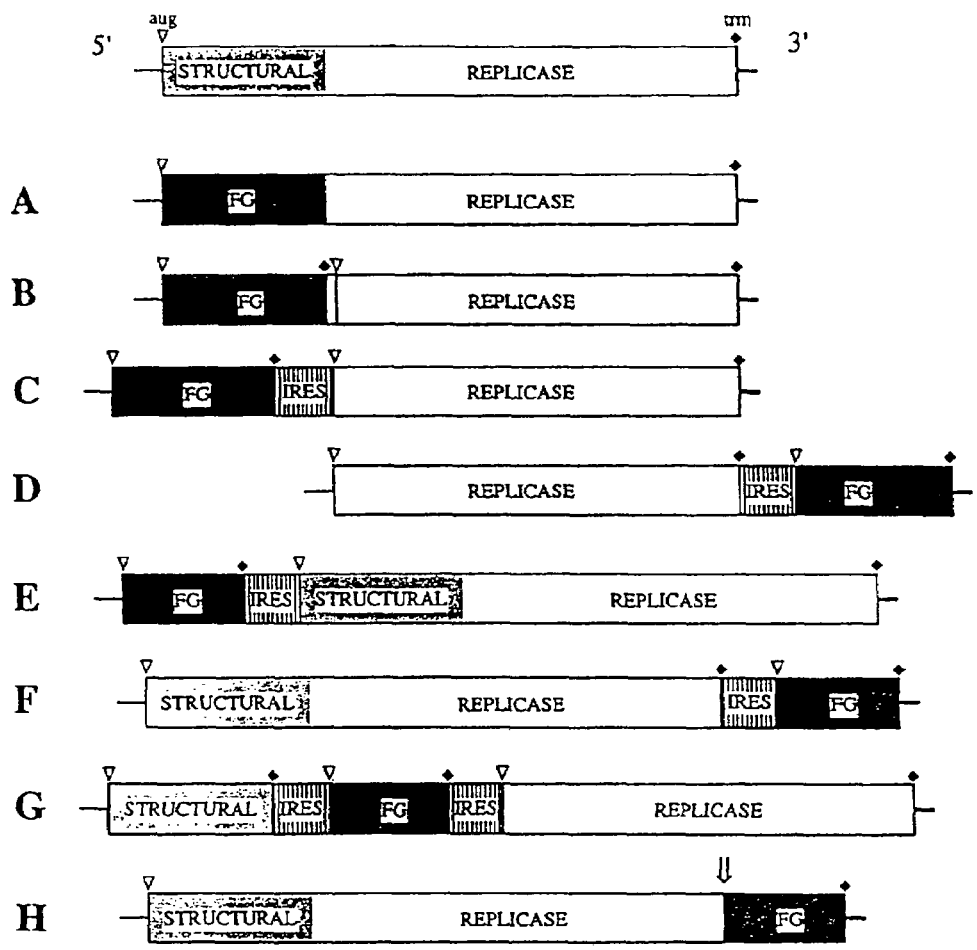

Some of the same properties of HCV leading to chronic liver infection of humans may also be of great utility for designing vectors for gene expression in cell culture systems, genetic vaccination, and gene therapy. The functional clones described herein can be engineered to produce chimeric RNAs designed for the expression of heterologous gene products (RNAs and proteins). Strategies have been described above and elsewhere [Bredenbeek and Rice, (1992) supra; Frolov et al., (1996) supra] and include, but are not limited to (i) in-frame fusion of the heterologous coding sequences with the HCV polyprotein; (ii) creation of additional cistrons in the HCV genome RNA; and (iii) inclusion of IRES elements to create multicistronic self-replicating HCV vector RNAs capable of expressing one or more heterologous genes (FIG. 2). Functional HCV RNA backbones utilized for such vectors include, but are not limited to, (i) live-attenuated derivatives capable of replication and spread; (ii) RNA replication competent "dead end" derivatives lacking one or more viral components required (e.g. the structural proteins) required for viral spread; (iii) mutant derivatives capable of high and low levels of HCV-specific RNA synthesis and accumulation; (iv) mutant derivatives adapted for replication in different human cell types; (v) engineered or selected mutant derivatives capable of prolonged noncytopathic replication in human cells. Vectors competent for RNA replication but not packaging or spread can be introduced either as naked RNA, DNA, or packaged into virus-like particles. Such virus-like particles can be produced as described above and composed of either unmodified or altered HCV virions components designed for targeted infection of the hepatocytes or other human cell types. Alternatively, HCV RNA vectors can be encapsidated and delivered using heterologous viral packaging machineries or encapsulated into liposomes modified for efficient gene delivery. These packaging strategies, and modifications thereof, can be utilized to efficiently target HCV vectors RNAs to specific cell types. Using methods detailed above, similar HCV-derived vector systems, competent for replication and expression in other species, can also be derived.

Various methods, e.g., as set forth supra in connection with transfection of cells and DNA vaccines, can be used to introduce an HCV vector of the invention. Of primary interest is direct injection of functional HCV RNA or virions, e.g., in the liver. Targeted gene delivery is described in International Patent Publication WO 95/28494, published October 1995. Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988); Ulmer et al., *Science* 259:1745–1748 (1993)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically. Receptor-mediated DNA delivery approaches can also be used [Curiel et al., *Hum. Gene Ther.* 3:147–154 (1992); Wu and Wu, *J. Biol. Chem.* 262:4429–4432 (1987)].

Examples of applications for gene therapy include, but are not limited to, (i) expression of enzymes or other molecules to correct inherited or acquired metabolic defects; (ii) expression of molecules to promote wound healing; (iii) expression of immunomodulatory molecules to promote immune-mediated regression or elimination of human cancers; (iv) targeted expression of toxic molecules or enzymes capable of activating cytotoxic drugs in tumors; (v) targeted expression of anti-viral or anti-microbial agents in pathogen-infected cells. Various therapeutic heterologous genes can be inserted in a gene therapy vector of the invention, such as but not limited to adenosine deaminase (ADA) to treat severe combined immunodeficiency (SCID); marker genes or lymphokine genes into tumor infiltrating (TIL) T cells [Kasis et al., *Proc. Natl. Acad. Sci. U.S.A.* 87:473 (1990); Culver et al., ibid. 88:3155 (1991)]; genes for clotting factors such as Factor VIII and Factor IX for treating hemophilia [Dwarki et al. *Proc. Natl. Acad. Sci. USA,* 92:1023–1027 (19950); Thompson, *Thromb. and Haemostatis,* 66:119–122 (1991)]; and various other well known therapeutic genes such as, but not limited to, β-globin, dystrophin, insulin, erythropoietin, growth hormone, glucocerebrosidase, β-glucaronidase, α-antitrypsin, phenylalanine hydroxylase, tyrosine hydroxylase, ornithine transcarbamylase, apolipoproteins, and the like. In general, use U.S. Pat. No. 5,399,346 to Anderson et al.

Examples of applications for genetic vaccination (for protection from pathogens other than HCV) include, but are not limited to, expression of protective antigens from bacterial (e.g., uropathogenic *E. coli, Streptococci, Staphlococci, Nisseria*), parasitic (e.g., *Plasmodium, Leishmania, Toxoplama*), fungal (e.g., *Candida, Histoplasma*), and viral (e.g., HIV, HSV, CMV, influenza) human pathogens. Immunogenicity of protective antigens expressed using HCV-derived RNA expression vectors can be enhanced using adjuvants, including co-expression of immunomodulatory molecules, such as cytokines (e.g., IL-2, GM-CSF) to facilitate development of desired Th1 versus Th2 responses. Such adjuvants can be either incorporated and co-expressed by HCV vectors themselves or administered in combination with these vectors using other methods.

Diagnostic Methods for Infectious HCV

Diagnostic cell lines. The invention described herein can also be used to derive cell lines for sensitive diagnosis of infectious HCV in patient samples. In concept, functional HCV components are used to test and create susceptible cell lines (as identified above) in which easily assayed reporter systems are selectively activated upon HCV infection. Examples include, but are not restricted to, (i) defective HCV RNAs lacking replicase components that are incorporated as transgenes and whose replication is upregulated or induced upon HCV infection; (ii) sensitive heterologous amplifiable reporter systems activated by HCV infection. In the first manifestation, cis RNA signals required for HCV RNA amplification flank a convenient reporter gene, such as luciferase, green fluorescent protein (GFP), β-galactosidase, or a selectable marker (see above). Expression of such chimeric RNAs is driven by an appropriate nuclear promoter and elements required for proper nuclear processing and transport to the cytoplasm. Upon infection of the engineered cell line with HCV, cytoplasmic replication and amplification of the transgene is induced, triggering higher levels of reporter expression, as an indicator of productive HCV infection.

Figure 3A:
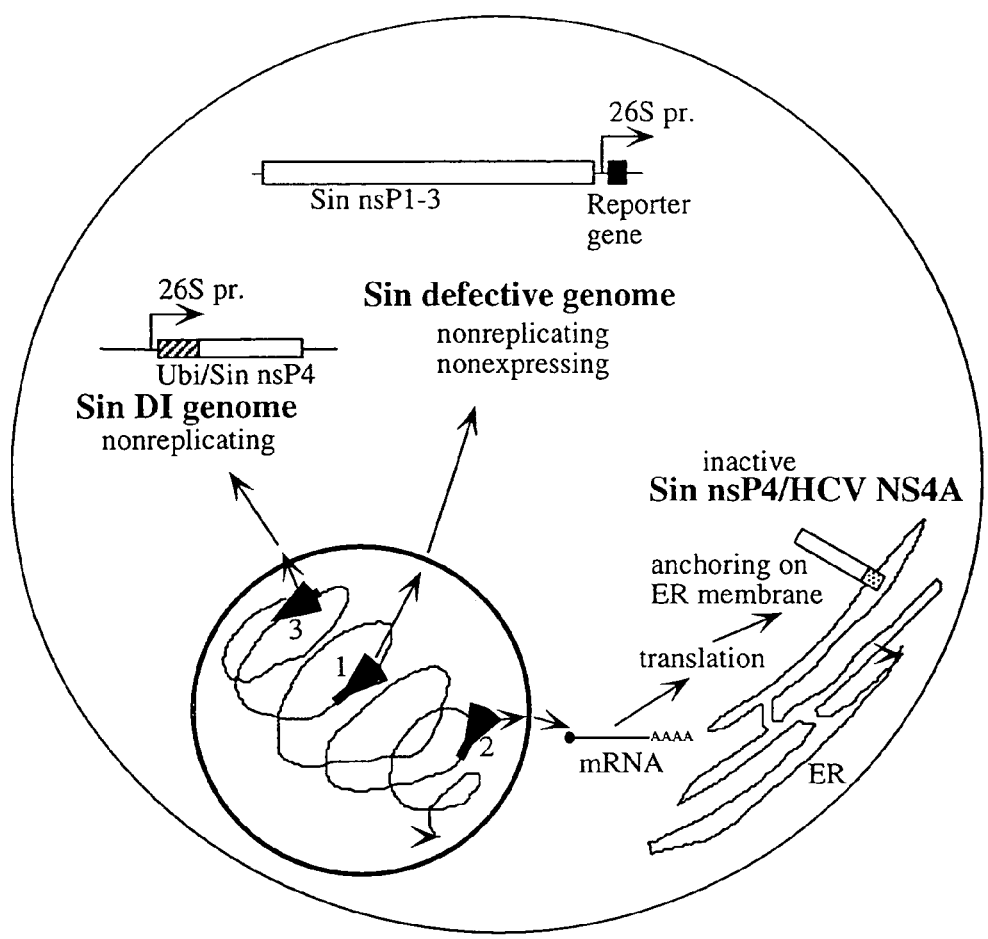
Figure 3B:
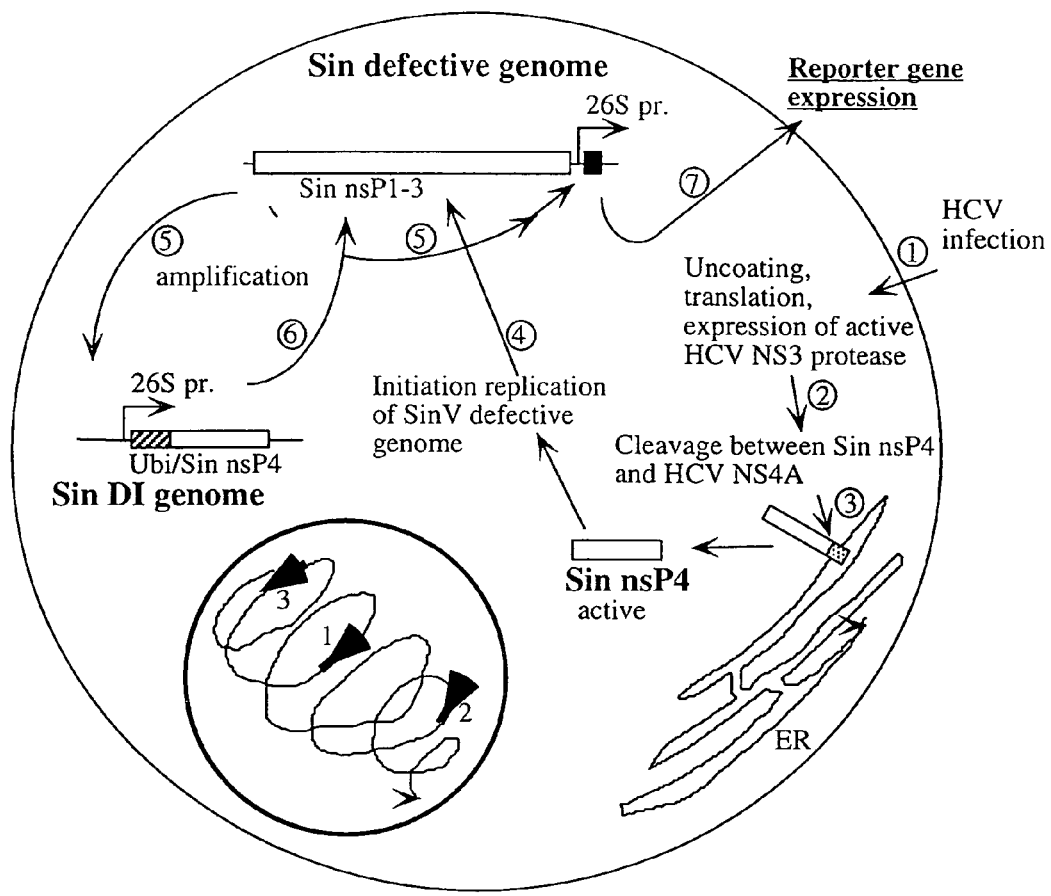

In the second example, cell lines are designed for more tightly regulated but highly inducible reporter gene amplification and expression upon HCV infection. Although this amplified system is described in the context of specific components, other equivalent components can be used. In one such system, diagrammed in FIG. 3, an engineered alphavirus replicon transgene is created which lacks the alphavirus nsP4 polymerase, an enzyme absolutely required for alphavirus RNA amplification and normally produced by cleavage from the nonstructural polyprotein. Additional features of this defective alphavirus replicon include a subgenomic RNA promoter, driving expression of a luciferase or GFP reporter gene. This promoter element is quiescent in the absence of productive cytoplasmic alphavirus replication. The cell line contains a second transgene for expression of gene fusion consisting of the HCV NS4A protein and the alphavirus nsP4 RDRP. This fused gene is expressed and targeted to the cytoplasmic membrane compartment, but this form of nsP4 would be inactive as a functional component of the alphavirus replication complex because a discrete nsP4 protein, with a precise N terminus is required for nsP4 activity [Lemm et al., *EMBO J.* 13:2925 (1994)]. An optional third transgene expresses a defective alphavirus RNA with cis signals for replication, transcription of subgenomic RNA encoding a ubiquitin-nsP4 fusion, and an alphavirus packaging signal. Upon infection of such a cell line by HCV, the HCV NS3 proteinase is produced and mediate trans cleavage of the NS4A-nsP4 fusion protein, activating the nsP4 polymerase. This active polymerase, which functions in trans and is effective in minute amounts, then forms a functional alphavirus replication complex leading to amplification of the defective alphavirus replicon as well as the defective alphavirus RNA encoding ubiquitin-nsP4. Ubiquitin-nsP4, expressed from its subgenomic RNA, is cleaved efficiently by cellular ubiquitin carboxyterminal hydrolase to product additional nsP4, in case this enzyme is limiting. Once activated, this system would produce extremely high levels of the reporter protein. The time scale of such an HCV infectivity assay is expected to take just hours (for sufficient reporter gene expression).

Antibody diagnostics. In addition to the cell lines described here, HCV virus particles (virions) produced by the transfected or infected cell lines, or isolated from an infected animal, may be used as antigens to detect anti-HCV antibodies in patient blood or blood products. Because the HCV virus particles are derived from an authentic HCV genome, they are likely to have structural characteristics that more closely resemble or are identical to natural HCV virus. These reagents can be used to establish that a patient is infected with HCV by detecting seroconversion, i.e., generation of a population of HCV-specific antibodies.

Alternatively, antibodies generated to the authentic HCV products prepared as described herein can be used to detect the presence of HCV in biological samples from a subject.

The present invention may be better understood by reference to the following non-limiting Examples, which are provided as exemplary of the invention.

EXAMPLES

The following examples report on the background experimental work, initial unsuccessful efforts to prepare an HCV DNA encoding infectious HCV RNA, and finally generation of a functional clone.

Example 1

Analysis of HCV-H Genome Structure and Expression

Rationale for the HCV-H strain, cDNA cloning, sequence analysis, and assembly of nearly full-length cDNA clones. HCV-H strain was chosen for the initial studies since this isolate has been extensively characterized in chimpanzees by Purcell and colleagues [see Shimizu et al., (1990) supra] and more recently in vitro by Shimizu and coworkers [Hijikata et al., (1993) supra; Shimizu et al., *J. Virol.* 68: 1494–1500 (1994); Shimizu et al., *Proc. Natl. Acad. Sci USA* 89: 5477–5481 (1992); Shimizu et al., *Proc. Natl. Acad. Sci. USA* 90, 6037–6041 (1993)]. HCV-H is a genotype 1a human isolate from an American with posttransfusion NANB hepatitis [Feinstone et al., *J. Infect. Dis.* 144: 588–598 (1981)].

Initial cDNA cloning and sequence analysis of HCV-H. The original HCV-H77 isolate was passaged twice in chimpanzees, both of whom developed elevated serum ALT levels and acute hepatitis. Liver tissue from the second chimpanzee passage was used for preparation of crude RNA suitable for cDNA synthesis and nested PCR amplification. PCR-amplified cDNA was cloned into plasmid expression vectors and several independent clones were isolated and used for sequence analysis, expression studies and reconstructing longer cDNA clones. Utilizing partial sequence data and restriction enzyme mapping, a clone containing the nearly the entire HCV-H cDNA, called pTET/T7HCVFLCMR, was assembled and sequenced [Daemer et al., unpublished; Grakoui et al., *J. Virol.* 67: 1385–1395 (1993c)]. The HCV sequence contained in this plasmid is subsequently referred to as HCV-H CMR (SEQ ID NO:19). The sequence of this clone is colinear and 98.5% homologous (at the nucleotide level) to the chimp-passaged HCV-H77 sequence published by Inchauspe et al. [Inchauspe et al., *Proc. Natl. Acad. Sci. USA* 88: 10292–10296 (1991)] and shows even greater similarity to the partial HCV-H90 sequences published by Ogata et al. [Ogata et al., (1991) supra].

Characterization of a prototype HCV-H clone. HCV-H cDNA clones and immune reagents have been used in cell-free translation and cell culture transient expression assays to provide a fairly detailed picture of HCV-H gene expression. In general terms, these results are similar to those obtained by others for different HCV genotypes. This work included: (i) the identification and mapping of HCV-H polyprotein cleavage products [Grakoui et al., (1993c) supra; Lin et al., (1994a) supra]; (ii) determining the sites of proteolytic processing [Grakoui et al., *J. Virol.* 67: 2832–2843 (1993a); Grakoui et al., *Proc. Natl. Acad. Sci. USA* 90: 10583–10587 (1993b); Lin et al., (1994a) supra]; (iii) characterization of the NS2-3 autoproteinase [Grakoui et al., (1993b) supra; Reed et al., *J. Virol.* 69: 4127–4136 (1995)], the NS3-4A serine proteinase [Grakoui et al., (1993a) supra; Lin et al., *J. Virol.* 68: 8147–8157 (1994b); Lin and Rice, *Proc. Natl. Acad. Sci. USA* 92: 7622–7626 (1995); Lin et al., *J. Virol.* 69: 4373–4380 (1995)] and their cleavage requirements [Kolykhalov et. al., *J. Virol.* 68: 7525–7533 (1994); Reed et al., (1995) supra]; (iv) studies on the NS4A serine proteinase cofactor and its association with NS3 [Lin et al., (1994b) supra; Lin and Rice, (1995) supra; Lin et al., (1995) supra]; and (v) an examination of HCV glycoprotein biogenesis including folding and association with calnexin, oligomer formation, and subcellular localization [Dubuisson et al., (1994) supra; Dubuisson and Rice, (1996) supra]. Assays for other biologically important activities have been developed using the prototype HCV-H cDNA clones, including RNA-stimulated NTPase and RNA helicase activities associated with partially purified NS3 [Suzich et al., (1993) supra] and an RNA-dependent RNA polymerase activity. Antigens expressed from this cloned cDNA can also be recognized by sera [see Ref. Grakoui et al., (1993c) supra] and cytotoxic T lymphocytes [Battegay et al., *J. Virol.* 69: 2462–2470 (1995); Koziel et al., *J. Clin. Invest.* 96:2311–21 (1995)] from patients with chronic HCV infections.

For the present invention, the work in HCV polyprotein processing provided a means of prescreening candidate full-length clones for a functional IRES element, an intact ORF, and proper membrane topology and active viral proteinases as evidenced by the production of all 10 polyprotein cleavage products.

Example 2

First Attempt at Recovery of Functional HCV from cDNA

Plasmid constructions. The preferred strategy for production of high specific infectivity potentially infectious HCV RNA transcripts [see Ahlquist et al., *Proc. Natl. Acad. Sci. USA* 81: 7066–7070 (1984); Rice et al., *New Biol.* 1: 285–296 (1989); Rice et al., (1987) supra and refs. therein], involved cloning of candidate full-length HCV cDNAs immediately downstream from a bacteriophage promoter (SP6 or T7) with a unique restriction site following the HCV 3' terminus for production of run off RNA transcripts (FIG. 4). The T7 or SP6 transcription systems were chosen for production of potentially infectious RNAs for several reasons. First, numerous examples exist for other RNA viruses where either T7 or SP6 have been successfully used to transcribe high yields of relatively high specific infectivity capped or uncapped RNA transcripts [Boyer and Haenni, *J. Gen. Virol.* 198: 415–426 (1994)]. In addition, the T7 system is particularly useful since it allows not only in vitro synthesis of defined RNAs for transfection, but also several in vivo approaches using transfection of plasmid DNA. One example is the vaccinia-T7 system where a vaccinia recombinant expressing the T7 RNA polymerase allows cytoplasmic transcription of transfected plasmid templates [Fuerst et al., *Proc. Natl. Acad. Sci. USA* 83: 8122–8126 (1986)]. A second in vivo approach, obviating the need for vaccinia virus, is cotransfection of a plasmid expressing T7 RNA polymerase [Chen et al., (1994) supra]. Transfection with HCV plasmid DNAs, designed for production of transcripts with defined 5' and 3' termini, might be advantageous given the susceptibility of long RNAs to degradation during transfection procedures [Ball, (1992) supra; Pattnaik et al., (1992) supra]. However, these in vivo methods do not allow precise control over the structure of the transcribed RNA and their export to the cytoplasm where HCV RNA replication is believed to occur. Hence, the in vitro transcription method has usually employed in our work.

Figure 4:
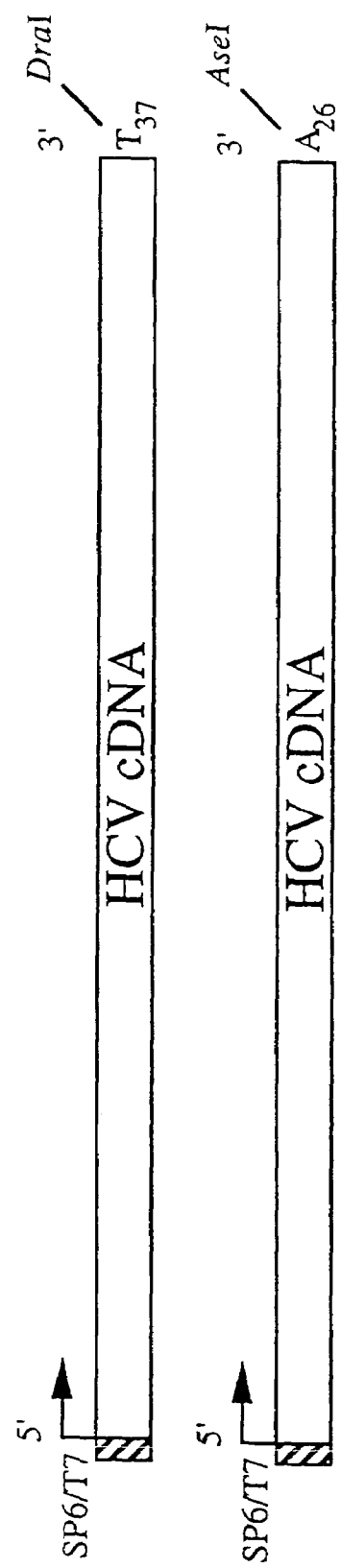

The sequenced prototype HCV-H cDNA clone used for the majority of the processing studies was the starting material for these constructions. Since the terminal sequences of the HCV-H genome RNA were unknown when these experiments were initiated, sequences reported for other isolates were used to engineer the 5' and 3' ends by PCR. For the first set of constructs tested (FIG. 4), the additional 5' terminal sequence was derived from HCV-1 isolate [Han et al., (1991) supra]. For the 3' NTR, plasmids with two alternative structures were constructed. One pair (SP6 or T7) contained the 3' NTR and terminal poly (A) tract reported for HCV-1 by Han [Han et al., (1991) supra]. A second pair was constructed using a consensus 3' NTR sequence for all other isolates followed by a 3' terminal poly (U) tract.

Methods for assaying infectivity of HCV RNA. A desirable method for initial identification of potentially functional clones would be to screen for RNA replication after transfection of permissive cell cultures. While several laboratories have reported infection and replication in various cell cultures (see Background of the Invention, supra, and below), these systems are extremely inefficient, poorly characterized, and difficult to reproduce. Factors precluding efficient replication in vitro are unknown but may involve one or multiple stages in the virus life cycle (attachment, entry, RNA replication, assembly or release). Furthermore, no one has shown that HCV produced in cell culture is "authentic", e.g., capable of causing disease in the chimpanzee model. For these reasons, as well the technical difficulties associated with unambiguously demonstrating replication after RNA transfection, the chimpanzee model was used to identify functional clones from the library. Surgical procedures and direct intrahepatic inoculation were used, since this technique had been successful for demonstrating infectivity of rabbit hemorrhagic disease virus virion RNA [Ohlinger et al., *J. Virol.* 64: 3331–3336 (1990)] and for hepatitis A virus RNA produced by in vitro transcription [Emerson et al., *J. Virol.* 66: 6649–6654 (1992)].

Chimpanzee Experiment I

Capped or uncapped full-length RNA transcripts were synthesized from each of the four linearized plasmid templates and assayed for infectivity by direct intrahepatic inoculation of chimpanzee liver using a percutaneous liver biopsy technique. Briefly, after RNA transcription, reactions were digested with DNase, extracted with phenol, and the RNAs collected by ethanol precipitation. The yield and integrity of each transcript RNA was determined by agarose gel electrophoresis under denaturing conditions. Equal amounts of each of the poly (U)- or poly (A)-containing transcripts (SP6, T7, capped, uncapped) were pooled and assayed separately in two animals. These animals had not previously been exposed to HCV or pooled blood products and were HCV antibody and RNA negative. For each animal, two injection sites were used. At one site, 200 µg pooled RNA in 1 ml RNase-free PBS was injected. At the second site, 200 µg pooled RNA mixed with 0.8 ml RNase-free PBS and 200 µl LIPOFECTIN (BRL) was injected. Pre- and post-inoculation plasma and liver biopsy samples were collected weekly. Plasma samples were assayed for ALT and GGTP (indicators of liver damage), for HCV-specific antibodies using available serological assays, and for evidence of circulating HCV RNA by RT/PCR. Besides histologic examination of liver biopsy tissue, samples were also stored for possible analysis by immunofluorescence and electron microscopy. Despite following the animals for 6 months, no evidence of productive HCV infection was found using any of these assays.

Using methods described more fully below, transcripts from these clones were also assayed for infectivity in several different cell types. In some cases, HCV antigens could be detected in transfected cells for several days; however, similar results were obtained using control HCV transcripts containing a deletion in the NS5B RDRP, which should be inactive for replication. Thus, no convincing evidence for replication was obtained in the first set of experiments.

Example 3

Second Attempt to Recover HCV from cDNA

Possible reasons for failure of Attempt I. Several possible explanations, alone or in combination, could account for previous unsuccessful attempts to recover infectious HCV RNA from prototype HCV-H clones (pTET/HCVFLCMR). These include missing or incorrect terminal sequences, internal errors deleterious or lethal for HCV replication, or inadequate methods for assaying infectivity and replication. To address the first concern, the HCV-H 5' and 3' terminal sequences were rigorously determined. To increase the chances of recovering a full-length clone free of deleterious errors, high fidelity RT/PCR and assembly PCR was used to construct a new library of full-length HCV-H clones which included the new terminal sequences. Multiple clones from the library were tested for infectivity in the chimpanzee model.

Rationale for rigorously determining the HCV-H termini. As mentioned above, the 5' and 3' terminal sequences of HCV-H were unknown; the previous attempts (Example 2) to generate functional transcripts were from cDNA clones bearing terminal sequences determined for other HCV isolates. Study in other RNA virus systems has shown that specific terminal sequences are critical for the generation of functional, replication competent RNAs [reviewed in Boyer and Haenni, (1994) supra]. Such sequences are believed to be involved in initiation of negative- and positive-strand RNA synthesis. In some cases, a few additional bases, or even longer non-viral sequences, are tolerated at the 5' and 3' termini; these sequences are typically lost or selected against during authentic viral replication. For other RNA viruses, extra bases, particularly at the 5' terminus, are deleterious. In contrast, transcripts lacking authentic terminal sequences are usually non-functional. For instance, deletion of the 3' terminal secondary structure or conserved sequence elements in the 3' NTR of flavivirus genome RNA is lethal for YF or TBE RNA replication. Given the importance of these sequence elements for other viruses, we have attempted to more rigorously determine the HCV-H terminal sequences.

Structure of the HCV-H 5' NTR. Methods used to amplify and clone the extreme 5' termini of RNAs include homopolymer tailing or ligation of synthetic oligonucleotides to first-strand cDNA (5' RACE) [Schaefer, *Anal. Biochem.* 227: 255–273 (1995)], cyclization of first-strand cDNA followed by inverse PCR [Zeiner and Gehring, *BioTechniques* 17: 1051–1053 (1994)], or cyclization of genome RNA with RNA ligase (after treatment to remove 5' cap structures, if necessary) followed by cDNA synthesis and PCR amplification across the 5'-3' junction [Mandl et al., *Biotechniques* 10: 486 (1991)]. Each of these approaches has its own set of problems, especially for rare RNAs. Despite this, 5' terminal sequences have been determined for a number of HCV isolates and are in general agreement. For HCV-H, both the cyclization/inverse PCR and 5' RACE methods were used to determine a 5'-terminal consensus sequence for HCV-H RNA from high titer H77 plasma (new data for HCV-H are shown in bold):

5'-GCCAGCCCCCTGATGGGGGCGACACTC-
CACCATGAATC....-3'  (SEQ ID NO:3)

This sequence is highly homologous to those determined for other isolates, but differs from our prototype full-length cDNA sequence at two positions (underlined). At lower frequency, clones with additional 5' residues (usually 1 additional G) were also recovered. Table 1 summarizes the results of the 5' terminal analyses.

TABLE 1

Results of the 5' end analysis of the HCV H cDNA clones.

| Number of Clones | 5' end |
|---|---|
| 18 | GCCAGCC... |
| 3* | NCCAGCC... |
| 18* | NNCCAGCC... |
| 9 | GGCCAGCC... |
| 3 | TGCCAGCC... |
| 1 | AGCCAGCC... |
| 2 | AAGCCAGCC... |
| 1 | GCGCCAGCC... |

*Sequences were not determined; the number of nucleotides on the 5' end was determined by relative electrophoretic mobility of restriction fragments.

Eighteen clones began with the sequence 5'-GCCAGC-C....-3'; nine clones with the sequence 5'-GGCCAGC-C....-3'; three clones with the sequence 5'-UGCCAGC-C....-3'; one clone with the sequence 5'-AGCCAGC-C....-3'; two clones with the sequence 5'-AAGCCAGC-C....-3'; and three clones with the sequence 5'-GCGC-CAGCC....-3'. Besides these sequenced clones, eighteen clones with one additional 5' base were identified by restriction analysis. Of note is the observation that a sequence reported for a genotype 1b isolate initiates with a U residue (5'-UGCCA....-3'). Although these results might indicate the presence of additional sequences or heterogeneity at the HCV 5' terminus, the additional bases may be artifactual and created by partial copying of a 5' cap structure or addition of non-templated 3' bases by reverse transcriptase during first-strand cDNA synthesis. It cannot be excluded that the 5' terminus of HCV genome RNA contains a 5' cap structure or a covalently linked terminal protein such as VPg of the picornaviruses [Vartapetian and Bogdanov, *Prog Nucleic Acid Res Mol Biol* 34: 209–51 (1987)]. These possibilities will remain unresolved until it becomes possible to directly determine the structure of the 5' terminus of HCV genome RNA. For the pestiviruses, recent results suggest that genome RNAs may not contain a 5' cap [Brock et al., *J. Virol. Meth.* 38: 39–46 (1992)] and that this structure is not required for infectivity of transcribed RNA [Meyers et al., *J. Virol.* 70: 8606–8613 (1996a); Meyers et al., *J Virol* 70: 1588–95 (1996b); Moormann et al., J Virol 70: 763–70 (1996); Ruggli et al., *J Virol* 70: 3478–87 (1996); Vassilev et al., *J. Virol.* 71: 471–478 (1997)].

Structure of the HCV-H 3' NTR. Determination of the extreme 3' terminal HCV sequences is described in co-pending, co-owned U.S. patent application Ser. No. 08/520,678, filed Aug. 29, 1995, now U.S. Pat. No. 5,874,565, which is incorporated herein by reference in its entirety, and PCT International Application No. PCT/US96/14033, filed Aug. 28, 1996. Briefly, these results showed that the HCV 3' NTR consists of three elements (positive-sense, 5' to 3'); (i) a short sequence with significant variability among genotypes; (ii) a homopolymeric poly (U) tract followed by a polypyrimidine stretch consisting of mainly U with interspersed C residues and; (iii) a novel sequence of 98 bases. This novel 98-base sequence was not present in human genomic DNA and is highly conserved among HCV genotypes. The 3'-terminal 46 bases are predicted to form a stable stem-loop structure. Using a quantitative-competitive RT/PCR assay, a substantial fraction of HCV genome RNAs from a high specific-infectivity inoculum were found to contain this 3' terminal sequence element. These results indicated that the HCV genome RNA terminates with a highly conserved RNA element, which is likely to be required for authentic HCV replication and therefore, for recovery of infectious RNA from cDNA. These results have been confirmed by two other groups [Tanaka et al., (1995) supra; Tanaka et al., (1996) supra; Yamada et al., (1996) supra]. A large number of clinical isolates have also been examined and shown to contain the novel conserved 3' terminal element Umlauft et al., J. Clin. Microbiol. 34: 2552–2558 (1996).

Recipient vector containing the HCV H77 5' and 3' consensus sequences. Based on our analysis of the HCV H terminal sequences, a recipient vector was constructed that contained the determined consensus H77 sequences 5' to the KpnI (580) and 3' fo the NotI (9219) site (these terminal HCV sequences are identical to those in p90/HCVFlong pU, see below, SEQ ID NO:5). This vector is designated pTET/T7HCVΔBglII/5'3' corr. and was used for construction of the combinatorial full-length library described below.

Additional considerations for construction of full-length cDNA libraries for the HCV-H strain. As for the previous attempt (Example 2), the strategy for the second try involved the construction of full-length cDNA templates in plasmid vectors that could be transcribed in vitro or in vivo using bacteriophage DNA-dependent RNA polymerases. Besides having correct 5' and 3' termini, RNA transcripts must also encode a full complement of functional HCV polypeptides. To minimize the possibility of cloning defective HCV genomes, high specific infectivity HCV-H plasma (H77) was used as a source of virion RNA for our new libraries (as mentioned earlier, the previous clone was assembled from cDNA made from infected chimp liver RNA). However, reverse transcription and multiple cycles of amplification prior to cDNA cloning raised the chances that HCV cDNA templates would contain one or more mutations deleterious for virus replication. For these reasons, complex libraries of full-length clones were constructed using high fidelity assembly PCR and then screened in pools for production of infectious RNA.

Figure 5:
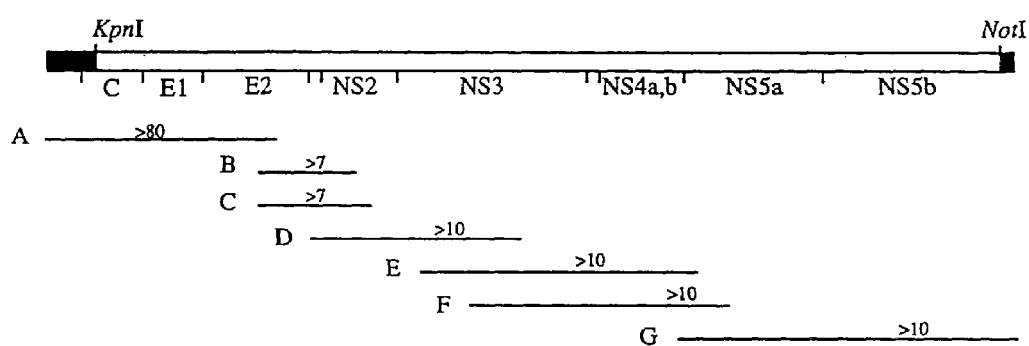
Figure 5:
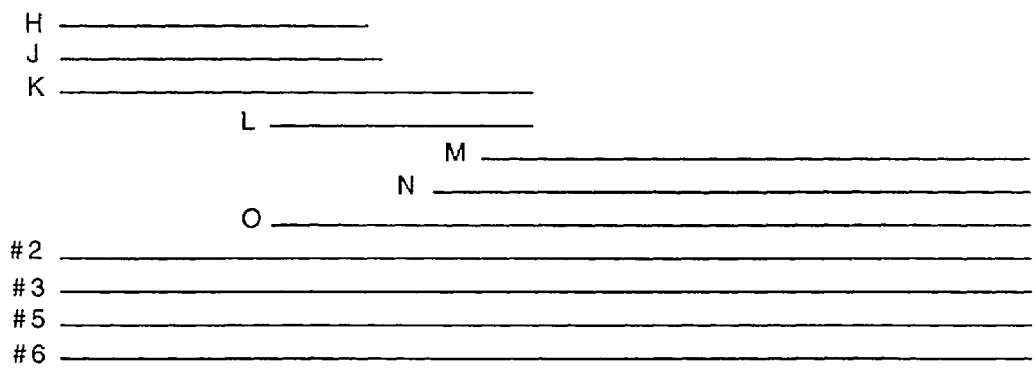

Construction of a new library of full-length HCV-H cDNA clones. We screened 41 HCV primer pairs and found 11 sets useful for amplifying overlapping 1–4 kb portions of the genome RNA (FIG. 5 and Tables 2 and 3).

TABLE 2

Oligonucleotides used for amplification of HCV-H cDNA.

| Name | Sequence (5' to 3') | SEQ ID NO: | position in HCV-H and orientation |
|---|---|---|---|
| SF49 | GGCGACACTCCACCATAGATC | 6 | (+) 18–38 |
| SF128 | TGGCACTACCCTCCAAGACC | 7 | (+) 1800–1819 |
| SF162 | ATGACACAAGGOGGCGCTCCGCACACT | 8 | (−) 2027–2053 |
| SF131 | TCCTGCTTGTGGATGATG | 9 | (+) 2538–2555 |
| SF152 | TAGTTTGGTGATGTCA | 10 | (−) 2999–3014 |
| PCL10067 | ACATAGGTGCCAGTAAG | 11 | (−) 3171–3188 |
| PCL10066 | CTGGCAACGTGCATCA | 12 | (+) 3549–3564 |
| CMR115 | GGGTGAGAACAATTACCA | 13 | (+) 4183–4200 |
| CMR117 | ATTGATGCCCAATGCG | 14 | (−) 4565–4580 |
| SF140 | ACTGCCTGGGATTCCCT | 15 | (+) 6347–6363 |
| SF155 | CCACAGTGGCAGCGAGTG | 16 | (−) 6419–6436 |
| SF156 | CATGGACGTCAACACG | 17 | (−) 6848–6863 |
| SF1045 | AATCTTCACCGGTTGGGGAGGAGGTAGATG | 18 | (−) 9353–9391 |

TABLE 3

Fragments and primers used in original and assembly PCR.

| Fragments in assembly | Primer pairs | Resulting fragment‡ | Position in start* | HCV genome end* |
|---|---|---|---|---|
| Original PCR | SF49, SF162 | A | 39 | 2026 |
| Original PCR | SF128, SF152 | B | 1820 | 2998 |
| Original PCR | SF128, PLC10067 | C | 1820 | 3170 |
| Original PCR | SF131, CMR117 | D | 2556 | 4564 |
| Original PCR | PCL10066, SF155 | E | 3565 | 6418 |
| Original PCR | CMR115, SF156 | F | 4201 | 6847 |
| Original PCR | SF140, SF1045 | G | 6364 | 9352 |
| A + B | SF49, SF152 | H | 39 | 2998 |
| A + C | SF49, PCL10067 | J | 39 | 3170 |
| B + D | SF128, CMR117 | L | 1820 | 4564 |
| J + L | SF49, CMR117 | K | 39 | 4564 |
| F + G | CMR115, SF1045 | M | 4201 | 9352 |
| E + G | PCL10066, SF1045 | N | 3565 | 9352 |
| L + M | SF128, SF1045 | O | 1820 | 9352 |
| H + O | SF49, SF1045 | #2 | 39 | 9352 |
| J + O | SF49, SF1045 | #3 | 39 | 9352 |
| K + N | SF49, SF1045 | #5 | 39 | 9352 |
| K + M | SF49, SF1045 | #6 | 39 | 9352 |

*excluding primer
‡see FIG. 5

Figure 6:
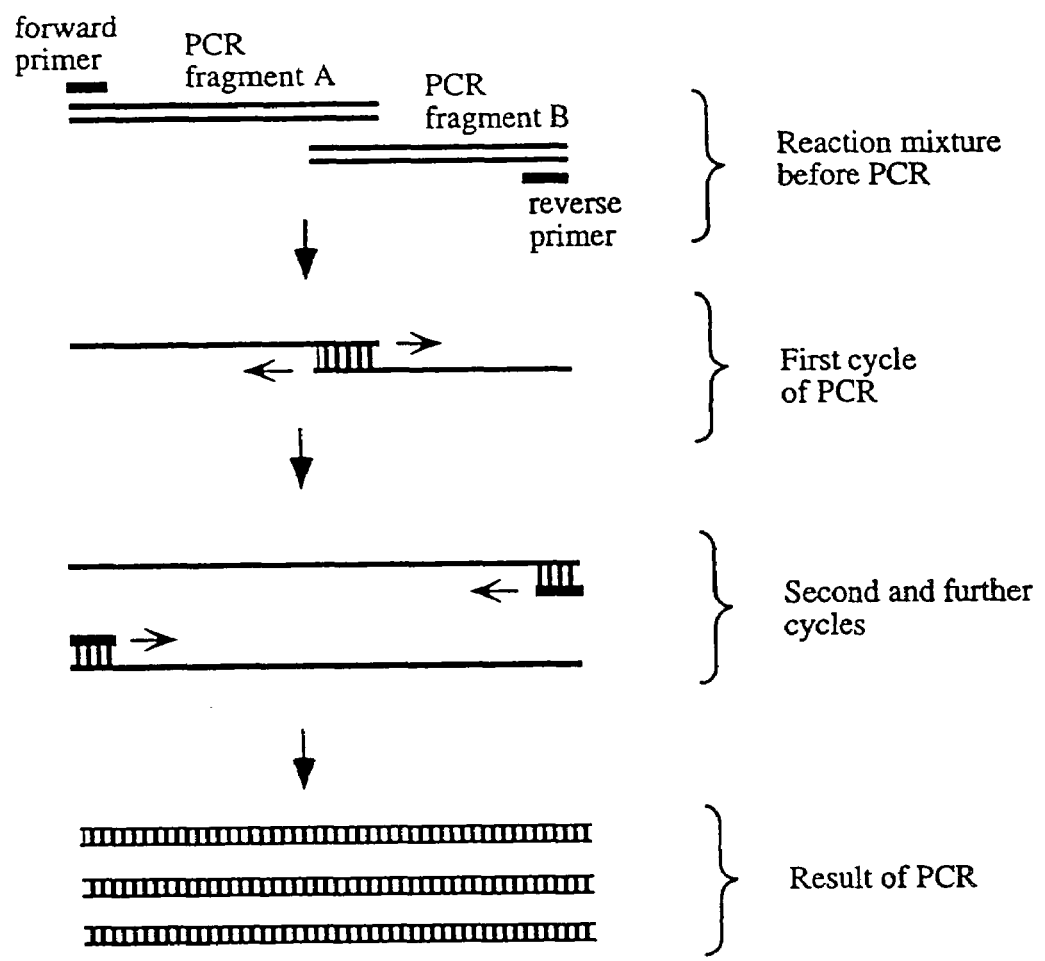
Figure 7:
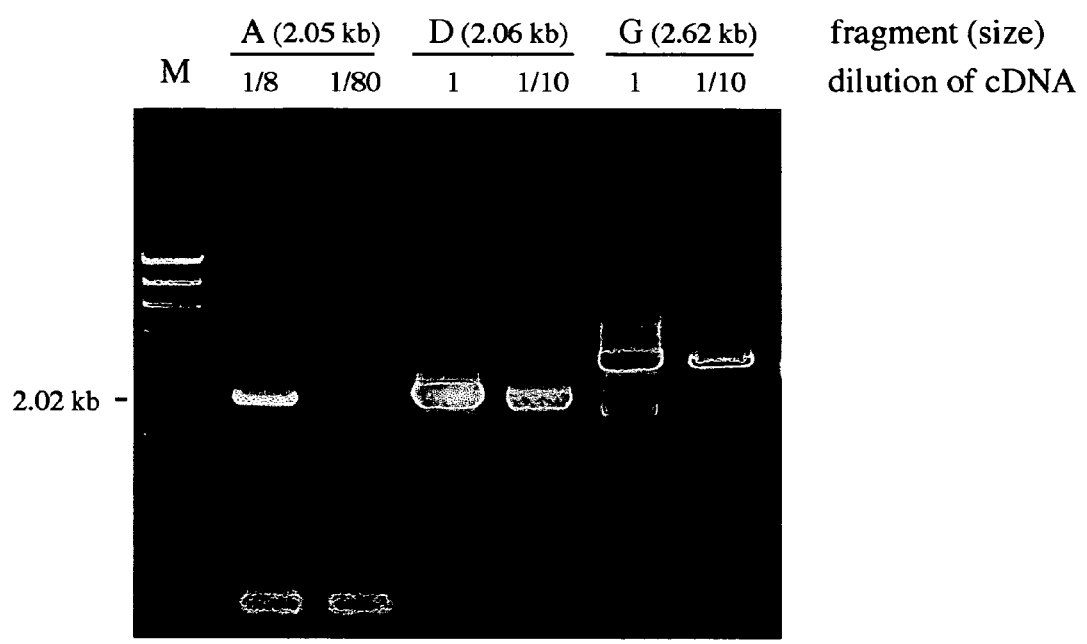

A mixture of thermostable enzymes were used to reduce error frequency and enhance synthesis of full-length products [Barnes, Proc. Natl. Acad. Sci. USA 91: 2216–2220 (1994); Lundberg et al., Gene 108: 1–6 (1991)]. Such intermediate PCR products were combined to produce full-length HCV cDNA using sequential rounds of assembly PCR [Mullis et al., Cold Spring Harbor Symp. 51: 263–273 (1986); Stemmer, (1994) supra]. Assembly PCR utilized primers at the extreme termini of the two overlapping fragments to be combined and a limited number of amplification cycles (FIG. 6). This approach has the advantage of generating complex combinatorial libraries which should contain some fraction of functional error-free HCV cDNA templates. A prime consideration for this approach is making sure that the library contains sufficient complexity to assure that some clones will be error-free. For each of the initial amplification reactions, dilutions of the first-strand cDNA were tested (FIG. 7) to show that multiple independent cDNA molecules were being amplified (greater than 7 to 100; indicated in FIG. 5). As shown in FIG. 7, the full-length library contained greater than $5.6 \times 10^5$ ($80 \times 7 \times 10 \times 10 \times 10$) different combinations. Possible deleterious mutations could have been introduced into half of the clones if the primer sequences chosen for PCR amplification and assembly were incorrect. However, it was later verified that no heterogeneity existed in the sequences corresponding to the primers used for PCR.

The majority of the HCV-H77 genome (from nucleotide 39-9352) was assembled and amplified in this manner and cloned as a KpnI (580)-NotI (9219) fragment into recipient plasmid (pTET/T7HCVΔBglII5'3'corr.) to produce the full-length library. As described above, pTET/T7HCVΔBglII5'3'corr. contains the T7 promoter, the consensus HCV-H 5' and 3'-terminal sequences 5' to the KpnI site and 3' from the NotI site, and a HpaI site for template linearization and production of run-off RNA transcripts. It should be noted that linearization with HpaI is predicted to produce run-off transcripts that contain one extra 3' U residue.

Clones from the library were chosen for infectivity assays based on two criteria. First, series of restriction digests were performed to eliminate clones that had obvious deletions or insertions in the HCV cDNA. Two hundred thirty-three clones were analyzed and clones passing this screen were then analyzed using the vaccinia-T7 transient expression system [see Grakoui et al., (1993a) supra; Grakoui et al., (1993c) supra] for production of the expected HCV polyprotein cleavage products. Full-length clones could be analyzed directly using this technique, since preliminary studies in BHK cells showed that the HCV IRES functions nearly as efficiently as the EMCV IRES for expression of HCV polypeptides. One hundred twenty-nine clones were screened using a polyclonal antiserum from a patient with chronic HCV (JHF: Grakoui et al., 1993c); 49 clones were analyzed for production of NS5B, the C-terminal protein in the HCV-H ORF [Grakoui et al., 1993a; Grakoui et al., 1993c). Thirty-four clones passing these tests (expected restriction pattern; intact ORF and proper processing; NS5B production) were selected for in vitro transcription of potentially infectious RNA and infectivity analysis.

Figures 8A, 8B:
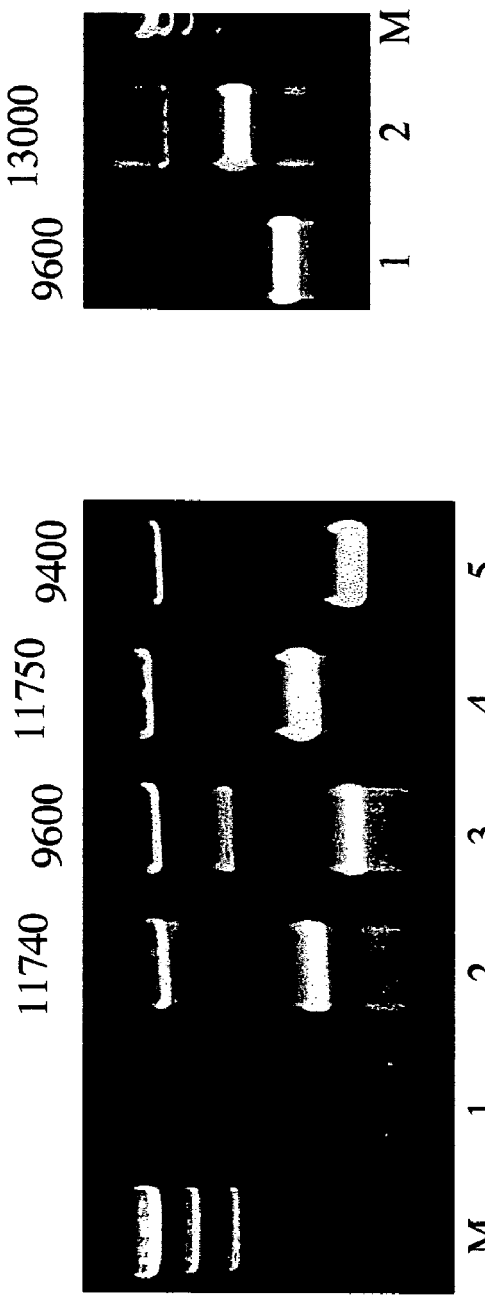

Special conditions for transcription of full-length HCV RNA containing the internal poly (U/UC) tract and the 98-base element. For T7-driven transcription, in vitro transcription conditions were optimized and showed that the resulting RNAs contain the extreme 3' terminal sequence. This was of special concern since the T7 RNA polymerase termination signals (a secondary structure followed by poly- U) resemble the HCV sequences preceding the 3' novel element and we observed termination at this site. In addition, the enzyme seemed to be prone to premature termination inside the poly (U/UC) tract. As shown in FIG. 8A, by raising the UTP concentration to 3 mM in the transcription reaction, high yields of full-length HCV RNA transcripts were obtained. T7 polymerase was clearly better in this regard than SP6 polymerase, which exhibited significant premature termination in the poly (U) tract even at relatively high concentrations of UTP.

Chimpanzee Experiment II

Essentially as described above (example 2), surgical procedures and direct intrahepatic inoculation were used to assay the infectivity of transcribed RNAs. Three animals, not previously used for HCV work and negative for HCV serology and RNA, were inoculated. Each of two of the animals were injected with RNA transcripts from 17 independent clones, with inoculations at 34 separate sites in the liver. Two separate inoculations used for each transcript preparation were: 50–100 µg RNA in PBS injected at one site and 1 µg RNA mixed with 10 µg lipofectin (a cationic liposome which enhances RNA transfection [see Rice et al., (1989) supra] at a second site. This procedure was intended to maximize the chances of productive transfection for each clone/RNA preparation. As a negative control, a third animal (Chimp 1557) was similarly inoculated at 34 sites with transcripts (~1500 µg) which contained a 21 residue in-frame deletion in NS5B encompassing the active site of the HCV RNA-dependent RNA polymerase (called ΔGDD). Following inoculation, serum samples were collected (at weekly intervals) and analyzed for HCV RNA, elevation of liver transaminases, and HCV-specific antibody. Neither experimental animal nor the negative control animal (ΔGDD) exhibited signs of productive infection (circulating HCV RNA, elevated liver enzymes, histopathology). Of note for future experiments was the complete absence of detectable circulating HCV RNA even as early as one week after inoculation.

Example 4

Successful Recovery of Infectious HCV from cDNA

Determination of the HCV-H consensus sequence. Since the limited pool screening approach was unsuccessful, we determined a complete consensus sequence for the HCV-H strain. Segments of these sequenced clones were used for directed assembly of full-length HCV-H clones having the consensus sequence. This procedure was expected to eliminate lethal mutations, which might have occurred during cDNA synthesis or PCR amplification, or which existed in the original HCV population. Accordingly, the consensus method had a strong change of producing functional HCV.

TABLE 4

Sequence information used to determine an HCV-H consensus sequence

| Designation | Description |
| --- | --- |
| HCV-H CMR | CMR prototype HCV-H cDNA clone; infected chimp liver RNA (SEQ ID NO: 19) |
| HCV-H GenBank | HCV-H sequence |
| AAK#83 | Combinatorial library clone #83; H77 serum |
| AAK#84 | Combinatorial library clone #84; H77 serum |
| AAK#86 | Combinatorial library clone #86; H77 serum |
| AAK#87 | Combinatorial library clone #87; H77 serum |
| AAK#89 | Combinatorial library clone #89; H77 serum |
| AAK#90 | Combinatorial library clone #90; H77 serum |
| AAK#92 | Combinatorial library clone #92; H77 serum |
| AAK#93 | Combinatorial library clone #93; H77 serum |
| AAK#96 | Combinatorial library clone #96; H77 serum |
| AAK#99 | Combinatorial library clone #99; H77 serum |
| AAK#101 | Combinatorial library clone #101; H77 serum |
| AAK#248 | Combinatorial library clone #248; H77 serum |
| AAK#227 | Combinatorial library clone #227; H77 serum |
| AAK#213 | Combinatorial library clone #213; H77 serum |
| AAK#211 | combinatorial library clone #211 H77 serum |
| AAK#209 | Combinatorial library clone #209; H77 serum |
| AAK#12 | Combinatorial library clone #12; H77 serum |

Complete sequences between the KpnI (580) and NotI (9219) sites in the HCV cDNA were determined for clones AAK#248, AAK#227, AAK#213, AAK#211, AAK#209, and AAK#12. Sequences for the prototype HCV-H CMR [Daemer et al., supra; Grakoui et al., (1993c) supra] and HCV-H GenBank [Inchauspe et al., (1991) supra] had been determined previously. These sequences are aligned in FIG. 9. Dots indicate positions identical to the HCV-H CMR sequence, shown at the bottom (SEQ ID NOS:19 and 20); dashes indicate gaps; the sequence "PCR seq" was determined by direct sequencing of PCR-amplified HCV-H77 cDNA. Sequences of additional clones from our combinatorial library (AAK#83, #84, #86, #87, #89, #90, #92, #93, #95, #96, #99, #101) were determined for the HVR1 hypervariable region in E2 (most were sequenced between nucleotides 1464–1823; see below). Inspection of the alignment reveals an HCV H77 consensus sequence (SEQ ID NO:1) at most positions. At some positions, however, no clear consensus sequence emerged. These variable positions were: 2170 (Gac versus Aac; variable base is indicated in upper case type), 3940 (gAg versus gGg), and 5560 (caA versus caT). In these cases, the sequence used in the consensus clone corresponded to the nucleotide yielding the amino acid found at that position for the majority of sequenced HCV isolates.

Regarding determination of a consensus sequence, additional areas of the HCV genome deserve further comment. First, the N-terminal portion of E2 is highly variable and believed to be the target of immune selection [Houghton, (1996) supra]. In the H77 sample, considerable variability exists in HVR1 [see Nakajima et al., *J Virol* 70: 3325–9 (1996); Ogata et al., (1991) supra]. Multiple independent clones from this region were sequenced and the predominant HVR1 sequence in each position was used in the consensus clones. The predominant sequence utilized differs in one position from that determined by others [Inchauspe et al., (1991) supra; Nakajima et al., (1996) supra; Ogata et al., (1991) supra. However, it is highly similar to that of the prototype HCV-H clone, which was derived from liver RNA isolated from an H77-inoculated chimpanzee. Hence, it seemed that this sequence would be tolerated for HCV replication in chimps. As shown below, this sequence was functional but it is likely that many other HVR sequence variations will also be tolerated.

A second region of the HCV-H sequence, the length and composition of the 3' NTR poly (U/UC) tract, was not determined unambiguously. Sufficient quantities of double-stranded cDNA could not be obtained for direct cloning of this region without resorting to PCR amplification. PCR amplification can contract and possibly expand the length of this homopolymer tract. Thus, clones resulting from this procedure may not reflect the native HCV genome RNA structure. In multiple independent clones derived by PCR amplification, the length of this tract varied from 41 to 133 nucleotides (see Kolykhalov et al., 1996 and patent application Ser. No. 08/520,678). Hence, two different lengths of poly (U/UC) tract were tested: "short" (75 bases) or "long" (133 bases). The length of the "short" tract is actually about the medium length for all sequences (from different genotypes) reported by us [Kolykhalov et al., (1996) supra] or others [Tanaka et al., (1995) supra; Tanaka et al., (1996) supra; Yamada et al., (1996), supra]. The "long" tract was only recovered in one HCV-H clone (pGEM3Zf(−)HCV-H3'NTR#10); a tract of similar length was recovered in one clone of genotype 4 isolate WD [Kolykhalov et al., (1996) supra]. Such long poly (U/UC) tracts have not yet been reported by others Tanaka et al., (1995) supra; Tanaka et al., (1996) supra; Yamada et al., (1996) supra].

Variations in 5'-terminal sequences, silent markers, length of 3' NTR poly (U/UC) tracts, and 3' run-off site. Given that additional bases were found at the 5' end of some HCV cDNA clones and the uncertainty about the length of the poly (U/UC) tract, several alternative clones were created. Silent nucleotide substitutions were incorporated in the ORF to serve as markers for identifying which derivatives were functional in later analyses and to demonstrate that replicating virus was in fact recovered from the assembled cDNA clones. Replacing the previously used HpaI site, a BsmI site was created following the 3' end of the HCV cDNA to allow for production of run-off transcripts corresponding to the precise 3' end of HCV genome RNA. Details describing these constructions follow:

Additional bases at the 5' terminus. A recipient clone containing the most frequent 5' terminal sequence (5'-GCCA . . . -3') called pTET/T7HCVΔBglII/5'+3'corr. was modified by subcloning a BssHII (479) to KpnI (580) fragment from pTET/HCV5'T7G3'AFL, one of the prototype HCV-H cDNA clones tested in chimpanzees, to create p67/HCVΔBglII/5'+3'/XhoI-. These clones differ by presence of a XhoI site at position 514 (pTET/T7HCVΔBglII/5'+3'corr.) or its absence (p67/HCVΔBglII/5'+3'/XhoI-). p67/HCVΔBglII/5'+3'/XhoI- was then used as the vector for construction of four derivatives with different 5' terminal sequences. These are:

| Plasmid | 5' sequence of T7 transcript | Marker (position) |
|---|---|---|
| p70/HCVΔBglII/5'+ 3'/XhoI−/GG | 5'-GGCCA . . . -3' | XhoI-(514) |
| p71/HCVΔBglII/5' + 3'/XhoI−/GAG | 5'-GAGCCA . . . -3' | XhoI-(514) |
| p72/HCVΔBglII/5' + 3'/XhoI−/GUG | 5'-GUGCCA . . . -3' | XhoI-(514) |
| p73/HCVΔBglII/5' + 3'/XhoI−/GCG | 5'-GCGCCA . . . -3' | XhoI-(514) |

These derivatives were constructed using appropriate synthetic oligonucleotides and PCR amplification and their structures verified by sequence analysis.

Figure 10:
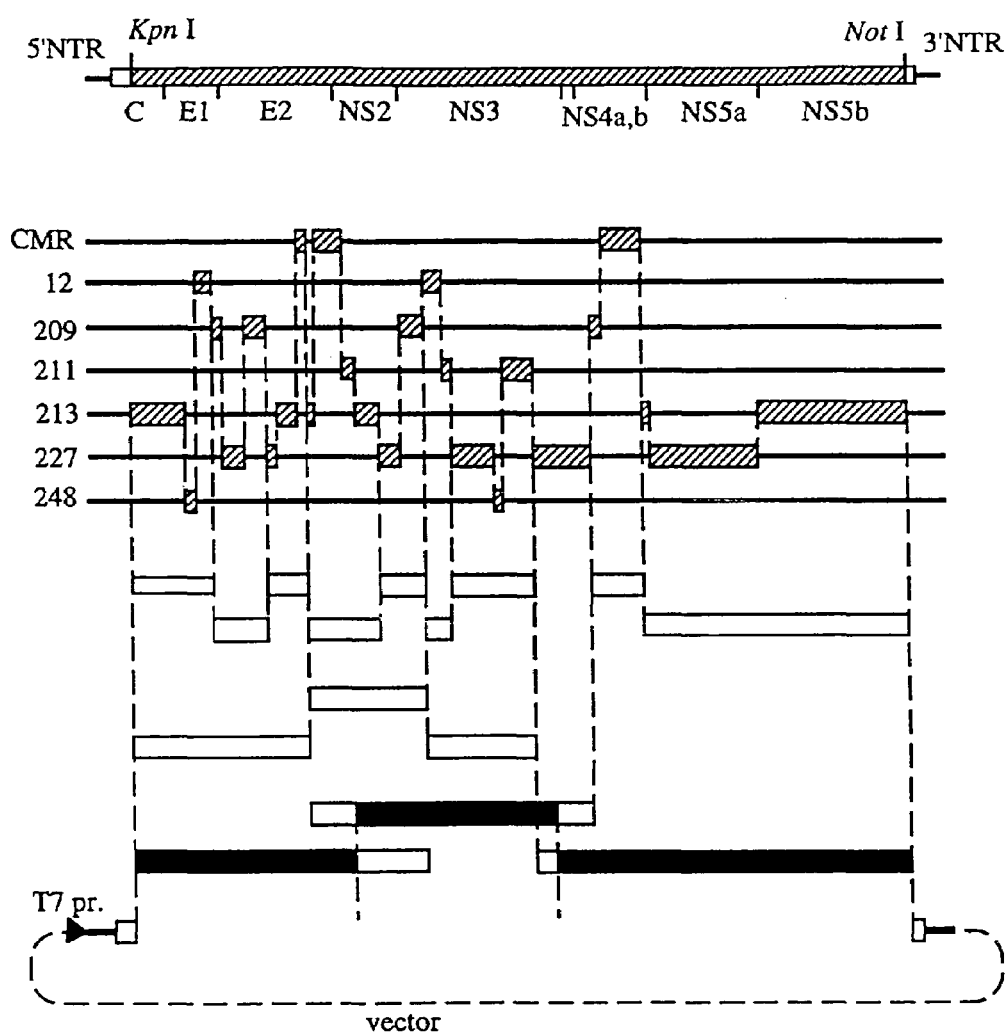

Assembly of a clone containing the consensus sequence between KpnI (580) and NotI (9219). A schematic of the assembly steps is shown in FIG. 10. The 7 sequenced HCV-H clones were used to assemble a prototype consensus clone. The plasmid source, position in the HCV cDNA, and restriction sites used for assembly are summarized in Table 5.

TABLE 5

Clones, fragments, and restriction sites used for consensus clone construction.

| Source of fragment number of clones | Position in HCV genome | Restriction sites used |
|---|---|---|
| 313 | 580–1046 | KpnI-Xho I |
| 248 | 1046–1174 | Xho I-PpuM I |
| 12 | 1174–1357 | PpuM I-BamH I |
| 209 | 1357–1482 | BamH I-Sal I |
| 227 | 1482–1748 | Sal I-PpuM I |
| 209 | 1748–1908 | PpuM I-Asc I |
| 227 | 1908–2108 | Asc I-BspE I |
| 312 | 2108–2322 | BspE I-Sst I |
| CMR | 2322–2440 | Sst I-Sca I |
| 213 | 2440–2526 | Sca I-BssH II |
| CMR | 2526–2828 | BssH II-Hinf I |
| 211 | 2828–2978 | Hinf I-BsrG I |
| 209 | 2978–3236 | BsrG I-Bgl II |
| 227 | 3236–3478 | Bgl II-Bgl I |
| 209 | 3478–3733 | Bgl I-SexA I |
| 12 | 3733–3942 | SexA I-Bfa I |
| 211 | 3942–4069 | Bfa I-Spl I |
| 227 | 4069–4545 | Spl I-Sst I |
| 248 | 4545–4646 | Sst I-Sal I |
| 211 | 4646–4976 | Sal I-Sma I |
| 227 | 4976–5610 | Sma I-Xho I |
| 209 | 5610–5750 | Xho I-Eae I |
| CMR | 5750–6209 | Eae I-Bsu36 I |
| 213 | 6209–6302 | Bsu36 I-Blp I |
| 227 | 6302–7529 | Blp I-Blp I-BamH I |
| 213 | 7529–9219 | BamH I-Not I |
| 209 | 7861–8205 | Hind III-EcoR I |

The final step in the assembly involved subcloning the KpnI-NotI consensus region into recipient vector pTET/T7HCVΔBglII/5'+3'corr to produce p61/HCVFLcons.

Introduction of a BsmI substitution in the HCV cDNA and a BsmI run off site. Since the previously used HpaI run off site resulted in transcripts with an additional 3' terminal U residue which might be deleterious, clones were re-engineered so that transcripts terminating at the exact HCV 3' nucleotide could be synthesized. This was accomplished by positioning a BsmI site at an appropriate position downstream from the HCV 3' terminus. Cleavage with BsmI produces a template strand which terminates at the position corresponding to the HCV 3' terminus. Since the H77 consensus sequence contains a BsmI site at position 5934, this site was inactivated with a translationally silent substitution engineered by site-directed mutagenesis.

The first step in this series of constructions was to inactivate the BsmI site in the HCV H77 cDNA. This clone, called p62/HCVFLcons/Bsm(−) was created in a four fragment ligation which included: (1) annealed synthetic oligos between SacI (5923) and Sau3AI (5942) which contained a silent substitution inactivating the BsmI site (C instead of A at position 5934); (2) NstI (5282) to SacI (5923) fragment from p61/HCVFLcons; (3) Sau3AI (5942) to Bsu36I (6209) from p61/HCVFLcons; (4) Bsu36I (6209) and NsiI (5282) digested p61/HCVFLcons. p62/HCVFLcons/Bsm(−) was sequenced completely verifying the structure of the assembled consensus clone, the presence of a silent marker mutation at position 899 (C instead of T), the ablated BsmI site, and a silent marker mutation at position 8054 (see below).

Intermediate plasmid p65/3'HCVBsm(+)/Not-Mlu, containing the 3' BsmI run off site, was created by the following three fragment ligation: (1) annealed synthetic oligos between Sau3AI (9639) and MluI (9656) containing the BsmI site [5'-tgTcgcattc-3' (SEQ ID NO:21); the nucleotides in bold indicate the BsmI site, the upper case nucleotide corresponds to the 3' terminal base of the HCV genome]; (2) NotI (9219) to Sau3AI (9639) fragment from p62/HCV-FLcons/Bsm(−); (3) MluI (9656) to NotI (9219) from p61/HCVFLcons. Note that this clone contains both the internal BsmI site (5934) and the engineered BsmI run-off site.

The original consensus full-length clone, p61/HCV-FLcons, contained a silent substitution in the NS5B coding region (A instead of G at positions 8054). This substitution was used as a marker to distinguish between clones containing "short" poly (U/UC) tracts (these clones contain A at position 8054) or "long" poly (U/UC) tracts (with G at position 8054). p90/HCVFLlong pU (SEQ ID NO:5), containing long poly (U/UC) and G at position 8054, was constructed by ligation of four fragments: (1) XbaI (−20) to HindIII (7861) from p62/HCVFLcons/Bsm(−); (2) HindIII (7861) to EcoRI (8205) from library clone AAK#209 (FIG. 9) containing the G residue at position 8054; EcoRI (8205) to NotI (9219) from p62/HCVFLcons/Bsm(−); NotI (9219) to XbaI (−20) from p65/3'HCVBsm(+)/Not-Mlu.

p91/HCVFLshort pU, a derivative containing the "short" poly (U/UC) tract and the silent marker A at position 8054, was created by ligation of the following fragments: (1) BglI (9398) to NheI (9520) from pGEM3Zf(−)HCV-H3'NTR#8; (2) NheI (9520) to MluI (9597) from p65/3'HCVBsm(+)/Not-Mlu; MluI (9597) to NotI (9219) from p62/HCV-FLcons/Bsm(−). Note that numbering for this construction refers to the final p91/HCVFLshort pU sequence.

To generate the final set of full-length constructs with long poly (U/UC) and additional nucleotides at the 5' terminus, the KpnI (580) to MluI (9656) fragment from p90/HCV-FLlong pU was cloned into p70/HCVΔBglII/5'+3'/XhoI-/GG, p71/HCVΔBglII/5'+3'/XhoI-/GAG, p72/HCVΔBglII/5'+3'/XhoI-/GUG, and p73/HCVΔBglII/5'+3'/XhoI-/GCG to create p92/HCVFLlong pU/5'GG, p93/HCVFLlong pU/5'GAG, p94/HCVFLlong pU/5'GUG, p95/HCVFLlong pU/5'GCG, respectively.

To generate the analogous set of full-length constructs with short poly (U/UC), the KpnI (580) to MluI (9597) fragment from p91/HCVFLshort pU was cloned into p70/HCVΔBglII/5'+3'/XhoI-/GG, p71/HCVΔBglII/5'+3'/XhoI-/GAG, p72/HCVΔBglII/5'+3'/XhoI-/GUG, and p73/HCVΔBglII/5'+3'/XhoI-/GCG to create p96/HCVFLshort pU/5'GG, p97/HCVFLshort pU/5'GAG, p98/HCVFLshort pU/5'GUG, p99/HCVFLshort pU/5'GCG, respectively.

Figure 11:
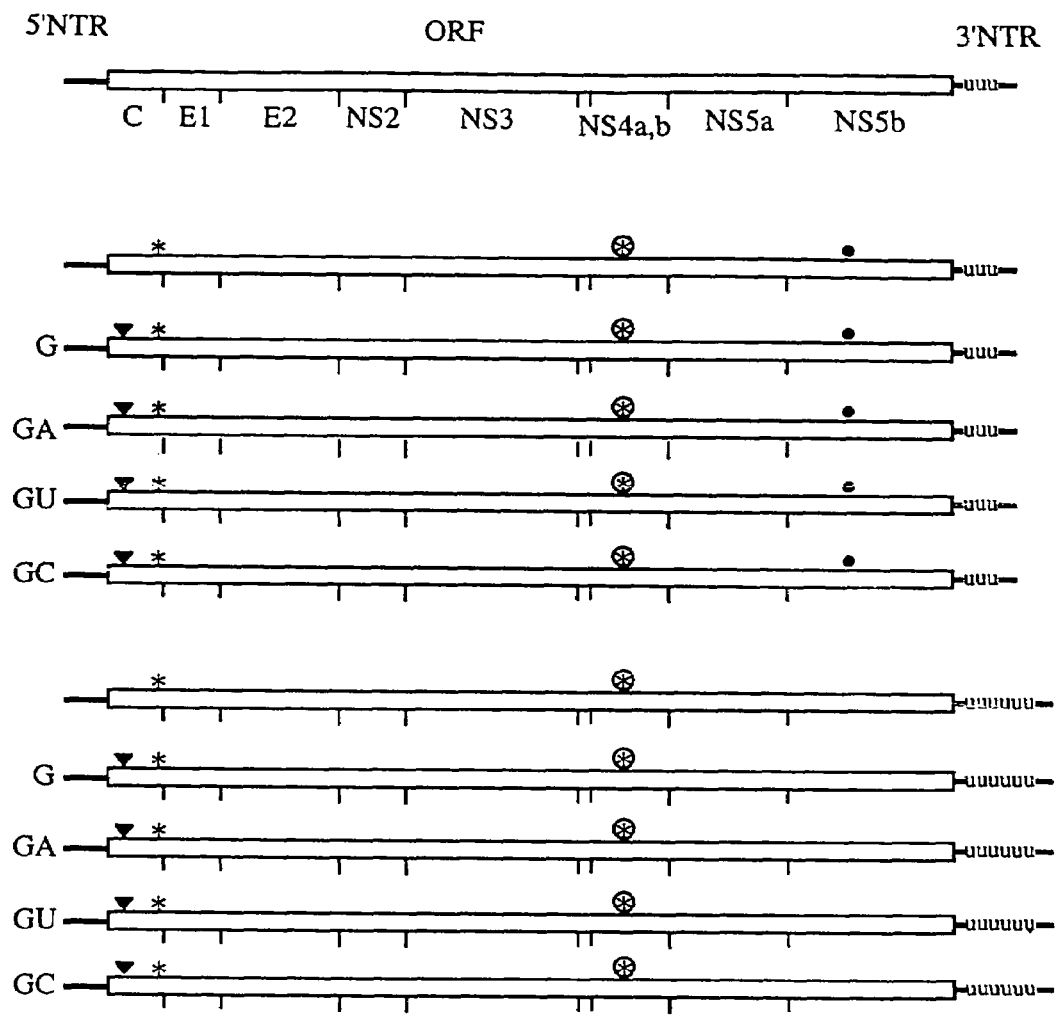

The salient features of these 10 clones [5' bases, silent markers, poly (U/UC) length] are summarized in FIG. 11. Plasmids were propagated in *E. coli* (tet$^s$ SURE strain) and purified plasmid DNAs were prepared by standard methods, including twice banding on CsCl gradients [Ausubel et al., Current protocols in molecular biology, eds. Green Publishing Associates, New York (1993); Sambrook et al., Cold Spring Harbor Laboratory, Cold Spring Harbor, N.Y. (1989)].

Transcription of full-length RNAs. As mentioned above, increasing the UTP concentration to 3 mM in T7 transcription reactions increased the yield of full-length HCV RNAs, by facilitating readthrough of the poly (U/UC) tract. The skewed ratio of UTP (3 mM) to the other rNTPs (1 mM) could lead to increased misincorporation of U residues, in particular late in the transcription reaction when the other NTPs were substantially depleted. This concern was avoided by increasing the concentration of the other three NTPs to 3 mM. Purified plasmid DNAs were digested to completion with BsmI, extracted once with phenol-chloroform and precipitated with ethanol [Ausubel et al., (1993) supra; Sambrook et al., (1989) supra]. DNA pellets were washed with EtOH to remove salts and resuspended in RNase-free $H_2O$. Transcription reactions (100 µl) contained the following components: 10 µg BsmI-linearized template DNA, 40 mM Tris-Cl, pH 7.8, 16 mM $MgCl_2$, 5 mM DTT, 10 mM NaCl, 3 mM each rNTP, 100 units T7 RNA polymerase, and 0.02 U inorganic pyrophosphatase. After a 1 hour incubation at 37° C., typical yields were approximately 300 µg with greater than 80% full-length RNA as estimated by gel electrophoresis (FIG. 8B).

Chimpanzee Experiment III

Transcripts from the ten consensus clones were used to inoculate two different animals, using essentially the same surgical procedures described above. Protocols were reviewed and approved by the FDA and NIH Animal Studies Committees. Animals were seronegative for all hepatitis viruses, negative for HCV RNA by nested RT-PCR, and had normal baseline levels of liver enzymes. Two different inoculation/transfection protocols were employed. For chimpanzee #1535, the 100 µl transcription reactions were diluted with 400 µl PBS and stored frozen at −80° C. until used for inoculation. These storage conditions were tested and shown to have no observable effect on the integrity of HCV RNA transcripts. Prior to inoculation, samples were thawed and each sample was injected intrahepatically at two sites (~0.25 ml/site). Injection sites for the 10 clones were distributed in three lobes of the liver. As a positive control for this procedure, chimpanzee #1557 was inoculated similarly with RNA transcripts from two different hepatitis A virus clones. In this case, 80–100 µg of transcribed RNA per clone was inoculated at two sites. A third animal, chimpanzee #1536, was inoculated with smaller amounts of RNA which had been mixed with lipofectin. In this case, the same transcript RNAs from the 10 full-length HCV-H77 clones were treated with DNaseI to remove template DNA and 0.15 µg, 0.5 µg, and 1.5 µg portions were diluted to 50 µl with PBS and stored at −80° C. until used for inoculation. After thawing, 100 µl PBS containing 9 µg lipofectin (Bethesda Research Laboratory) was added to each sample, mixed, and injected into a single site. Hence, each clone/transcript preparation with different RNA/lipofectin ratios was injected at three separate sites.

Serum samples and liver biopsies were taken pre-inoculation and at weekly intervals thereafter. For nearly two months post-inoculation, samples have been assayed for liver enzymes (ALT, ICD, GGTP) hepatitis virus serology, and viremia by quantitative competitive RT-PCR [Kolykhalov et al., (1996) supra].

Evidence for successful initiation of infection and replication. The results of our analyses thus far are summarized in Table 6.

TABLE 6

Results of chimpanzee experiment III.

Chimp 1535 (RNA-DNA IN PBS):

| week | ALT | ICD | GGTP | anti-HCV ab | HCV RNA bDNA (Meg/ml) | QC RT-PCR |
|---|---|---|---|---|---|---|
| −5 | 43 | 453 | 28 | 0.2 | — | — |
| −2–3 | 32 | 325 | 27 | 0.1 | — | — |
| −1 | 36 | 600 | 27 | 0.2 | — | — |
| 0 | 40 | 430 | 28 | 0.1 | <0.2 | <$10^2$/ml |
| 1 | 42 | 490 | 24 | 0 | 0.445 | 1 × $10^5$/ml |
| 2 | 96C | 1000 | 53 | 0 | 0.283 | 3 × $10^5$/ml |

TABLE 6-continued

Results of chimpanzee experiment III.

| | | | | | | |
|---|---|---|---|---|---|---|
| 3 | 81C | 780 | 55 | 0 | 0.593 | 6 × 10⁵/ml |
| 4 | 78 | 640 | 52 | 0.2 | 2.026 | 1 × 10⁶/ml |
| 5 | 60 | 510 | 57 | 0.1 | 2.609 | 2 × 10⁶/ml |
| 6 | 49 | 670 | 50 | 0.1 | 3.286 | T.B.D. |
| 7 | 49 | 525 | 44 | 0 | 5.708 | T.B.D. |
| 8 | 56 | 485 | 50 | .01 | T.B.D. | T.B.D. |
| 9 | 67 | 500 | 67 | 0.1 | T.B.D. | T.B.D. |
| 10 | 98 | 725 | 79 | 0.2 | T.B.D. | T.B.D. |
| 11 | 86 | 525 | 85 | 0.2 | T.B.D. | T.B.D. |

Chimp 1536 (RNA + lipofectin):

| week | ALT | ICD | GGTP | anti-HCV ab | HCB RNA bDNA (Meg/ml) | QC RT-PCR |
|---|---|---|---|---|---|---|
| −9 | 27 | 368 | 33 | 0.1 | — | — |
| −5 | 45/45 | 524/496 | 82/77R | 0.2 | — | — |
| −2–3 | 28 | 375 | 52 | 0.1 | — | — |
| −1 | 34 | 475 | 41 | 0.1 | — | — |
| 0 | 36 | 680 | 44 | 0.1 | <0.2 | <10²/ml |
| 1 | 45 | 660 | 42 | 0 | <0.2 | 1 × 10⁴/ml |
| 2 | 44 | 875 | 51 | 0 | 0.252 | 3 × 10⁵/ml |
| 3 | 49 | 760 | 55 | 0 | 0.469 | 1 × 10⁶/ml |
| 4 | 41 | 465 | 52 | 0.2 | 0.862 | 2 × 10⁶/ml |
| 5 | 42 | 500 | 49 | 0.1 | 0.904 | 3 × 10⁶/ml |
| 6 | 50 | 730 | 60 | 0.00 | 1.489 | 6 × 10⁶/ml |
| 7 | 43 | 490 | 55 | 0.1 | 3.413 | T.B.D. |
| 8 | 53 | 700 | 64 | 0.1 | 13.00 | T.B.D. |
| 9 | 38 | 505 | 65 | 0.1 | 3.271 | T.B.D. |
| 10 | 133 | 1270 | 120 | 0.4 | T.B.D. | T.B.D. |
| 11 | 324 | 1485 | 258 | 1.3 | T.B.D. | T.B.D. |

Chimp 1557 (HAV RNA + DNA in PBS), positive control:

| week | ALT | ICD | GGTP | anti-HAV |
|---|---|---|---|---|
| 0 | 33 | 405 | 19 | (−) |
| 1 | 42 | 360 | 14 | (−) |
| 2 | 33 | 345 | 16 | 0.6 |
| 3 | 26 | 520 | 14 | 0.7 |
| 4 | 62 | 1330 | 24 | 3.5 |
| 5 | 43 | 700 | 28 | 21.4 |
| 6 | 23 | 650 | 27 | 27.9 |
| 7 | 22 | 540 | 25 | 14.6 |
| 8 | 20 | 490 | 22 | T.B.D. |

R = repeated
C = confirmed
T.B.D. = to be determined

Chimp #1535 showed a peak in liver enzymes at week 2 post-inoculation, which has gradually declined to the pre-inoculation baseline. At week 10, a second peak of liver enzymes was observed. HCV RNA titers were below our detection limit pre-inoculation (<10²), increased to 10⁵/ml by week 1, and continued to climb steadily reaching 2×10⁶/ml by week 5. This represents a 20-fold increase relative to week 1.

Chimp #1536 showed less evidence of early liver damage with only a minor peak in the ICD level at week 2 and fluctuating values thereafter. However, highly elevated levels of enzymes were observed in weeks 10 and 11. The animal also became HCV-seropositive on weeks 10 and 11. On week 1, the HCV RNA titer was 10⁴/ml and has climbed to 6×10⁶/ml by week 6. This represents a 600-fold increase relative to week 1.

The positive control inoculated with HAV transcripts (chimpanzee #1557) showed a sharp peak in liver enzymes on week 4 and had clearly seroconverted by this time. HAV-specific immunoreactivity increased sharply on week 5 and continued at high levels thereafter. These results show clear evidence of HAV infection and validate the inoculation method used for chimpanzee #1535.

Figure 12:
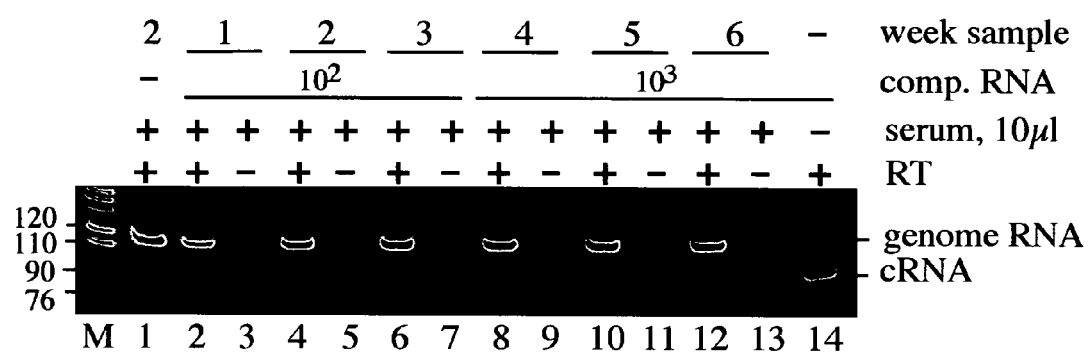
Figure 13:
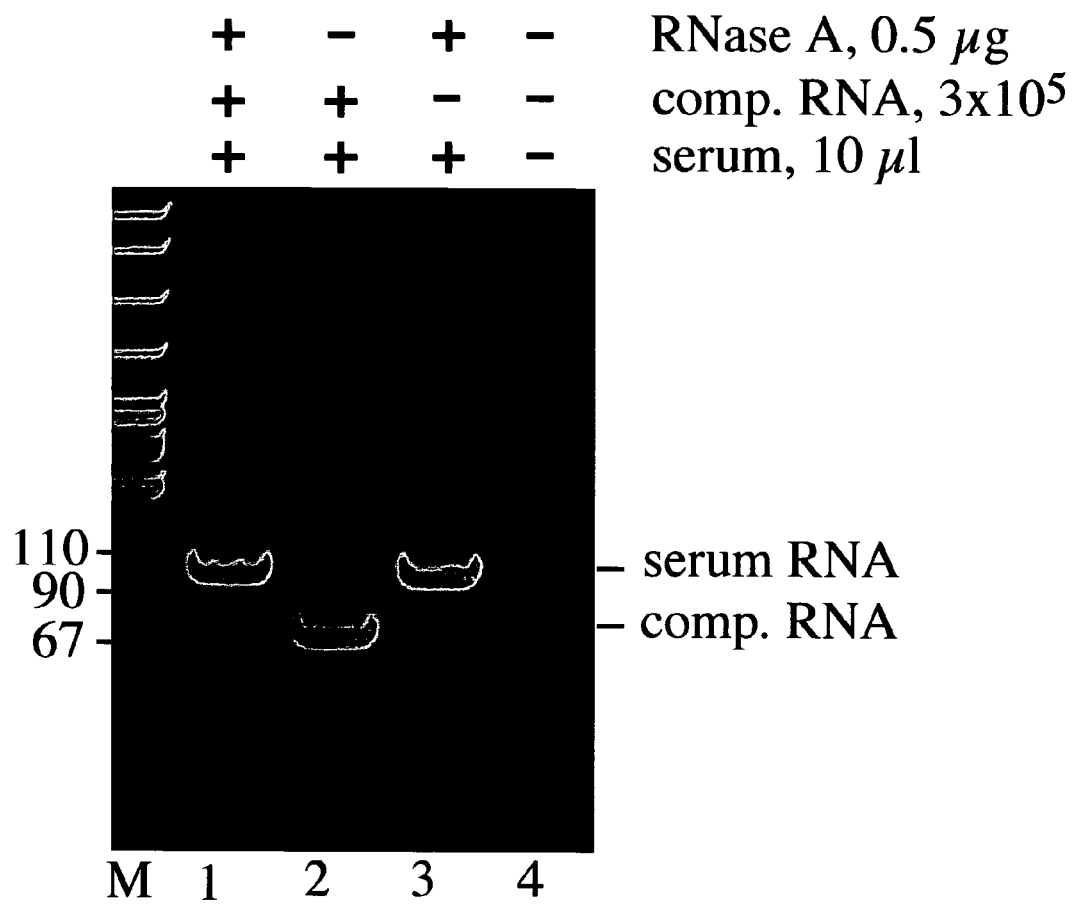

All of the samples analyzed for HCV RNA were also assayed for the presence of residual template DNA by omitting the enzyme in the reverse transcription step. No products were obtained, demonstrating that the signals detected in the quantitative competitive PCR assay were due to RNA (FIG. 12). In addition, the HCV RNA containing material in these samples was resistant to RNase digestion under the same conditions that completely degraded naked competitor RNA mixed with serum being analyzed (FIG. 13). These are the expected results if the RNAs are packaged into enveloped RNase-resistant virus particles, as opposed to residual inoculated RNA. Moreover, the total amount of transcript RNA used for inoculation was ~3000 μg, for chimpanzee #1535 and only ~22 μg for chimpanzee #1536. In spite of being inoculated with ~150-fold less RNA, chimpanzee #1536 showed higher levels of viremia than chimpanzee #1535. Thus the level of viremia does not correlate with input RNA, which is again indicative of virus amplification and spread. Finally, in the previous negative experiment using the non-consensus combinatorial library clones and the ΔGDD negative control (Example 3), 1000–2000 μg of HCV-specific RNA were inoculated per animal using similar procedures. No HCV RNA was detected at week 1 or thereafter, again suggesting that signal observed here is due to authentic virus replication and release into the serum.

Proof that the infections observed in these animals stemmed from the inoculated transcript RNA was obtained by restriction enzyme and sequence analysis of recovered virus for the presence of engineered markers. Two silent mutations marked all of the transfected RNAs. These were the substitution at position 899 (C instead of T) and the substitution at position 5936 (C instead of A) ablating the internal BsmI site (5934). For the nucleotide 899 marker, the region between 466 to 950 was amplified by nested RT-PCR, sequenced directly, and shown to have the expected H77 sequence including the silent C (instead of T) marker at position 899. The region from 5801 to 6257 was also amplified by nested RT-PCR and shown to be resistant to digestion with BsmI. The expected digestion products were obtained, however, for four other enzymes cleaving in this region [SstI (5923); BspHI (5944); Bsu36I (6209); RsaI (6244)] of the H77 cDNA sequence. These analyses were conducted for both chimpanzee #1535 (week 5) and chimpanzee #1536 (week 6).

The pathogenesis profiles for the RNA-inoculated animals are reminiscent of those obtained in previous experiments in which chimpanzees were inoculated with the H77 material or other HCV-containing samples. The course of this disease in chimpanzees, like man, is highly variable with respect to the extent of liver damage, progression to chronicity, level of viremia, and timing of seroconversion.

Identification of functional "infectious" clones by evaluating silent markers present in virus recovered from infected animals. As detailed above, additional silent markers were incorporated in order to help identify the 5' terminal sequence(s) and the length(s) of poly (U/UC) tract which were required or preferred for initiating infection.

Transcripts containing a single G (5'-GCCA . . . -3') were distinguished from those with additional 5' residues by the presence of the XhoI (514) silent marker in the C protein coding region. The region containing this marker was amplified by RT-PCR under conditions that ensured that a representative number of independent cDNAs were analyzed (greater than 50 in this case). The resulting products were analyzed for digestion with either XhoI or as a control, AccI, an enzyme which should digest this fragment for all input clones. For chimpanzee #1535 (week 3 sample), the fraction of the products digested with XhoI paralleled the input inoculum: approximately 20% was digested with XhoI (both 4 U and 30 U); 80% was resistant to digestion (values were determined by scanning ethidium bromide-stained digestion patterns with an IC1000 Imaging System). Complete digestion was observed for AccI. In the week 4 sample analyzed for chimpanzee #1536, 55% was digested with XhoI; 45% was resistant to digestion. Again, complete digestion was observed for AccI. Thus, in the second animal an advantage was observed for transcripts with only a single G (5'-GCCA . . . -3'). Although it is not possible to draw firm quantitative conclusions from these data regarding possible differences in specific infectivity, the results clearly demonstrate that the transcripts without additional nucleotides are infectious (clones p90/HCVFLlong pU and p91/HCV-FLshort pU). Furthermore, transcripts with additional nucleotides can also initiate infection, although our analysis thus far does not allow us to distinguish among the various clones.

Transcripts containing "short" or "long" poly (U/UC) tracts were distinguished by the silent marker at position 8054 of the NS5B coding region. The region between 7955 and 8088 was amplified by RT-PCR, using enough cDNA to ensure the amplification of greater than 100 independent cDNA molecules, and molecularly cloned. Sequences of ten and nine independent clones were determined for chimpanzee #1535 (week 3) and chimpanzee #1536 (week 4), respectively. Nine of ten clones (90%) for chimpanzee #1535 contained the G at position 8054, indicative of the "long" poly (U/UC) tract. Six of nine clones (66%) for chimpanzee #1536 contained the G at position 8054, indicative of the "long" poly (U/UC) tract. The results demonstrate that transcripts containing either "short" or "long" poly (U/UC) tracts are infectious but that the "long" poly (U/UC) tract appears to be preferred. We can not, however, rule out the possibility that this effect is due to deleterious effects of the marker mutation at 8054. These additional analyses provide further confirmation that the viremia observed in these animals was initiated by transcripts derived from our full-length clones.

The functional genotype 1a cDNA clones described in this Example, or functional clones for other HCV genotypes (constructed and verified using similar methods), have a variety of applications for development of (i) more effective HCV therapies; (ii) HCV vaccines; (iii) HCV diagnostics; and (iv) HCV-based gene expression vectors.

Example 5

Productive HCV Infection of a Hepatocyte Line

The EcoRI-BstBI fragment from pCEN was cloned into the unique SfiI site of p90/HCVFLlong pU. Prior to ligation, protruding termini were blunt ended using T4 DNA polymerase in the presence of dNTPs. The EcoRI-BstBI fragment from pCEN contains the EMCV IRES element followed by the neomycin-resistance (NEO) coding region. This IRES NEO cassette is essentially identical to that described in Ghattas et al. [*Mol. Cell. Biol.* 11:5848 (1991)]. A clone containing this cassette in the correct orientation (positive-sense with respect to HCV genome RNA) was identified by digestion with appropriate restriction enzymes.

EMCV IRES NEO cassette was inserted into the SfiI site in the 3' NTR of p90/HCVFL long pU. This transcribed RNA was used to transfect a human hepatocyte cell line, which was then selected for neomycin resistance using G418. Most cells died, but a G418 population grew up over the course of a few months. Remarkably, HCV RNA appears to be still present in these cells at a copy number of ~1000 RNA molecules per cell. It is believed that the neomycin resistance is mediated by HCV RNA because there is no evidence for integration of contaminating template DNA in the genome of these cells.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

The invention claimed is:

1. A method of selecting for an HCV sequence with an adaptive mutation that permits higher levels of HCV replication in a cell line, said method comprising:
   (a) transfecting a cell line in culture with a polynucleotide that comprises a non-naturally occurring HCV sequence capable of replication, said sequence comprising from 5' to 3' on the positive-sense nucleic acid:
      (i) an HCV 5' non-translated region (5' NTR) sequence, wherein said HCV 5'NTR sequence comprises at the 5' terminus at least one of NCCAGCC, GCCAGCC; GGCCAGCC; UGCCAGCC; AGCCAGCC; AAGCCAGCC; GAGCCAGCC; GUGCCAGCC; and GCGCCAGCC;
      (ii) an HCV non-structural protein coding region consensus sequence comprising an NS3 serine proteinase/helicase and an NS5B RNA-dependent RNA polymerase encoding region;
      (iii) a selectable marker under the control of the HCV replication machinery; and
      (iv) an HCV 3' non-translated region (3' NTR) that comprises a poly (u/c) tract of variable length and an HCV extreme 3' terminal conserved sequence of about 98 nucleotides; wherein said HCV 5' NTR, said HCV non-structural protein coding region, said selectable marker and said 3' NTR are operably associated;
   (b) culturing said cell line in vitro;
   (c) selecting for cell populations displaying the phenotype conferred by said selectable marker; and
   (d) isolating an adaptive HCV sequence from said cell populations of (c), thereby selecting for an HCV sequence with an adaptive mutation that permits higher levels of HCV replication in a cell line.

2. The method of claim 1, wherein said selectable marker is selected from the group consisting of the genes encoding dihydrofolate reductase, thymidine kinase, puromycin acetyl transferase, neomycin resistance (neo), G418 resistance (neo) hygromycin resistance, mycophenolic acid resistance (gpt), and zeocin resistance protein.

3. The method of claim 1, wherein said selectable marker is an antibiotic resistance gene.

4. The method of claim 3, wherein said selectable marker is a neomycin resistance gene.

5. The method of claim 4, wherein said gene is a neo gene.

6. The method of claim 3, wherein said culturing of (b) comprises culturing said cell line on media containing an antibiotic.

7. The method of claim 6, wherein said antibiotic is neomycin.

8. A method for selecting for an HCV sequence with an adaptive mutation that permits higher levels of HCV replication in a cell line, said method comprising:
   (a) providing a polynucleotide that comprises a non-naturally occurring HCV sequence capable of replication, said polynucleotide comprising from 5' to 3' on the positive-sense nucleic acid an HCV 5' non-translated region (5' NTR) sequence, wherein said HCV 5'NTR sequence comprises at the 5' terminus at least one of NCCAGCC, GCCAGCC; GGCCAGCC; UGCCAGCC; AGCCAGCC; AAGCCAGCC; GAGCCAGCC; GUGCCAGCC; and GCGCCAGCC, an HCV non-structural protein coding region consensus sequence comprising an NS3 serine proteinase/helicase and an NS5B RNA-dependent RNA polymerase encoding region, and an HCV 3' NTR that comprises a poly (u/c) tract of variable length and an HCV extreme 3' terminal conserved sequence of about 98 nucleotides, wherein the region of said HCV sequence encoding HCV structural proteins is replaced by a neomycin resistance gene, and wherein said HCV 5' NTR, said HCV non-structural protein coding region, said selectable marker and said 3' NTR are operably associated;
   (b) transfecting a cell line with the polynucleotide of (a);
   (c) culturing the transfected cell line in vitro on media containing neomycin;
   (d) identifying cell lines resistant to neomycin; and
   (e) isolating an adaptive HCV sequence from said cell lines of (d), thereby selecting for an HCV sequence with an adaptive mutation that permits higher levels of HCV replication in a cell line.

9. The method of claim 8, wherein the HCV further comprises an internal ribosome entry site (IRES) of a non-HCV virus, wherein said IRES directs translation of a sequence of the HCV that encodes non-structural proteins.

10. The method of claim 9 wherein the non-HCV virus is Encephalomyocarditis virus (EMCV).

11. A method for selecting for an HCV sequence with an adaptive mutation that permits higher levels of HCV replication in a cell line, said method comprising:
   (a) providing a polynucleotide that comprises a non-naturally occurring HCV sequence capable of replication, said polynucleotide comprising from 5' to 3' on the positive-sense nucleic acid an HCV 5' non-translated region (5' NTR) sequence, wherein said HCV 5'NTR sequence comprises at the 5' terminus at least one of NCCAGCC, GCCAGCC; GGCCAGCC; UGCCAGCC; AGCCAGCC; AAGCCAGCC; GAGCCAGCC; GUGCCAGCC; and GCGCCAGCC, an HCV non-structural protein coding region consensus sequence comprising an NS3 serine proteinase/helicase and an NS5B RNA-dependent RNA polymerase encoding region, and an HCV 3' NTR that comprises a poly (u/c) tract of variable length and an HCV extreme 3' terminal conserved sequence of about 98 nucleotides, wherein an internal ribosome entry site (IRES) of a non-HCV virus, directs translation of said HCV non-structural protein coding region, said polynucleotide further comprising a selectable marker that is operably associated with said HCV 5' non-translated region (5' NTR);

(b) transfecting a cell line with the polynucleotide of (a);
(c) culturing the transfected cell line in vitro;
(d) identifying cell populations displaying the phenotype conferred by said selectable marker; and
(e) isolating an adaptive HCV sequence from said cell lines of (d), thereby selecting for an HCV sequence with an adaptive mutation that permits higher levels of HCV replication in a cell line.

12. The method of claim 11, wherein said selectable marker is an antibiotic resistance gene.

13. The method of claim 12, wherein said selectable marker is a neomycin resistance gene.

14. A method for selecting for an HCV sequence with an adaptive mutation that permits higher levels of HCV replication in a cell line, said method comprising:
(a) providing an original HCV sequence comprising from 5' to 3' on the positive sense strand nucleic acid:
  (i) an HCV 5' NTR sequence, wherein said HCV 5'NTR sequence comprises at the 5' terminus at least one of NCCAGCC, GCCAGCC; GGCCAGCC; UGCCAGCC; AGCCAGCC; AAGCCAGCC; GAGCCAGCC; GUGCCAGCC; and GCGCCAGCC;
  (ii) a gene encoding neomycin resistance;
  (iii) an IRES from an Encephalomyocarditis virus;
  (iv) an HCV non-structural protein coding sequence consensus sequence comprising an NS3 serine proteinase/helicase and an NS5B RNA-dependent RNA polymerase encoding region; and
  (v) an HCV 3' NTR that comprises a poly (u/c) tract of variable length and an HCV extreme 3' terminal conserved sequence of about 98 nucleotides, wherein said HCV 5' NTR, said gene encoding neomycin resistance, said IRES, said non-structural protein coding sequence, and said 3' NTR are operably associated;
(b) transfecting a cell line with the HCV replicon of (a);
(c) culturing said cell line in media containing neomycin;
(d) selecting cell colonies that are resistant to neomycin;
(e) isolating an adaptive HCV sequence from said cell colonies of (d); thereby selecting for an HCV sequence with an adaptive mutation that permits higher levels of HCV replication in a cell line.

15. The method of claim 14, wherein the HCV coding sequence comprises a sequence that encodes HCV non-structural proteins.

16. The method of claim 15 wherein the region of the HCV coding sequence that encodes structural proteins is replaced with the gene encoding neomycin resistance.

17. A method for identifying a cell line that is permissive for infection with HCV, said method comprising:
(a) transfecting a cell line with a polynucleotide that comprises a non-naturally occurring HCV sequence capable of replication, said sequence comprising from 5' to 3' on the positive-sense nucleic acid:
  (i) an HCV 5' non-translated region (5' NTR) sequence, wherein said HCV 5'NTR sequence comprises at the 5' terminus at least one of NCCAGCC, GCCAGCC; GGCCAGCC; UGCCAGCC; AGCCAGCC; AAGCCAGCC; GAGCCAGCC; GUGCCAGCC; and GCGCCAGCC;
  (ii) an HCV non-structural protein coding region consensus sequence comprising an NS3 serine proteinase/helicase and an NS5B RNA-dependent RNA polymerase encoding region;
  (iii) a selectable marker under the control of the HCV replication machinery; and
  (iv) an HCV 3' non-translated region (3' NTR) that comprises a poly (u/c) tract of variable length and an HCV extreme 3' terminal conserved sequence of about 98 nucleotides; wherein said HCV 5' NTR, said HCV non-structural protein coding region, said selectable marker and said 3' NTR are operably associated;
(b) culturing said cell line in vitro; and
(c) selecting for a cell line displaying the phenotype conferred by said selectable marker; thereby identifying a cell line that is permissive for infection with HCV.

18. A method of selecting for an HCV sequence with an adaptive mutation that permits higher levels of HCV replication in a permissive cell line, said method comprising:
(a) providing an HCV replicon comprising from 5' to 3' on the positive sense strand nucleic acid:
  (i) an HCV 5' NTR sequence, wherein said HCV 5'NTR sequence comprises at the 5' terminus at least one of NCCAGCC, GCCAGCC; GGCCAGCC; UGCCAGCC; AGCCAGCC; AAGCCAGCC; GAGCCAGCC; GUGCCAGCC; and GCGCCAGCC;
  (ii) an HCV non-structural protein coding consensus sequence comprising an NS3 serine proteinase/helicase and an NS5B RNA-dependent RNA polymerase encoding region; and
  (iii) an HCV 3' NTR that comprises a poly (u/c) tract of variable length and an HCV extreme 3' terminal conserved sequence of about 98 nucleotides, wherein said HCV 5' NTR, said HCV non-structural protein coding sequence, and said 3' NTR are operably associated;
(b) transfecting a cell line with the HCV replicon of (a);
(c) culturing said cell line in media; and
(d) detecting progressively increasing levels of HCV RNA in the cell line or the animal, thereby selecting for an HCV sequence with an adaptive mutation that permits higher levels of HCV replication in a permissive cell line.

19. The method of claim 18, wherein the HCV replicon further comprises an operably associated sequence that encodes HCV structural proteins.

20. The method of claim 18, wherein detection of progressively increasing levels of HCV RNA is effected by assaying for HCV RNA by RT-PCR or nucleic acid hybridization.

21. The method of claim 18, wherein detection of progressively increasing levels of HCV RNA is effected by assaying for activity of HCV virions or HCV viral proteins.

22. The method of claim 18, wherein detection of progressively increasing levels of HCV RNA is effected by assaying for immunological characteristics of HCV virions or HCV viral proteins.

23. The method of claim 18, wherein said HCV replicon further comprises an operably associated gene encoding neomycin resistance, wherein said media of step (c) comprises neomycin or G418, and wherein detection of progressively increasing levels of HCV RNA is effected by selecting cell colonies that are resistant to neomycin or G418.

* * * * *